(12) United States Patent
Hatakeyama et al.

(10) Patent No.: US 11,965,095 B2
(45) Date of Patent: Apr. 23, 2024

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Osamu Watanabe, Joetsu (JP); Joe Ikeda, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 636 days.

(21) Appl. No.: 17/195,004

(22) Filed: Mar. 8, 2021

(65) Prior Publication Data
US 2021/0371663 A1   Dec. 2, 2021

(30) Foreign Application Priority Data
Apr. 1, 2020  (JP) .................................. 2020-65962

(51) Int. Cl.
*C08L 87/00*      (2006.01)
*A61B 5/268*     (2021.01)
(Continued)

(52) U.S. Cl.
CPC ............ *C08L 87/005* (2013.01); *A61B 5/268* (2021.01); *A61B 5/28* (2021.01);
(Continued)

(58) Field of Classification Search
CPC .......... A61B 5/25; A61B 5/263; A61B 5/265; A61B 5/266; A61B 5/268;
(Continued)

(56) References Cited

U.S. PATENT DOCUMENTS 5,981,680 A    11/1999  Petroff et al.
10,734,132 B2 *  8/2020  Hatakeyama .......... H01B 1/122
(Continued)

FOREIGN PATENT DOCUMENTS

JP    H05-095924 A    4/1993
JP    2002-332305 A    11/2002
(Continued)

*Primary Examiner* — Eun Hwa Kim
(74) *Attorney, Agent, or Firm* — Oliff PLC

(57) ABSTRACT

A bio-electrode composition contains (A) an ionic polymer material. The component (A) is a polymer compound containing: a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a side chain with a radical-polymerizable double bond in a structure selected from the group consisting of (meth)acrylate, vinyl ether, and styrene. Thus, the present invention provides: a bio-electrode composition capable of forming a living body contact layer for a bio-electrode to enable signal collection immediately after attachment to skin and prevention of residue on the skin after peeling from the skin; a bio-electrode including a living body contact layer formed of the bio-electrode composition; and a method for manufacturing the bio-electrode.

20 Claims, 2 Drawing Sheets

(51) Int. Cl.
*A61B 5/28* (2021.01)
*C08F 220/18* (2006.01)
*C08F 220/38* (2006.01)
*C08F 265/06* (2006.01)
*C09D 5/24* (2006.01)
*C09D 187/00* (2006.01)

(52) U.S. Cl.
CPC .. *C08F 220/1808* (2020.02); *C08F 220/1809* (2020.02); *C08F 220/382* (2020.02); *C08F 220/387* (2020.02); *C08F 265/06* (2013.01); *C09D 5/24* (2013.01); *C09D 187/005* (2013.01); *A61B 2562/0209* (2013.01); *A61B 2562/125* (2013.01); *C08L 2203/02* (2013.01); *C08L 2203/20* (2013.01)

(58) Field of Classification Search
CPC ...... A61B 2562/0209; A61B 2562/125; C08L 87/005; C08L 2203/02; C08L 2203/20; C08L 101/02; C08F 220/1808; C08F 220/1809; C08F 220/382; C08F 220/387; C08F 265/06; C08F 212/30; C09D 5/24; C09D 187/005; C09D 4/06
See application file for complete search history.

(56) References Cited

U.S. PATENT DOCUMENTS

| | | | |
|---|---|---|---|
| 2002/0188069 | A1 | 12/2002 | Sugo et al. |
| 2015/0275060 | A1 | 10/2015 | Kuroda et al. |
| 2016/0155530 | A1 | 6/2016 | Someya et al. |
| 2017/0275510 | A1 | 9/2017 | Quan et al. |
| 2018/0072930 | A1 | 3/2018 | Hatakeyama et al. |
| 2018/0085019 | A1 | 3/2018 | Hatakeyama et al. |
| 2018/0086948 | A1 | 3/2018 | Hatakeyama et al. |
| 2018/0168470 | A1* | 6/2018 | Hatakeyama ......... A61L 31/028 |
| 2018/0215876 | A1 | 8/2018 | Hatakeyama et al. |
| 2018/0223133 | A1 | 8/2018 | Hatakeyama et al. |
| 2018/0229023 | A1 | 8/2018 | Hatakeyama et al. |
| 2018/0229024 | A1 | 8/2018 | Hatakeyama et al. |
| 2018/0240564 | A1* | 8/2018 | Hatakeyama ......... C08F 128/00 |
| 2018/0273811 | A1 | 9/2018 | Cura et al. |
| 2019/0106528 | A1 | 4/2019 | Hatakeyama et al. |

FOREIGN PATENT DOCUMENTS

| | | | |
|---|---|---|---|
| JP | 2003-225217 | A | 8/2003 |
| JP | 2004-033468 | A | 2/2004 |
| JP | 2005-320418 | A | 11/2005 |
| JP | 2011-079946 | A | 4/2011 |
| JP | 2015-019806 | A | 2/2015 |
| JP | 2015-100673 | A | 6/2015 |
| JP | 2015-193803 | A | 11/2015 |
| JP | 2016-011338 | A | 1/2016 |
| JP | 2016-065238 | A | 4/2016 |
| JP | 2018-044147 | A | 3/2018 |
| JP | 2018-059050 | A | 4/2018 |
| JP | 2018-059052 | A | 4/2018 |
| JP | 2018-099504 | A | 6/2018 |
| JP | 2018-123304 | A | 8/2018 |
| JP | 2018-126496 | A | 8/2018 |
| JP | 2018-130533 | A | 8/2018 |
| JP | 2018-130534 | A | 8/2018 |
| JP | 2019-503406 | A | 2/2019 |
| JP | 2019-070109 | A | 5/2019 |
| WO | 2013/039151 | A1 | 3/2013 |

* cited by examiner

[FIG. 1]
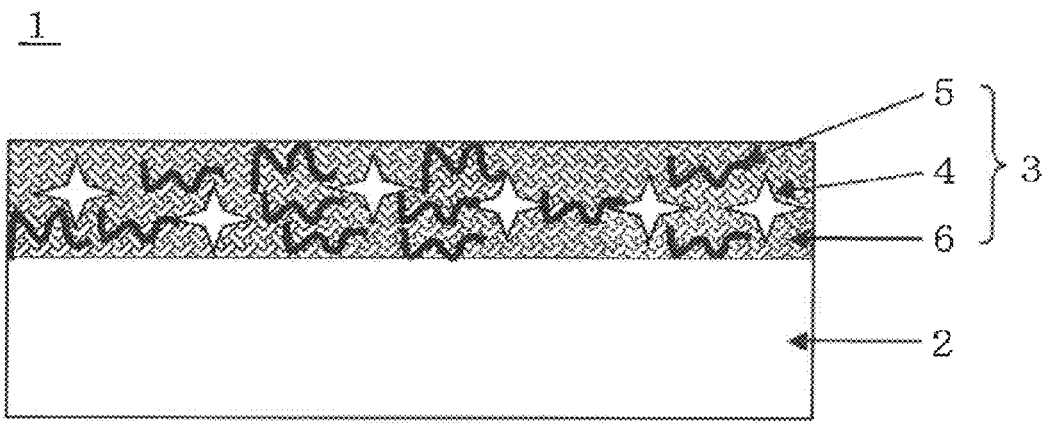
[FIG. 2]
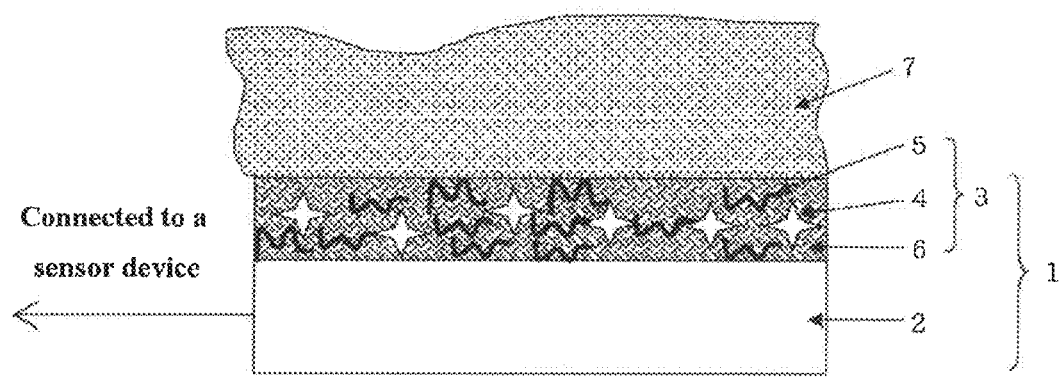
[FIG. 3]
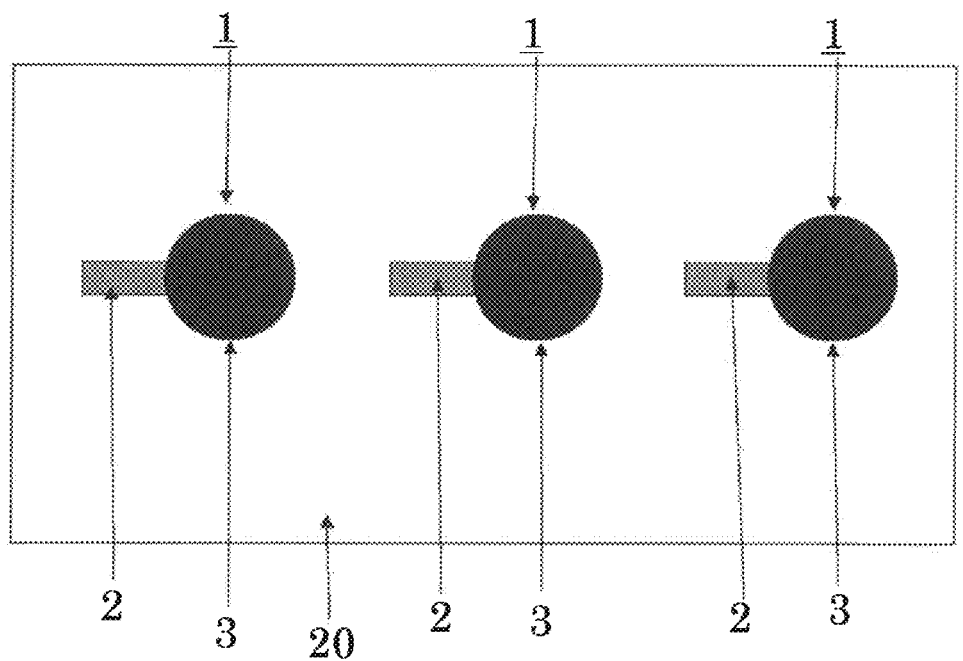

[FIG. 4]
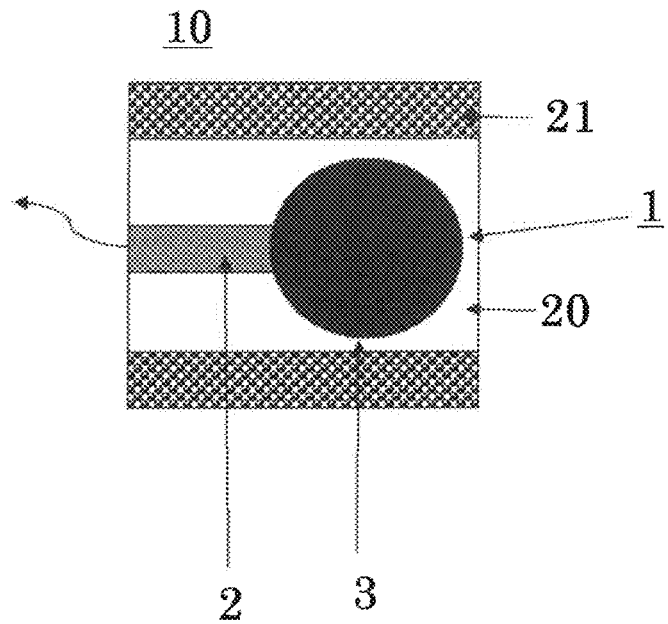
[FIG. 5]
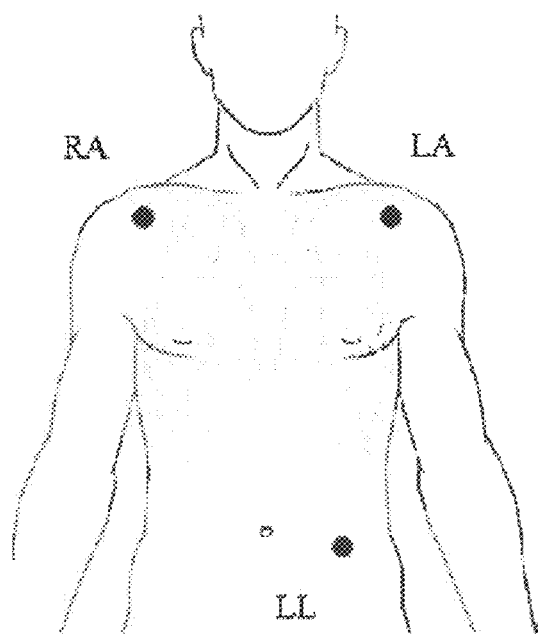
[FIG. 6]
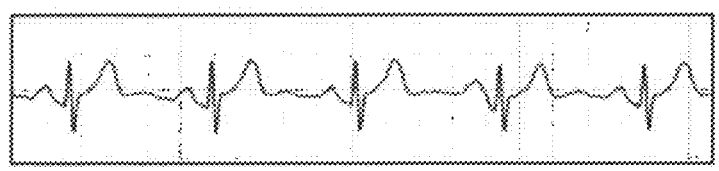

BIO-ELECTRODE COMPOSITION, BIO-ELECTRODE, AND METHOD FOR MANUFACTURING BIO-ELECTRODE

TECHNICAL FIELD

The present invention relates to a bio-electrode that is used in contact with the skin of a living body and capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of such major wearable devices as watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detect an electric signal to measure the motion of the heart. The electrocardiogram measurement is conducted by attaching an electrode coated with an electro-conductive paste to a body, but this is a single (not continuous), short-time measurement. On the other hand, the above medical wearable device is aimed at continuously monitoring the condition of health for a few weeks. Accordingly, a bio-electrode used in a medical wearable device is required to make no changes in electric conductivity even in long-time use and cause no skin allergy. In addition to these, it is required that a bio-electrodes is light-weight and can be produced at low cost.

Medical wearable devices are classified into two types: a type in which a device is directly attached to body and a type in which a device is incorporated into clothes. As the type in which a device is attached to a body, it has been proposed a bio-electrode using water soluble gel containing water and electrolyte, which are materials of the foregoing electro-conductive paste (Patent Document 1). The water soluble gel contains sodium, potassium, or calcium as the electrolyte in a water soluble polymer for retaining water, and converts changes of ion concentration from skin into electricity. On the other hand, as the type in which a device is incorporated into clothes, it has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. The carbon nanotubes can stimulate (irritate) a living body by the same reason. Although the carbon black is not as poisonous as carbon nanotube, it also stimulates the skin to a certain degree. Accordingly, even if these electrode materials themselves cause no allergic reaction, the biocompatibility may be degraded depending on the shape of a material and its inherent stimulation, thereby making it hard to satisfy both electric conductivity and biocompatibility.

Although metal films seem to function as an excellent bio-electrode thanks to extremely high electric conductivity, this is not always the case. Upon heartbeat, the human skin releases not only extremely weak current, but also a sodium ion, a potassium ion, and a calcium ion. It is thus necessary to convert changes in ion concentration into current. Noble metals, however, are difficult to ionize and are inefficient in converting ions from skin to current. Therefore, the resulting bio-electrode using the noble metal is characterized by high impedance and high resistance to the skin during electrical conduction.

There have been proposed bio-electrodes in each of which an ionic polymer (hereinafter, ionic polymer material) is added (Patent Documents 6, 7, 8). A bio-electrode obtained by mixing a silicone adhesive with an ionic polymer material and a carbon powder added thereto has adhesion and high water repellency so that biological signals can be stably collected even while taking a shower or when the bio-electrode is attached to the skin for a long time in a wet state by sweat. Ionic polymer materials do not permeate to the skin and hence do not stimulate the skin, and the biocompatibility is high. From these aspects, the bio-electrode enables long-time attachment.

Although silicones are inherently insulators, the ionic conductivity is improved by the combination with an ionic polymer material and a carbon powder, and thus the function as a bio-electrode is obtained. Nevertheless, it has been desired to improve the performance by further improving the ionic conductivity.

For improvement of the ionic conductivity, increasing the proportion of the ionic polymer material is effective. However, ionic polymer materials are poor in adhesion, and increasing the proportion thereof lowers the adhesive strength, or after the bio-electrode is peeled off, the component may remain sticking to the skin. Adhesion is necessary to obtain stable biological signals even when skin is stretched back and forth in human activities.

Bio-electrodes are required to collect signals immediately after attached to skin. A gel electrode has ion concentrations equivalent to those of skin, and ions move in and out smoothly. In a water-containing gel, ions move so fast that signals can be detected immediately after attachment to the skin. Meanwhile, it takes long time for a dry electrode to detect signals after attachment to skin. This is presumably because no signal is found until the dry electrode surface is saturated with ions released from skin.

CITATION LIST

Patent Literature

Patent Document 1: WO 2013-039151 A1
Patent Document 2: JP 2015-100673 A
Patent Document 3: JP H05-095924 A
Patent Document 4: JP 2003-225217 A
Patent Document 5: JP 2015-019806 A Patent Document 6: JP 2018-99504 A
Patent Document 7: JP 2018-126496 A
Patent Document 8: JP 2018-130533 A

SUMMARY OF INVENTION

Technical Problem

The present invention has been made to solve the above problems and has an object to provide: a bio-electrode composition capable of forming a living body contact layer for a bio-electrode to enable signal collection immediately after attachment to skin and prevention of residue on the skin after peeling from the skin; a bio-electrode including a living body contact layer formed of the bio-electrode composition; and a method for manufacturing the bio-electrode.

Solution to Problem

To achieve the object, the present invention provides a bio-electrode composition comprising (A) an ionic polymer material, wherein the component (A) is a polymer compound comprising:

a repeating unit-a having a structure selected from the group consisting of salts of ammonium, sodium, potassium, and silver formed with any of fluorosulfonic acid, fluorosulfonimide, and N-carbonyl-fluorosulfonamide; and a repeating unit-b having a side chain with a radical-polymerizable double bond in a structure selected from the group consisting of (meth)acrylate, vinyl ether, and styrene.

The inventive bio-electrode composition contains the component (A) that is an ionic polymer material containing the ionic repeating unit-a and the repeating unit-b having a side chain with a radical-polymerizable double bond. This makes it possible to provide a living body contact layer for a bio-electrode capable of exhibiting excellent ionic conductivity, and also capable of preventing residue on skin even when the bio-electrode is peeled from the skin after long-time attachment to the skin. Since the living body contact layer formed from the inventive bio-electrode composition is capable of exhibiting excellent ionic conductivity, this enables the signal collection immediately after attachment to skin. Accordingly, the inventive bio-electrode composition is capable of forming a living body contact layer for a bio-electrode to enable signal collection immediately after attachment to skin and prevention of residue on the skin after peeling from the skin.

Moreover, since the component (A) incorporated in the inventive bio-electrode composition is a polymer material, it is possible to exhibit low permeability to skin, thereby causing less irritation to a body. Thus, the inventive bio-electrode composition can form a living body contact layer for a bio-electrode capable of exhibiting not only excellent ionic conductivity but also excellent biocompatibility.

Further, the inventive bio-electrode composition enables low-cost formation of a living body contact layer for a light-weight bio-electrode. In addition, the living body contact layer for a bio-electrode formed from the inventive bio-electrode composition is capable of preventing significant reduction in electric conductivity (ionic conductivity) even when wetted with water or dried.

The repeating unit-a is preferably shown by any of the following general formulae (1)-1 to (1)-4,

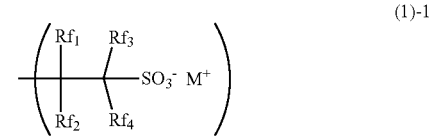

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; and $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms and at least one or more fluorine atoms; $M^+$ represents an ion selected from the group consisting of an ammonium ion, a sodium ion, a potassium ion, and a silver ion; and "m" represents an integer of 1 to 4.

The repeating unit-a having such structures enables the bio-electrode composition to form a living body contact layer for a bio-electrode that is more excellent in electric conductivity and biocompatibility.

The repeating unit-a further preferably comprises at least one repeating unit selected from the group consisting of repeating units-a1 to -a7 shown by the following general formula (2),

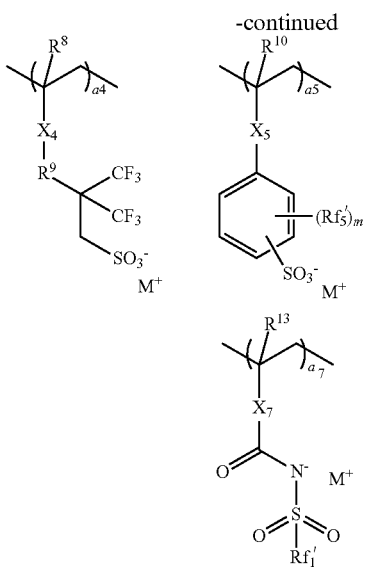
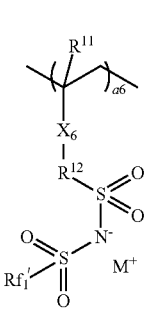
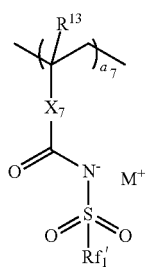

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent a single bond, or a linear, branched, or cyclic hydrocarbon group having 1 to 12 carbon atoms, the hydrocarbon group optionally having either or both of an ester group and an ether group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$, $X_6$, and $X_7$, each independently represent any of a single bond, a phenylene group, a naphthylene group, an ether group, an ester group, and an amide group; $X_5$ represents any of a single bond, an ether group, and an ester group; Y represents an oxygen atom or a —$NR^{19}$— group; $R^{19}$ represents a hydrogen atom, or a linear or branched alkyl group having 1 to 4 carbon atoms; $Rf_1'$ represents a fluorine atom or a trifluoromethyl group; $Rf_5'$ represents a fluorine atom, or a linear or branched alkyl group having 1 to 4 carbon atoms and at least one or more fluorine atoms; "m" represents an integer of 1 to 4; a1, a2, a3, a4, a5, a6, and a7 satisfy $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, and $0 < a1+a2+a3+a4+a5+a6+a7 < 1.0$; and $M^+$ represents an ion selected from the group consisting of an ammonium ion, a sodium ion, a potassium ion, and a silver ion.

The repeating unit-a having such structures enables the bio-electrode composition to form a living body contact layer for a bio-electrode that is further excellent in electric conductivity and biocompatibility.

The component (A) preferably comprises an ammonium ion shown by the following general formula (3) as the $M^+$,

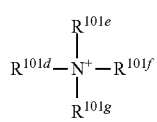 (3)

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula (3) within the ring.

The component (A) containing such an ammonium ion enables the bio-electrode composition to form a living body contact layer for a bio-electrode that is further excellent in electric conductivity and biocompatibility.

The repeating unit-b is preferably shown by the following general formula (4),

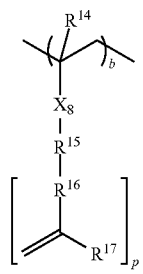 (4)

wherein $R^{14}$ and $R^{17}$ each represent a hydrogen atom or a methyl group; $X_8$ represents any of a single bond, a phenylene group, a naphthylene group, an ether group, an ester group, and an amide group; $R^{15}$ represents a single bond, a linear, branched, or cyclic alkylene group having 1 to 20 carbon atoms, or an aryl group having 6 to 10 carbon atoms, the alkylene group optionally having an ether group, an ester group, a hydroxy group, an alkoxy group, an alkoxycarbonyl group, a urethane group, a carbonate group, or an amino group; $R^{16}$ represents an ether group, an ester group, or a phenylene group; "p" represents an integer of 1 to 3; and "b" represents a number satisfying $0 < b < 1.0$.

The repeating unit-b having such a structure enables the bio-electrode composition to form a living body contact layer for a bio-electrode that can further suppress residue when the bio-electrode is peeled from skin.

In addition to the component (A), the bio-electrode composition preferably comprises (B) a component which is a resin containing any one or more of silicone, polyacrylate, and polyurethane.

The bio-electrode composition further containing such a component (B) is a bio-electrode composition capable of forming a living body contact layer for a bio-electrode that constantly adheres to skin and enables stable electric-signal collection for a long time.

The resin containing any one or more of silicone, polyacrylate, and polyurethane as the component (B) preferably has adhesion.

The component (B) can be such an adhesive resin.

The inventive bio-electrode composition may further comprise a radical generator.

Incorporating a radical generator allows effective cross-linking at the radical-crosslinkable moiety in the component (A).

The inventive bio-electrode composition may further comprise an organic solvent.

The bio-electrode composition containing an organic solvent can exhibit high coating properties.

The inventive bio-electrode composition may further comprise any one or more of a carbon material, a silicon powder, a silver powder, and a lithium titanate powder having a spinel structure.

A carbon material and a silver powder function as electric conductivity improvers, and can impart more excellent electric conductivity to the living body contact layer formed from the bio-electrode composition. A silicon powder and a lithium titanate powder can further enhance the ion reception sensitivity of the living body contact layer formed from the bio-electrode composition.

The present invention also provides a bio-electrode comprising an electro-conductive base material and a living body contact layer formed on the electro-conductive base material, wherein
the living body contact layer is a cured material of the inventive bio-electrode composition.

Since the inventive bio-electrode has the living body contact layer that is a cured material of the inventive bio-electrode composition, the inventive bio-electrode enables signal collection immediately after attachment to skin and prevention of residue on the skin after peeling from the skin. Moreover, the inventive bio-electrode is capable of exhibiting excellent ionic conductivity as well as excellent biocompatibility.

Further, the inventive bio-electrode is light-weight and manufacturable at low cost. Additionally, the living body contact layer of the inventive bio-electrode is capable of preventing significant reduction in electric conductivity (ionic conductivity) even when wetted with water or dried.

The electro-conductive base material can comprise one or more species selected from the group consisting of gold, silver, silver chloride, platinum, aluminum, magnesium, tin, tungsten, iron, copper, nickel, stainless steel, chromium, titanium, and carbon.

The inventive bio-electrode can include various electro-conductive base materials as described above.

Further, the present invention provides a method for manufacturing a bio-electrode having an electro-conductive base material and a living body contact layer formed on the electro-conductive base material, comprising:
applying the inventive bio-electrode composition onto the electro-conductive base material; and
curing the bio-electrode composition to form the living body contact layer.

The inventive bio-electrode can be manufactured according to inventive method for manufacturing a bio-electrode.

The living body contact layer can be formed by curing the bio-electrode composition through light irradiation.

In this manner, for example, light irradiation may be performed to cure the inventive bio-electrode composition to thus obtain the living body contact layer.

Preferably, after the living body contact layer is formed, the living body contact layer is immersed in water, or the living body contact layer is humidified.

Such a treatment improves the compatibility with skin, and it is possible to manufacture a bio-electrode having a living body contact layer that is capable of obtaining biological signals more quickly.

The electro-conductive base material can comprise one or more species selected from the group consisting of gold, silver, silver chloride, platinum, aluminum, magnesium, tin, tungsten, iron, copper, nickel, stainless steel, chromium, titanium, and carbon.

In the inventive method for manufacturing a bio-electrode, various electro-conductive base materials can be used as described above.

Advantageous Effects of Invention

As described above, the inventive bio-electrode composition makes it possible to form a living body contact layer for a bio-electrode that enables signal collection immediately after attachment to skin and prevention of residue on the skin after peeling from the skin. Moreover, the inventive bio-electrode composition can form a living body contact layer for a bio-electrode that is capable of exhibiting excellent ionic conductivity and excellent biocompatibility. Further, the inventive bio-electrode composition enables formation of a living body contact layer for a light-weight bio-electrode at low cost. Additionally, the living body contact layer for a bio-electrode formed from the inventive bio-electrode composition is capable of preventing significant reduction in the electric conductivity (ionic conductivity) even when the bio-electrode is wetted with water or dried.

Furthermore, the inventive bio-electrode is capable of collecting signals immediately after attachment to skin and preventing residue on the skin after peeling from the skin. Moreover, the inventive bio-electrode is capable of exhibiting not only excellent ionic conductivity but also excellent biocompatibility. Further, the inventive bio-electrode is light-weight and manufacturable at low cost. Additionally, the living body contact layer of the inventive bio-electrode is capable of preventing significant reduction in the electric conductivity (ionic conductivity) even when wetted with water or dried.

Furthermore, according to the inventive method for manufacturing a bio-electrode, the inventive bio-electrode can be manufactured.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer thereon;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As described above, it has been desired to develop: a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried and prevents residue from remaining on skin after peeling from the skin; a bio-electrode including a living body contact layer formed of the bio-electrode composition; and a method for manufacturing the bio-electrode.

The surface of skin releases ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions.

To stably obtain biological signals after attachment to skin, a bio-electrode film needs to have adhesion. Meanwhile, if a residue remains on skin when a bio-electrode is peeled after long-time attachment, the residue may cause rash or rough skin. To prevent such residue, the bio-electrode needs to be formed from crosslinkable ion polymer. The combination of an epoxy group, a hydroxy group and an isocyanate group as crosslinking groups is not preferable because if unreacted groups are present after the crosslinking reaction, these cause rough skin.

On the other hand, radical reactive groups, for example, a (meth)acrylate group, have a low possibility of causing rough skin even when the unreacted groups are present. This finding has led to the present invention.

In neutralized salts formed from highly acidic acids, the ions are strongly polarized, so that the ionic conductivity is improved. This is why lithium salts of bis(trifluoromethanesulfonyl)imidic acid and tris(trifluoromethanesulfonyl)methide acid show high ionic conductivity as electrolytes of a lithium ion battery. On the other hand, before the formation of the neutralized salt, the higher acidity of the acid makes the salt have stronger irritation to a body. That is, ionic conductivity and irritation to a body are in relation of trade-off. In a salt applied to a bio-electrode, however, higher ionic conductivity and lower irritation to a body have to be combined.

As the molecular weight of ionic compound increases, the permeability and the stimulus to skin tend to decrease. Accordingly, the ionic compound is preferably a polymer type with higher molecular weight.

Thus, the present inventors have conceived that such an ionic compound is prepared into a form having a polymerizable double bond and polymerized to form a polymer, and also that a radical crosslinking group is attached to this polymerized ionic polymer material and crosslinked during the curing reaction in the bio-electrode film formation process. Then, the present inventors have found that when this bio-electrode film is peeled after long-time attachment, no residue remains on skin.

Based on these discoveries, the present inventors propose: a bio-electrode composition that contains a radical-crosslinkable ionic polymer material; and a bio-electrode having a living body contact layer that is a cured material of the bio-electrode composition.

Further, the present inventors have found that when this ionic polymer material (salt) is mixed with, for example, a silicone, acrylic, or urethane based adhesive (resin), particularly a polyurethane acrylate resin, the use of this mixture enables the resulting bio-electrode to constantly adhere to skin and obtain stably electric signals for a long time.

Furthermore, the present inventors have found that it is preferable to enhance electron conductivity in addition to ionic conductivity so as to obtain a highly sensitive bio-electrode. To enhance electron conductivity, for example, adding a carbon material or a metal powder such as silver powder is effective. Moreover, ion receptivity can be enhanced by adding a silicon powder or a lithium titanate powder.

In sum, the present invention is a bio-electrode composition comprising (A) an ionic polymer material, wherein
the component (A) is a polymer compound comprising:
a repeating unit-a having a structure selected from the group consisting of salts of ammonium, sodium, potassium, and silver formed with any of fluorosulfonic acid, fluorosulfonimide, and N-carbonyl-fluorosulfonamide; and
a repeating unit-b having a side chain with a radical-polymerizable double bond in a structure selected from the group consisting of (meth)acrylate, vinyl ether, and styrene.

Hereinafter, the present invention will be described in detail, but the present invention is not limited thereto.

<Bio-Electrode Composition>

The inventive bio-electrode composition contains (A) an ionic polymer material. In addition to the component (A), the inventive bio-electrode composition can further contain any one or more optional components such as (B) a resin other than the component (A), a radical generator, an additive, and an organic solvent.

Hereinafter, each component will be further described in detail.

[(A) Ionic Polymer Material (Salt)]

A salt to be incorporated into the inventive bio-electrode composition as (A) the ionic polymer material (conductive material) is a polymer compound containing:
a repeating unit-a having a structure selected from the group consisting of salts of ammonium, sodium, potassium, and silver formed with any of fluorosulfonic acid, fluorosulfonimide, and N-carbonyl-fluorosulfonamide; and
a repeating unit-b having a side chain with a radical-polymerizable double bond in a structure selected from the group consisting of (meth)acrylate, vinyl ether, and styrene.

(Repeating Unit-a)

The repeating unit-a can be shown by any of the following general formulae (1)-1 to (1)-4.

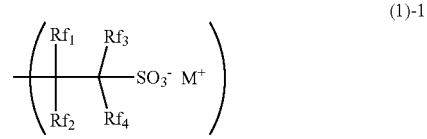

(1)-1

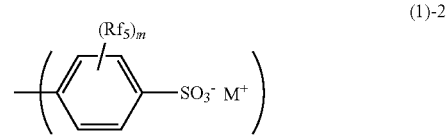

(1)-2

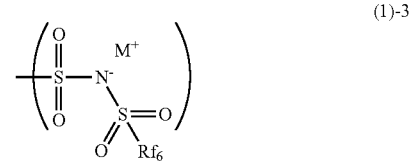

(1)-3

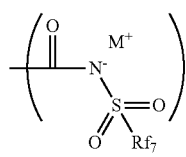

(1)-4

In the formula (1)-1, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group.

In the formulae (1)-2, (1)-3, and (1)-4, $Rf_5$, $Rf_6$, and $Rf_7$ each represent a fluorine atom, or a linear or branched alkyl group having 1 to 4 carbon atoms and at least one or more fluorine atoms.

In the formulae (1)-1 to (1)-4, $M^+$ represents an ion selected from the group consisting of an ammonium ion, a sodium ion, a potassium ion, and a silver ion.

In the formula (1)-2, "m" represents an integer of 1 to 4.

When the repeating unit-a has such structures, the resulting bio-electrode composition is capable of forming a living body contact layer for a bio-electrode that is more excellent in electric conductivity and biocompatibility.

One or more repeating units-a selected from the group consisting of salts of ammonium, sodium, potassium, and silver formed with any of fluorosulfonic acid as shown by the general formula (1)-1 or (1)-2, sulfonimide as shown by (1)-3, and N-carbonyl-fluorosulfonamide as shown by (1)-4 are preferably at least one repeating unit selected from the group consisting of repeating units-a1 to -a7 shown by the following general formula (2).

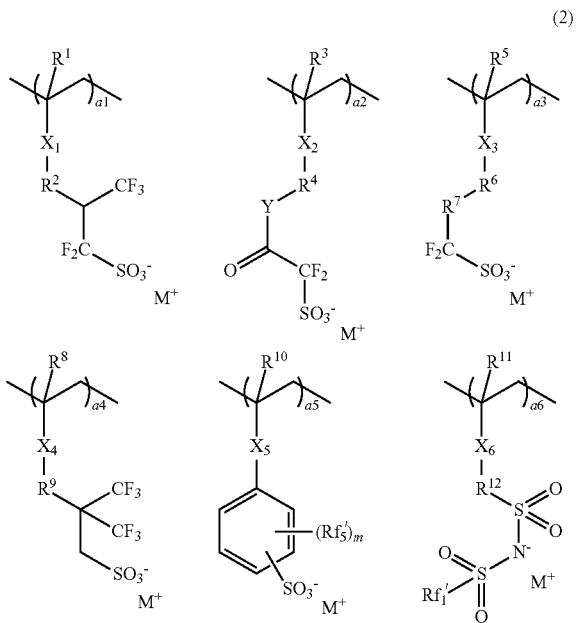

(2)

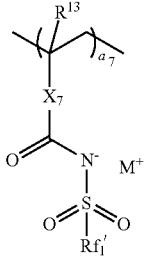

In the formula (2), $R^1$, $R^3$, $R^5$, $R^8$, $R^{10}$, $R^{11}$, and $R^{13}$ each independently represent a hydrogen atom or a methyl group. $R^2$, $R^4$, $R^6$, $R^9$, and $R^{12}$ each independently represent a single bond, or a linear, branched, or cyclic hydrocarbon group having 1 to 12 carbon atoms. The hydrocarbon group optionally has either or both of an ester group and an ether group. $R^7$ represents a linear or branched alkylene group having 1 to 4 carbon atoms, and one or two hydrogen atoms in $R^7$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. X represents any of a single bond, an ether group, and an ester group. Y represents an oxygen atom or a —$NR^{19}$— group. $R^{19}$ represents a hydrogen atom, or a linear or branched alkyl group having 1 to 4 carbon atoms. $Rf_1{'}$ represents a fluorine atom or a trifluoromethyl group. $Rf_5{'}$ represents a fluorine atom, or a linear or branched alkyl group having 1 to 4 carbon atoms and at least one or more fluorine atoms. "m" represents an integer of 1 to 4. a1, a2, a3, a4, a5, a6, and a7 satisfy $0 \le a1 < 1.0$, $0 \le a2 < 1.0$, $0 \le a3 < 1.0$, $0 \le a4 < 1.0$, $0 \le a5 < 1.0$, $0 \le a6 < 1.0$, $0 \le a7 < 1.0$, and $0 < a1+a2+a3+a4+a5+a6+a7 < 1.0$. $M^+$ represents an ion selected from the group consisting of an ammonium ion, a sodium ion, a potassium ion, and a silver ion.

When the repeating unit-a has such structures, the resulting bio-electrode composition is capable of forming a living body contact layer for a bio-electrode that is further excellent in electric conductivity and biocompatibility.

Note that a1, a2, a3, a4, a5, a6, and a7 are symbols to identify the respective repeating units, and also represent the proportions of the respective repeating units in the ionic polymer material (A). The formula (2) specifically illustrates: the repeating units-a1, -a2, -a3, -a4, and -a5 in this order from left to right at the top; and the repeating units-a6 and -a7 in this order from left to right at the bottom.

Among the repeating units-a1 to -a7 shown by the general formula (2), the repeating units-a1 to -a5 can be obtained from fluorosulfonic acid salt monomers specifically exemplified below.

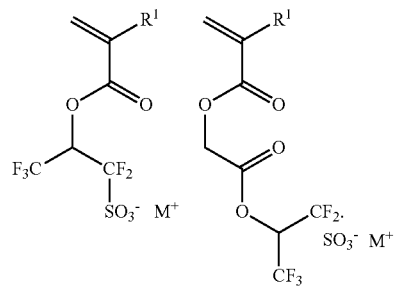

-continued
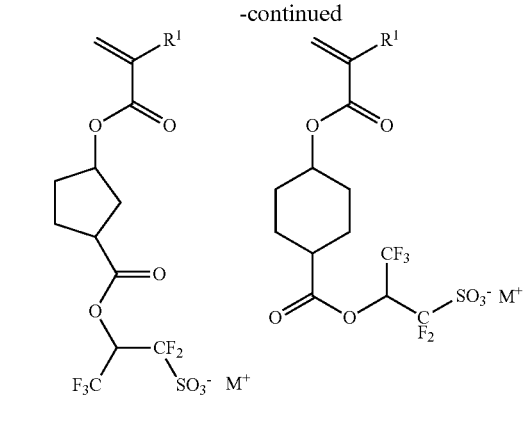
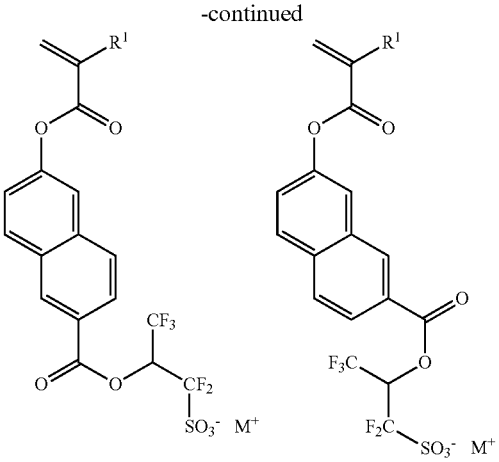
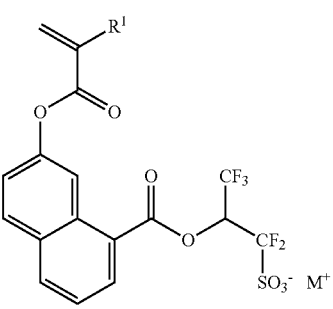
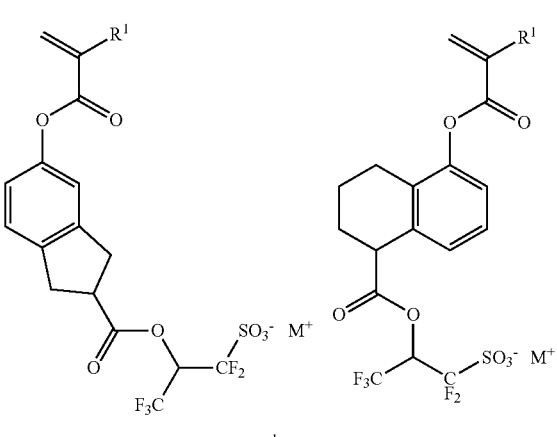
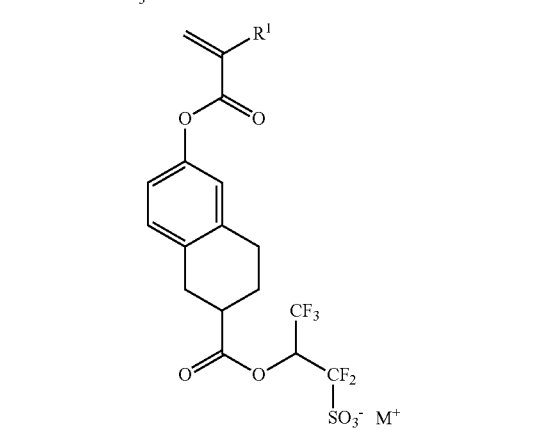

-continued
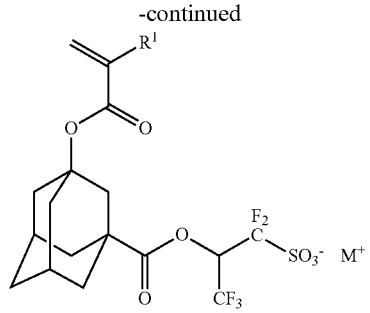
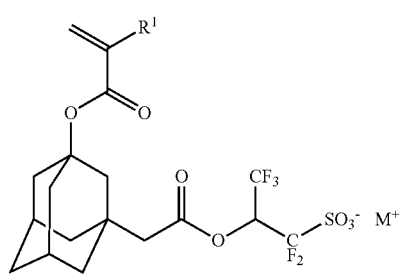
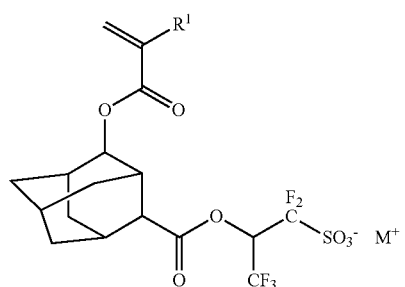
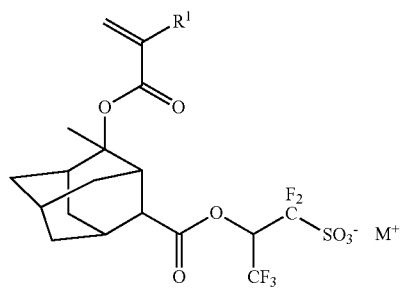
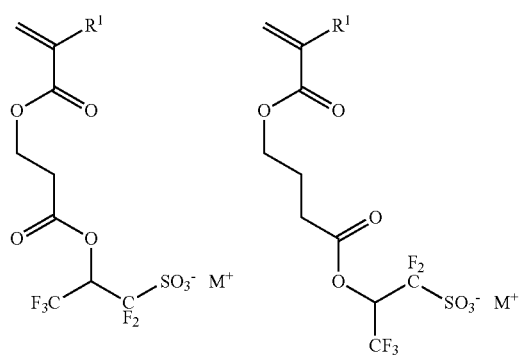
-continued
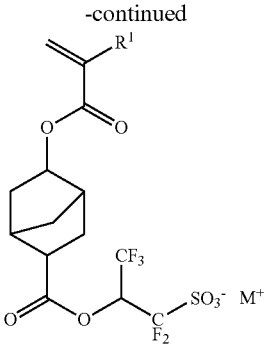
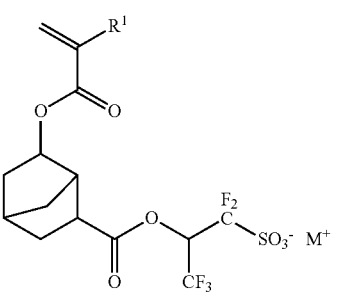
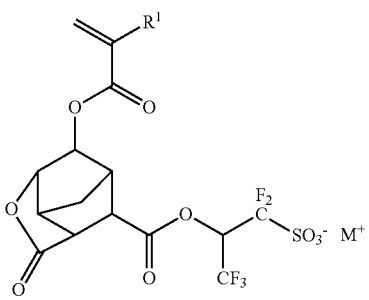
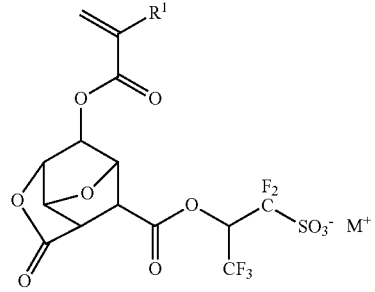
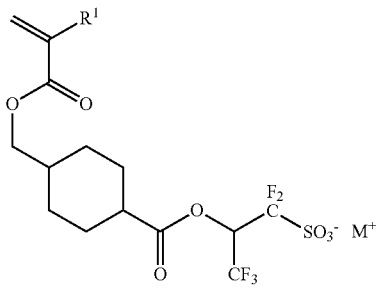

17
-continued
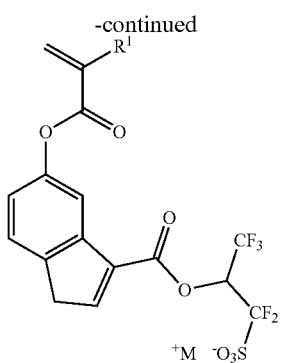
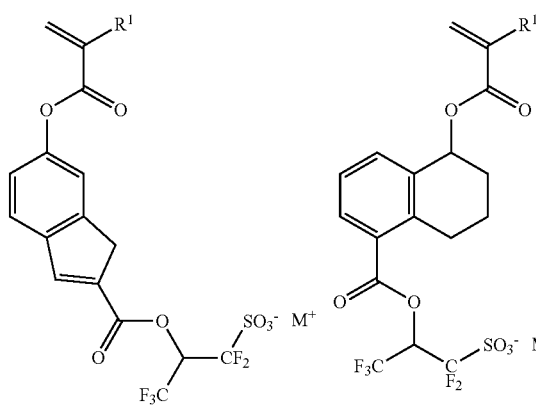
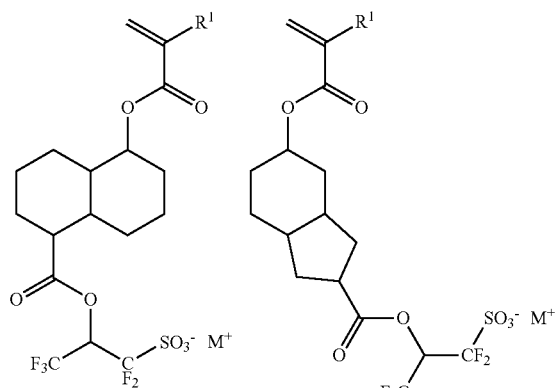
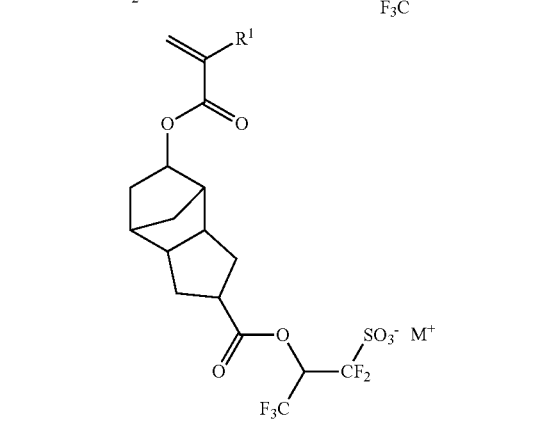
18
-continued
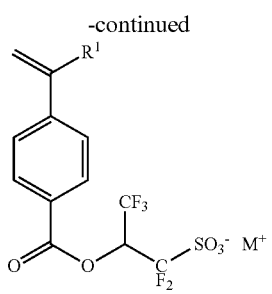
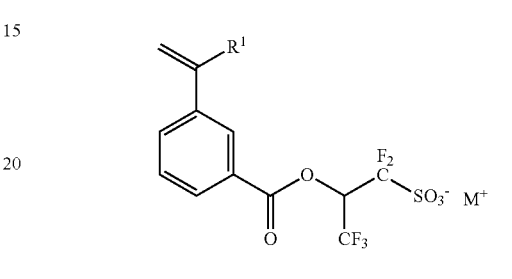
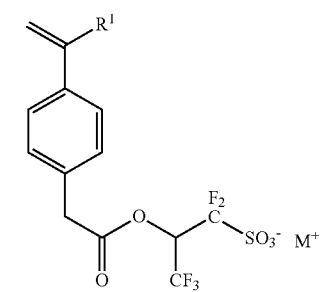
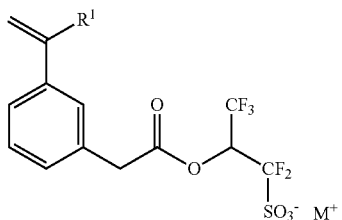
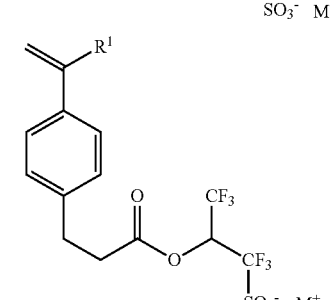
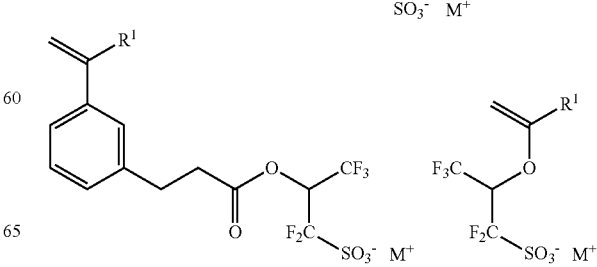

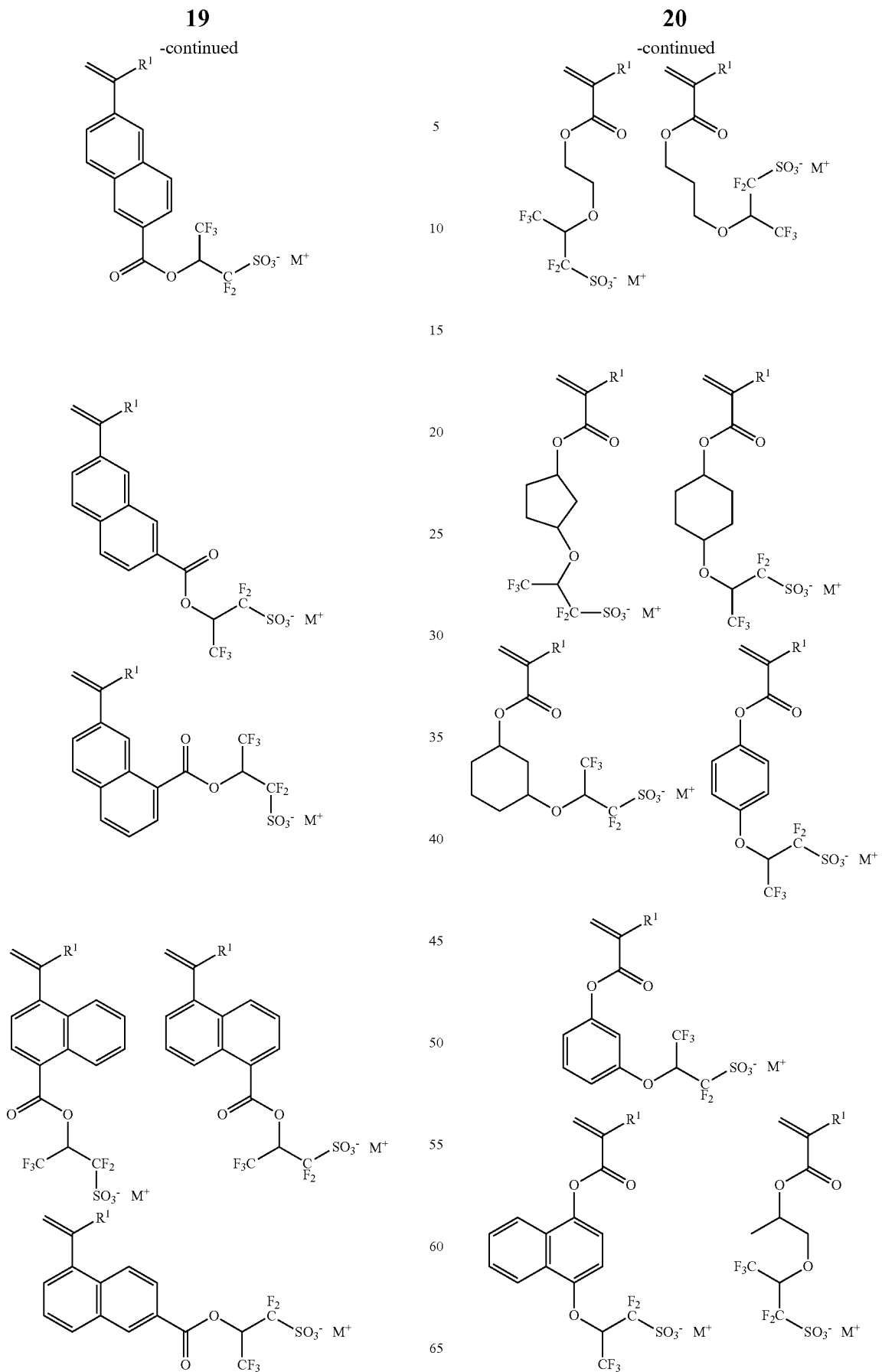

-continued
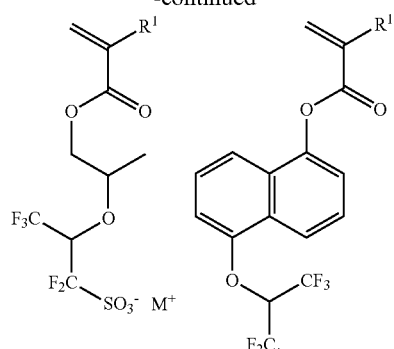
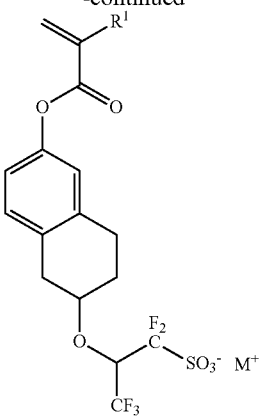
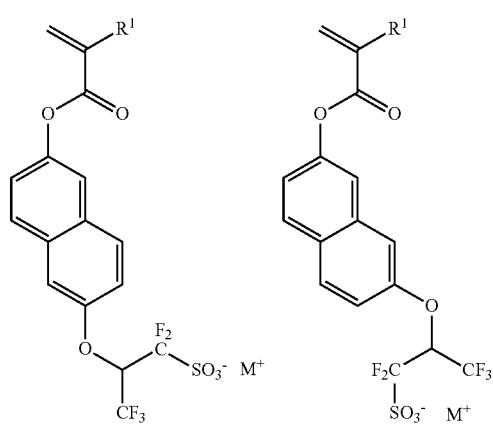
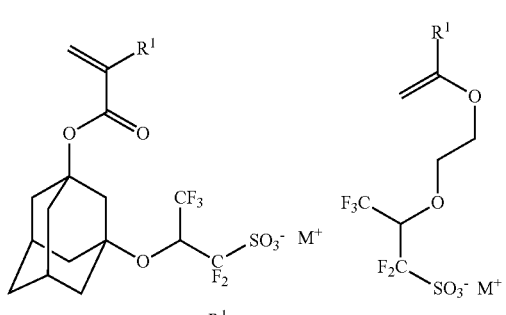
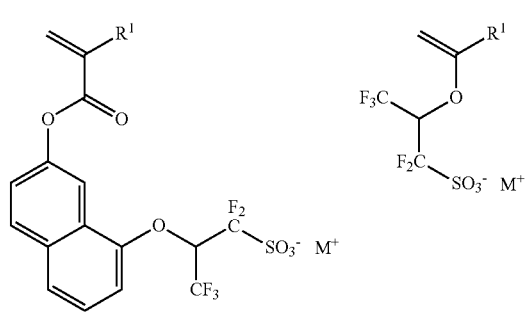
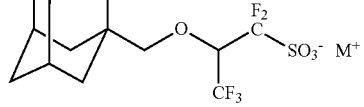
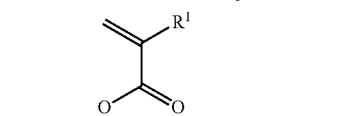
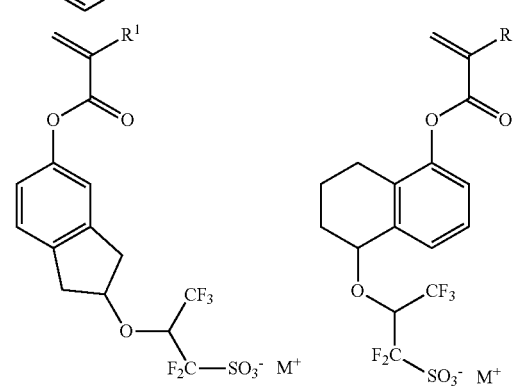
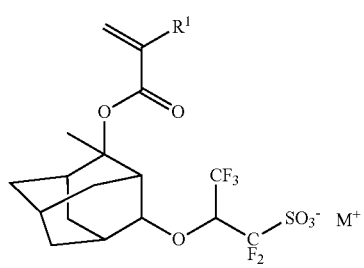

-continued
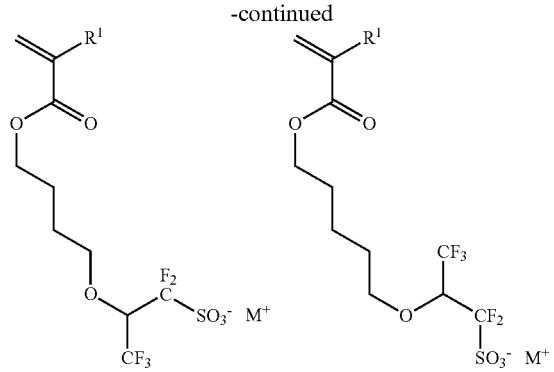
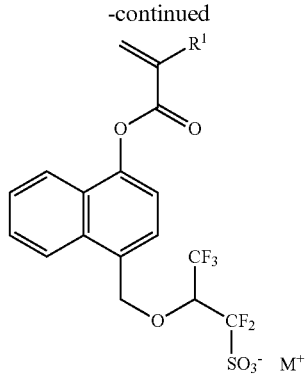
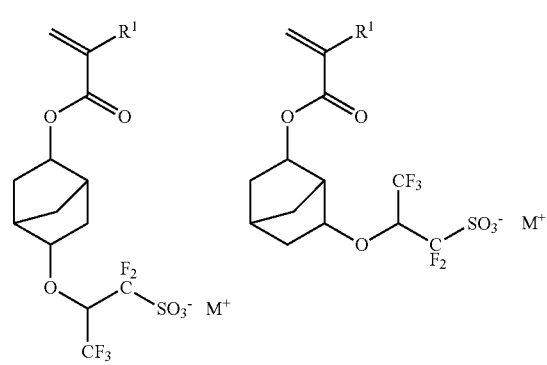
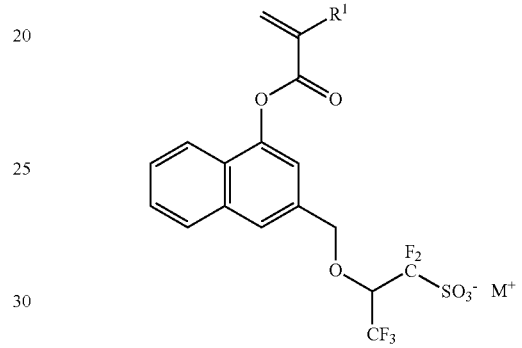
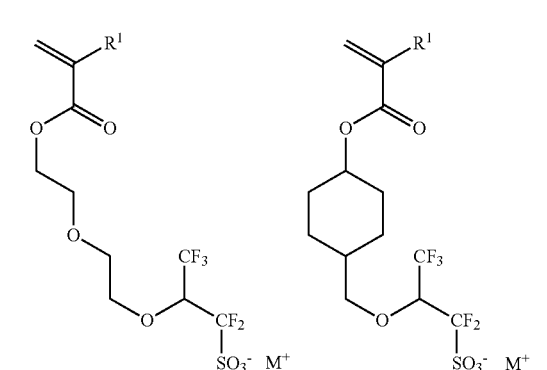
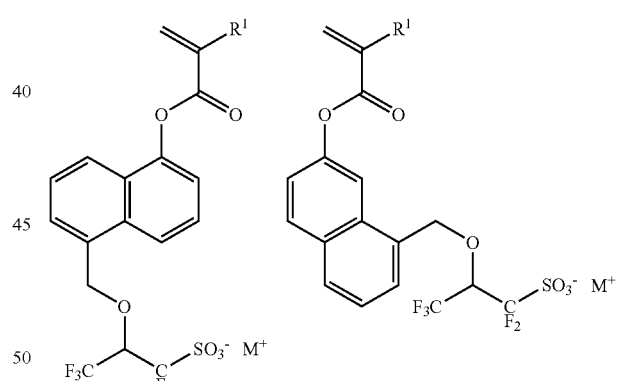
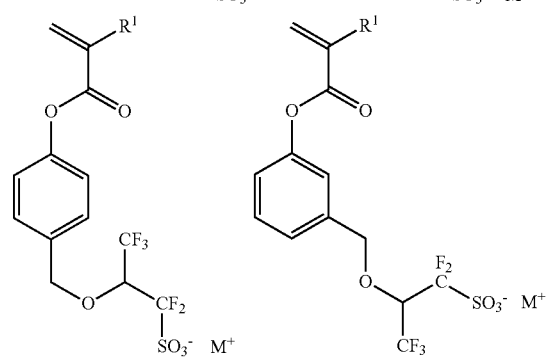
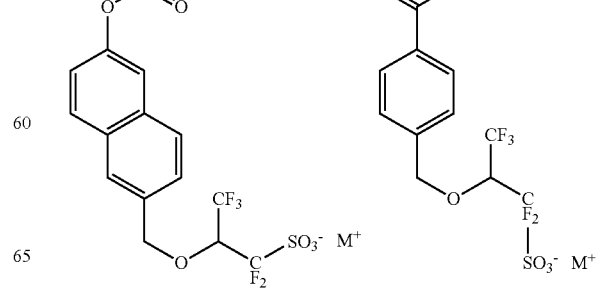

-continued
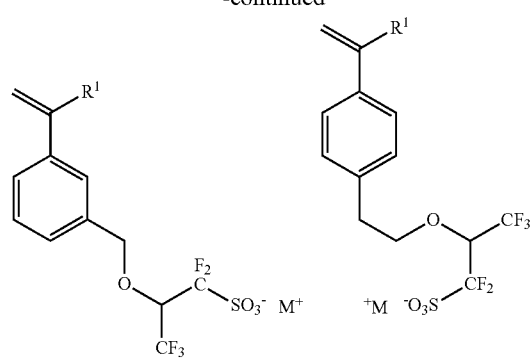
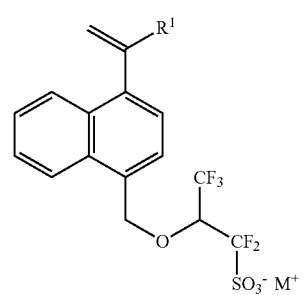
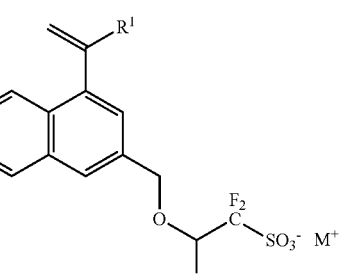
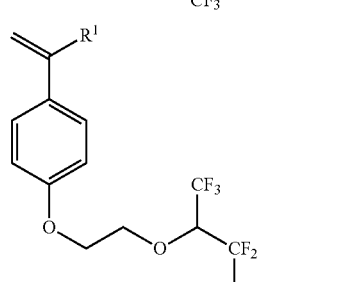
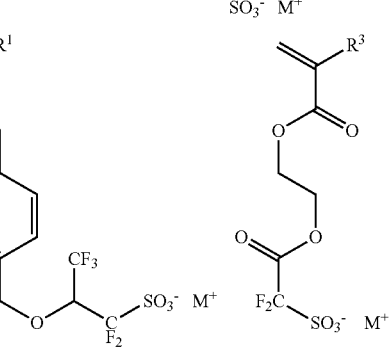
-continued
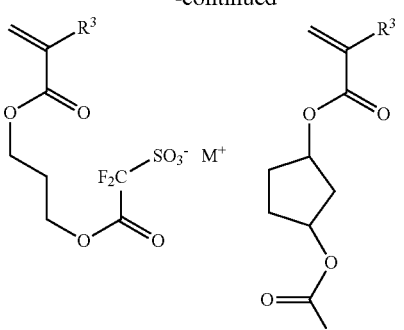
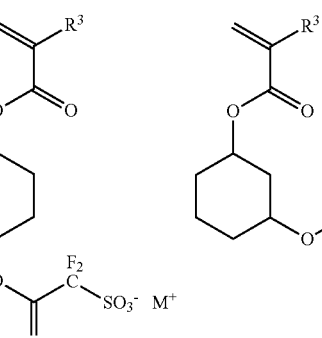
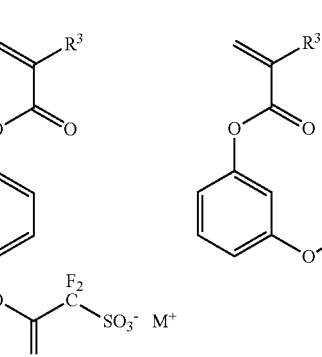
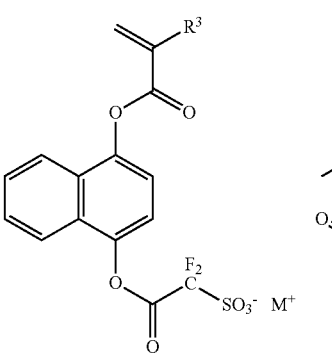

-continued
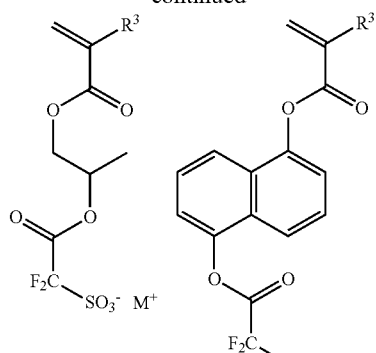
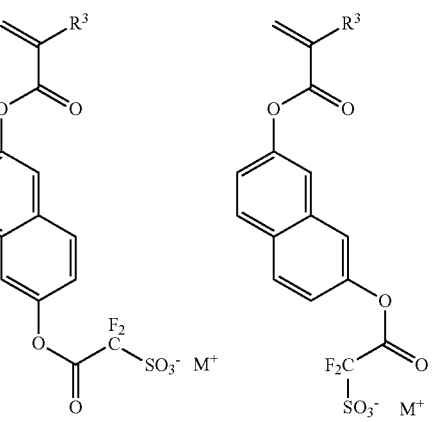
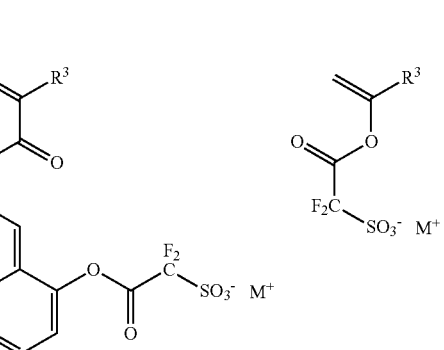
-continued
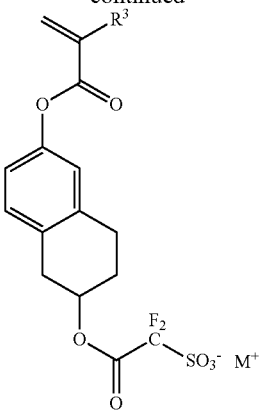
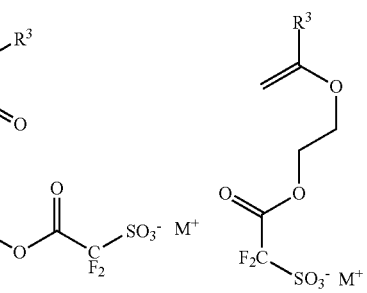

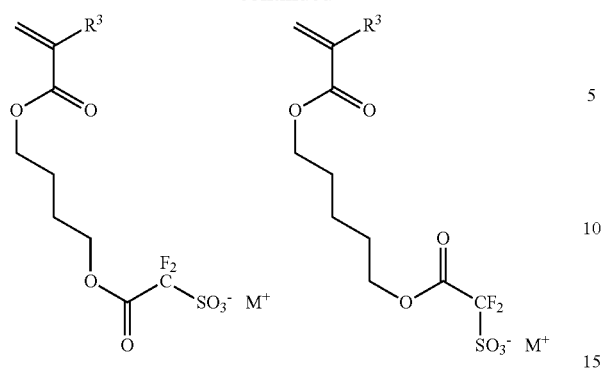
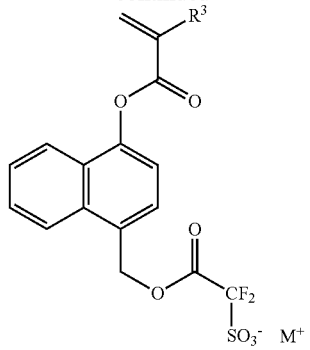
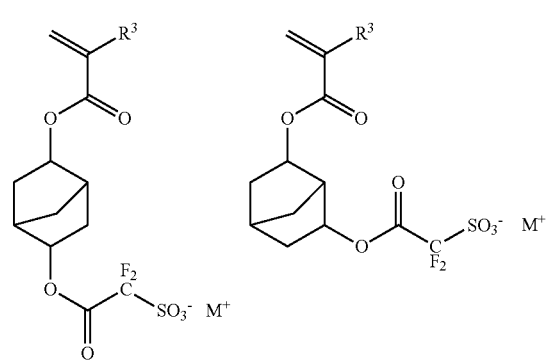
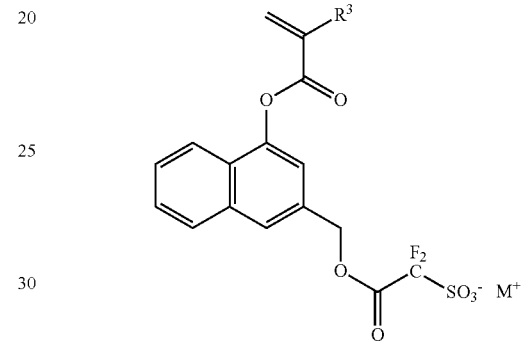
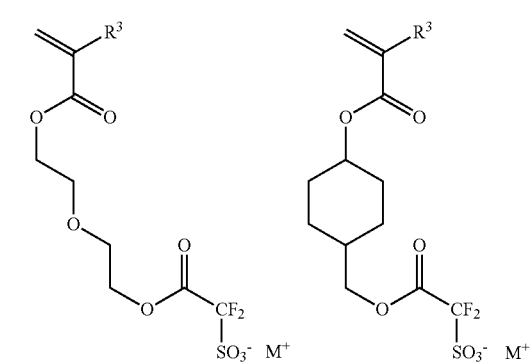
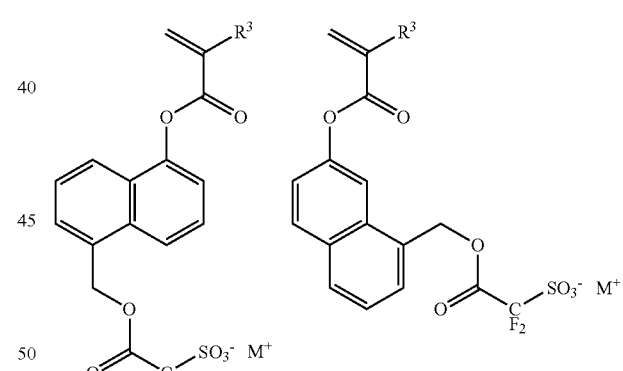
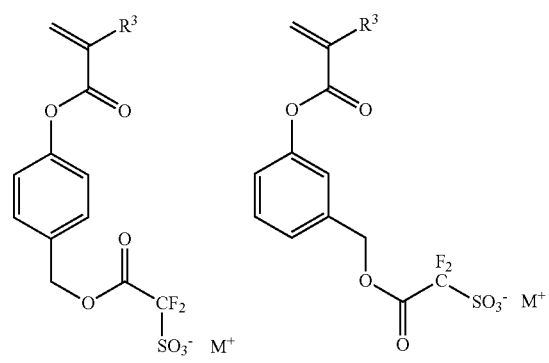
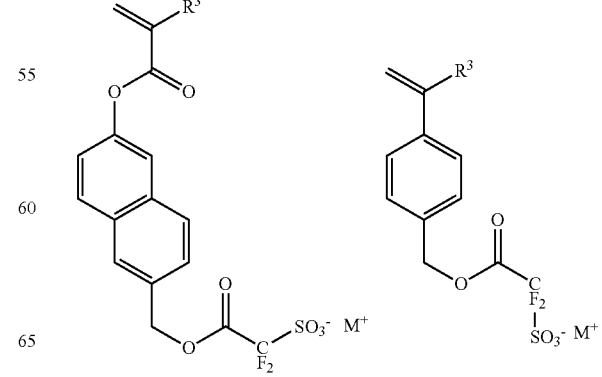

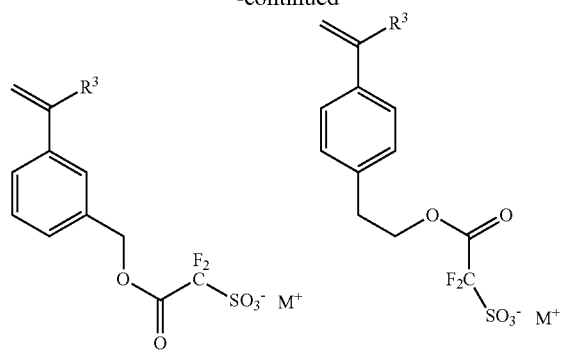
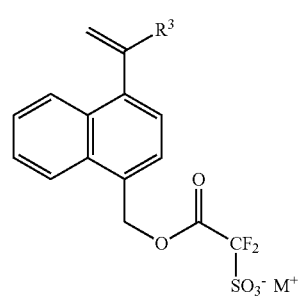
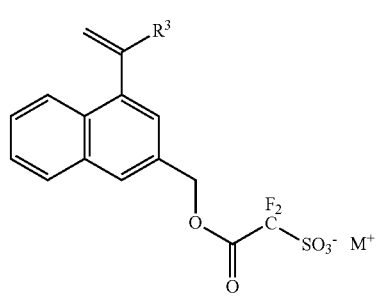
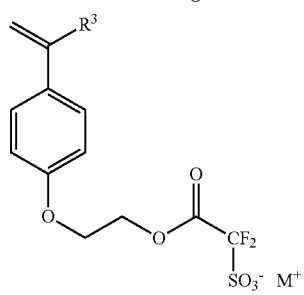
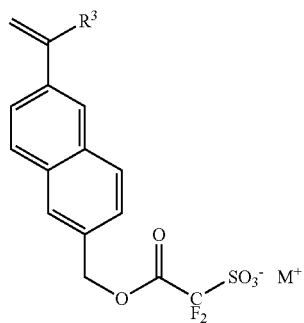
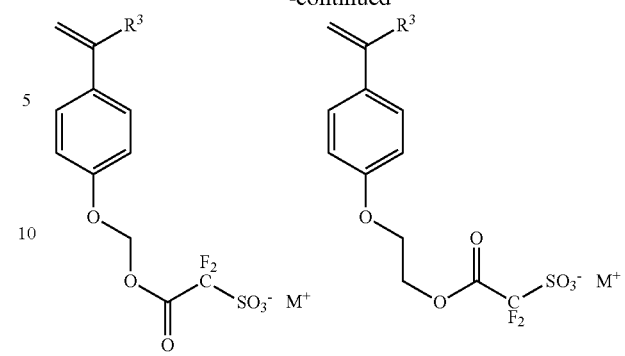
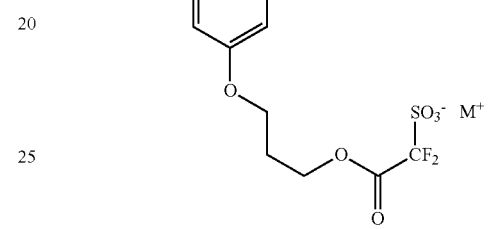
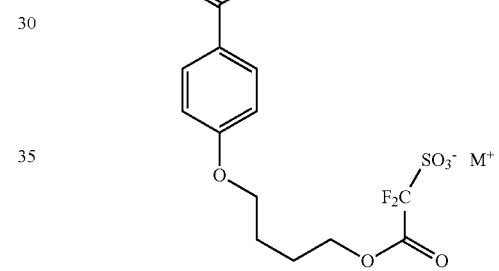
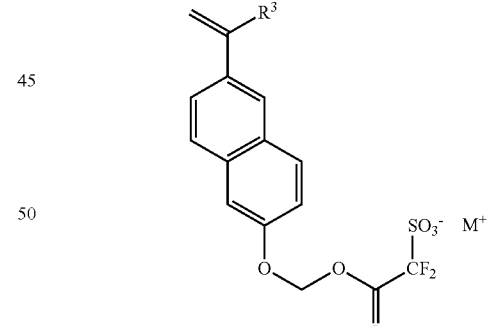
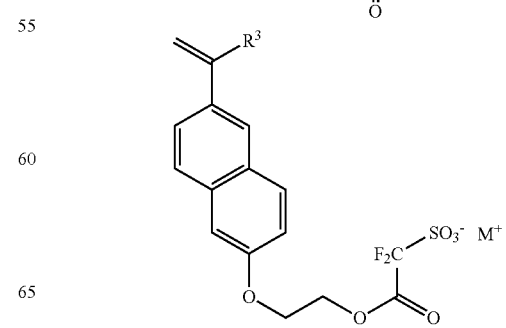

33
-continued
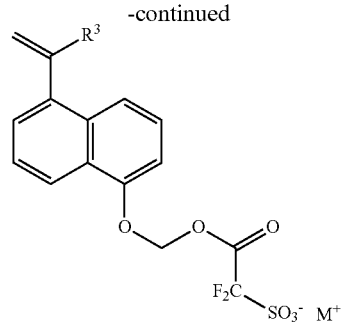
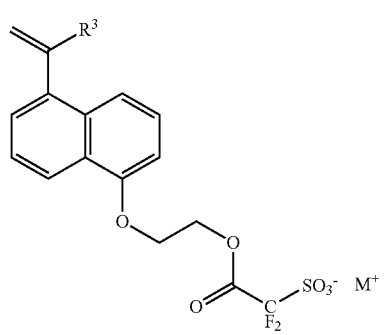
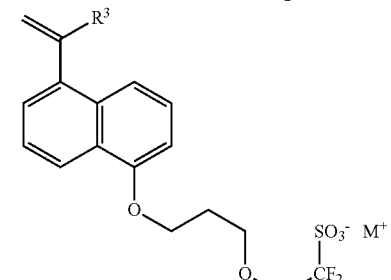
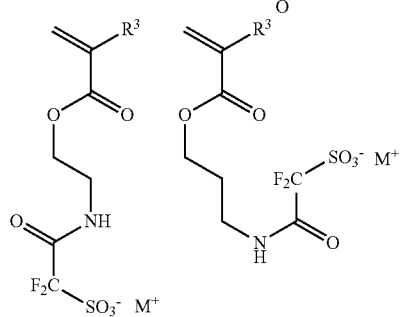
34
-continued
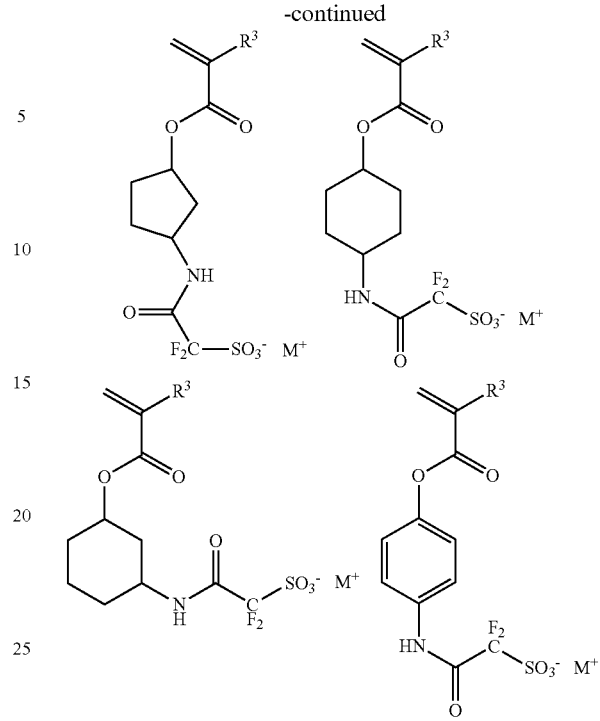
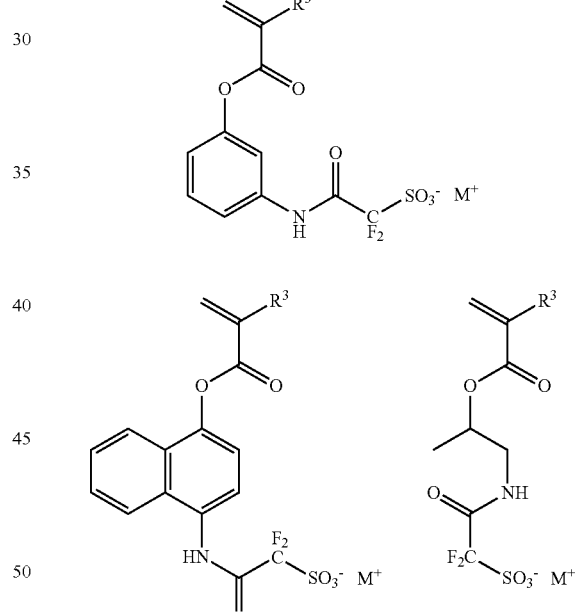
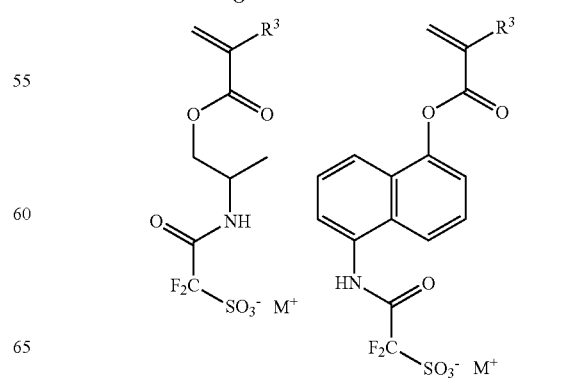

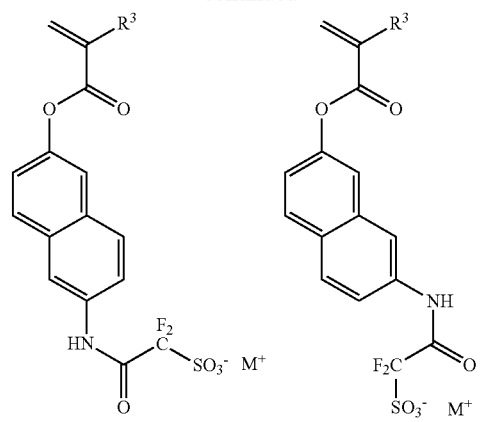
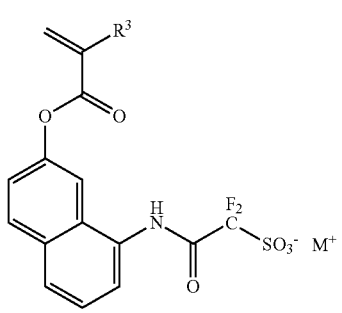
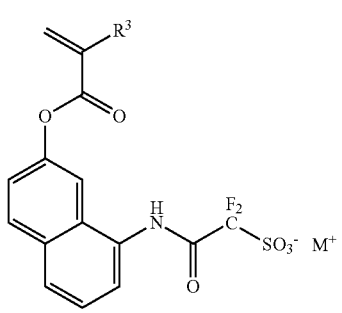
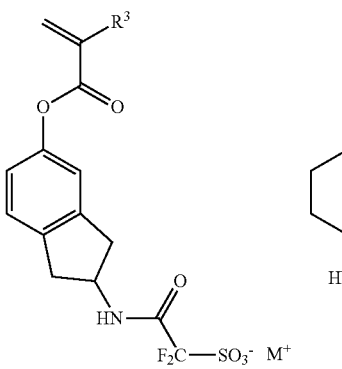
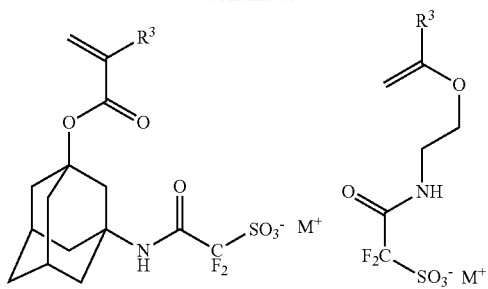
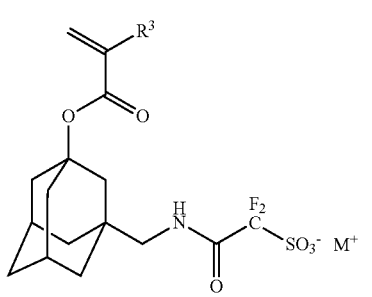
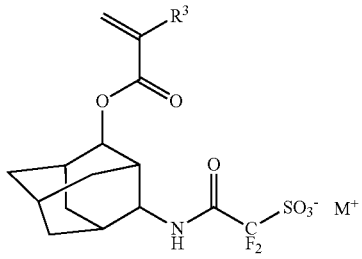
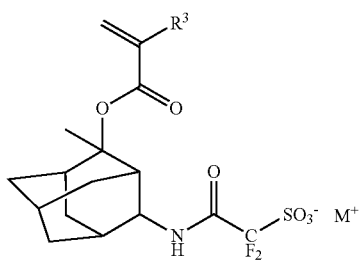
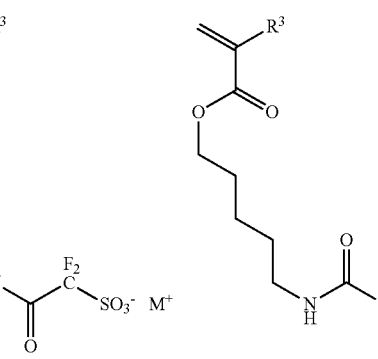

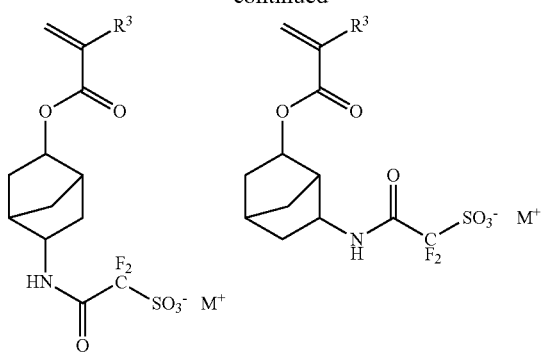
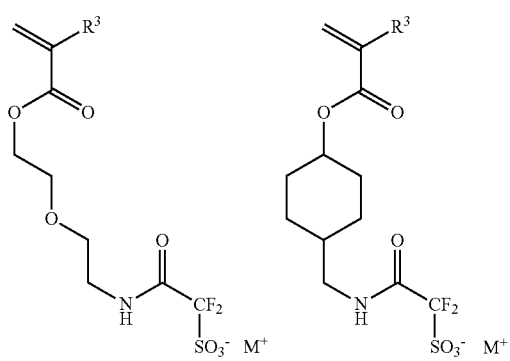
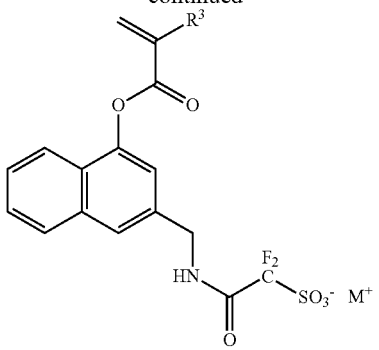
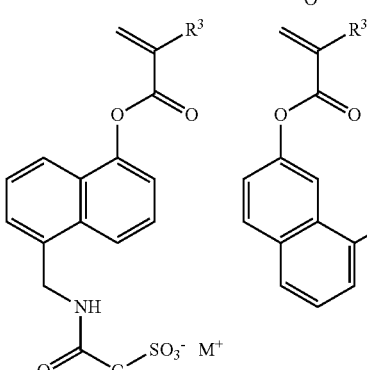
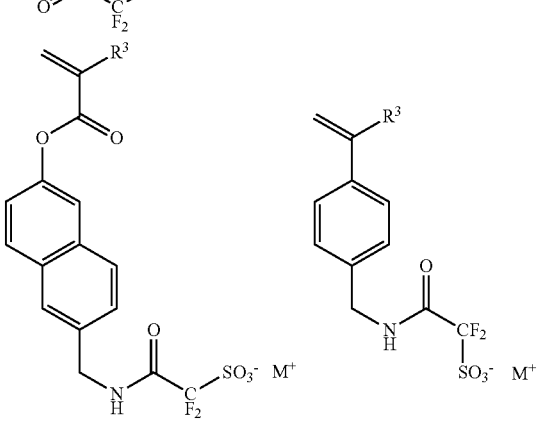
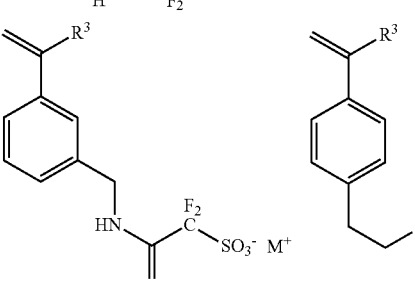
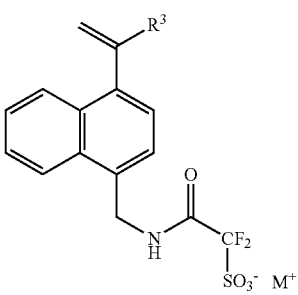

-continued
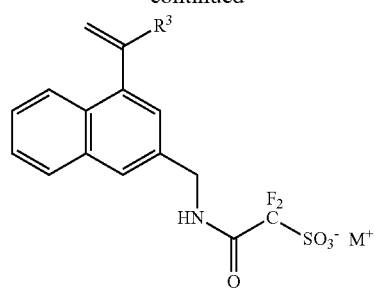
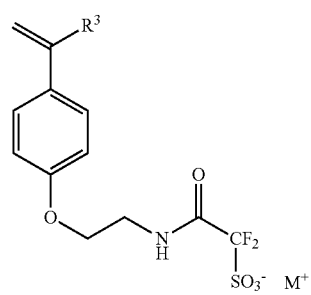
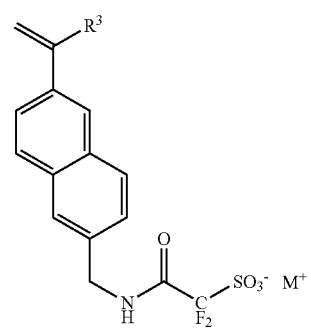
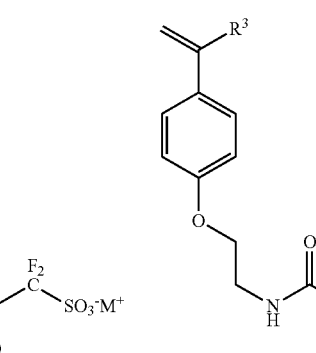
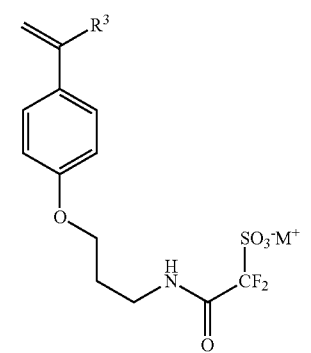
-continued
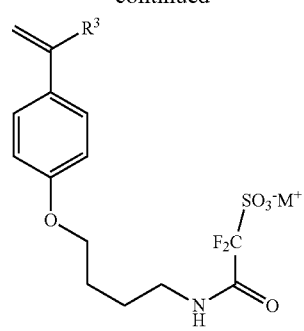
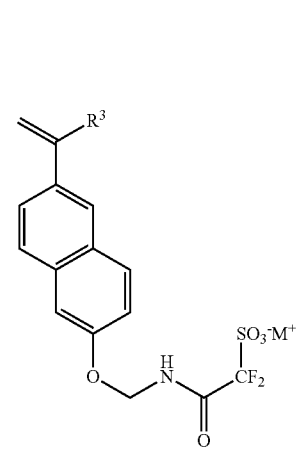
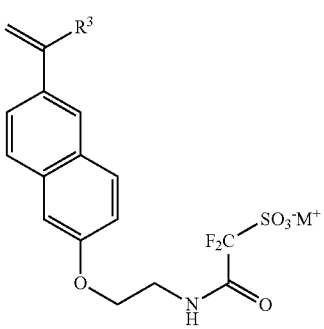
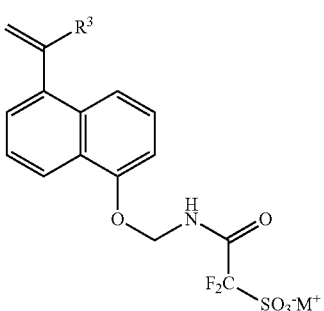
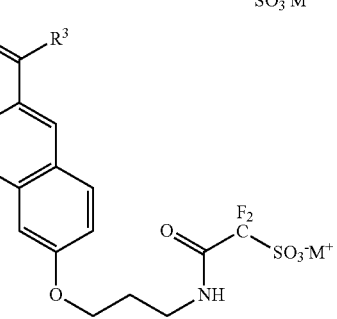

-continued
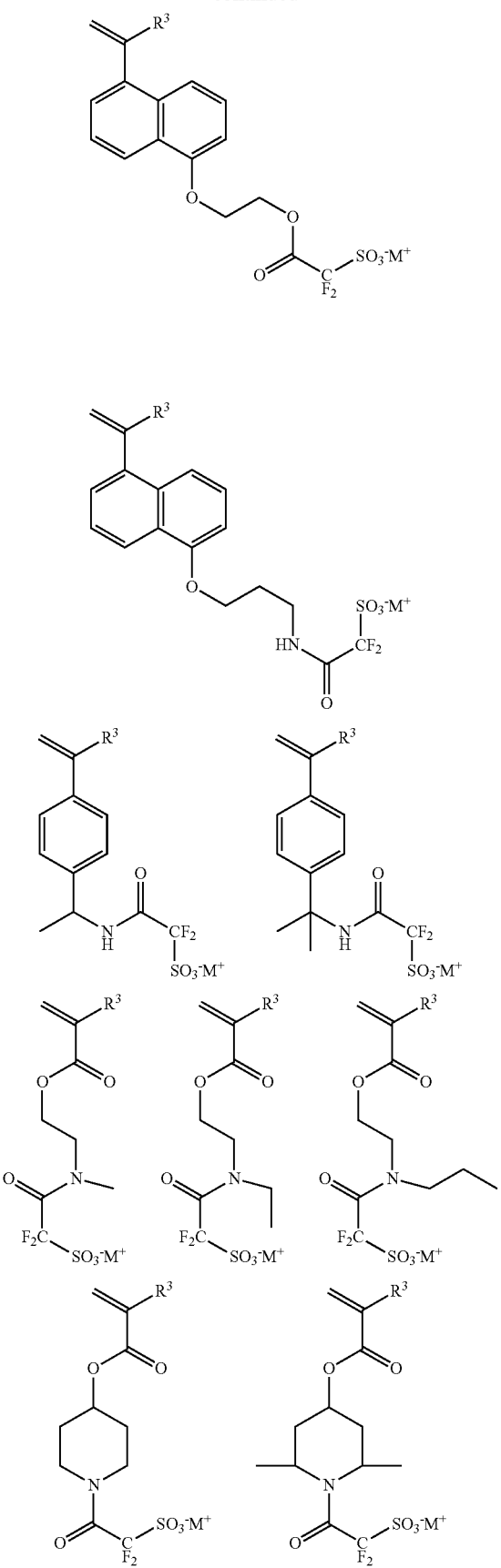
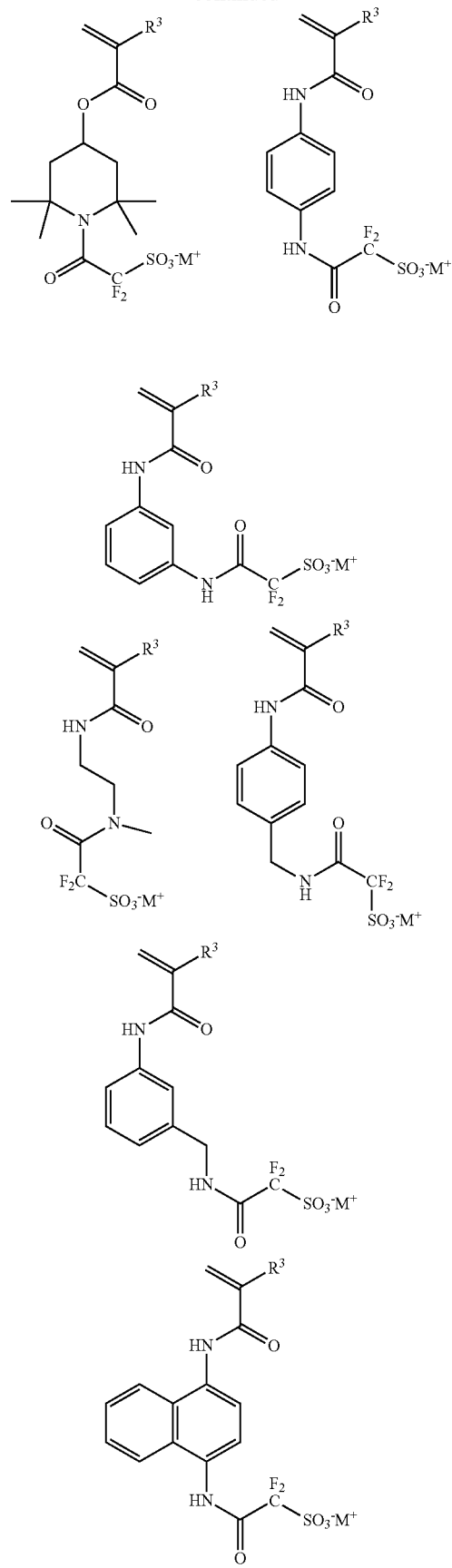

-continued
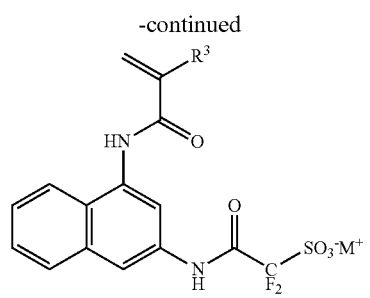
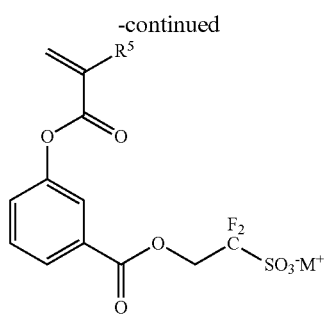
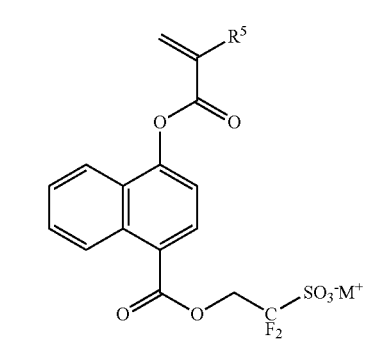
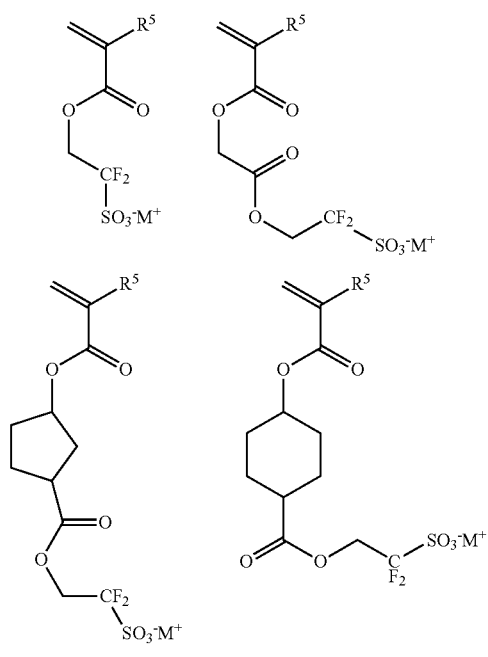
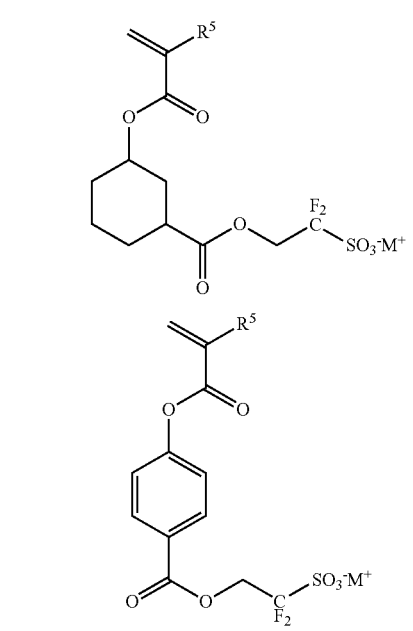
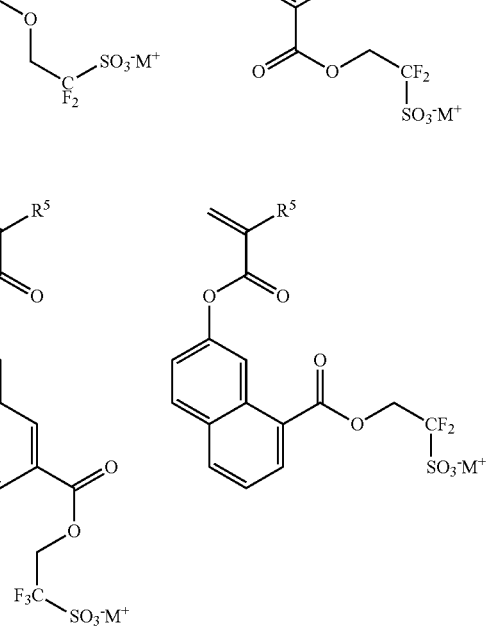

-continued
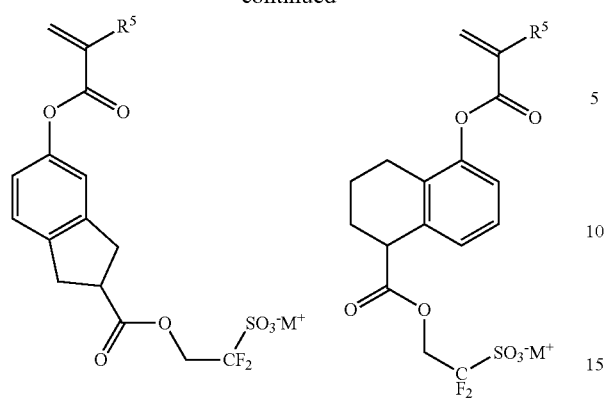
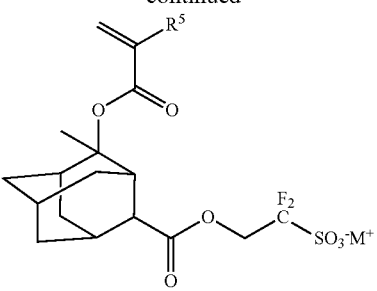
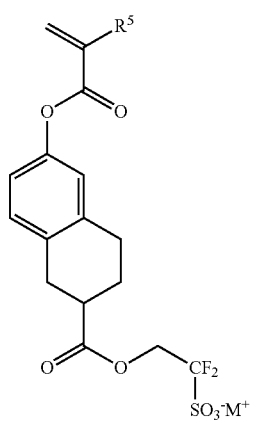
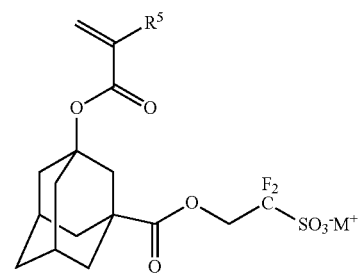
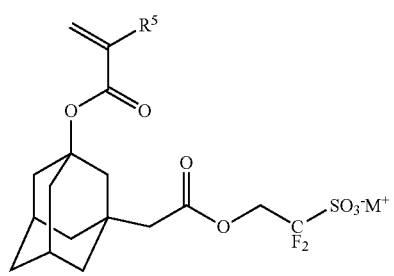
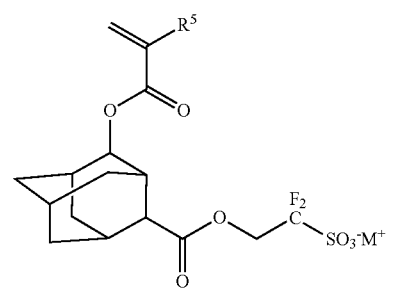
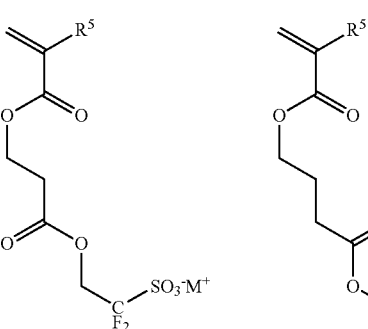
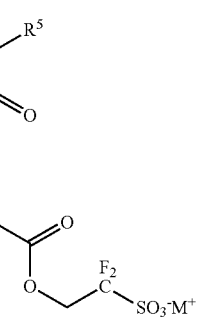
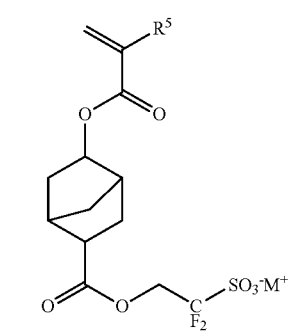
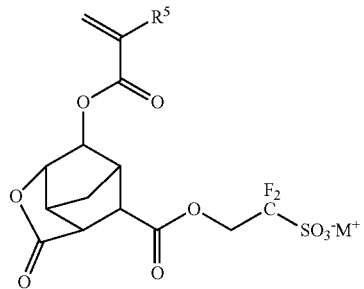

-continued
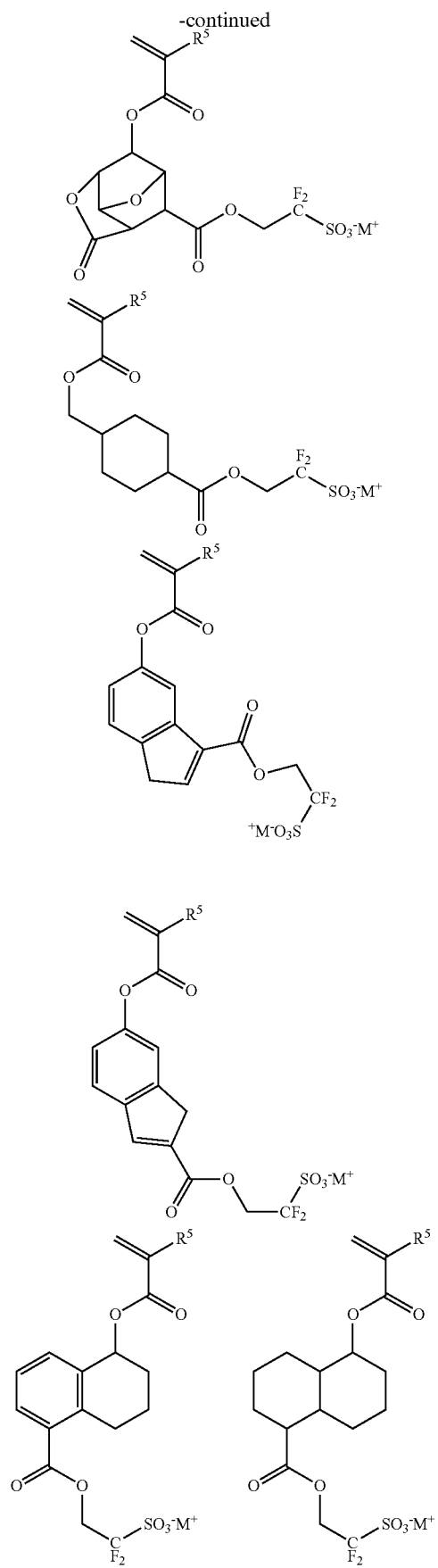
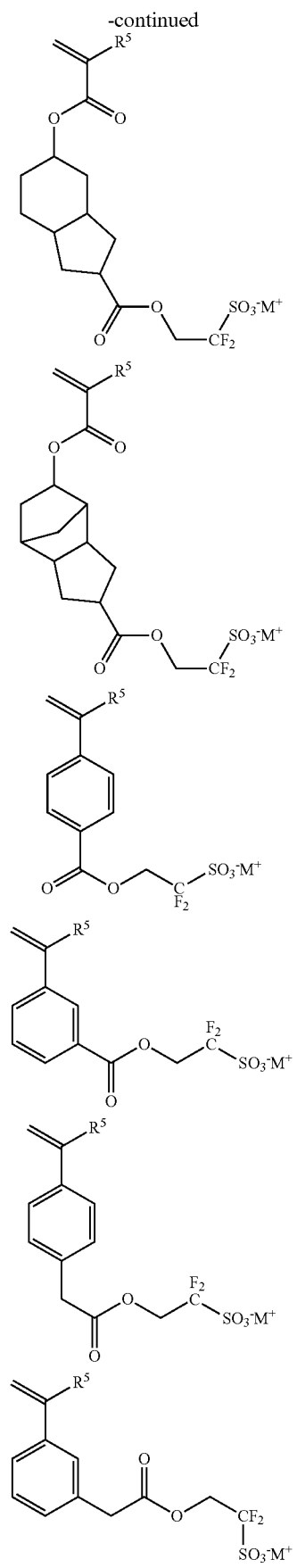

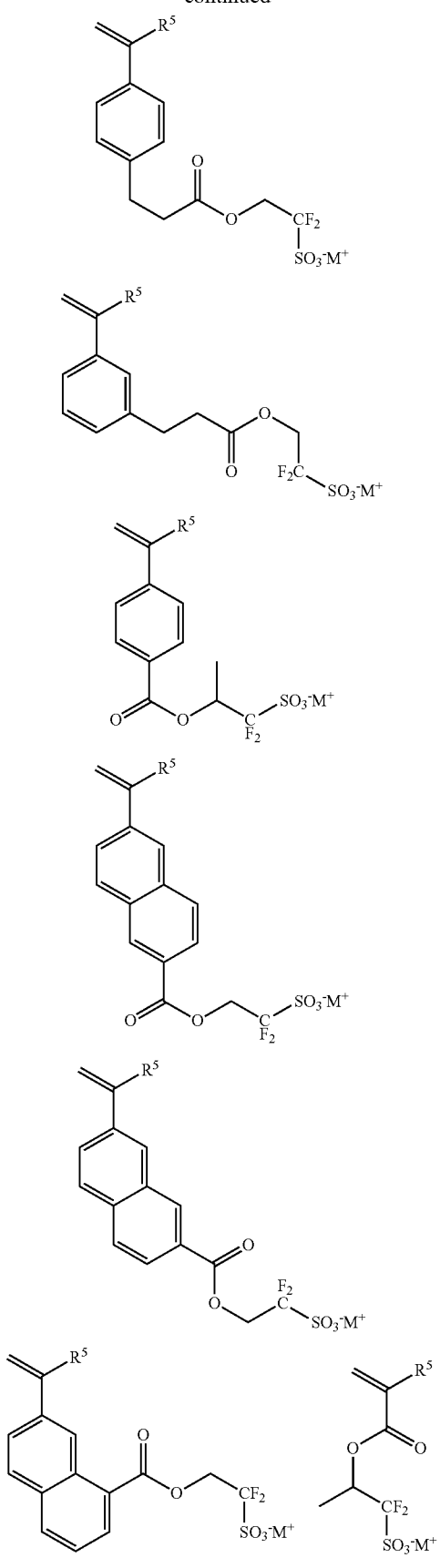
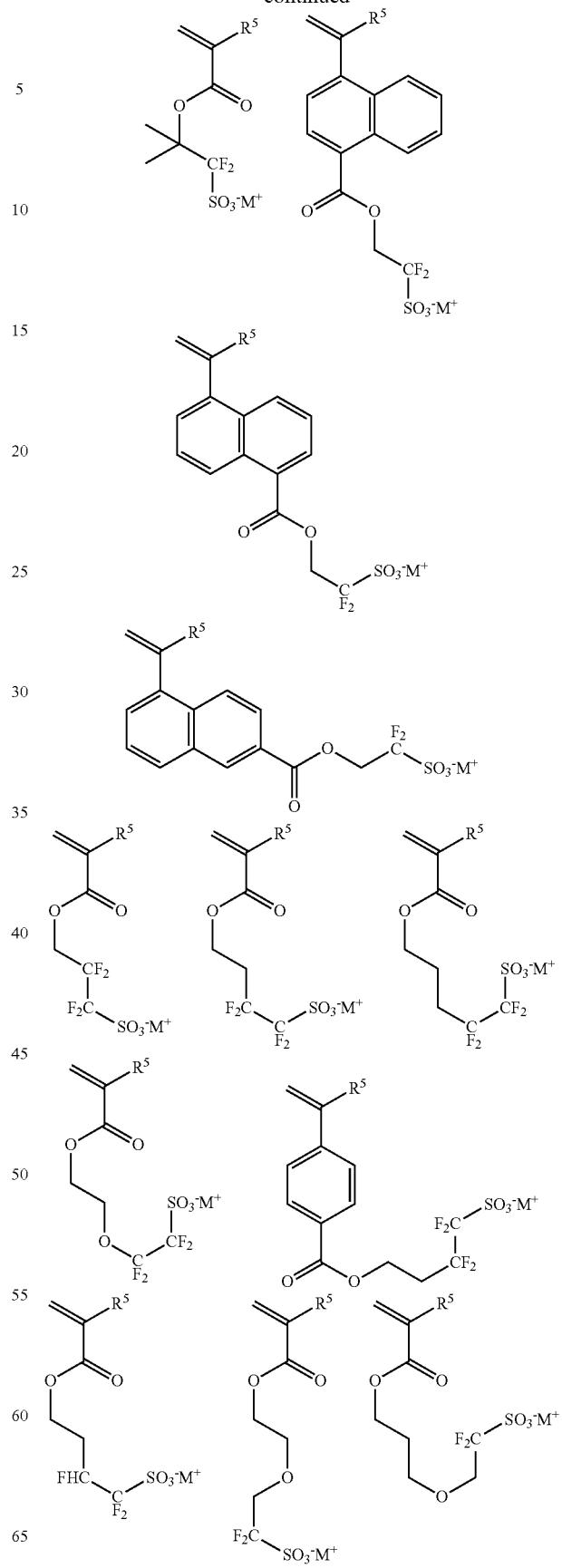

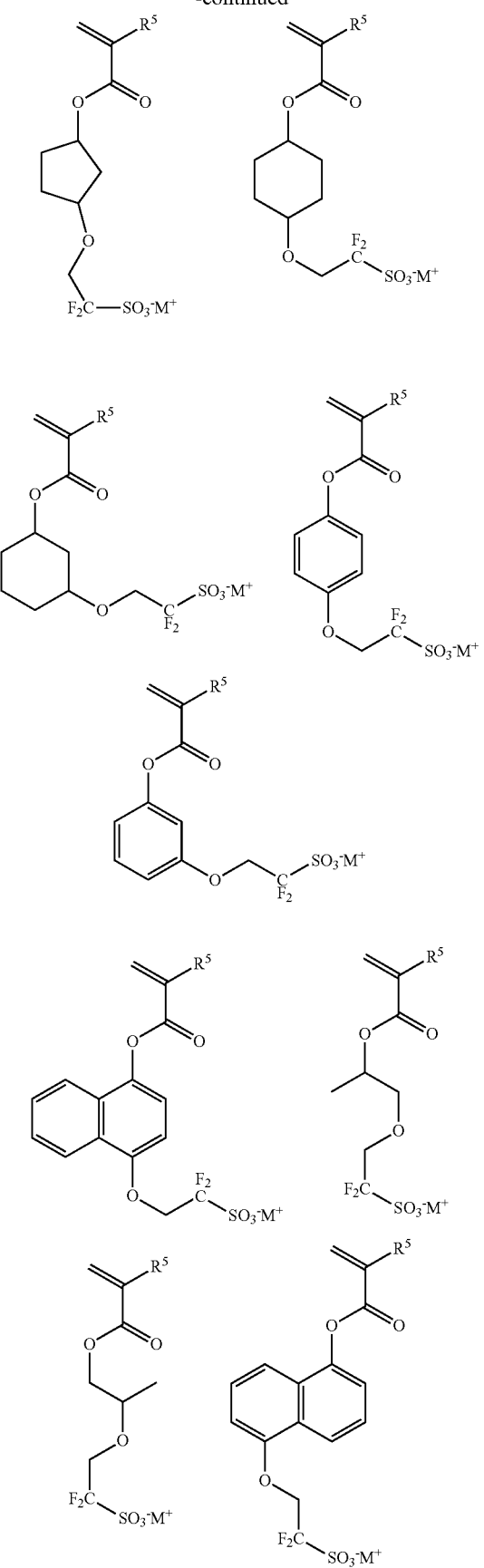
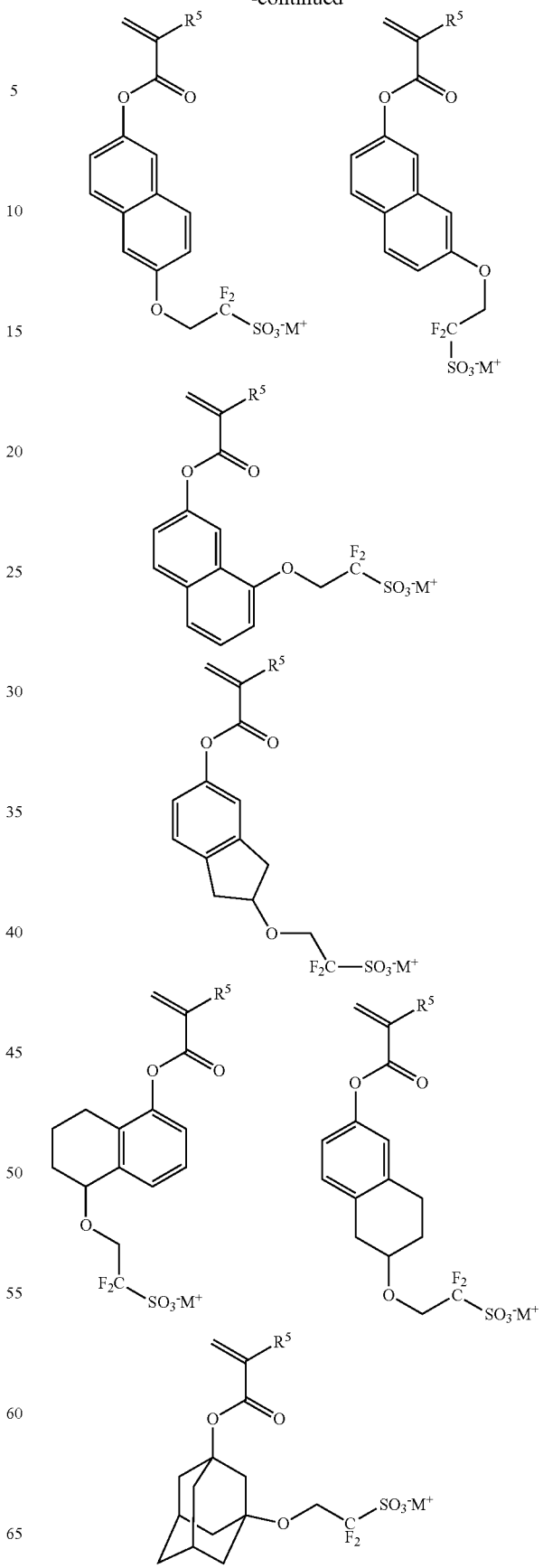

-continued
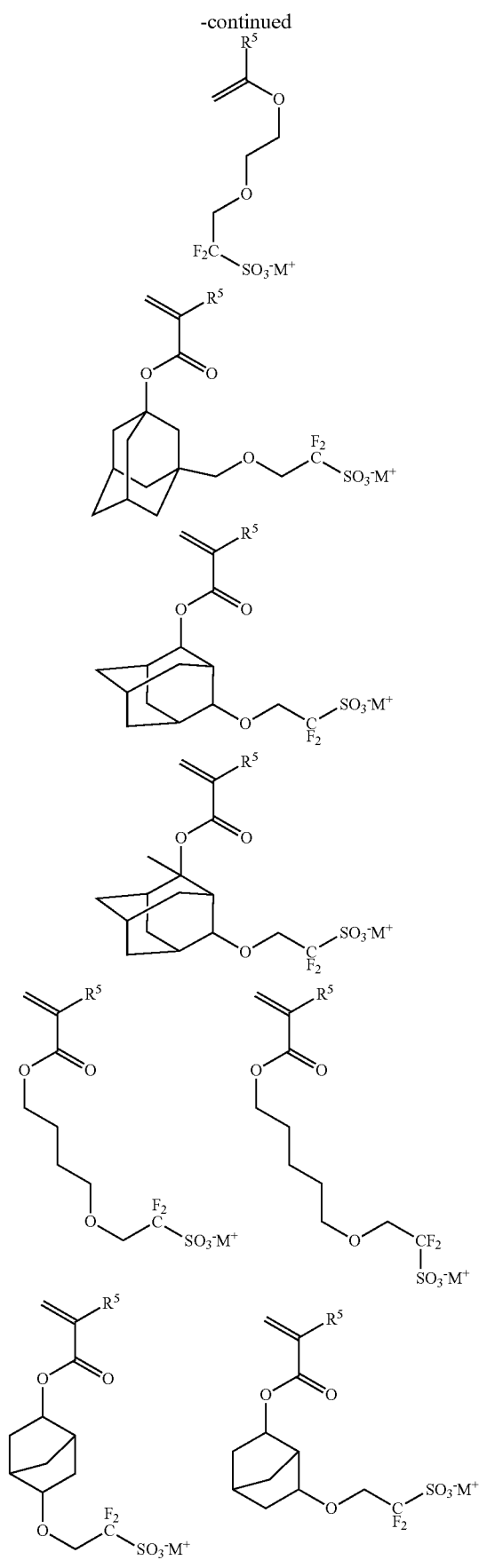
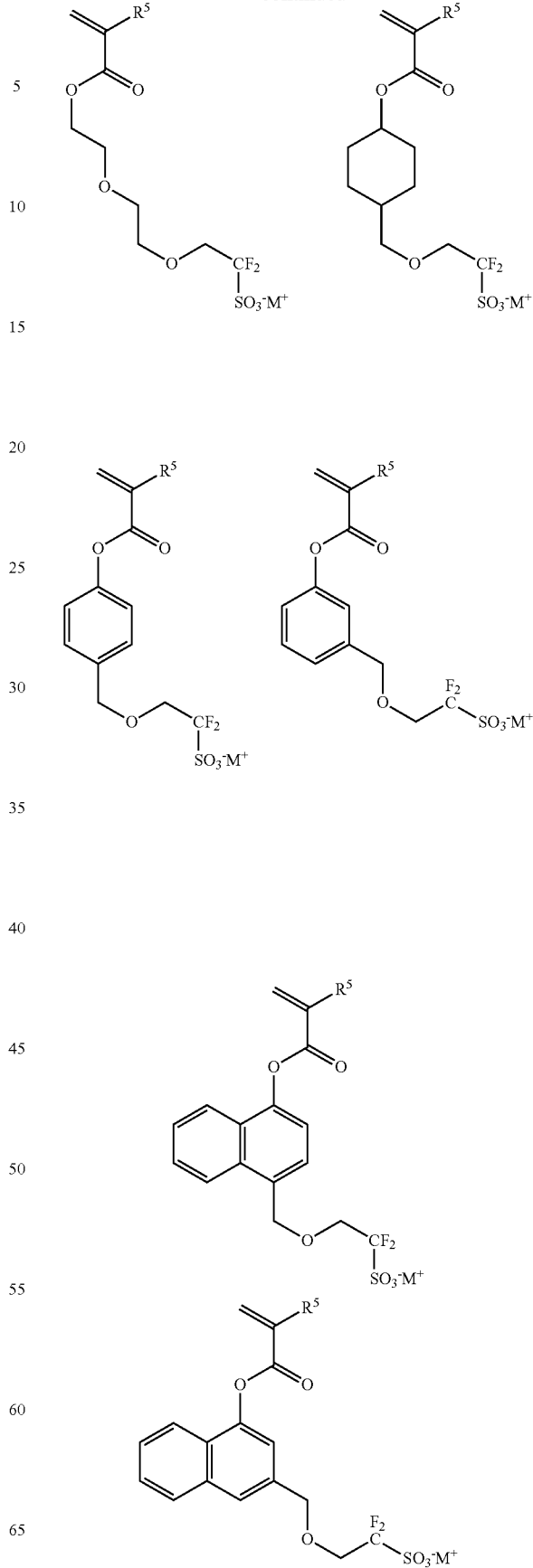

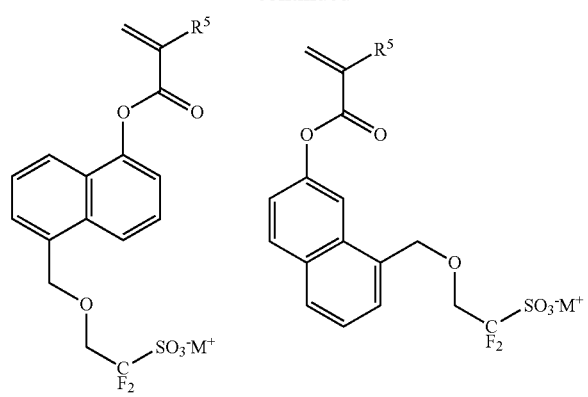
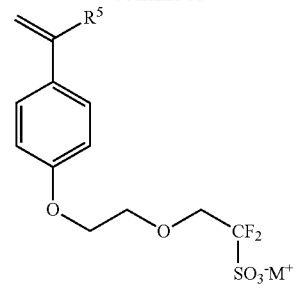
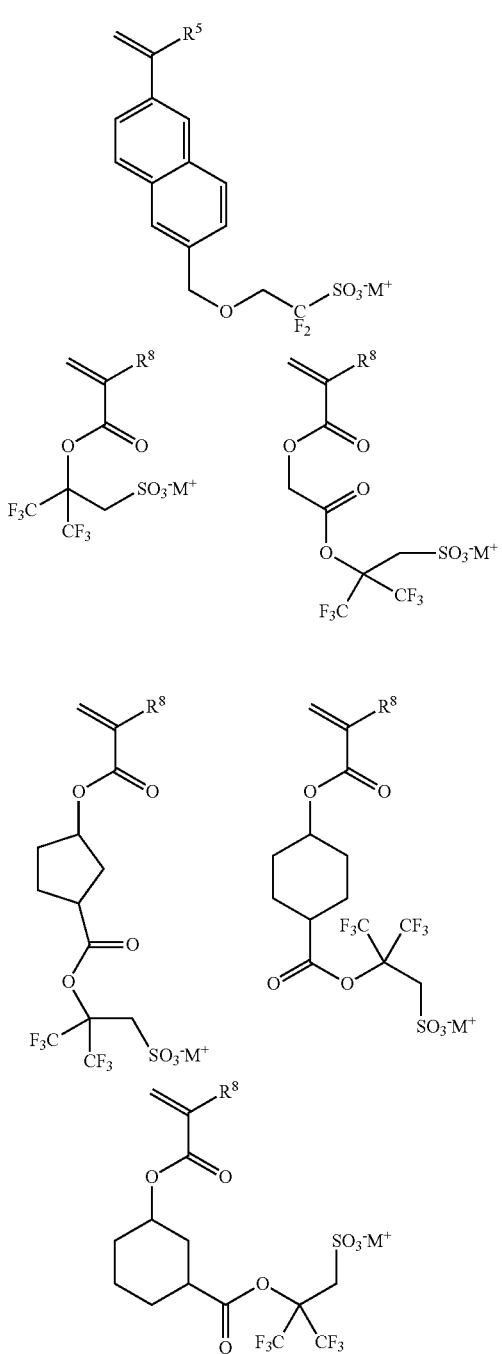

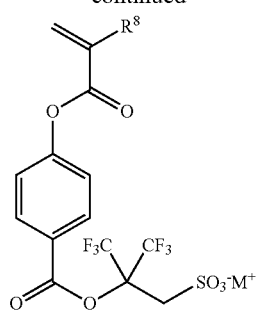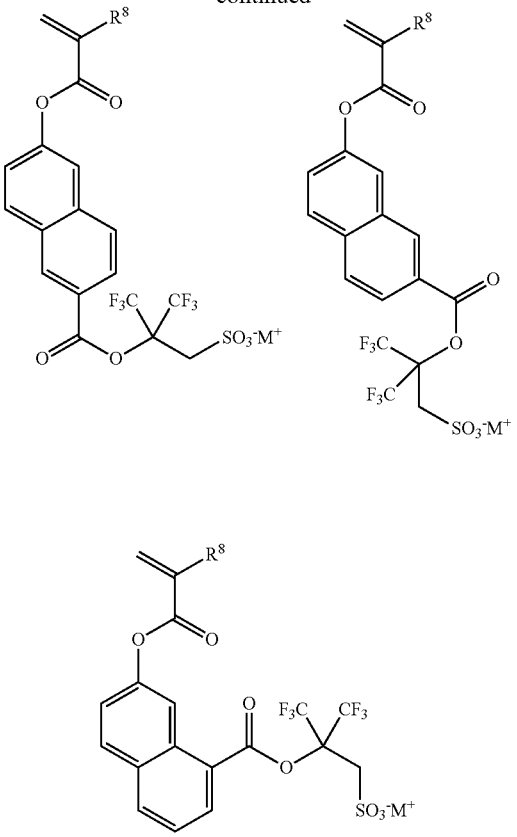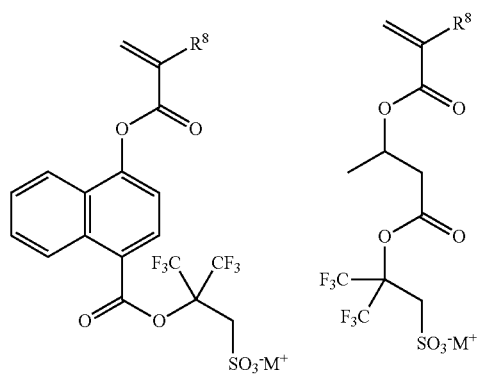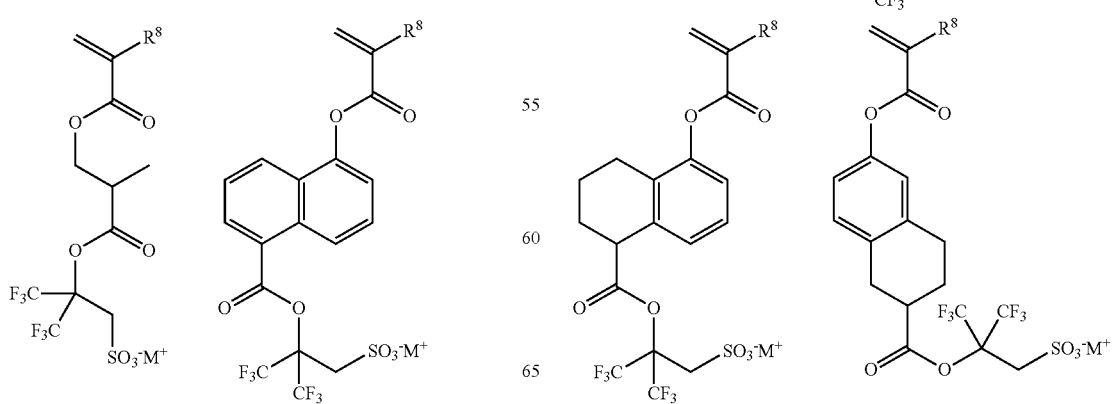

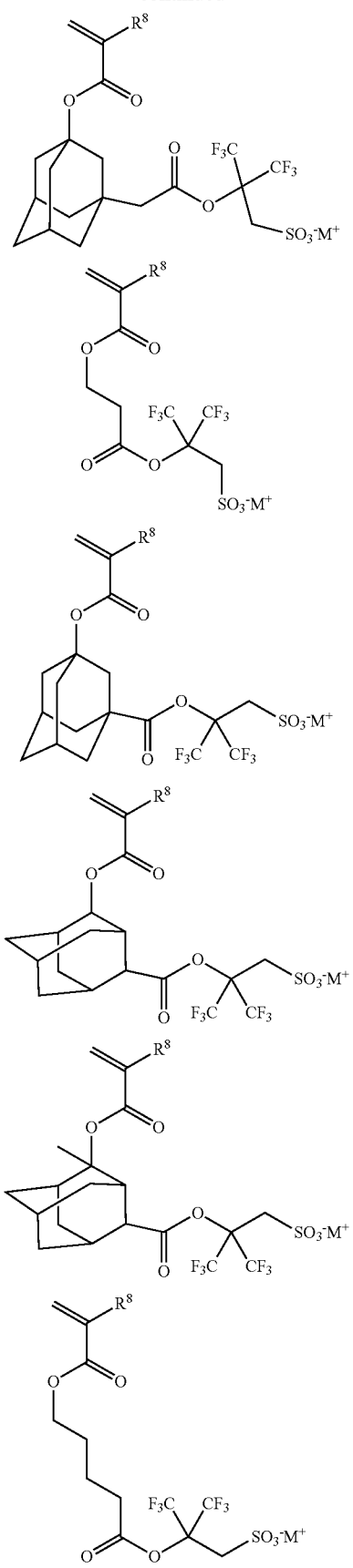
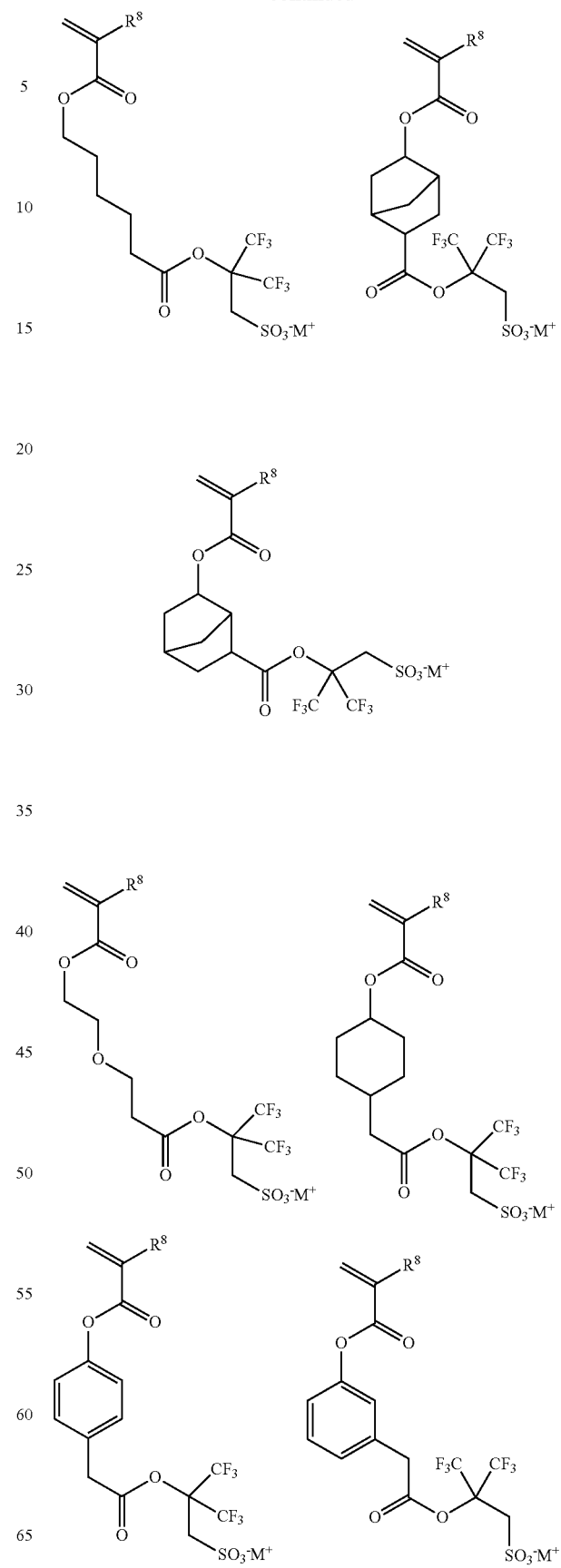

61
-continued
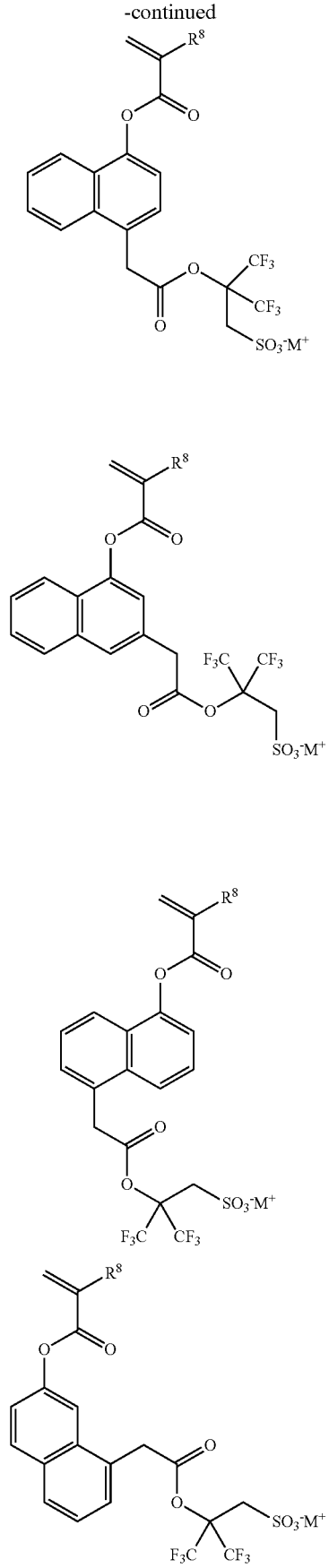
62
-continued
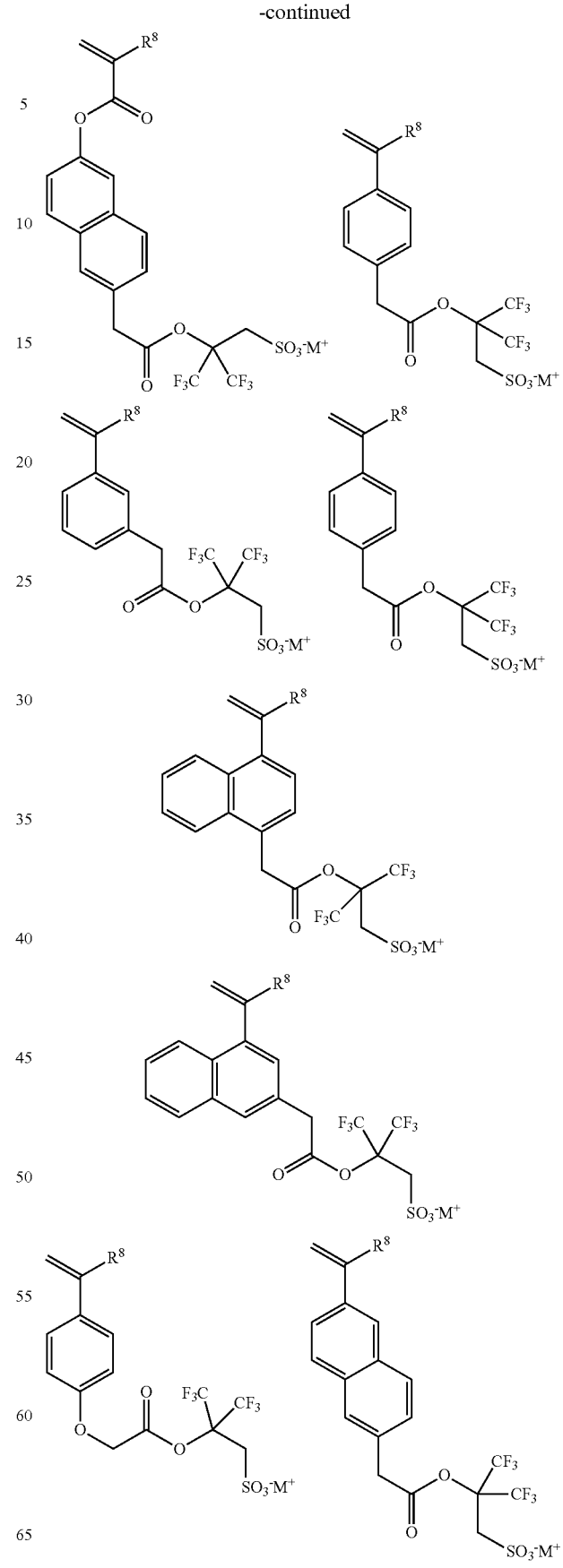

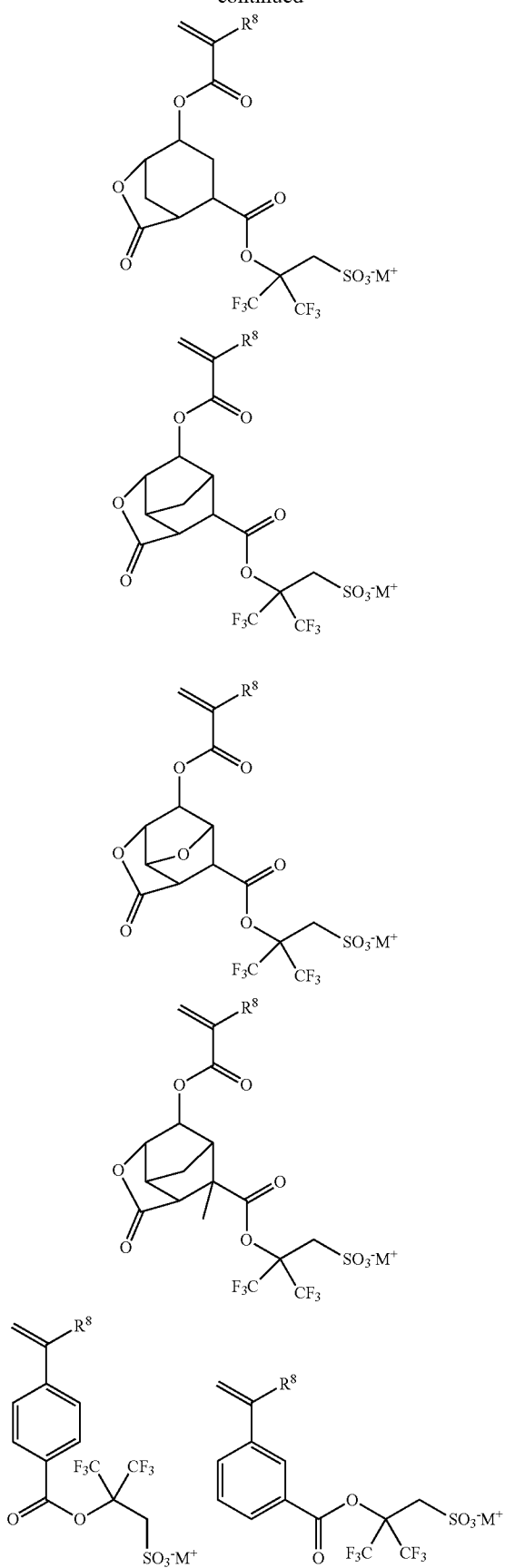

-continued
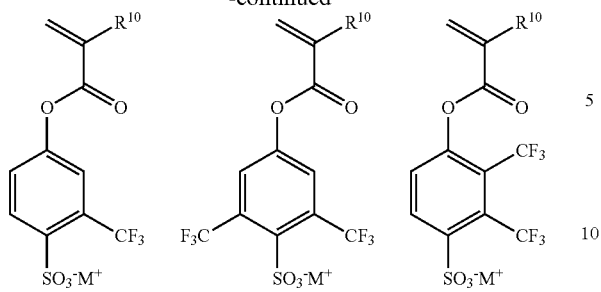
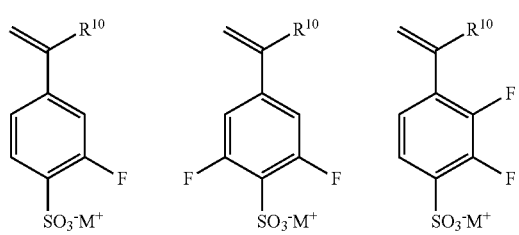
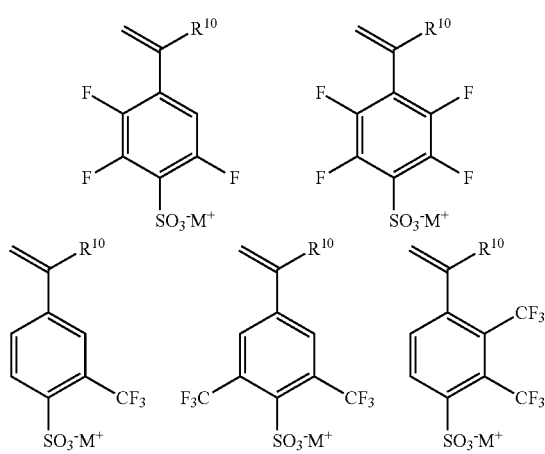
In the formulae, $R^1$, $R^3$, $R^5$, $R^8$, and $R^{10}$ are as defined above.
Specific examples of sulfonimide salt monomer to give the repeating unit-a6 in the above general formula include the following.
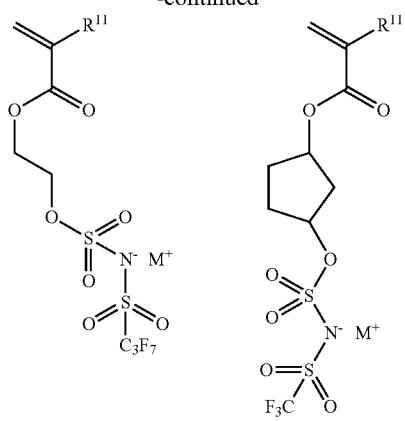
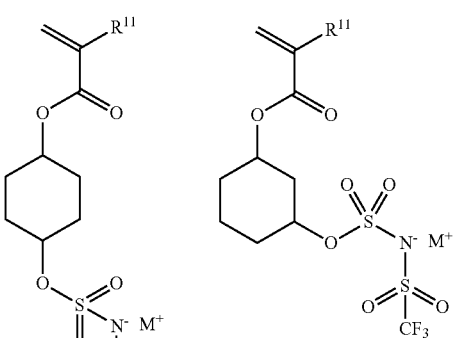
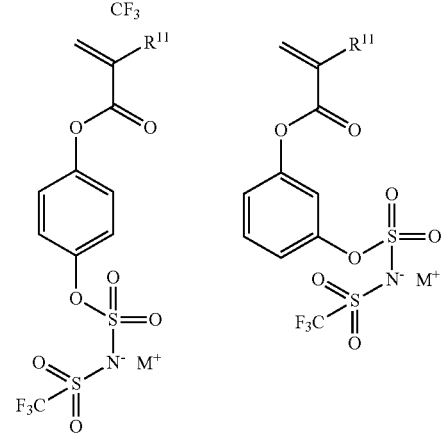
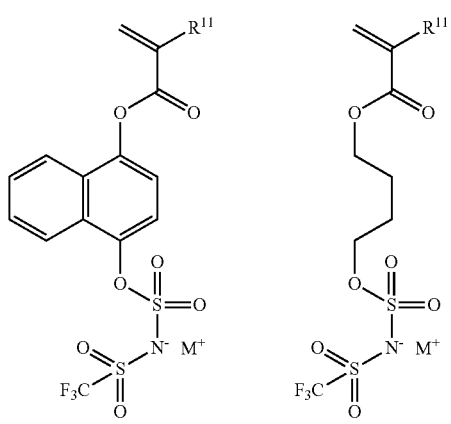

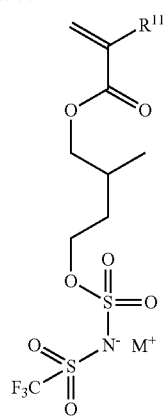
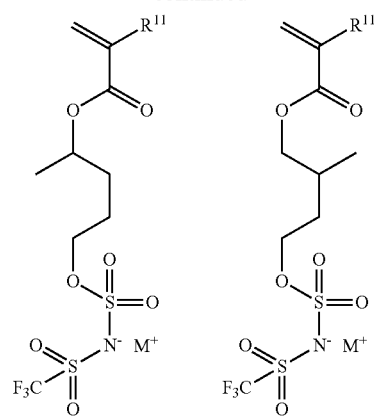
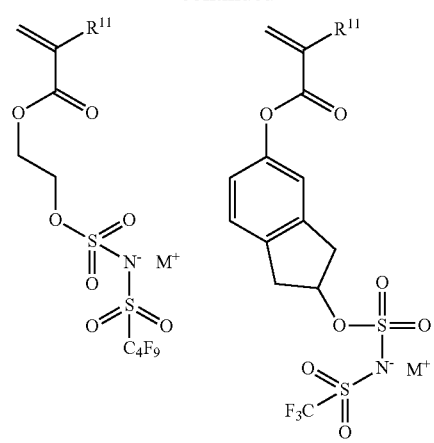
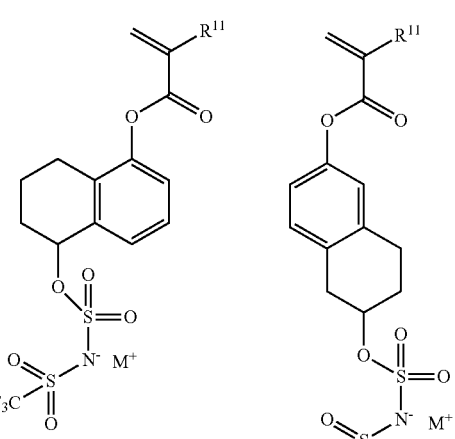
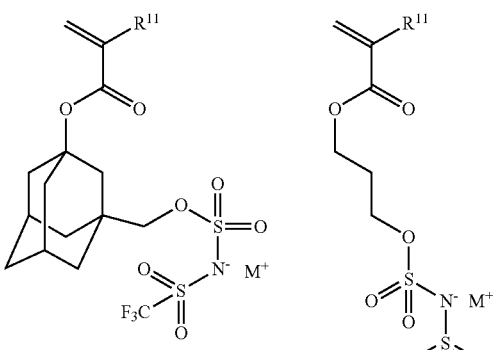
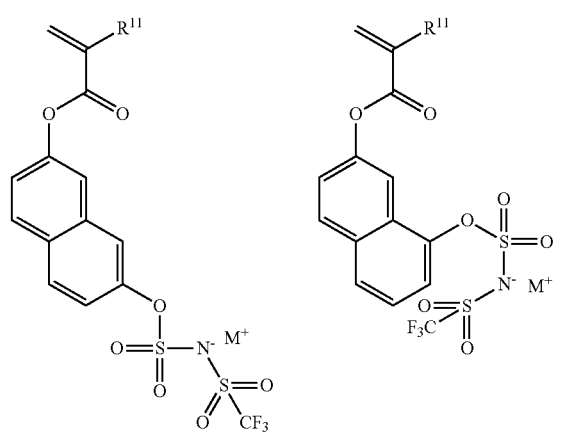
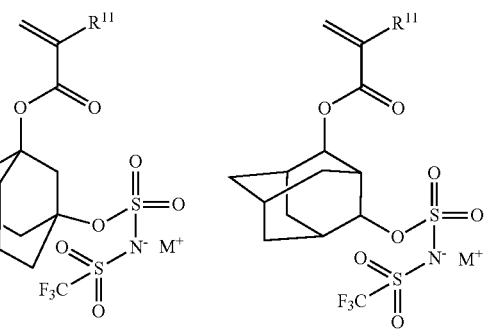

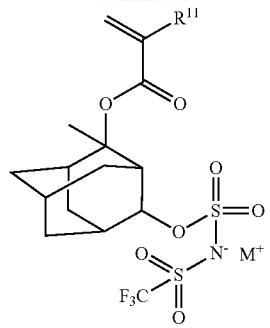
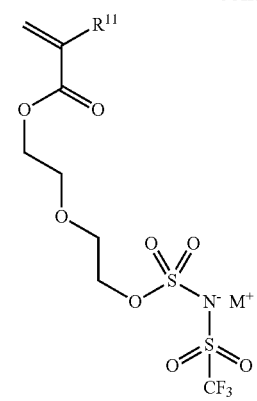
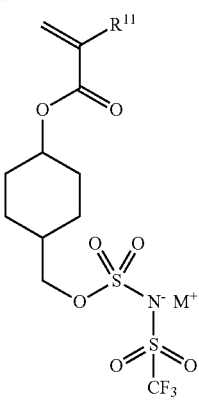
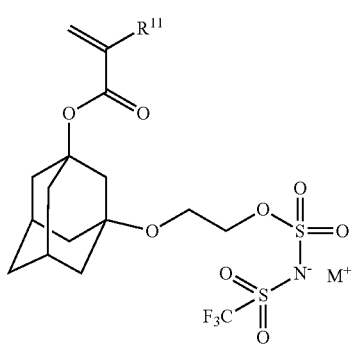
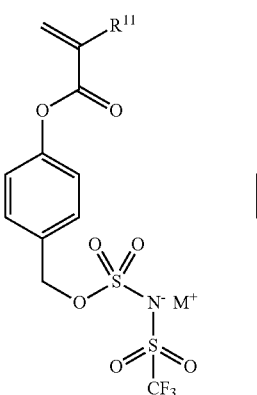
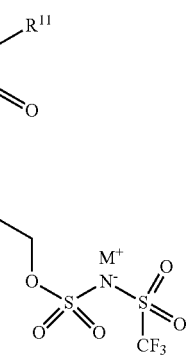
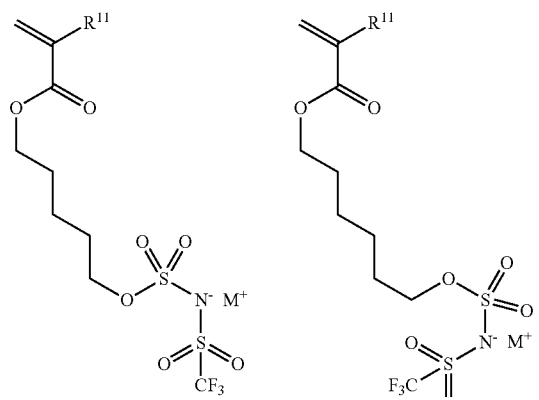
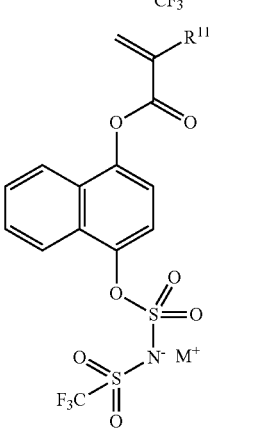
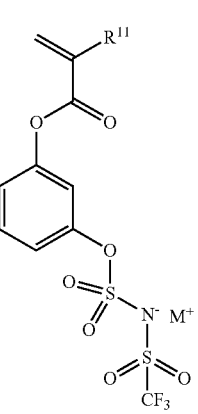
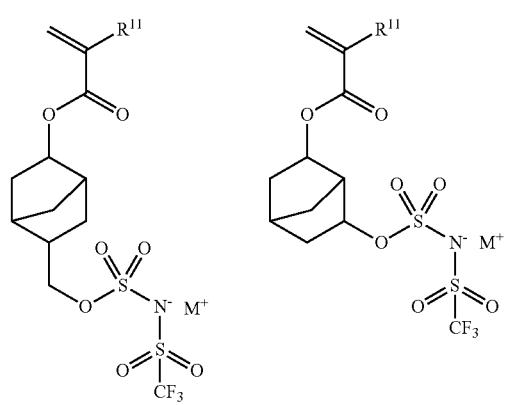
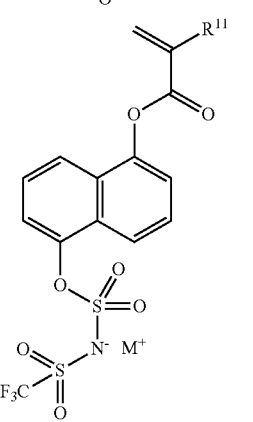
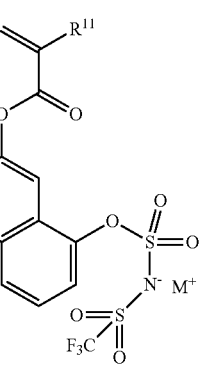

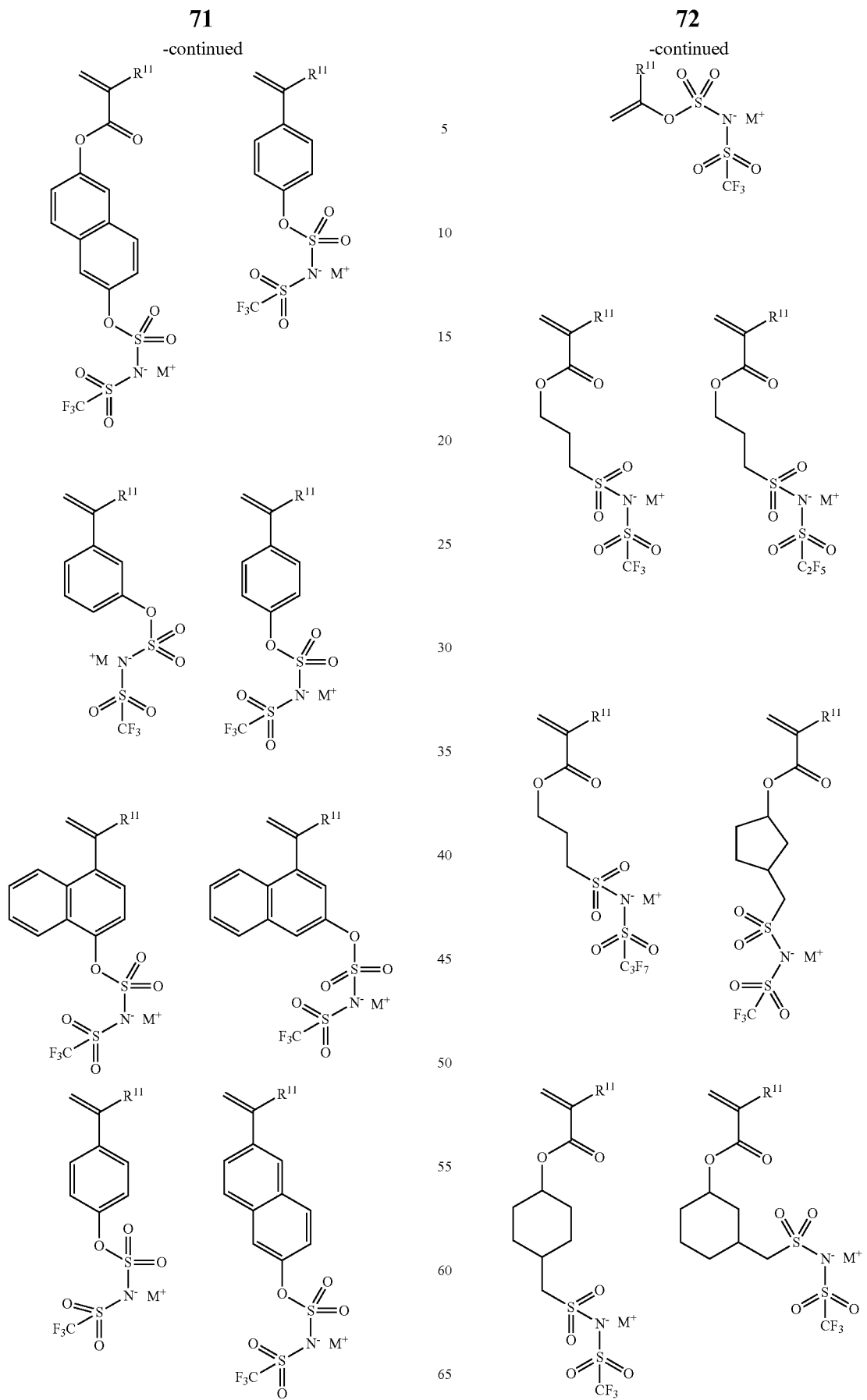

-continued
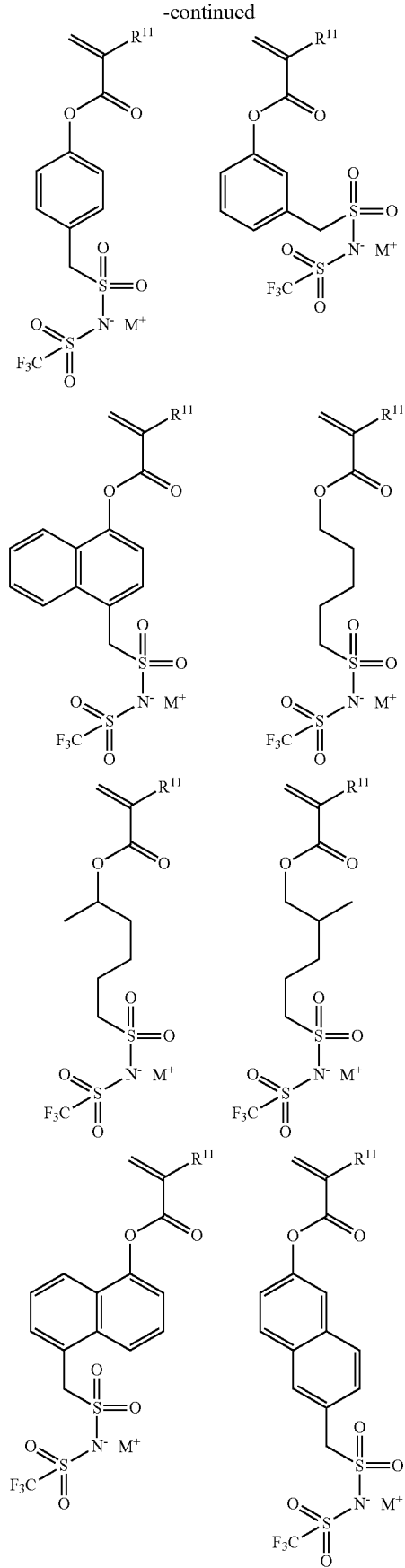
-continued
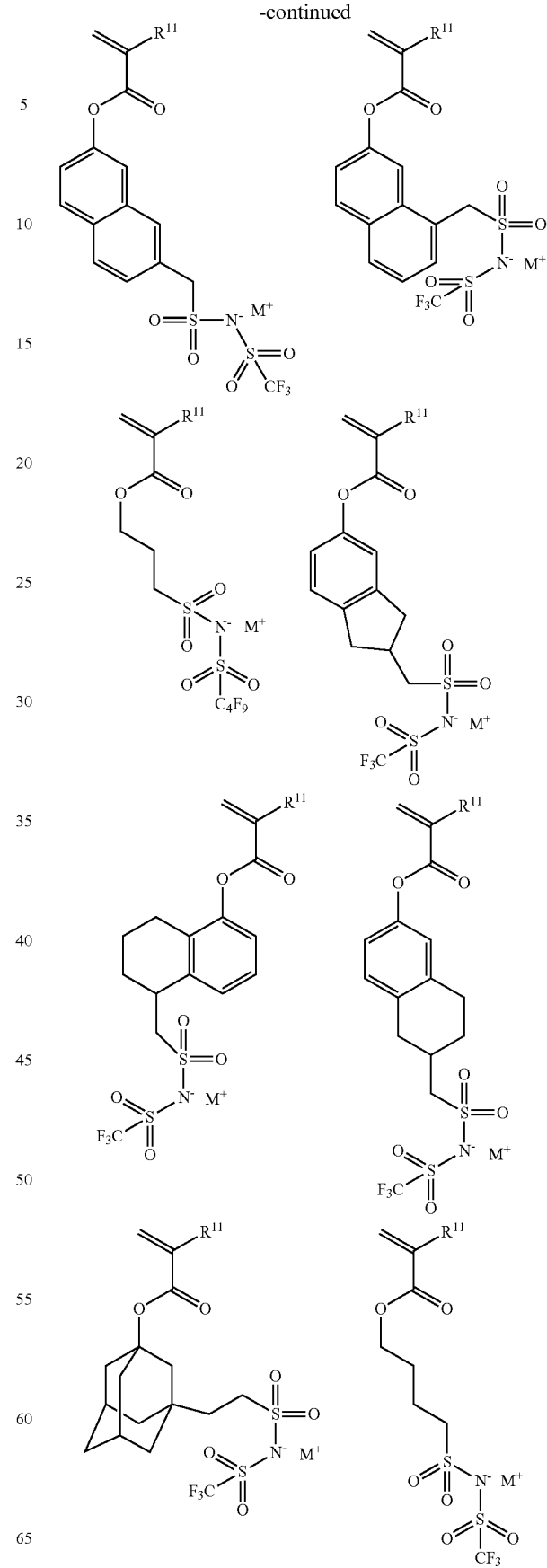

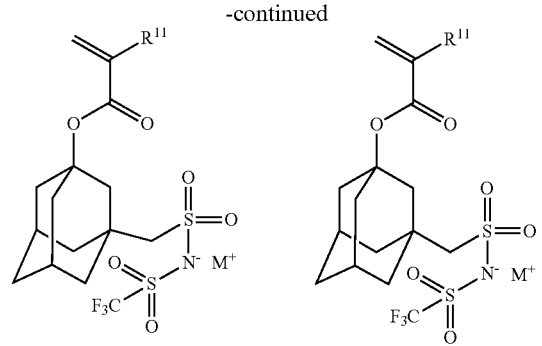
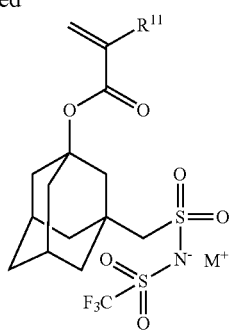
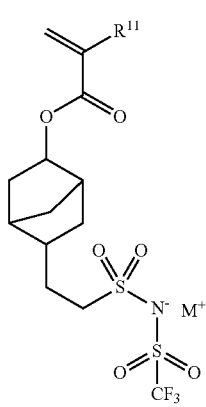
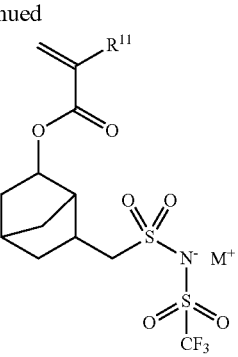
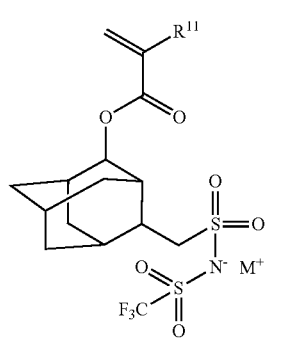
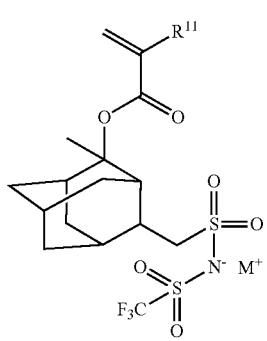
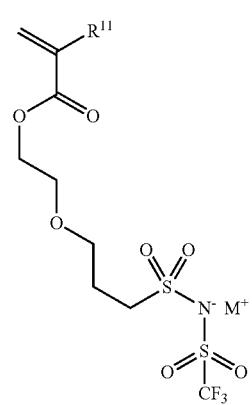
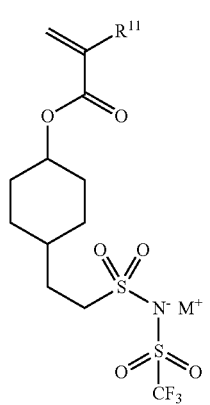
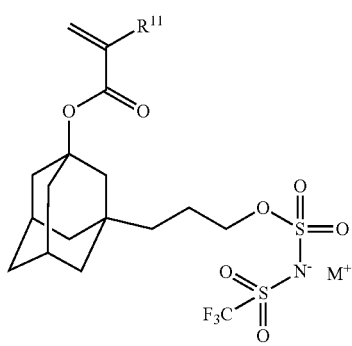
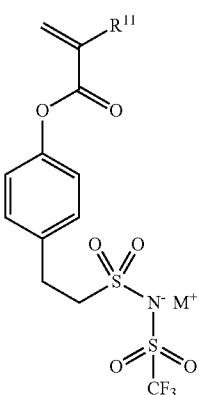
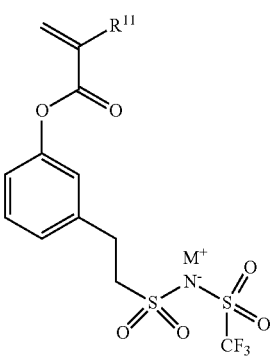
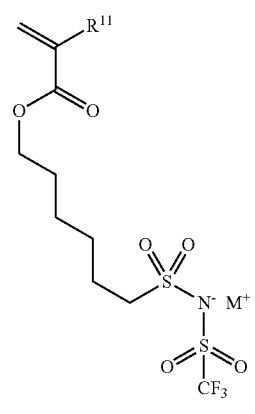
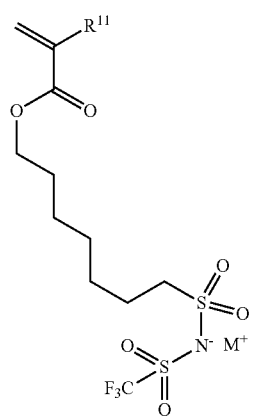
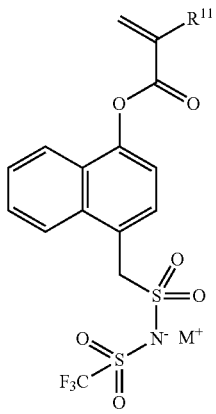
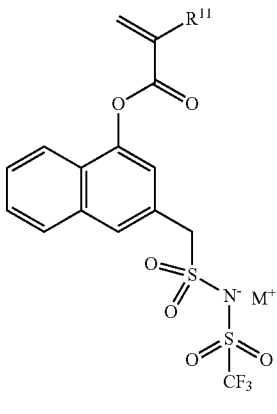

77
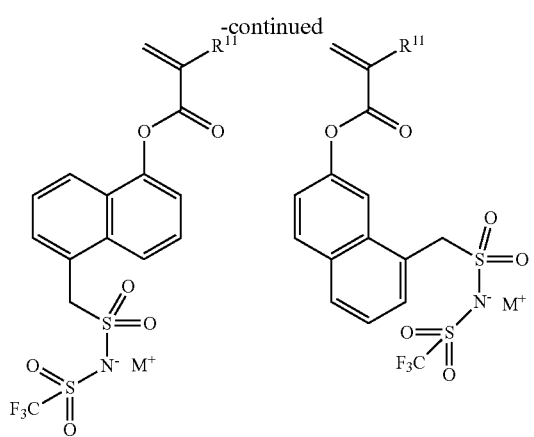
78
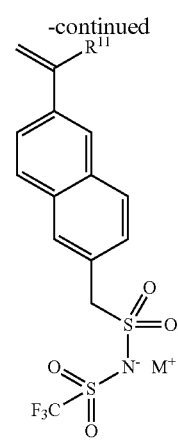
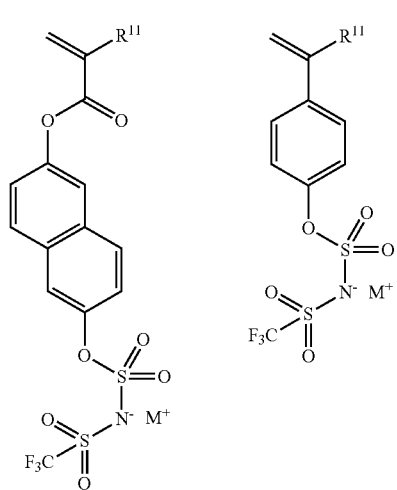
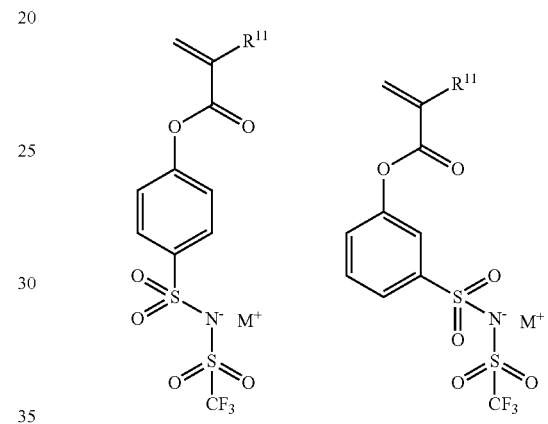
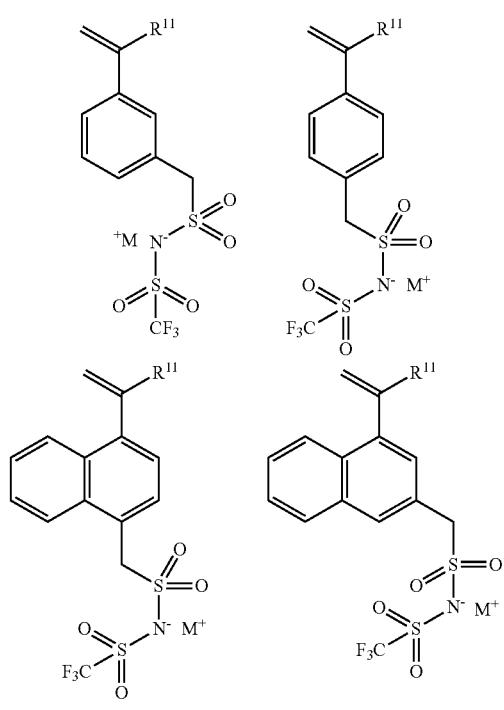
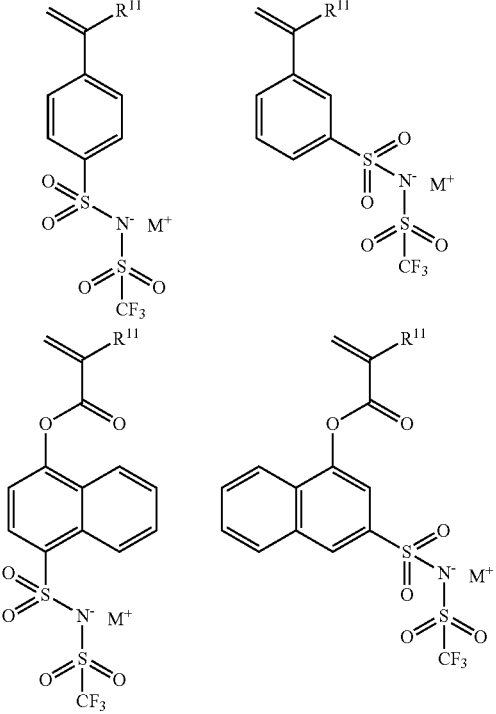

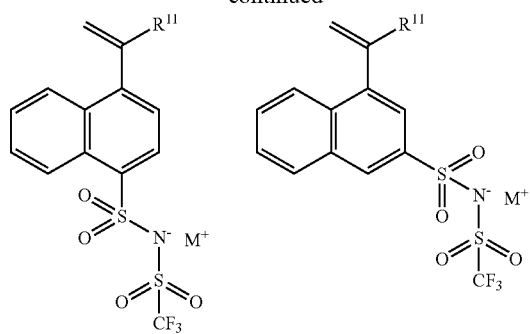
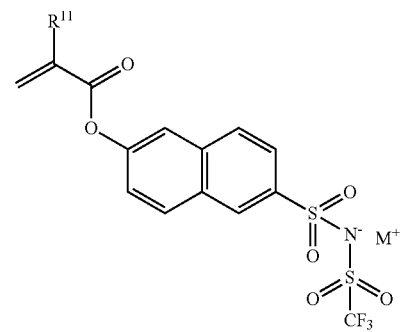
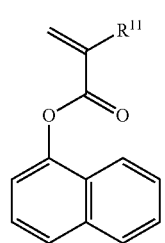
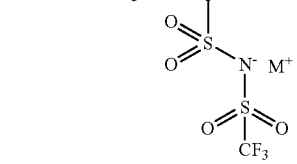
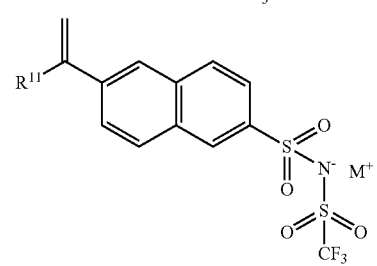
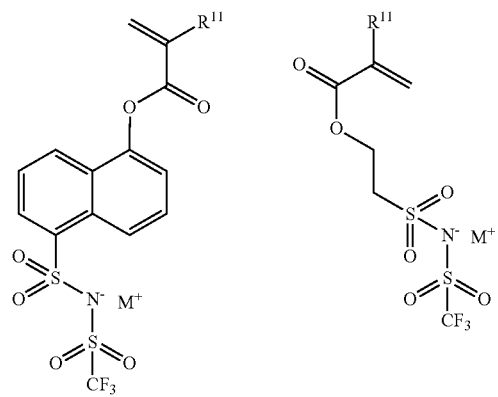
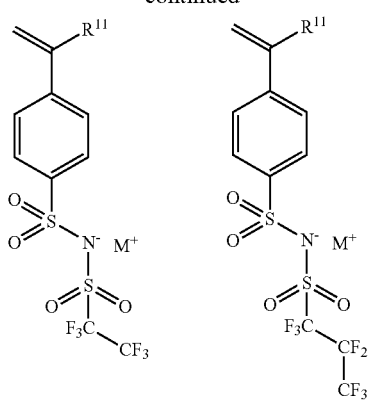
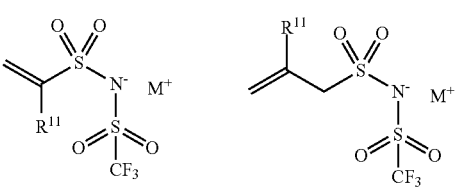
In the formulae, $R^1$ is as defined above.
Specific examples of N-carbonyl-fluorosulfonamide salt monomer to give the repeating unit-a7 in the above general formula include the following.
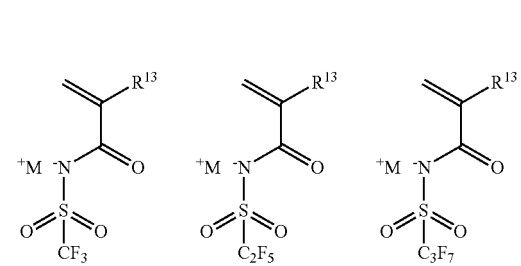
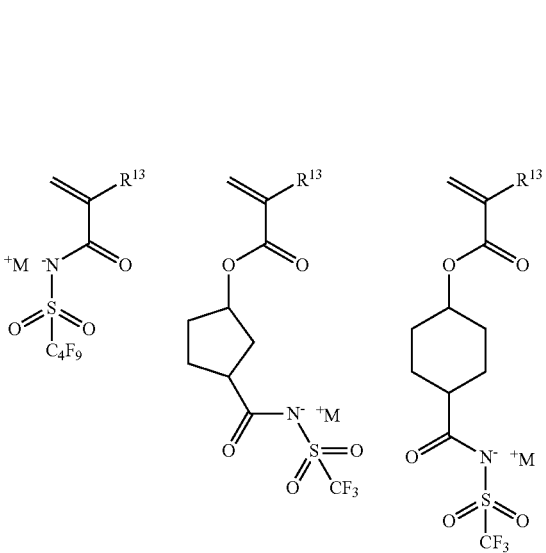

81
-continued
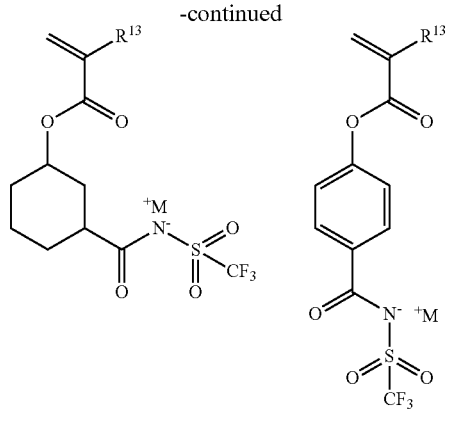
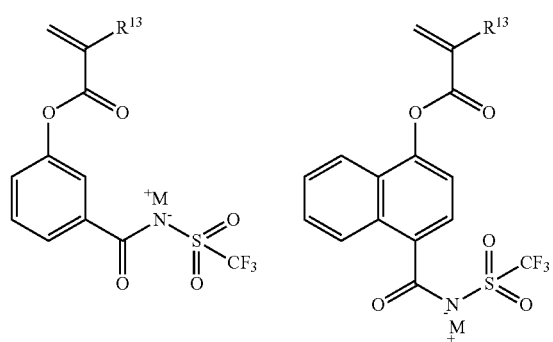
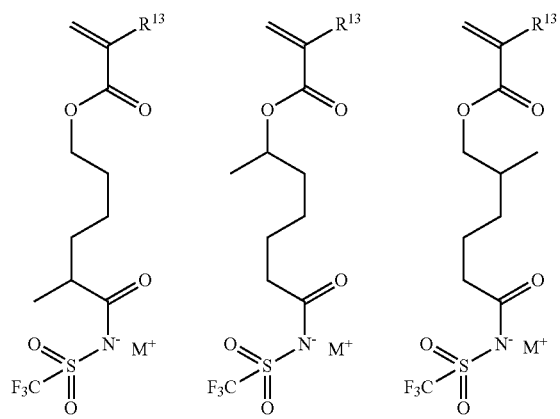
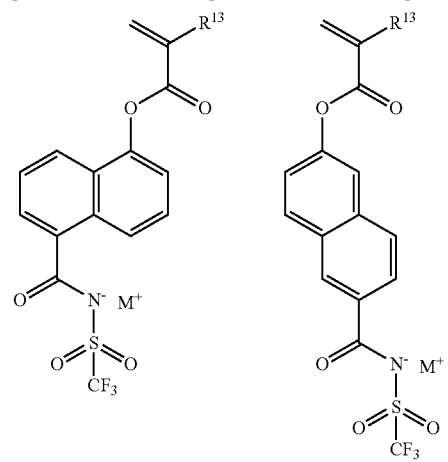
82
-continued
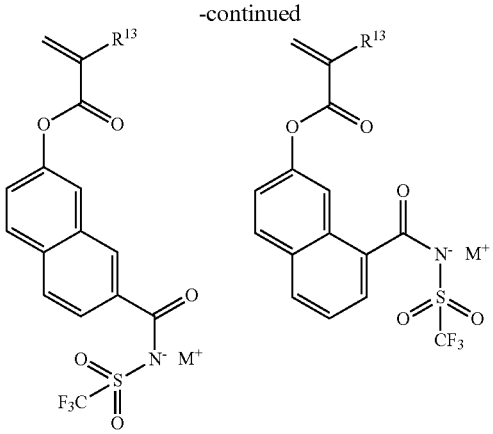
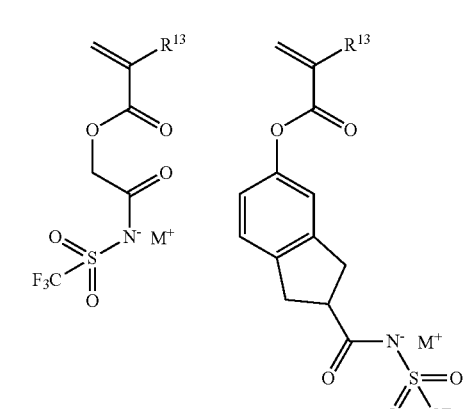
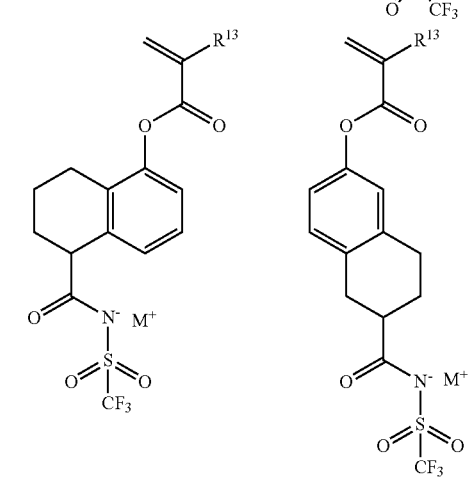
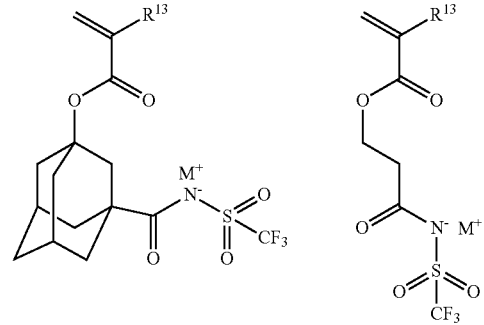

-continued
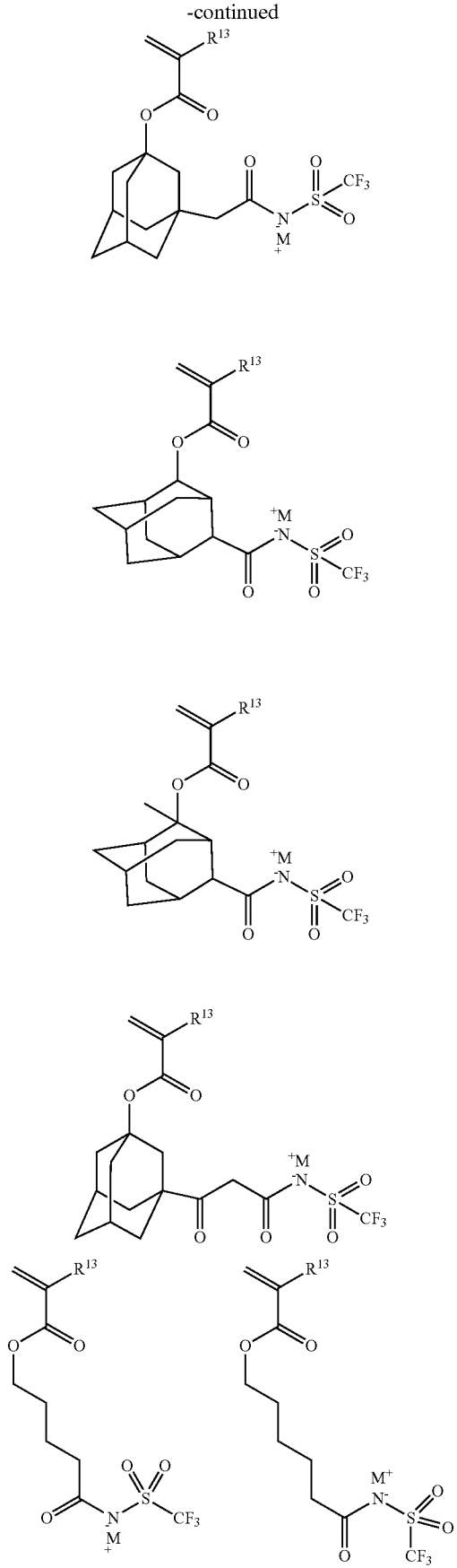
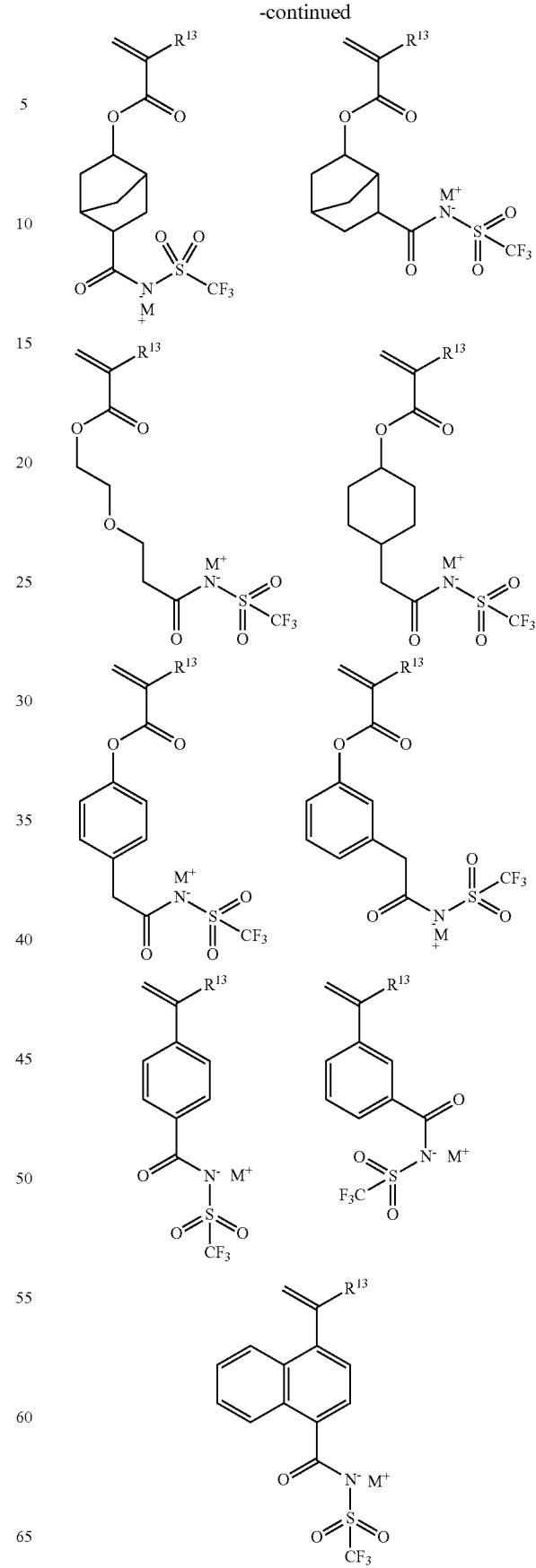

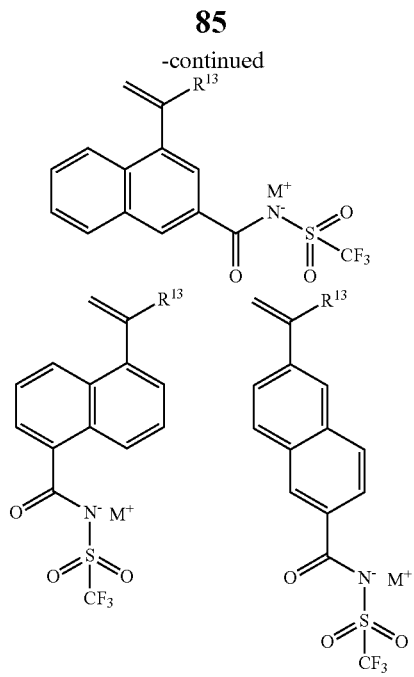

In the formulae, $R^{13}$ is as defined above.

The component (A) preferably contains an ammonium ion (ammonium cation) shown by the following general formula (3) as $M^+$ in the repeating unit-a (e.g., the repeating units-a1 to -a7).

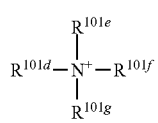
(3)

In the formula, $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom. $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula (3) within the ring.

Specific examples of the ammonium ion shown by the general formula (3) include the following.

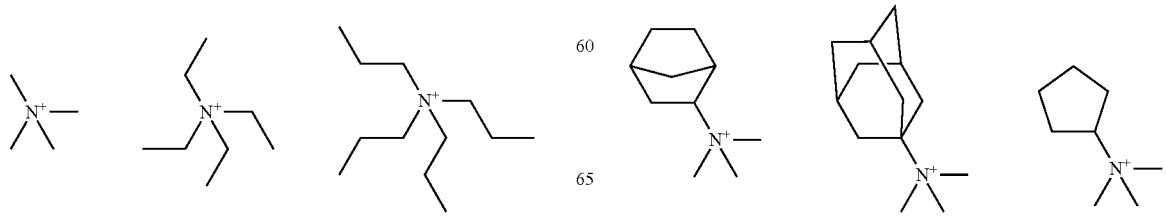

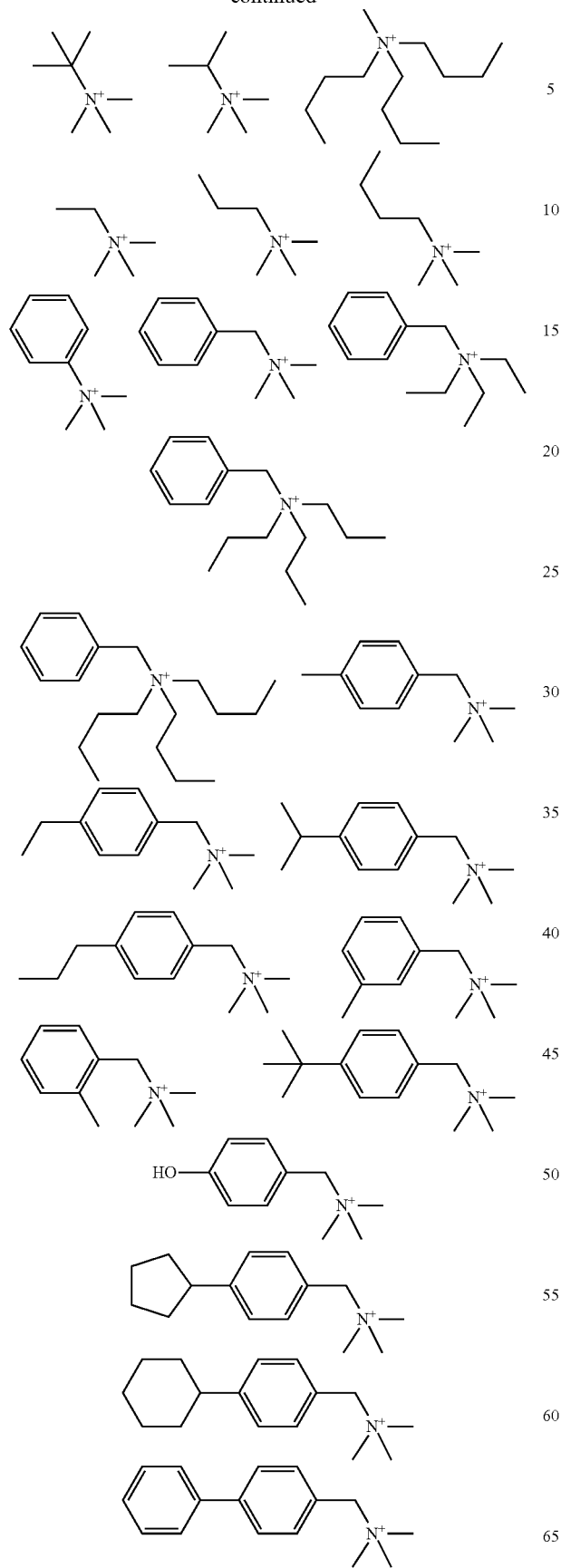
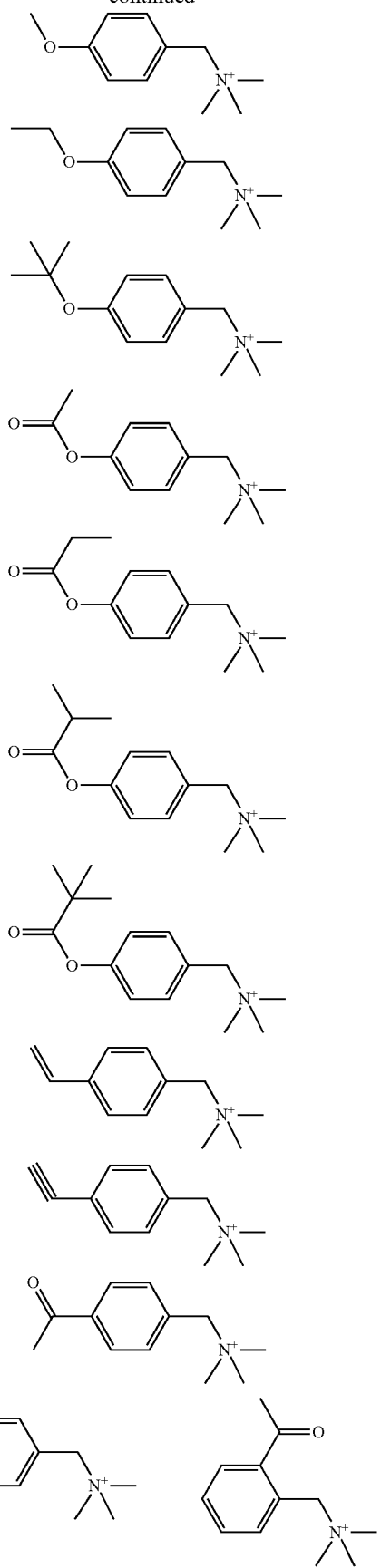

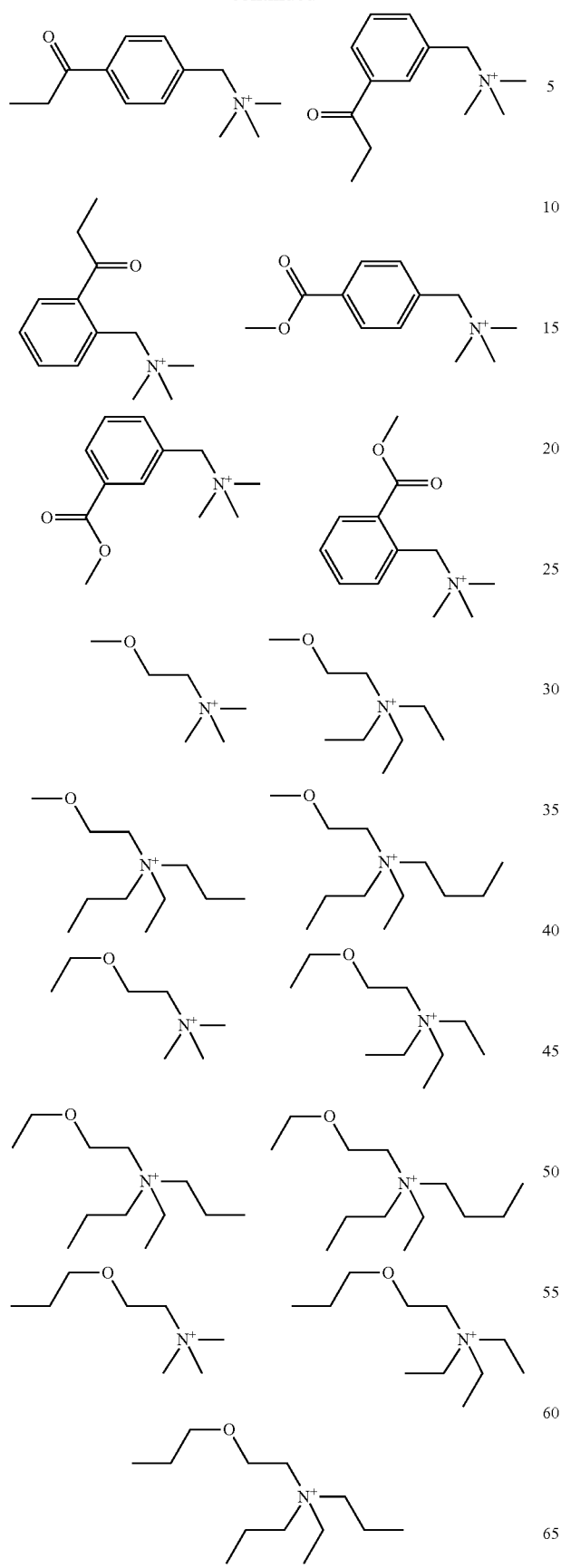
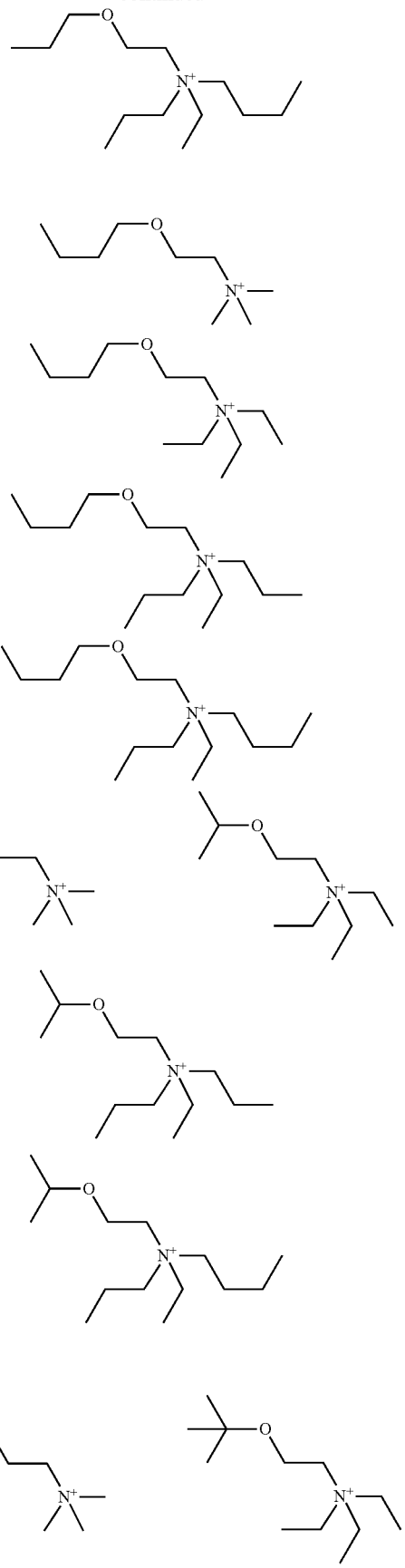

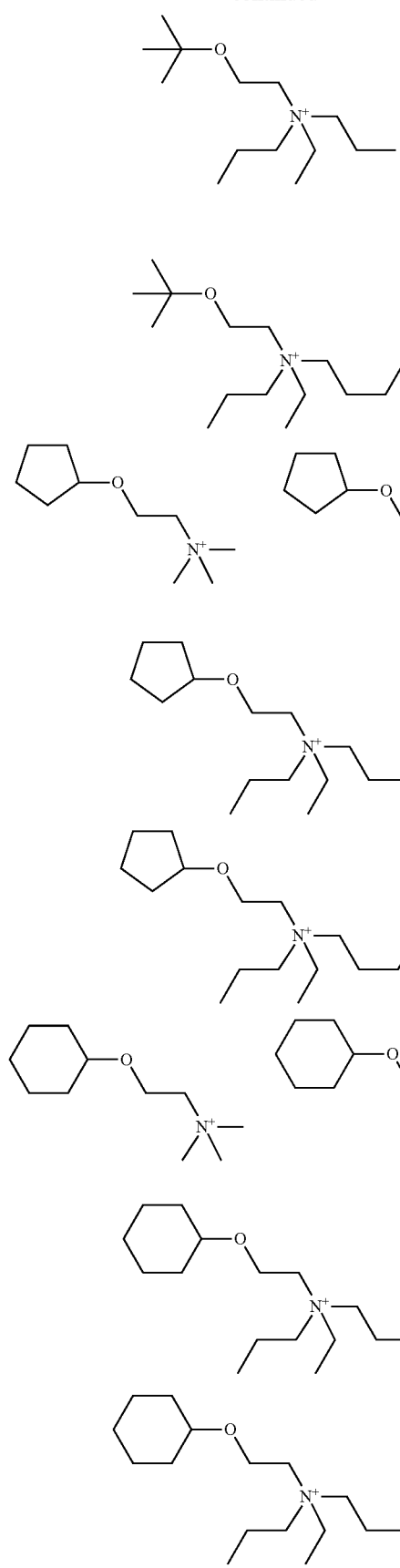

93
-continued
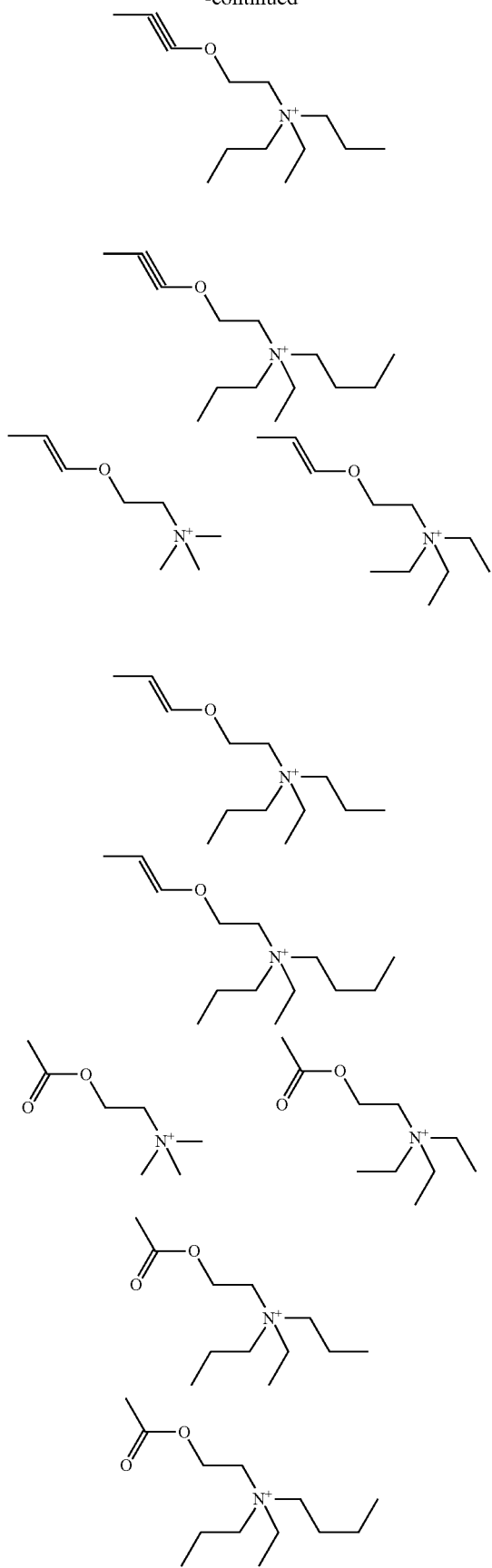
94
-continued
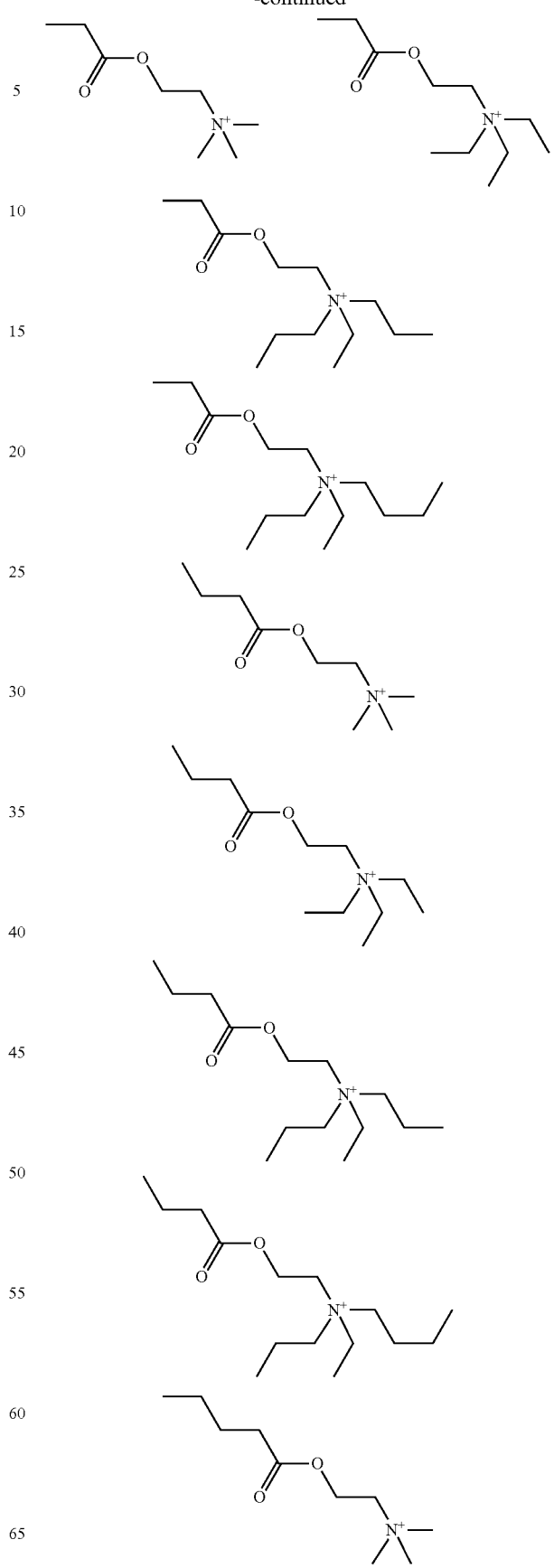

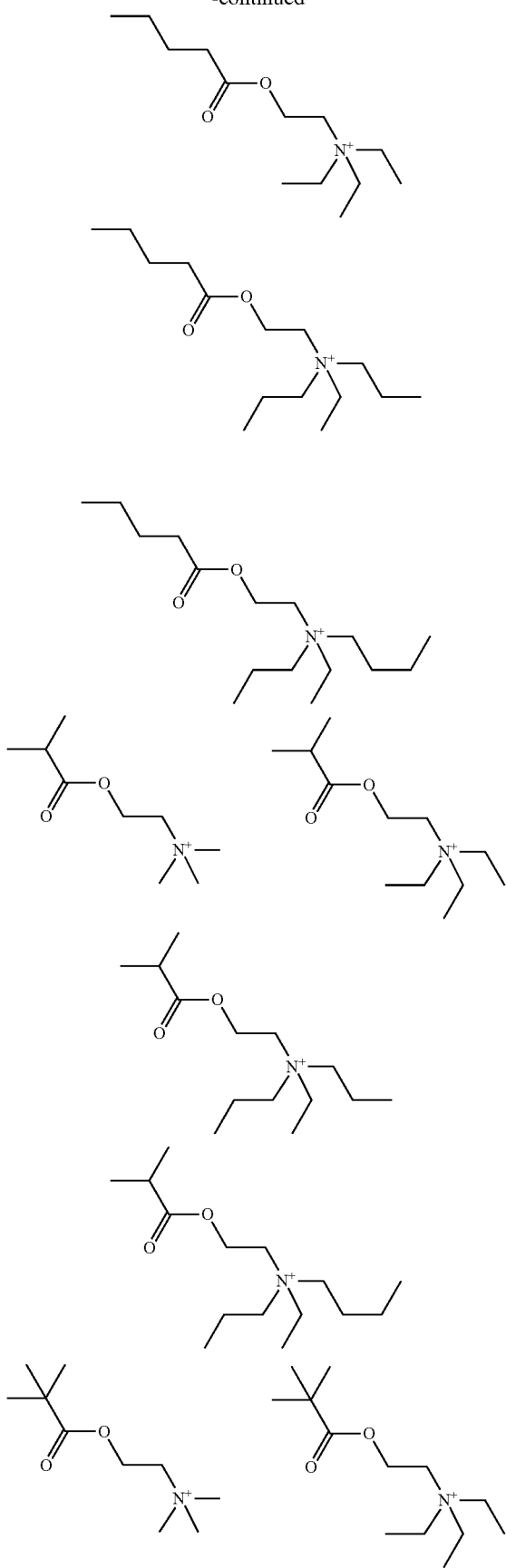
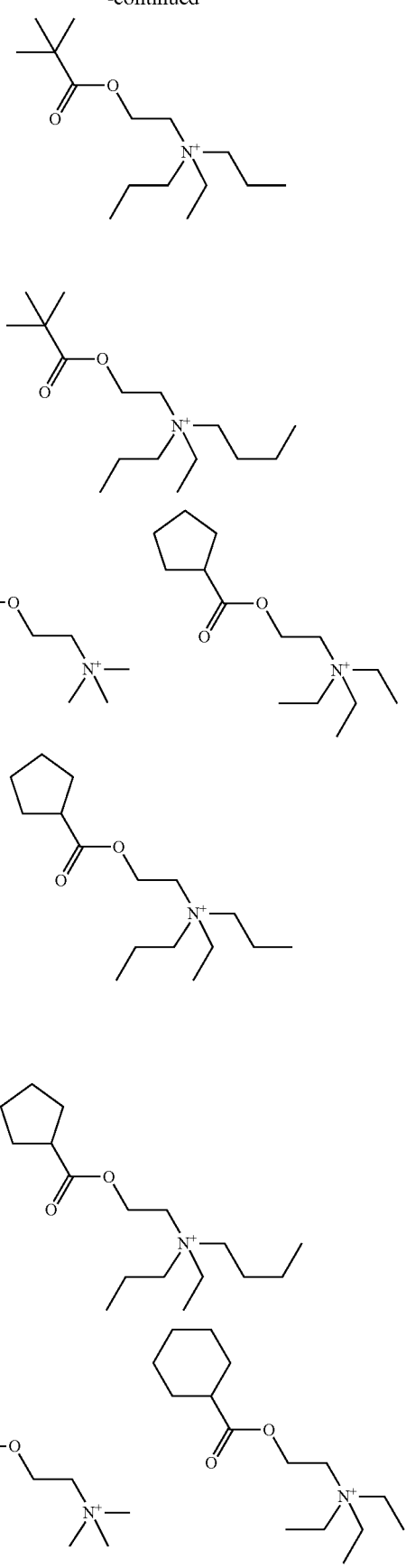

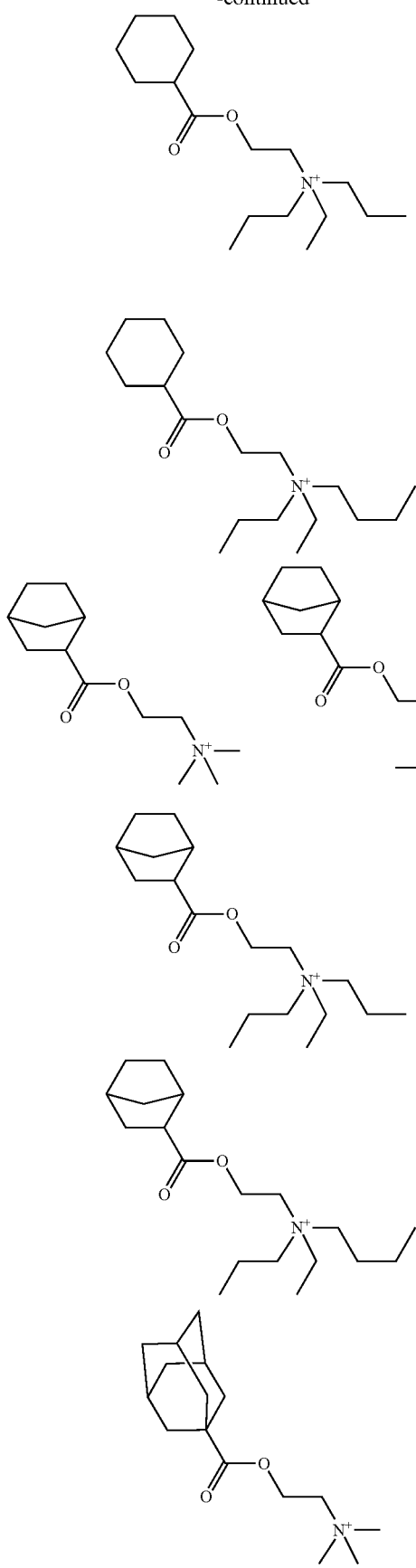

99
-continued
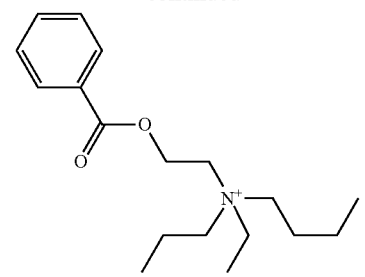
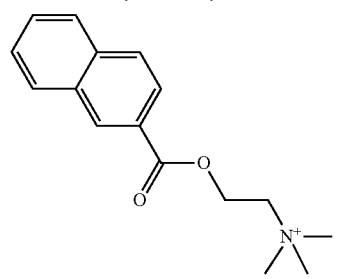
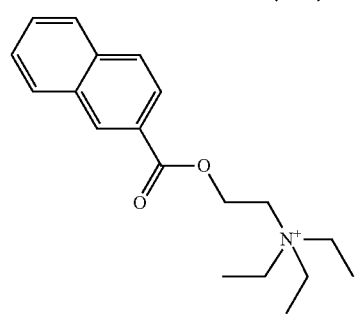
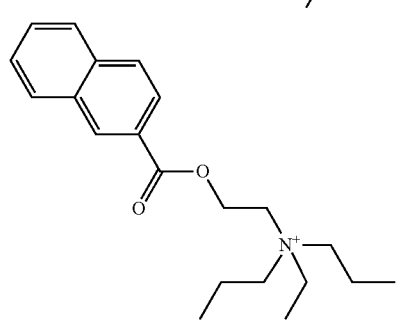
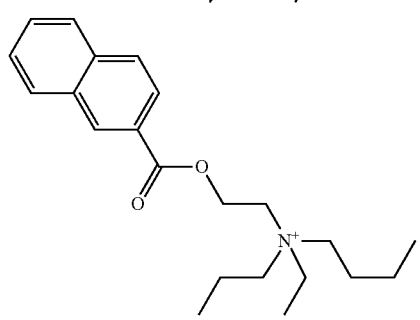
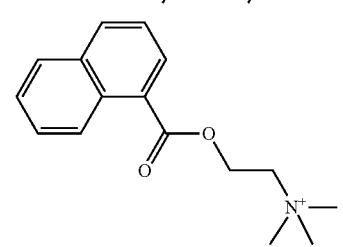
100
-continued
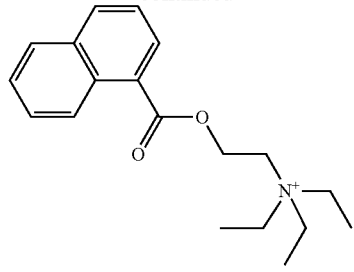
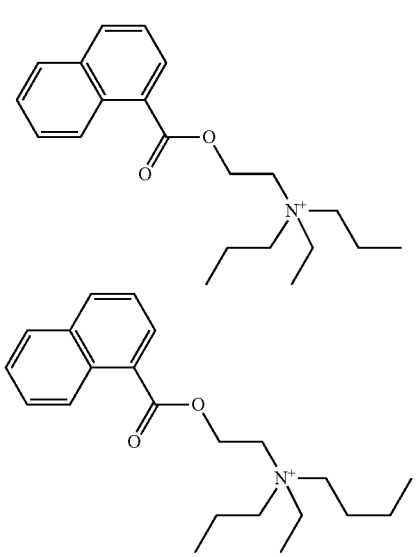
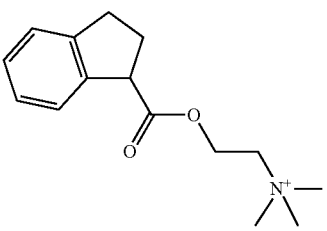
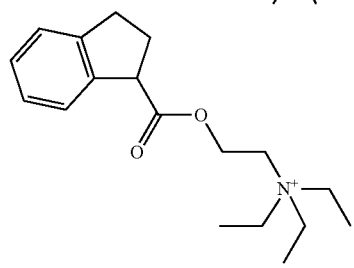
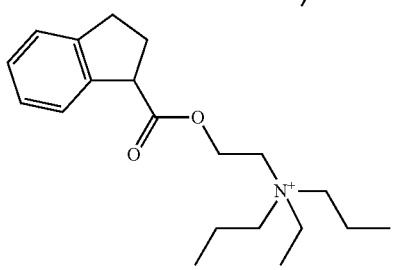

101
-continued
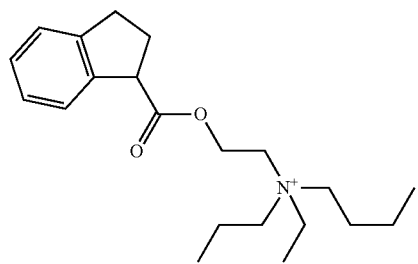
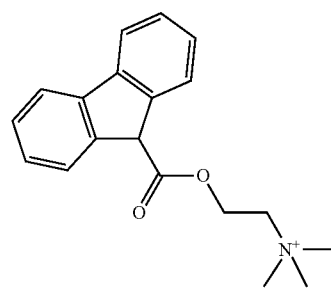
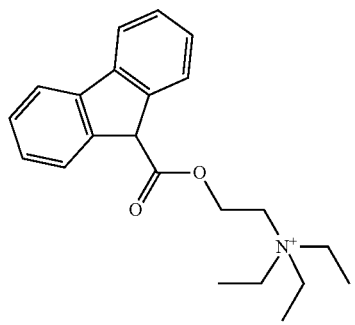
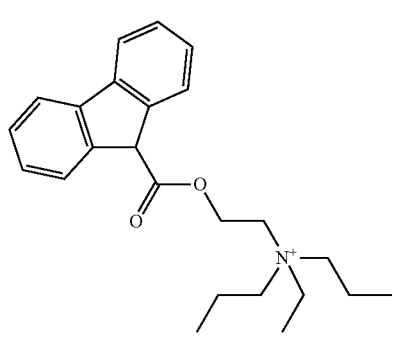
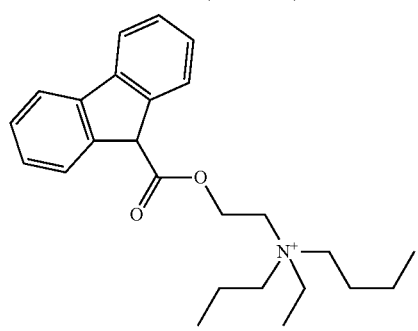
102
-continued
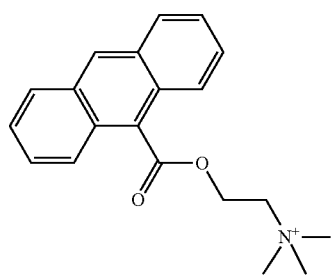
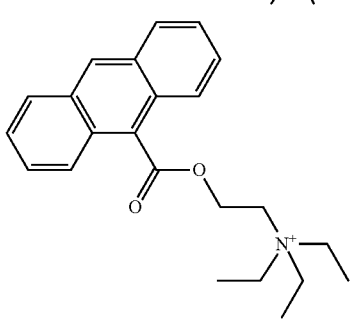
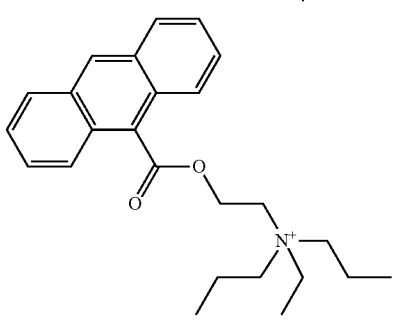
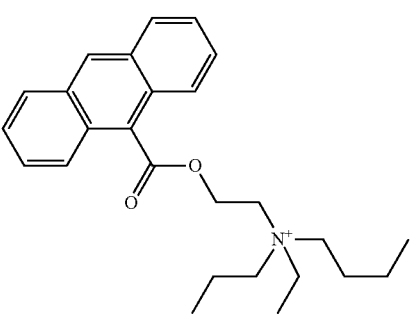
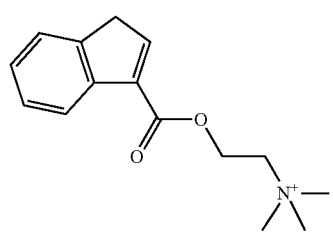
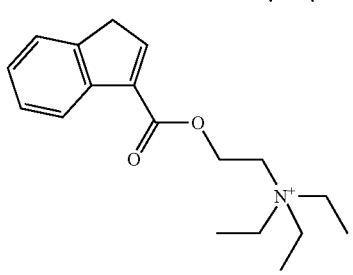

| 103 -continued | 104 -continued |
|---|---|
| 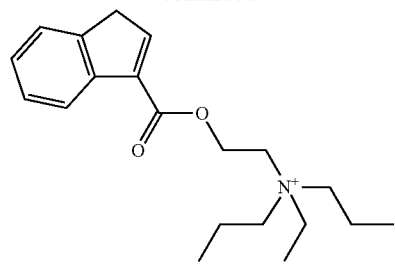 | 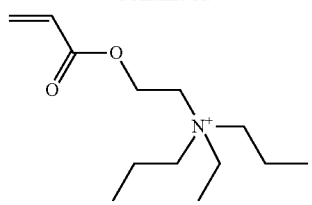 |
| 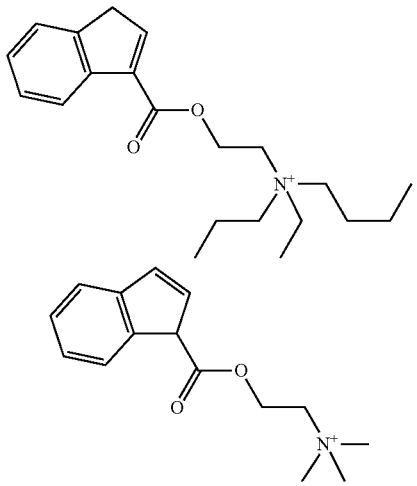 | 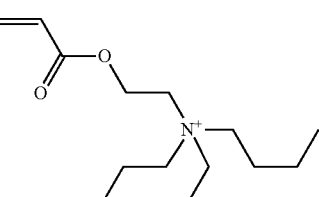 |
| 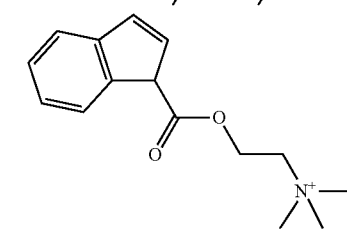 | 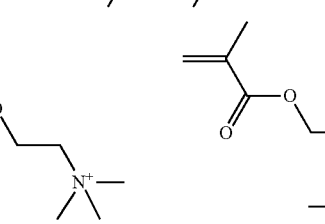 |
| 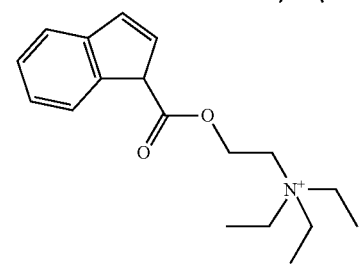 | 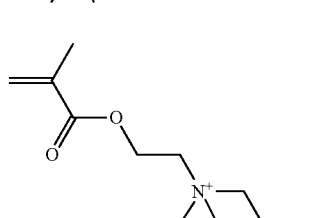 |
| 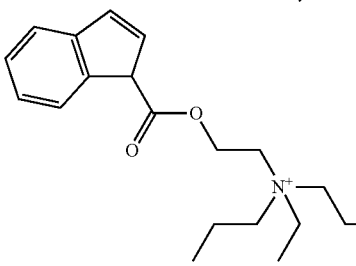 | 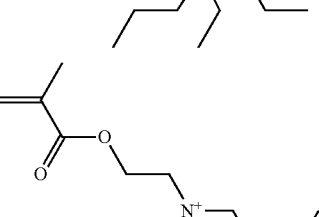 |
| 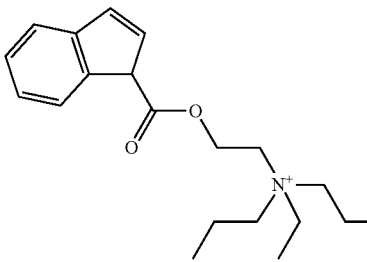 | 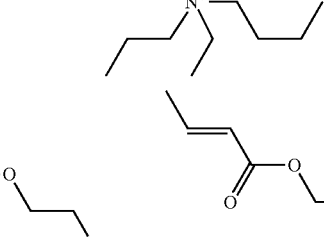 |
| 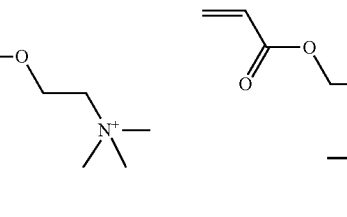 |  |
| | 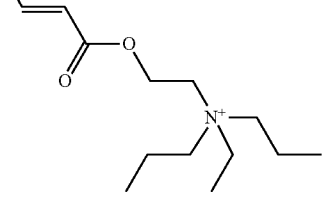 |

105
-continued
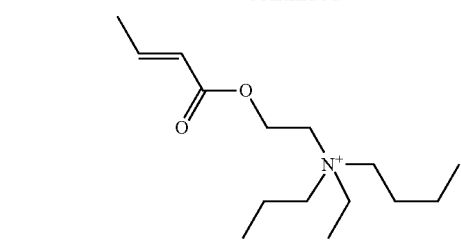
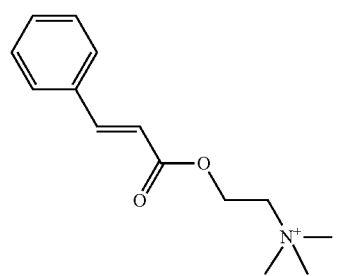
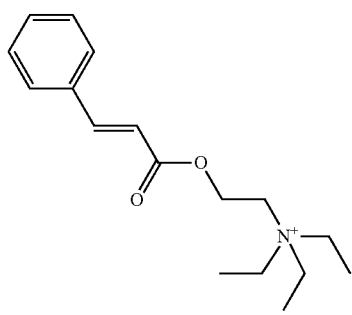
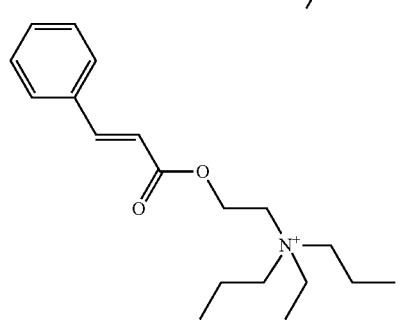
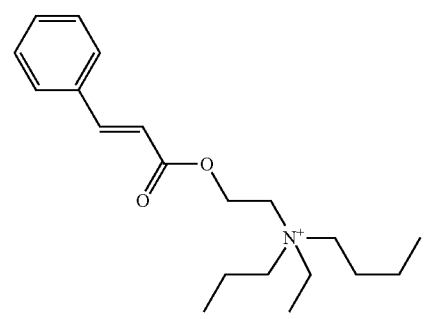
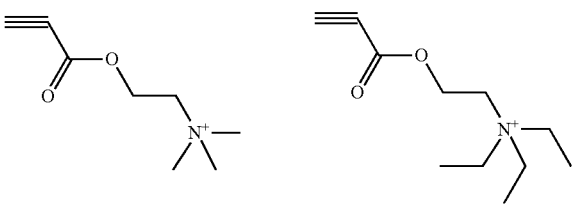
106
-continued
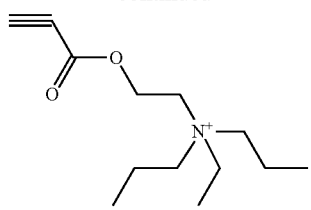
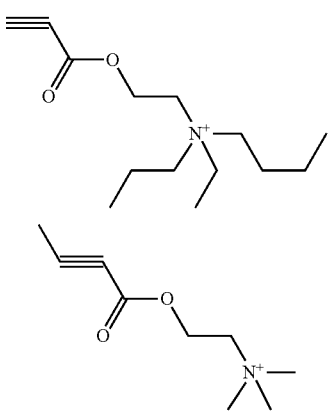
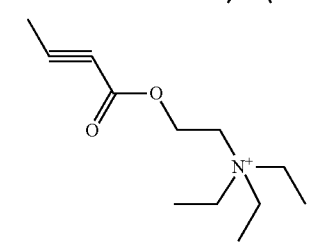
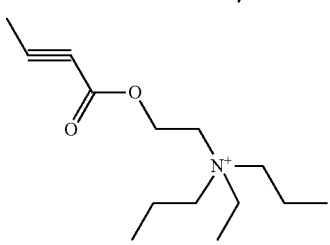
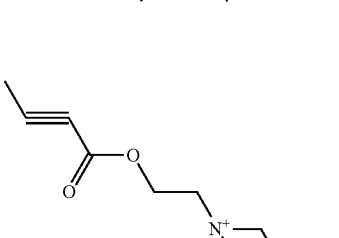
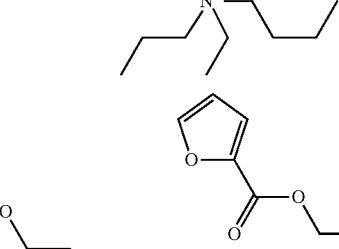
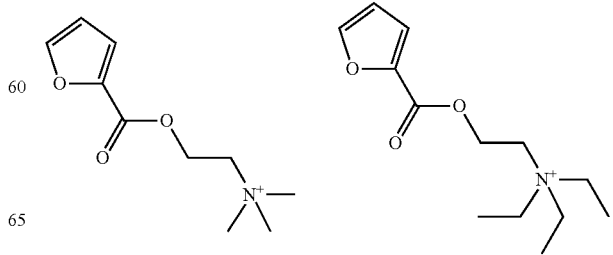

107
-continued
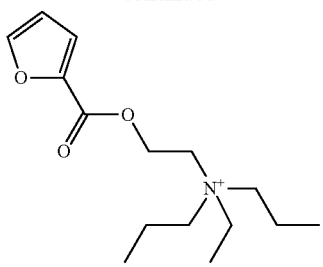
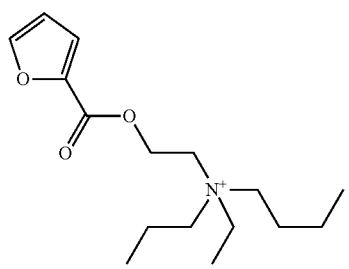
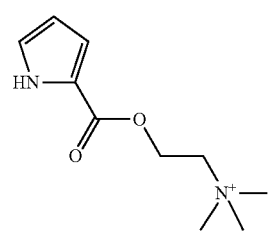  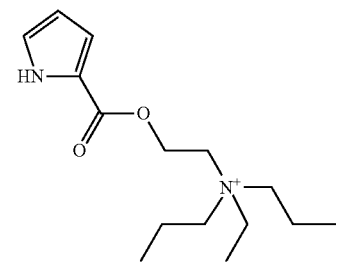
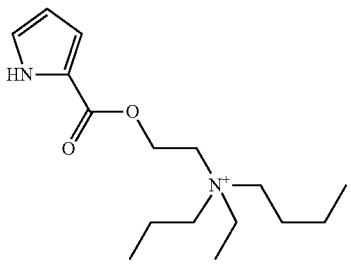
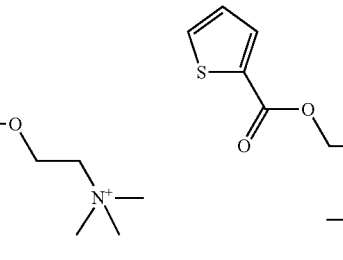  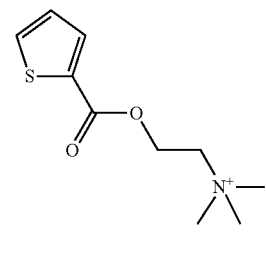
108
-continued
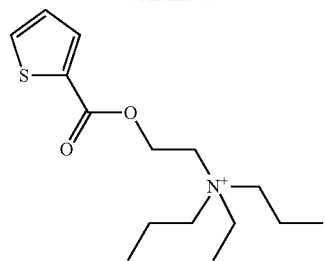
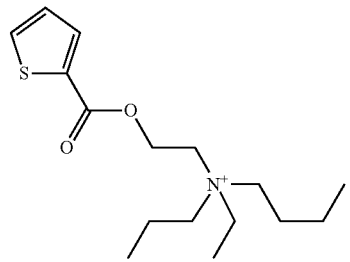
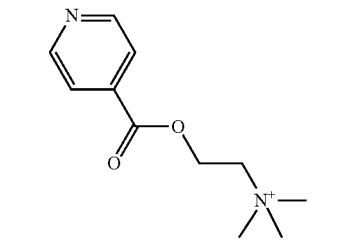
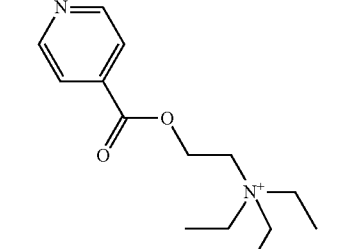
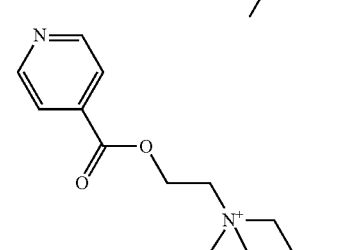
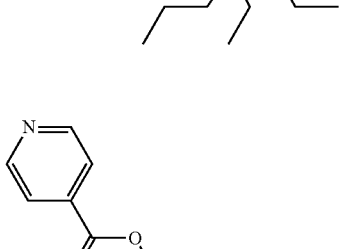
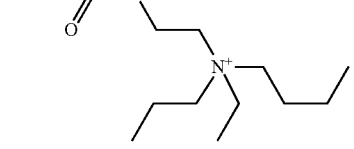

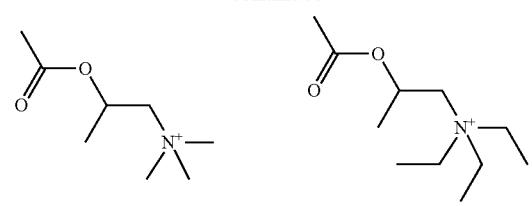
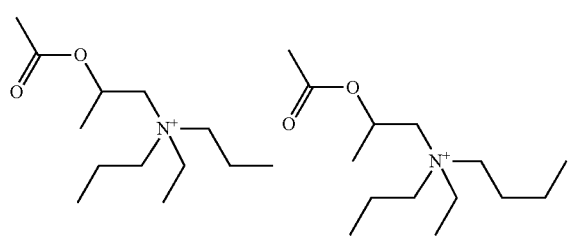
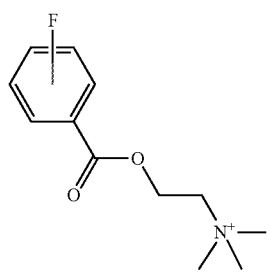
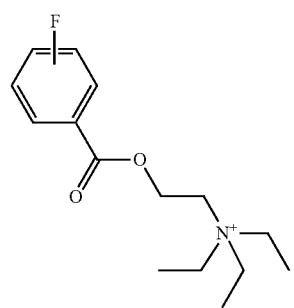
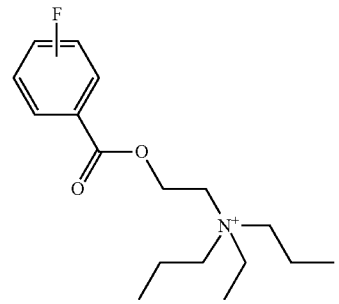
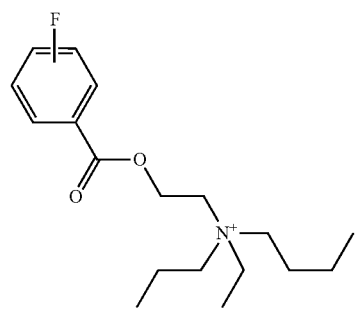
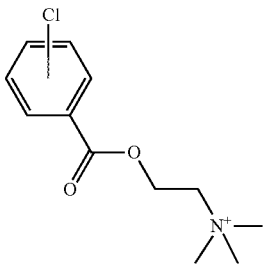
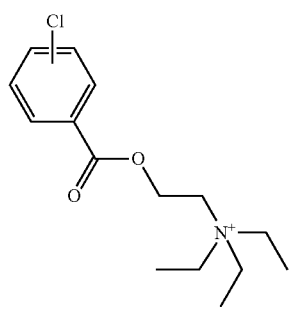
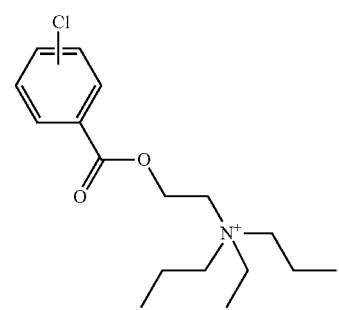
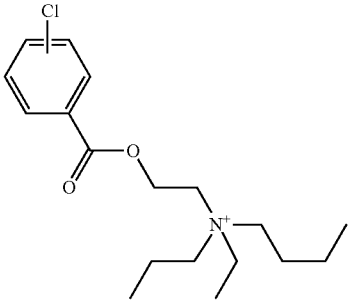
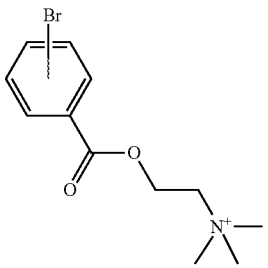

111
-continued
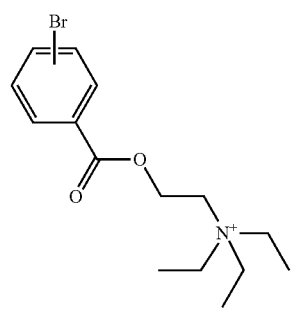
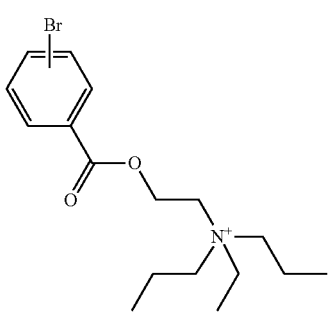
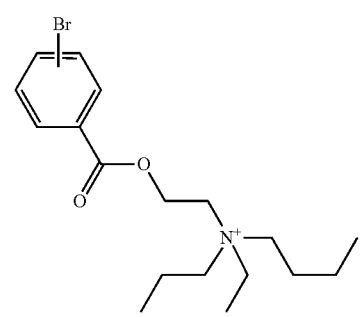
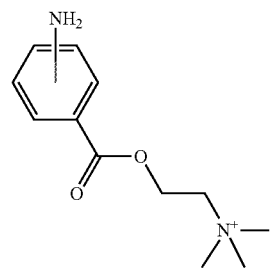
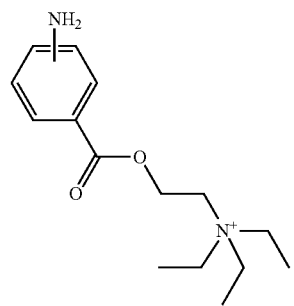
112
-continued
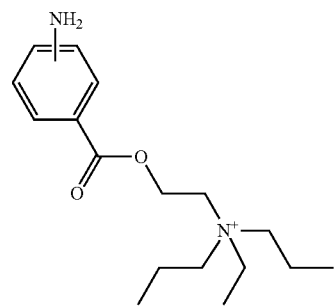
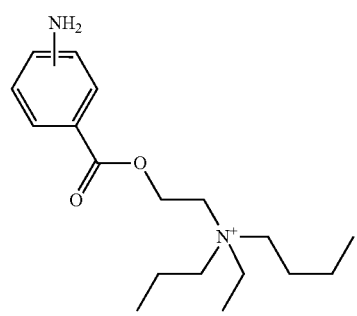
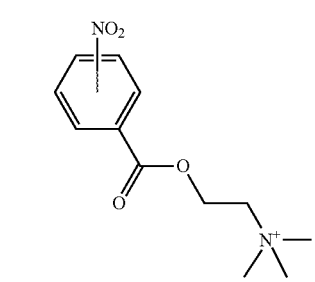
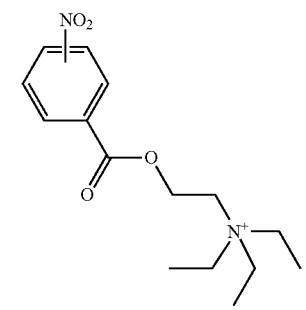
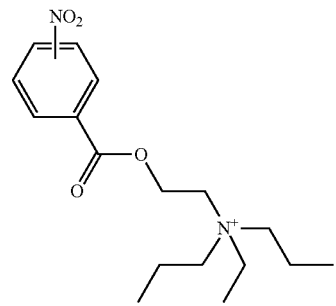

113
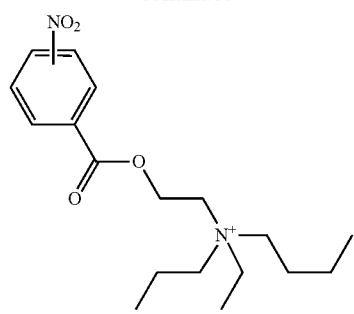
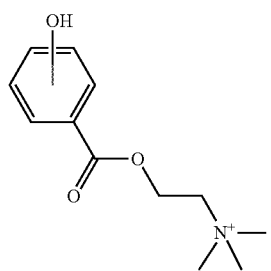
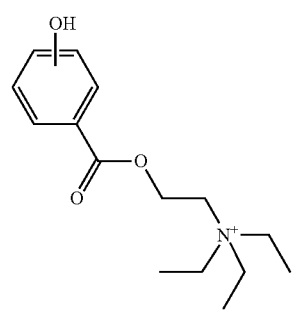
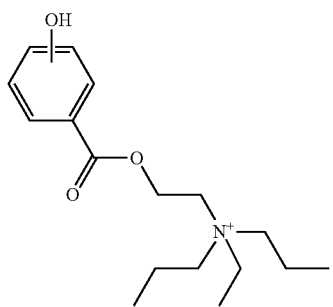
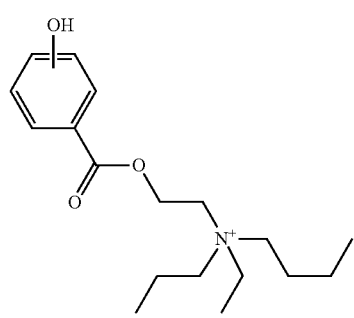
114
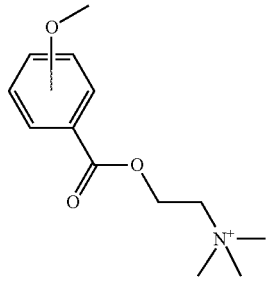
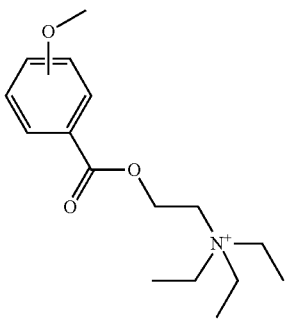
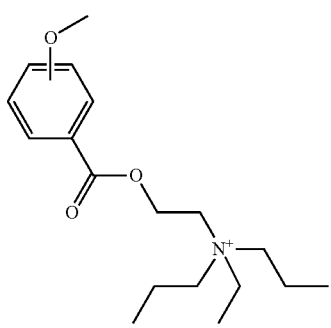
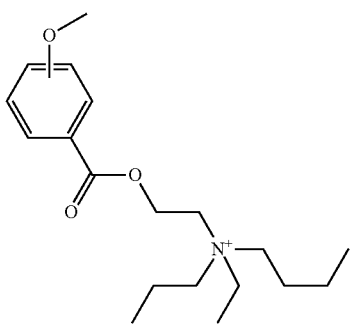
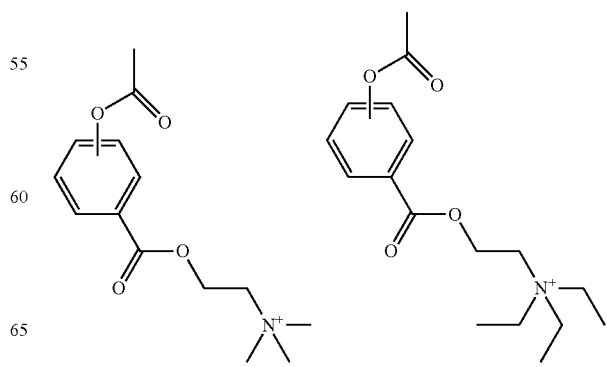

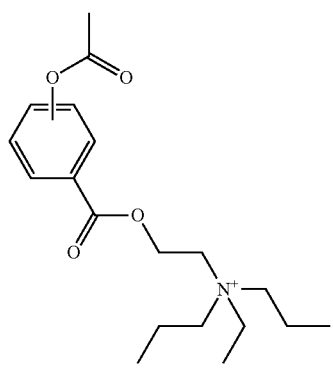
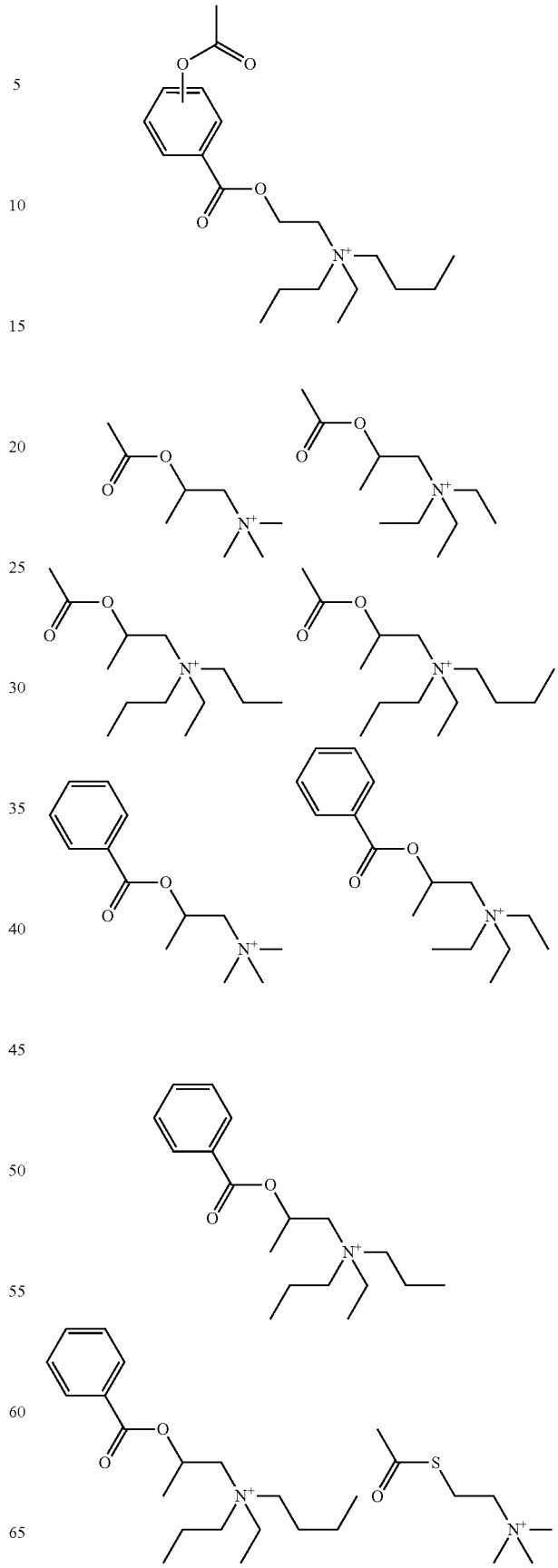

117
-continued
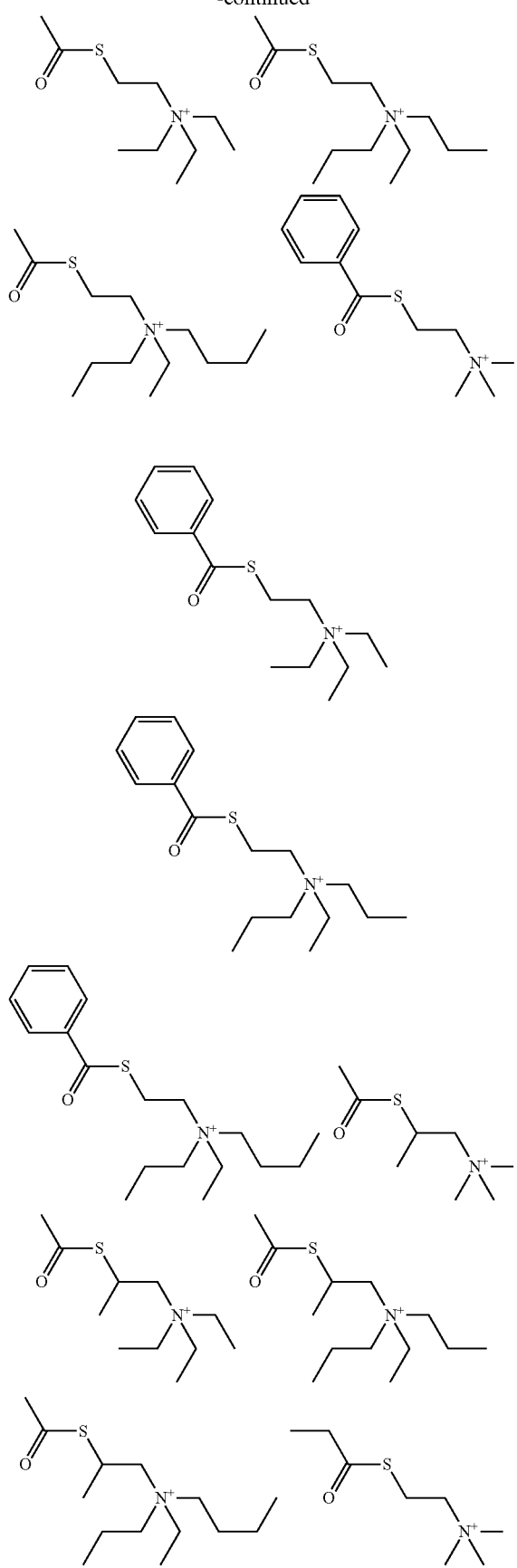
118
-continued
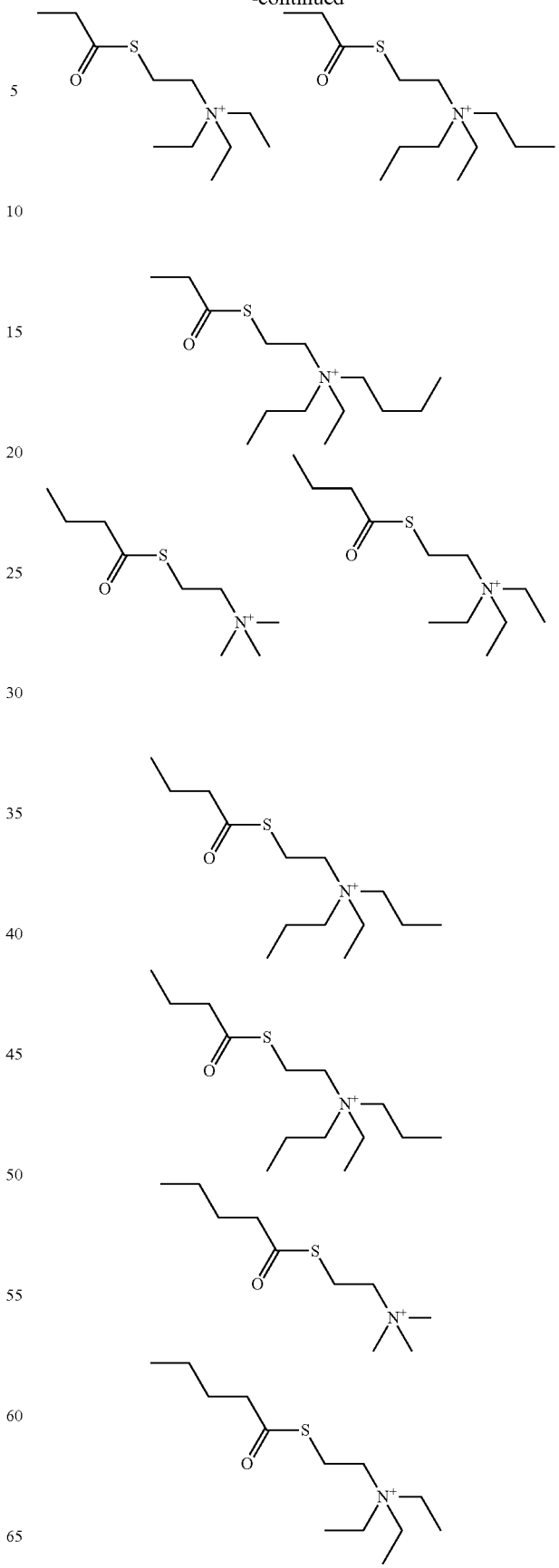

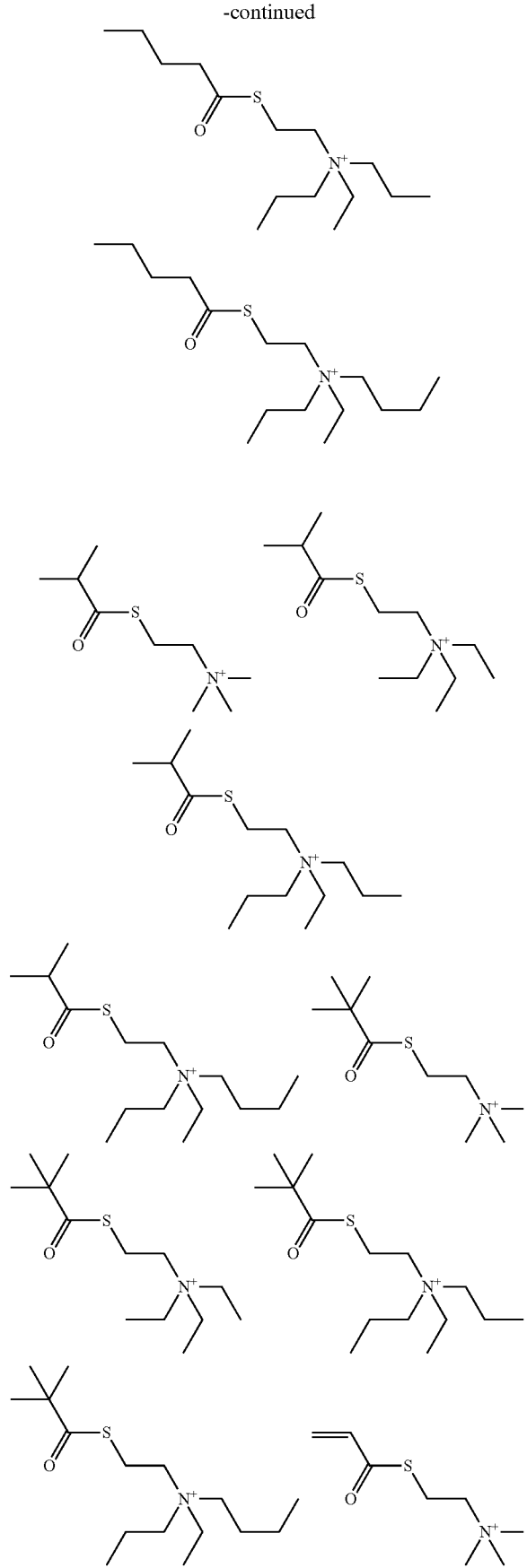

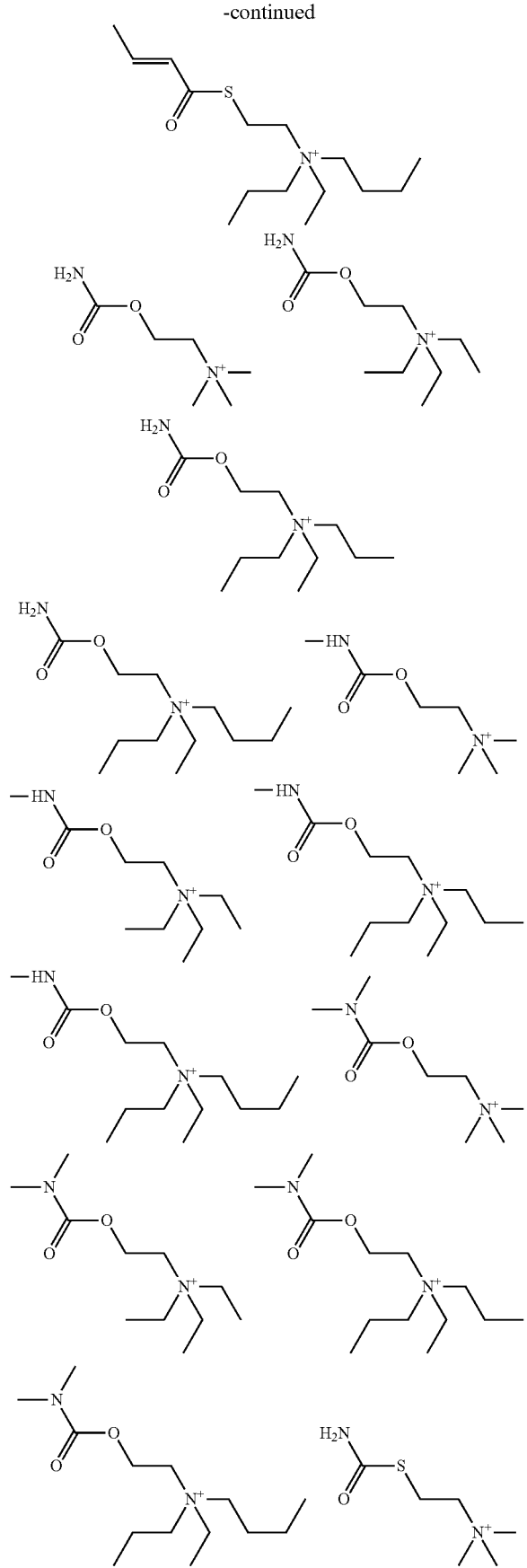
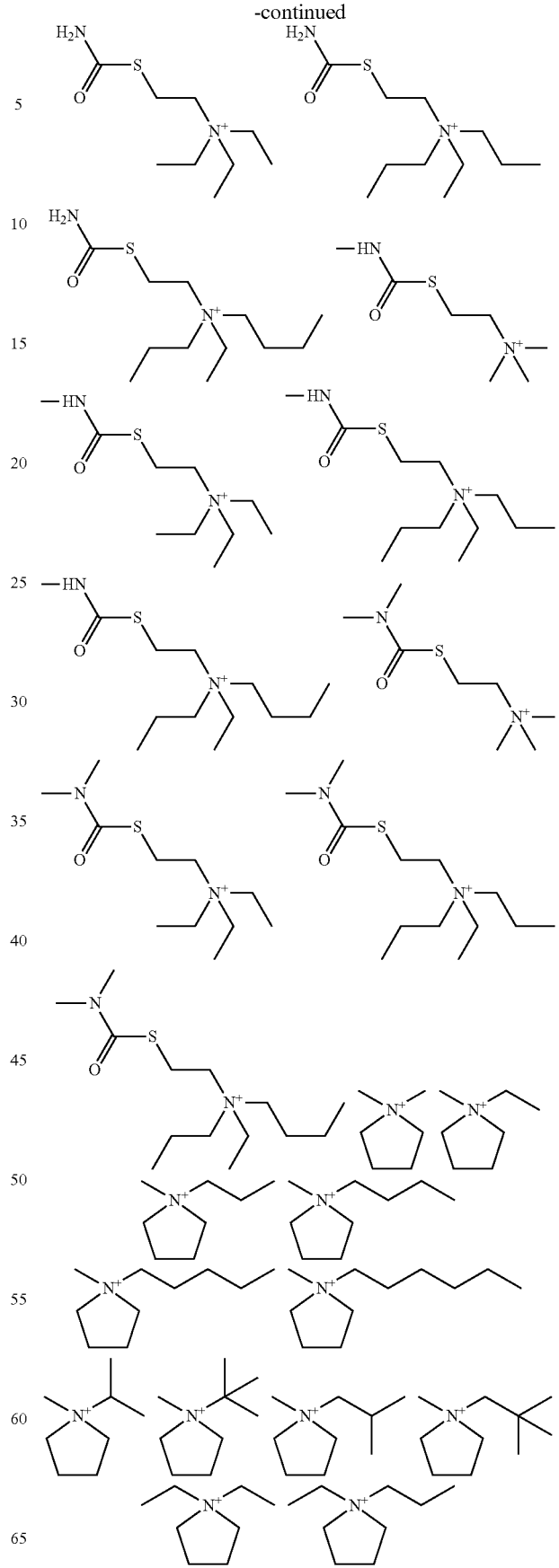

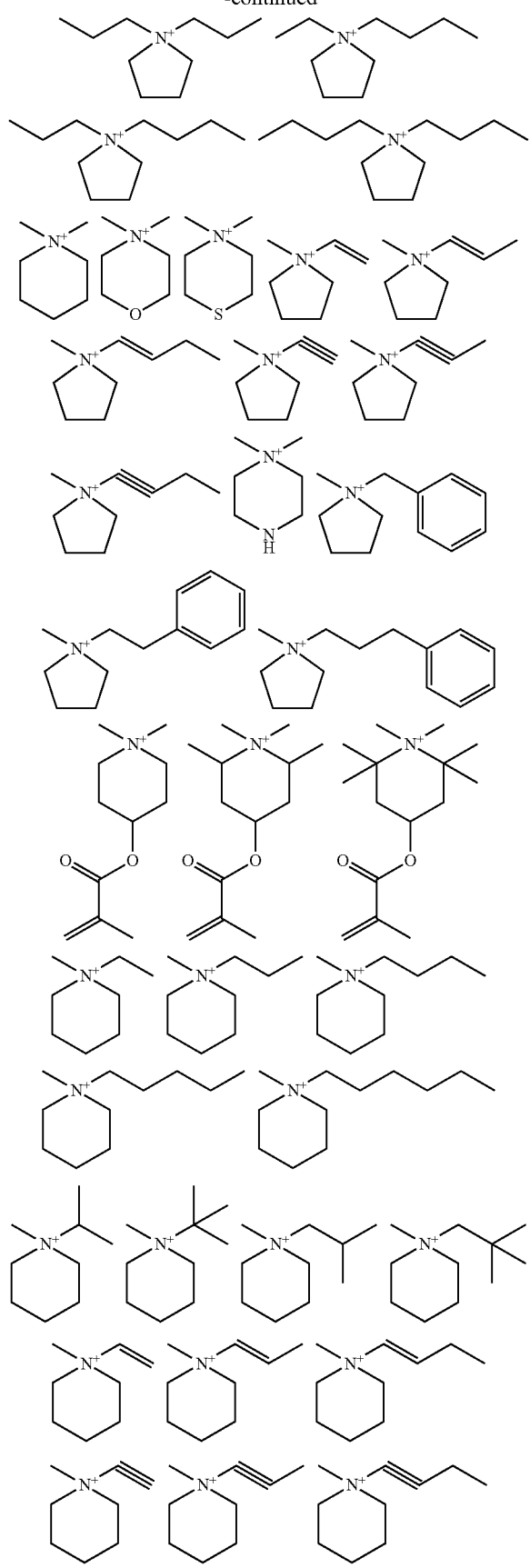
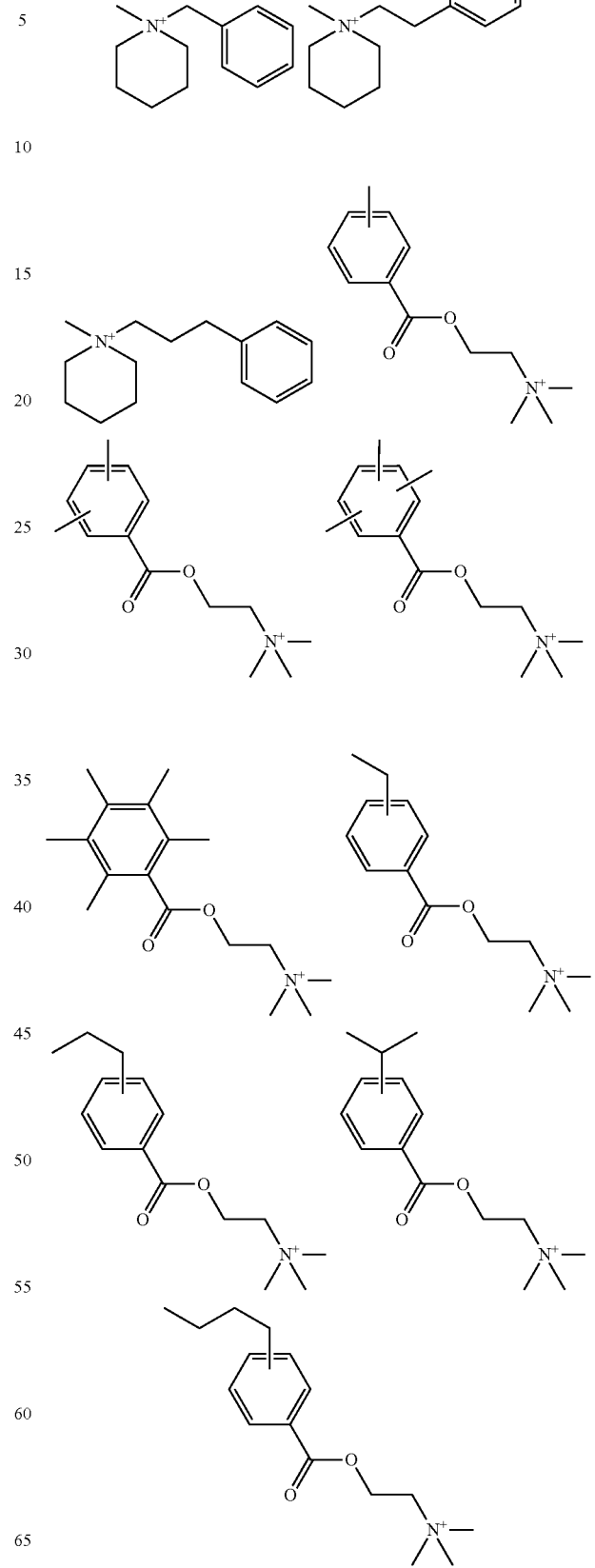

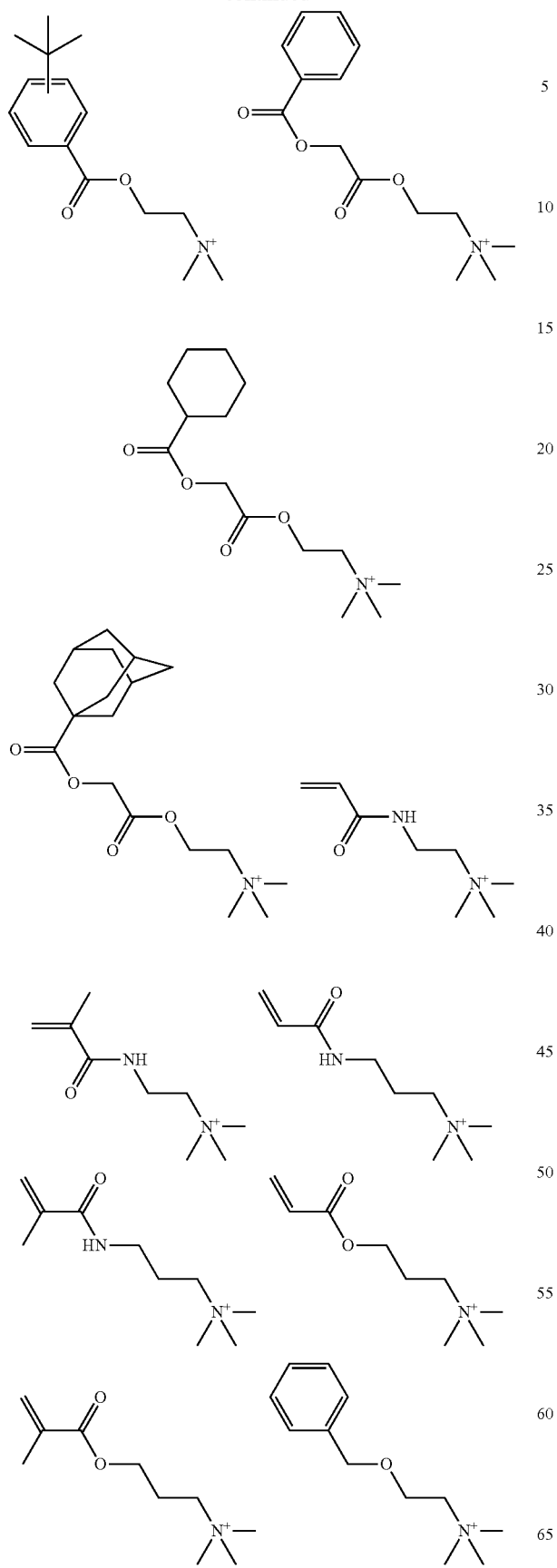
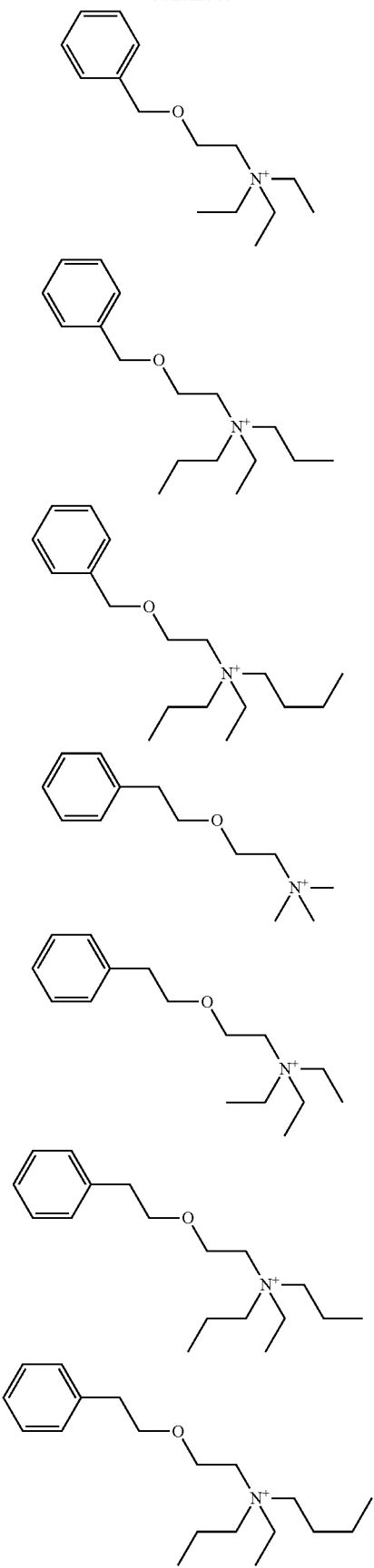

127
-continued
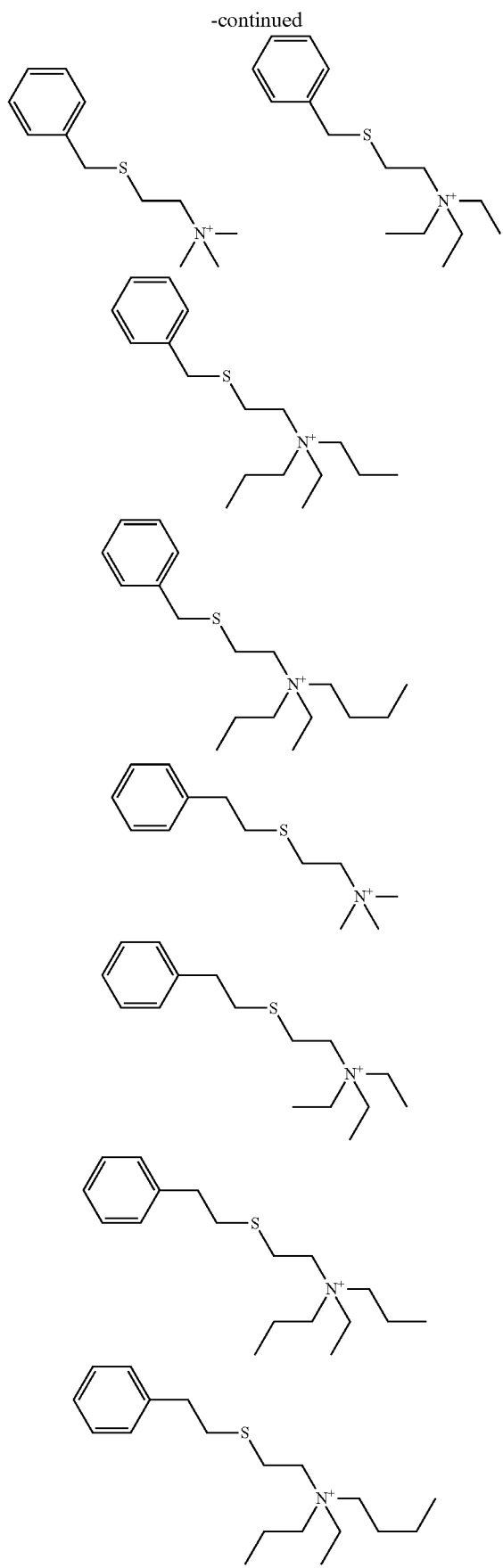
128
-continued
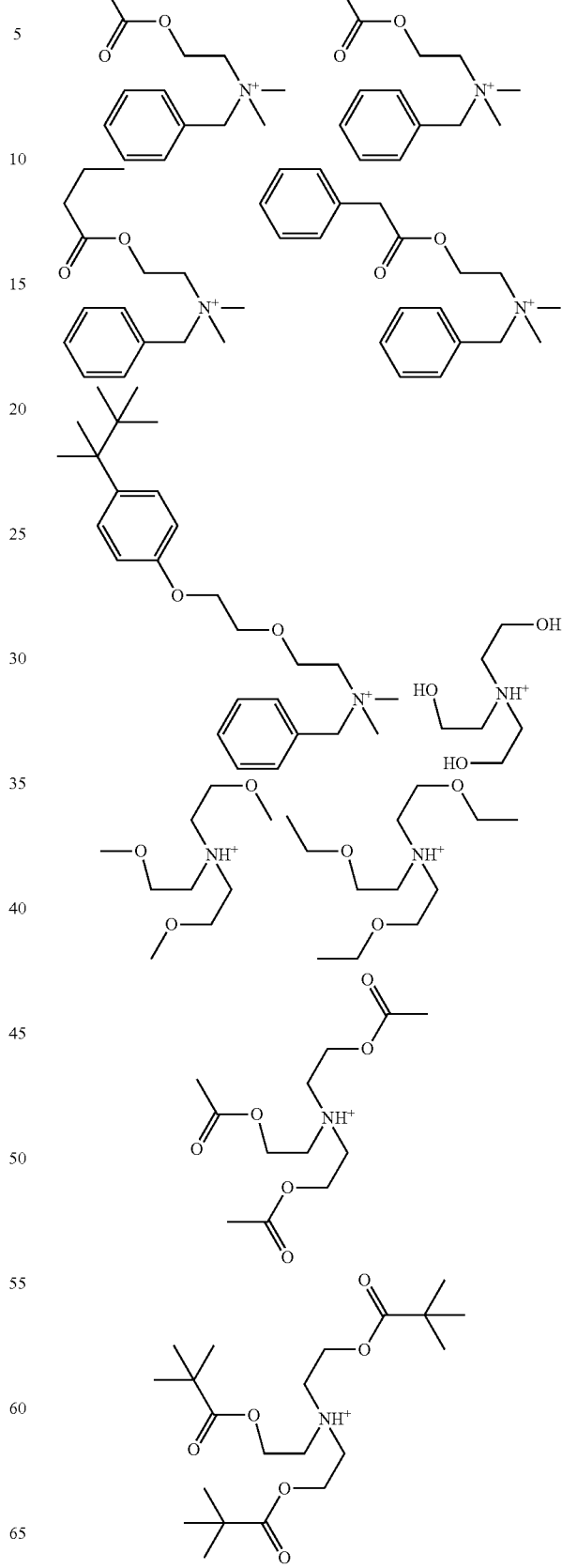

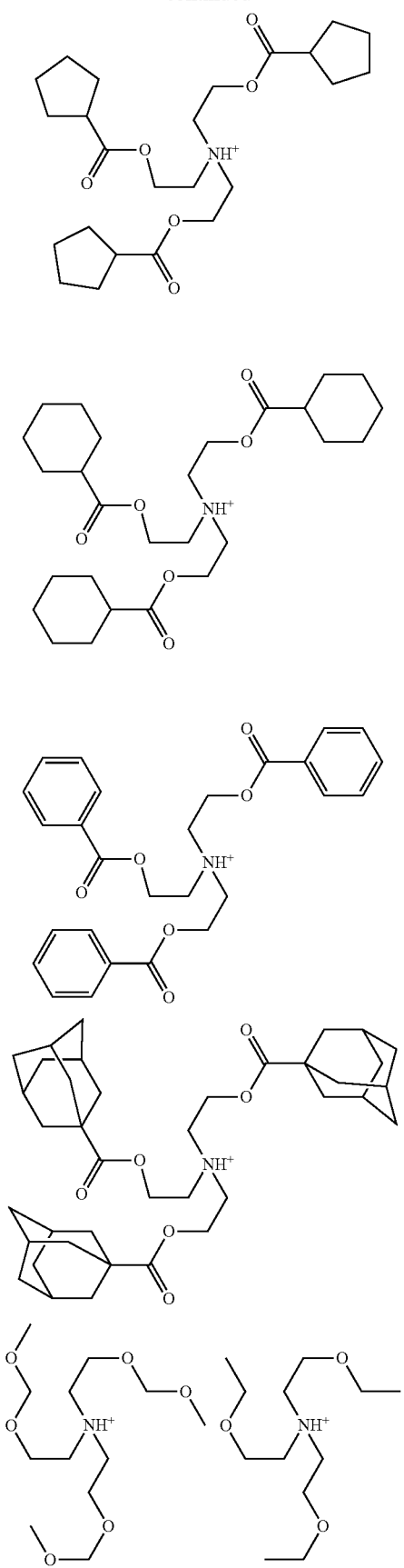
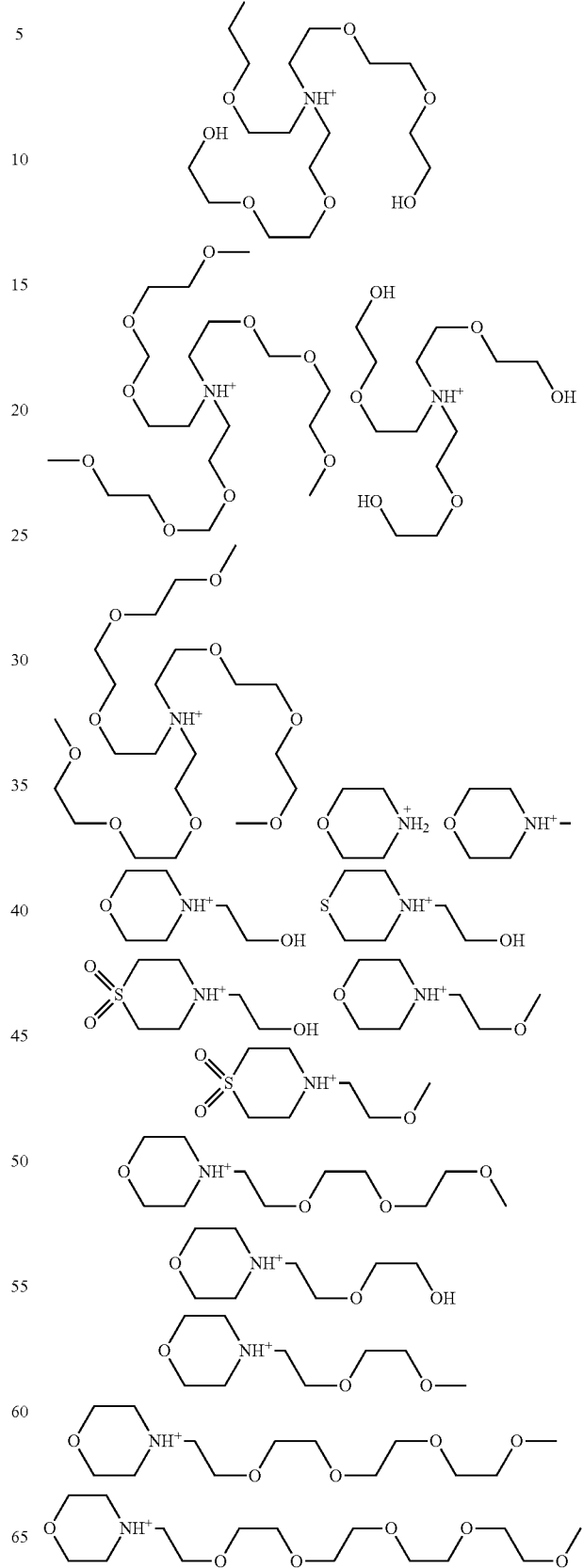

131
-continued

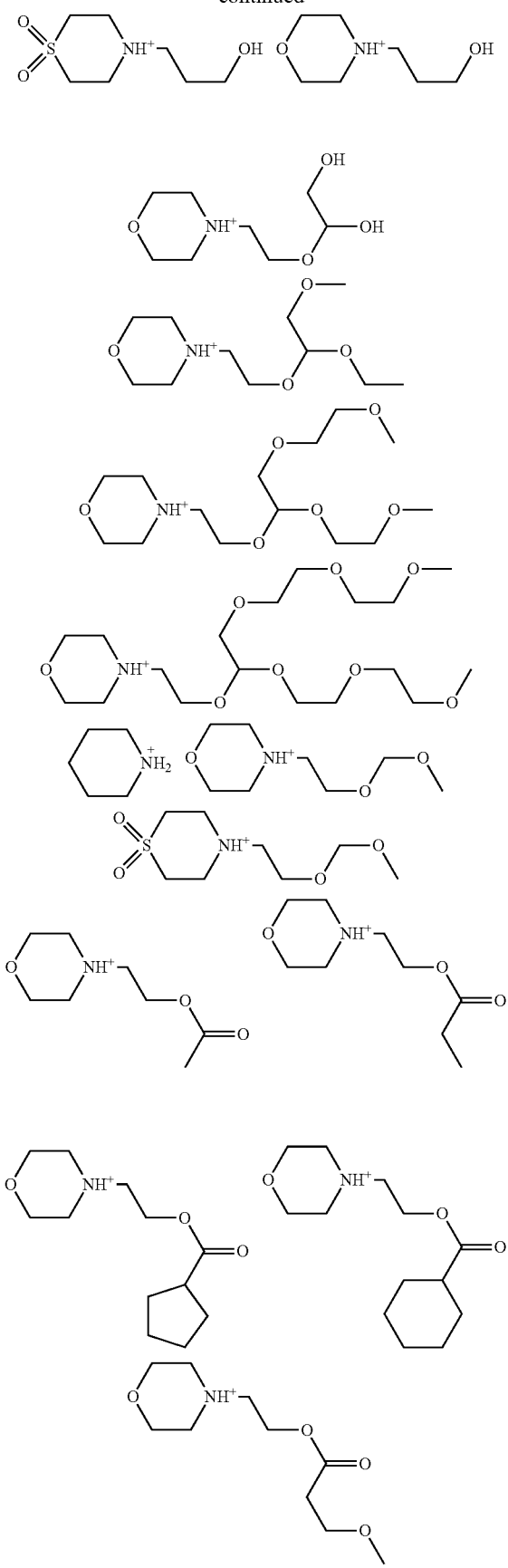

132
-continued

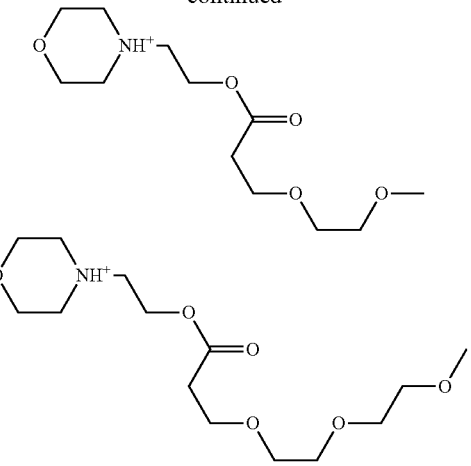

The ammonium ion shown by the general formula (3) is particularly preferably a tertiary or quaternary ammonium ion.

(Repeating Unit-b)

In addition to the repeating unit-a (e.g., the repeating units-a1 to -a7), the inventive ionic polymer material (ion polymer) essentially contains a repeating unit-b having a side chain with a radical-polymerizable double bond in a structure selected from the group consisting of (meth)acrylate, vinyl ether, and styrene. The repeating unit-b can be shown by the following general formula (4), for example.

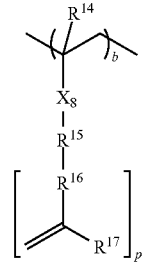

(4)

In the formula, $R^{14}$ and $R^{17}$ each represent a hydrogen atom or a methyl group. $X_8$ represents any of a single bond, a phenylene group, a naphthylene group, an ether group, an ester group, and an amide group. $R^{15}$ represents a single bond, a linear, branched, or cyclic alkylene group having 1 to 20 carbon atoms, or an aryl group having 6 to 10 carbon atoms. The alkylene group optionally has an ether group, an ester group, a hydroxy group, an alkoxy group, an alkoxycarbonyl group, a urethane group, a carbonate group, or an amino group. $R^{16}$ represents an ether group, an ester group, or a phenylene group. "p" represents an integer of 1 to 3. "b" represents a number satisfying $0<b<1.0$.

The repeating unit-b can be obtained by: polymerizing a precursor monomer thereof with the monomer(s), which are to give the repeating unit-a, and another optional monomer(s); and then attaching, to a side chain of the resulting polymerization product, a radical-polymerizable double bond of a structure selected from the group consisting of (meth)acrylate, vinyl ether, and styrene.

Specific examples of the repeating unit shown by the general formula (4) include the following.

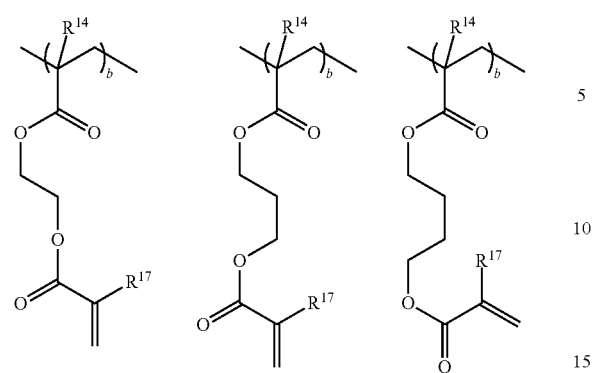
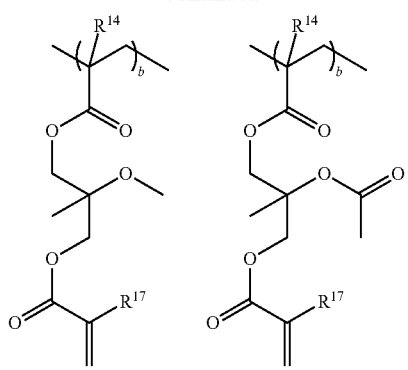
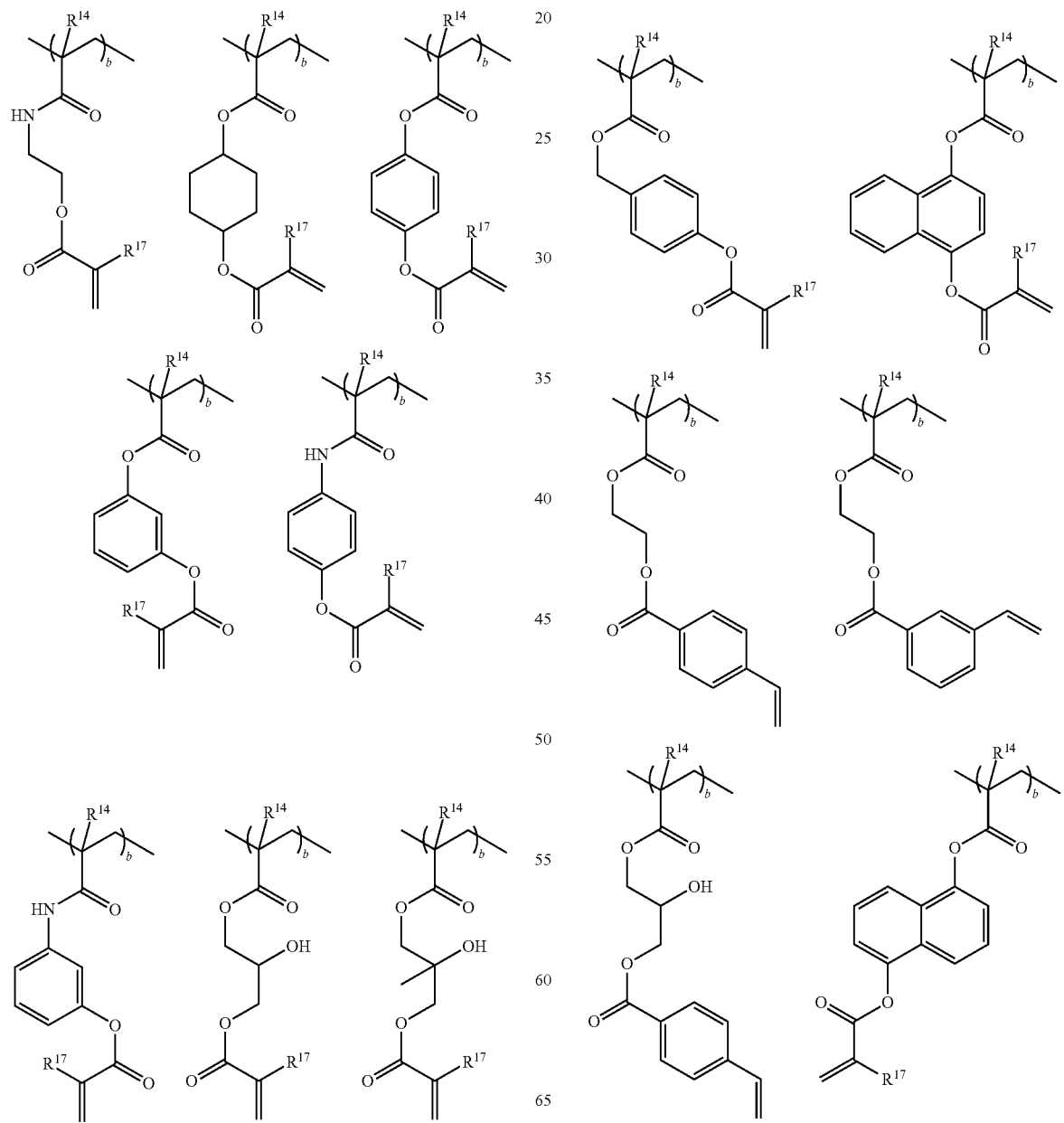

-continued
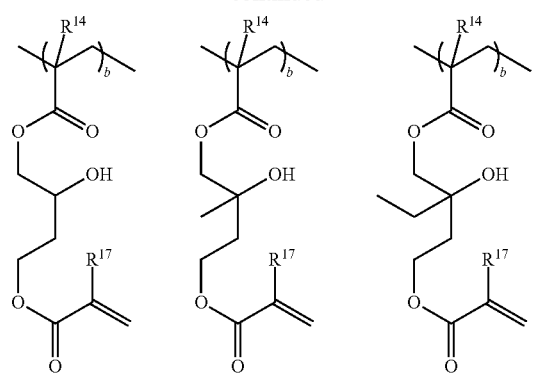
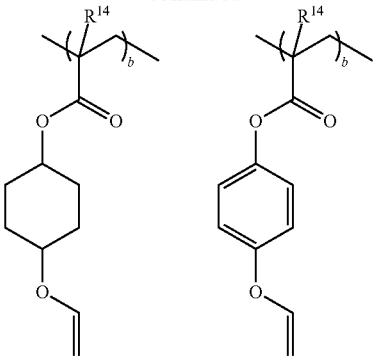
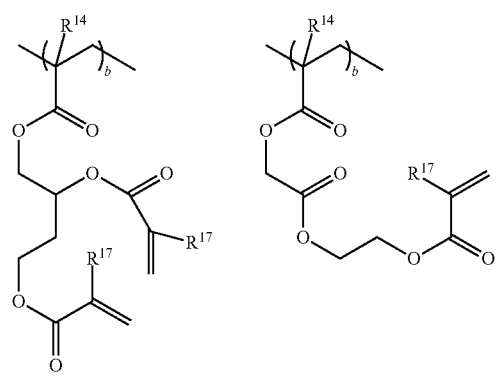
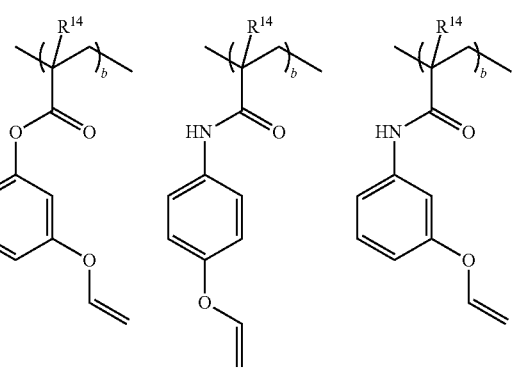
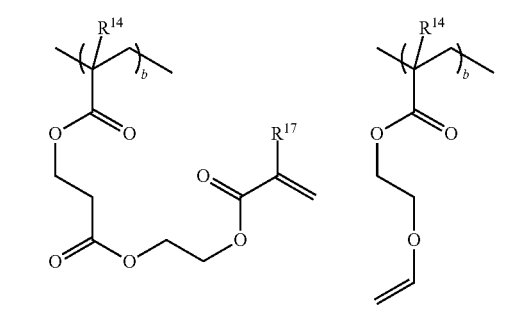
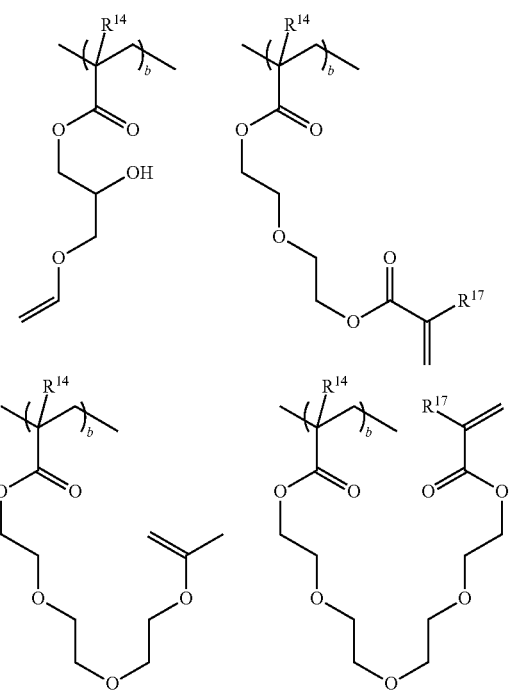

137
-continued
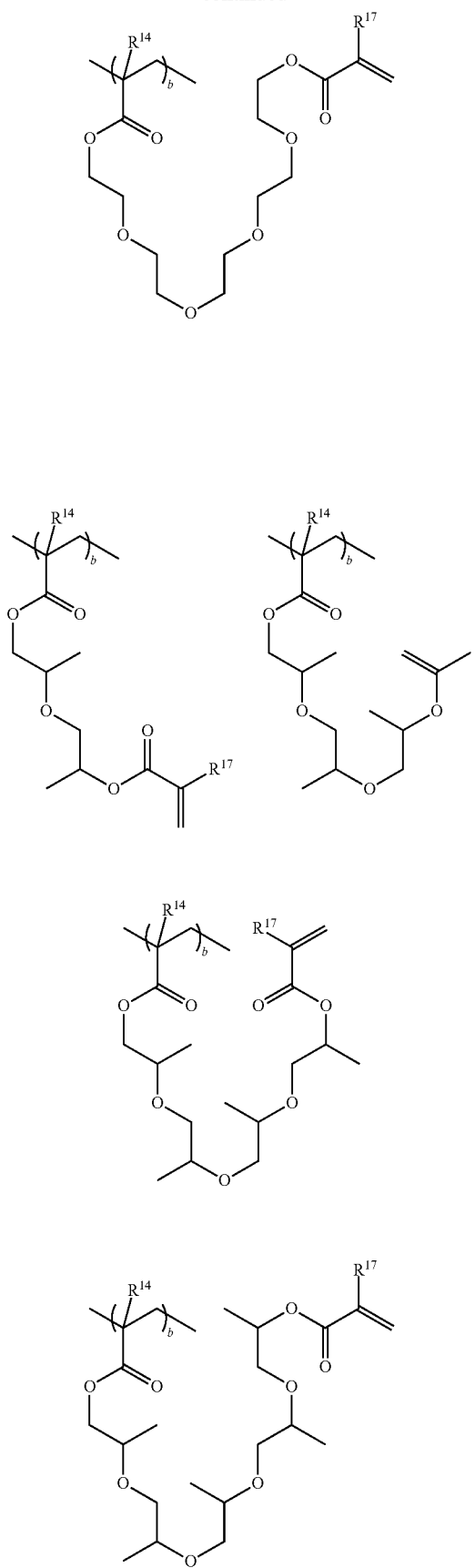
138
-continued
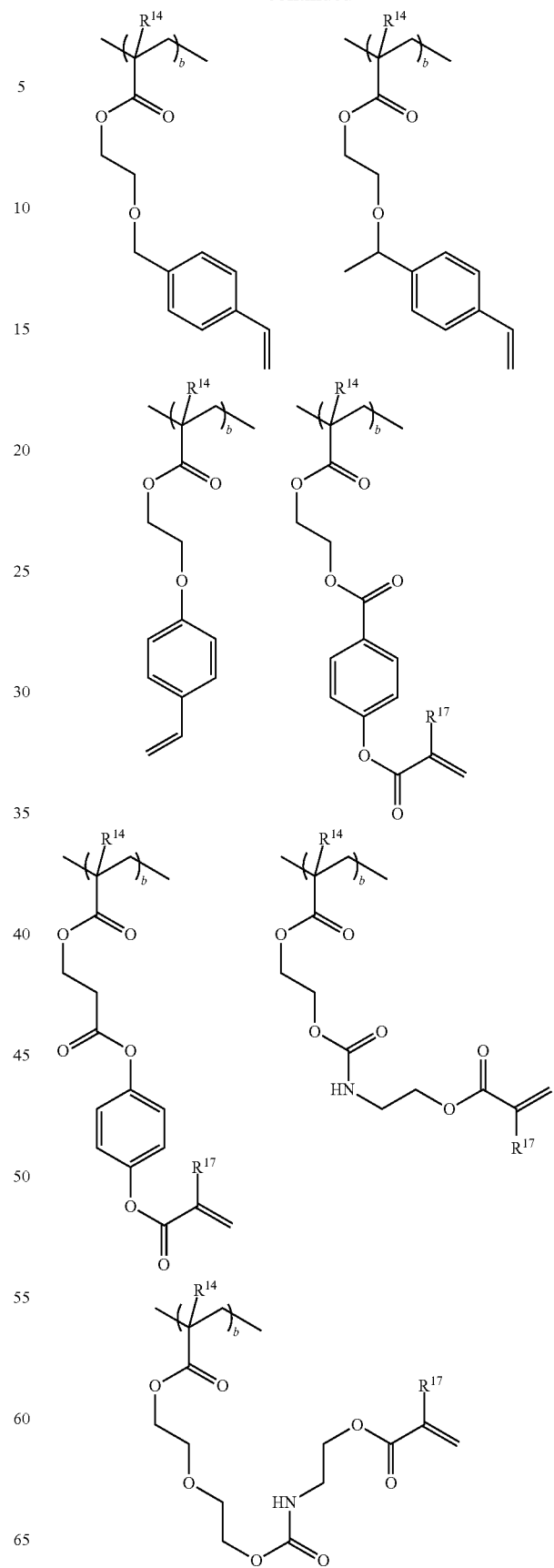

139
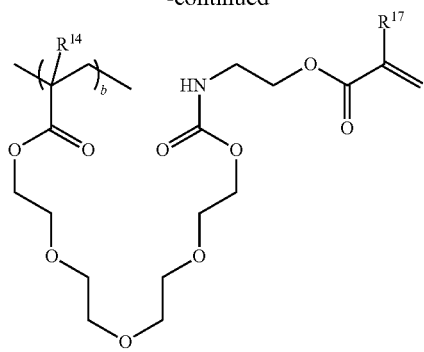
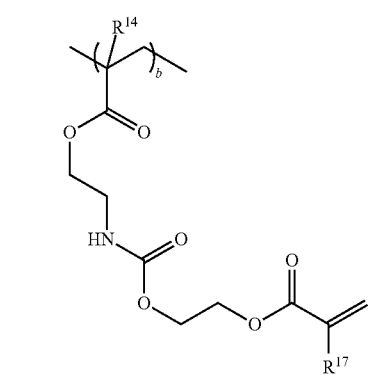
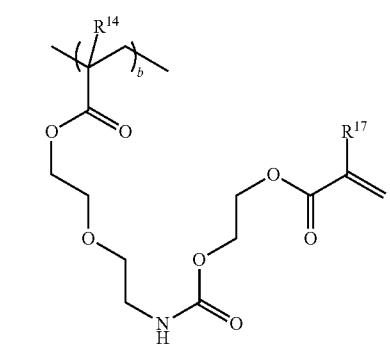
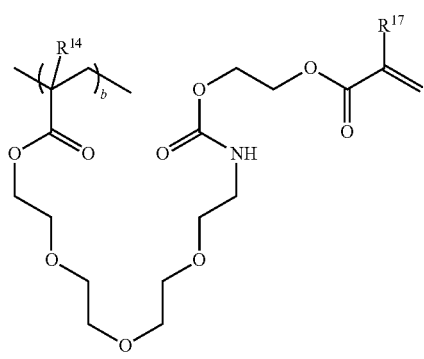
140
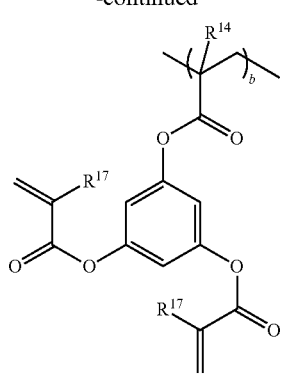
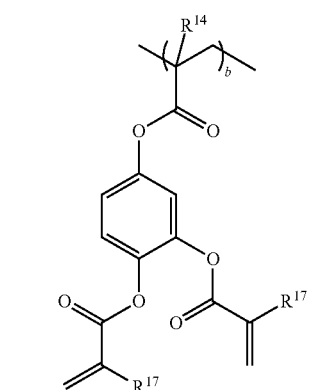
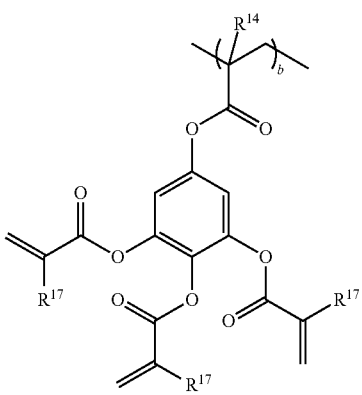
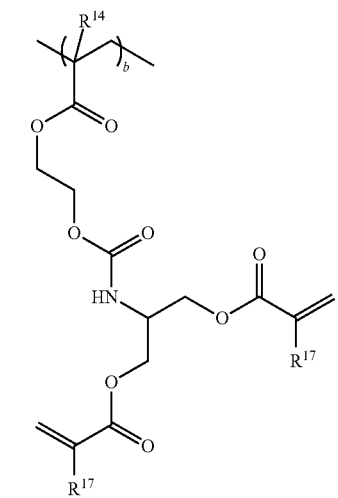

141
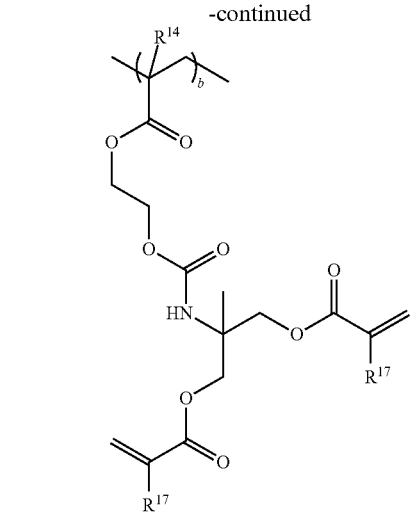
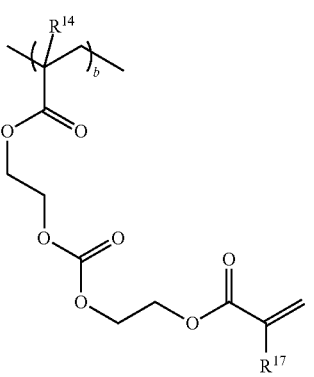
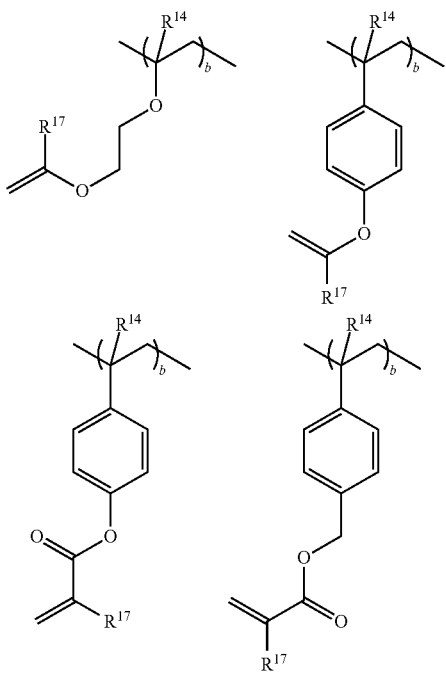
142
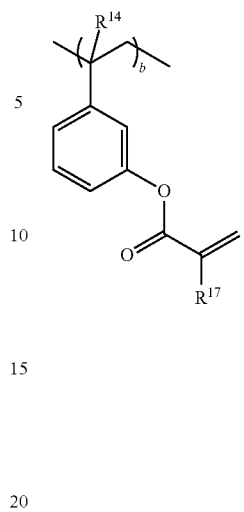
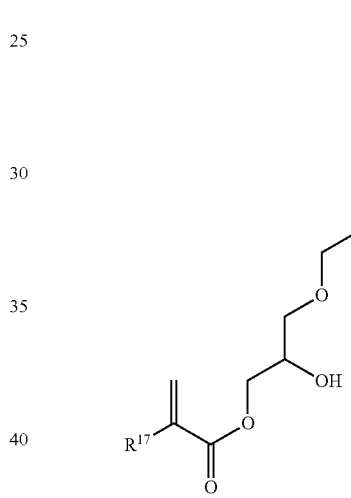
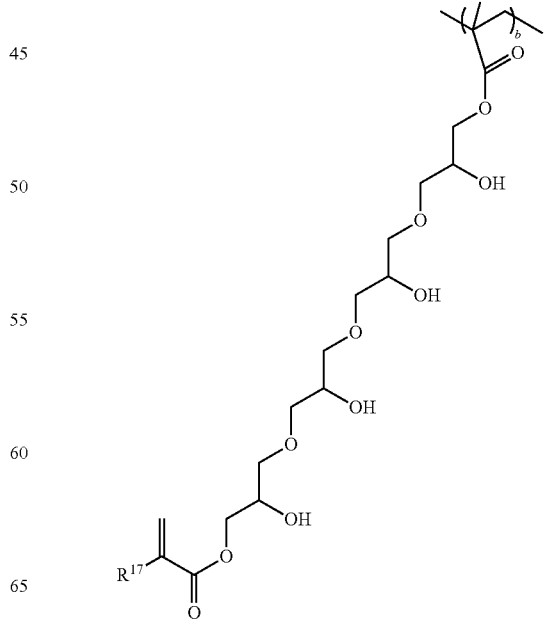

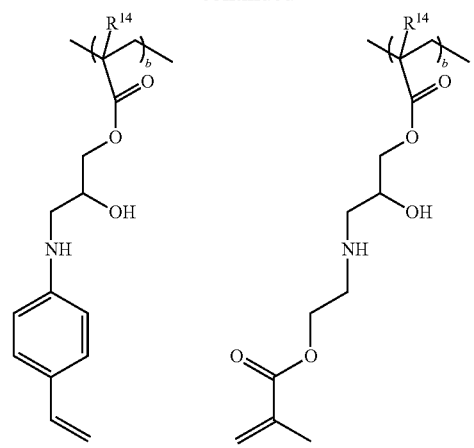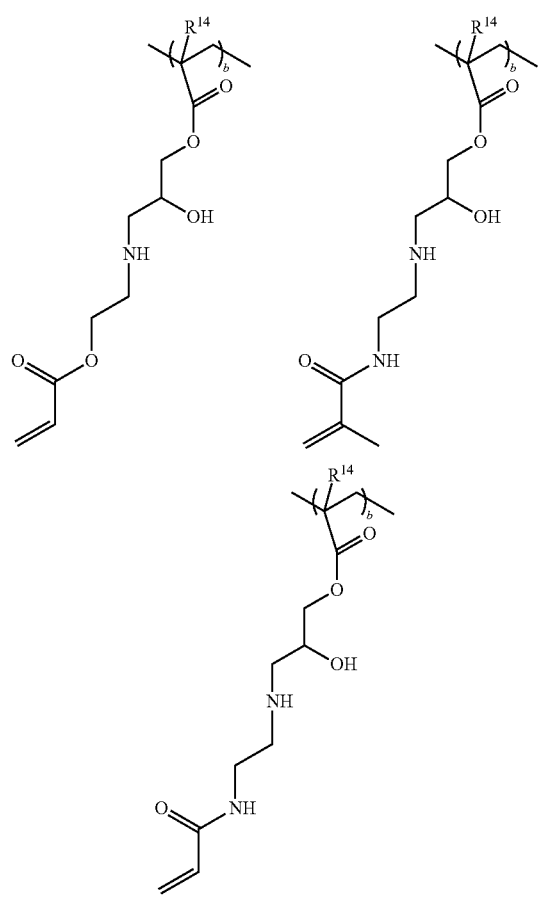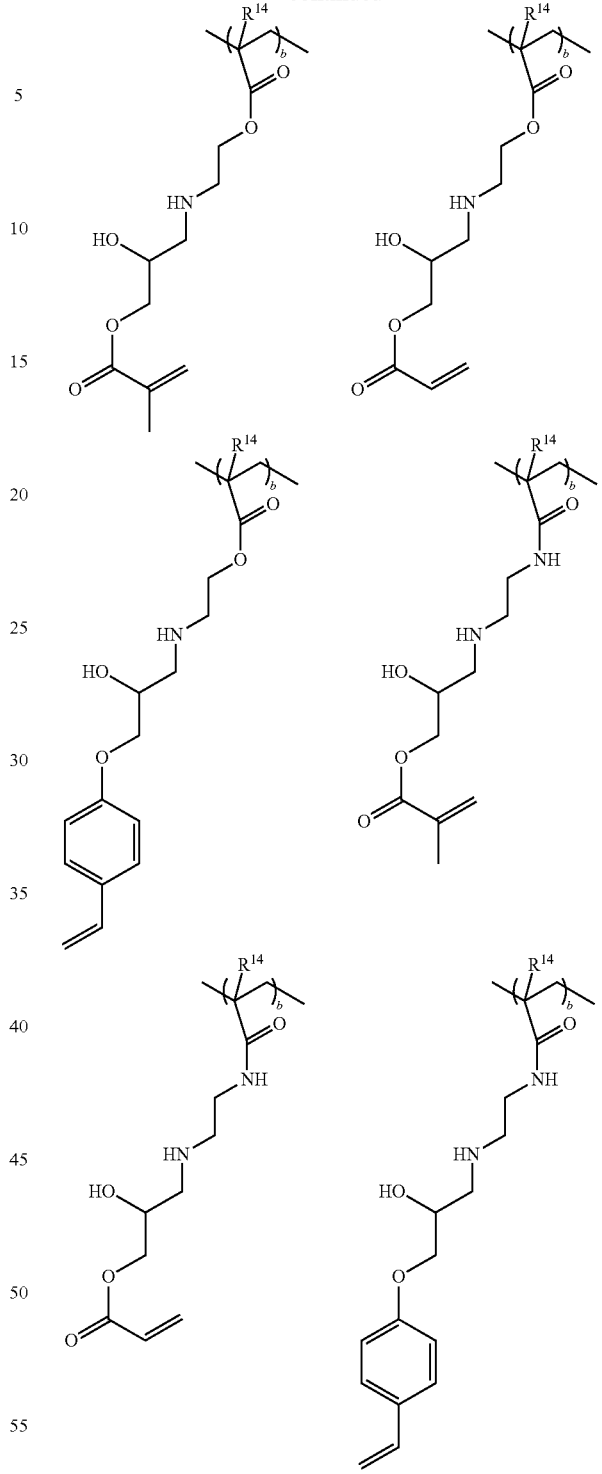

(Repeating Unit-c)

in the component (A) of the inventive bio-electrode composition, a repeating unit-c having a glyme chain can also be copolymerized in addition to the repeating unit-a (e.g., the repeating units-a1 to -a7) and the repeating unit-b in order to improve the electric conductivity.

Specific examples of a monomer to give the repeating unit-c having a glyme chain include the following. The copolymerization with a repeating unit having a glyme chain facilitates the movement of ions released from skin in the dry electrode film, and thus can increase the sensitivity of the dry electrode.
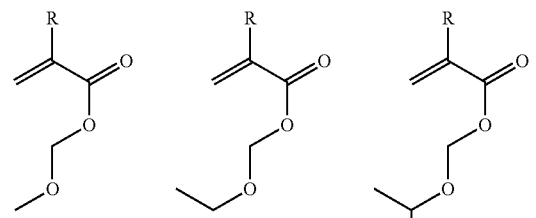
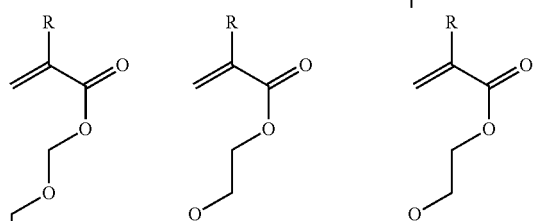
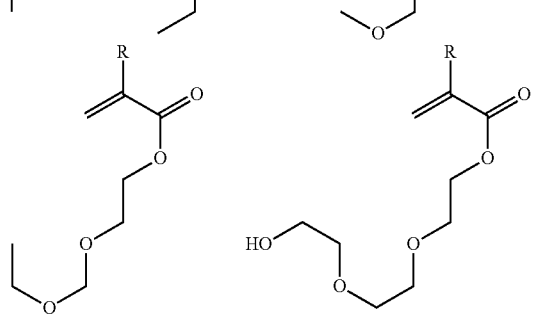
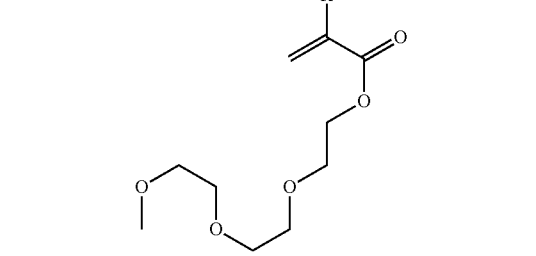
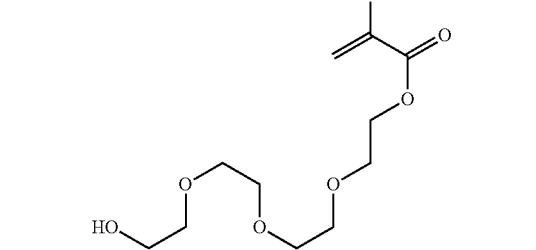
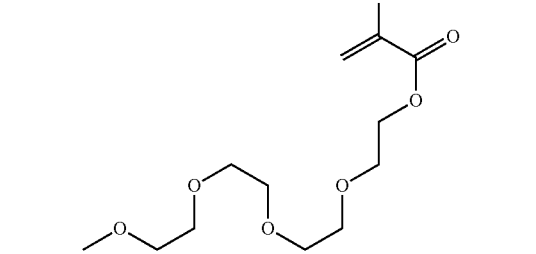
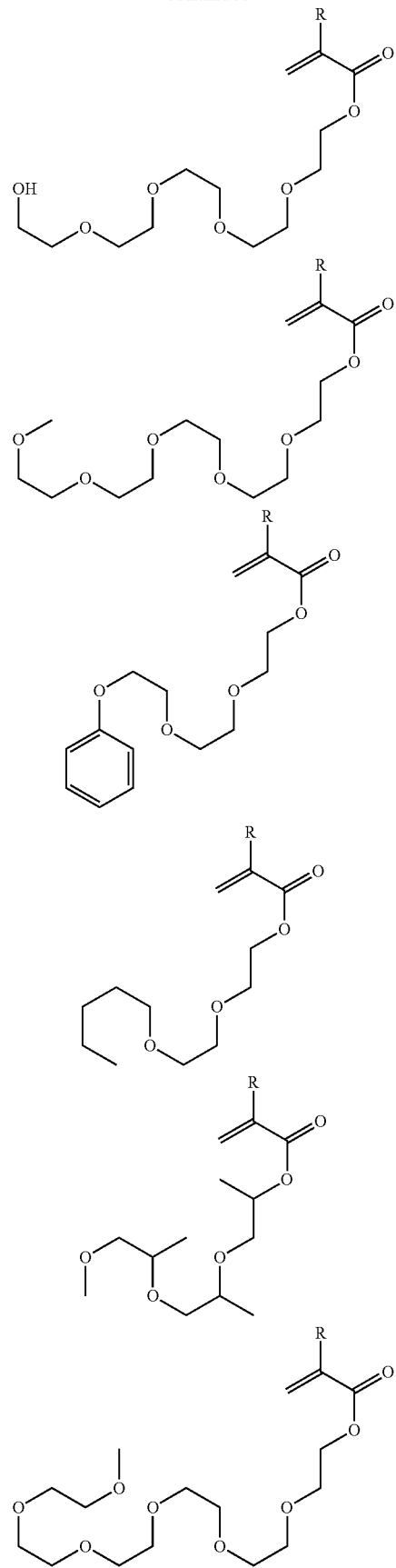

147
-continued
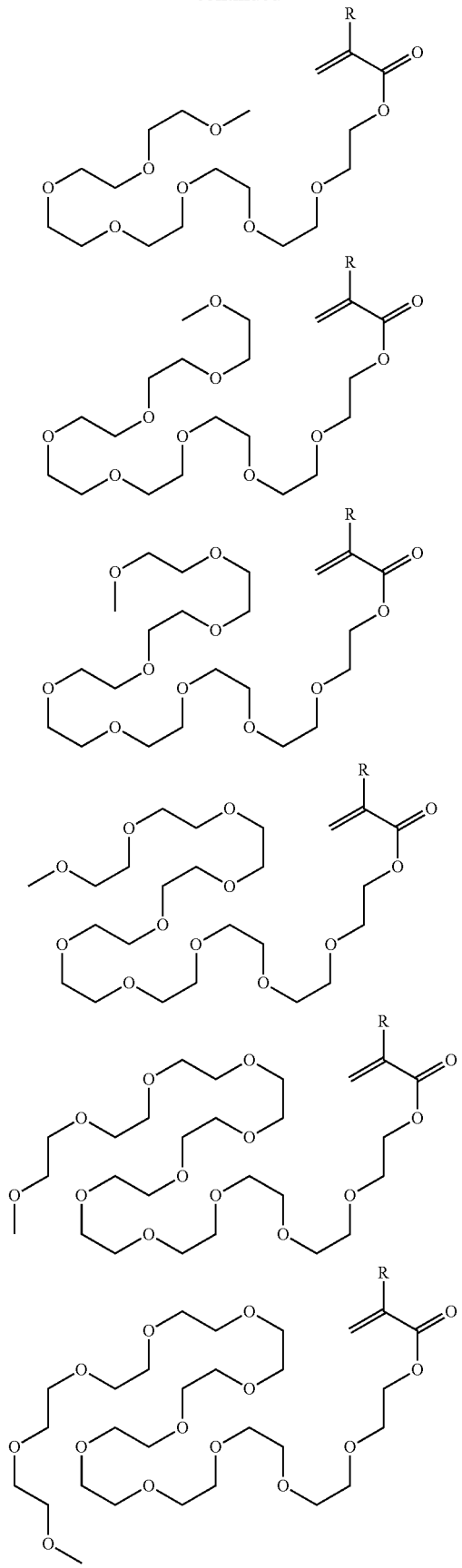
148
-continued
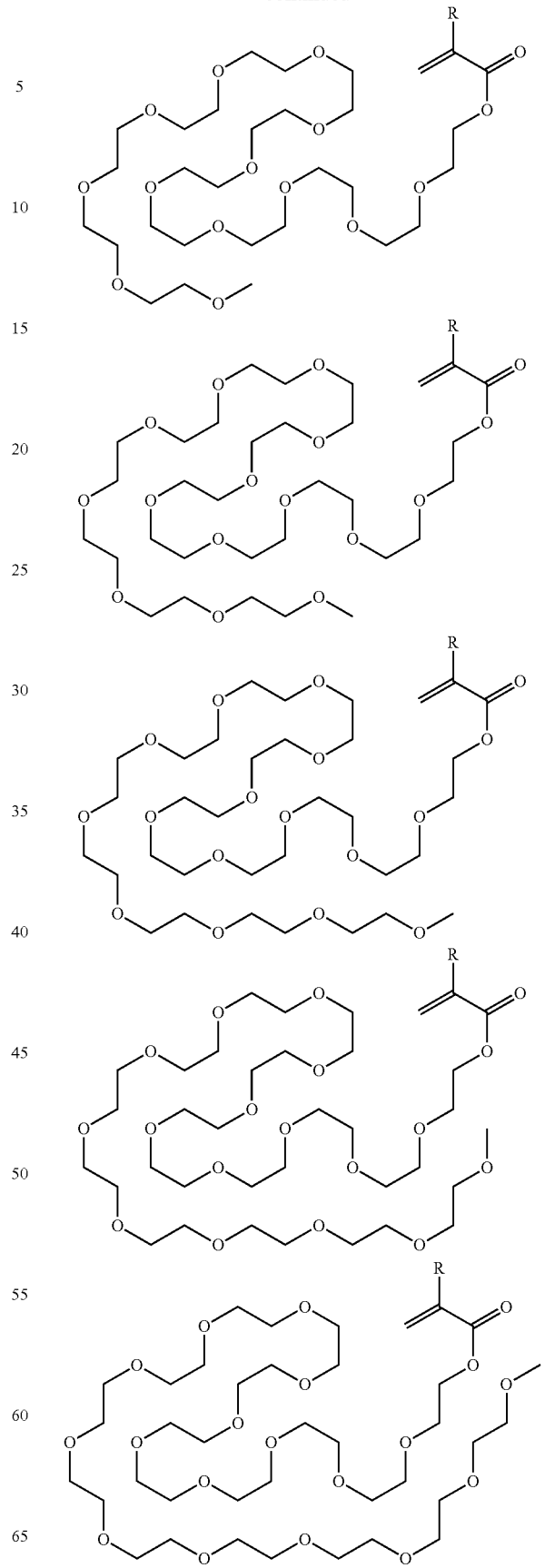

149
-continued
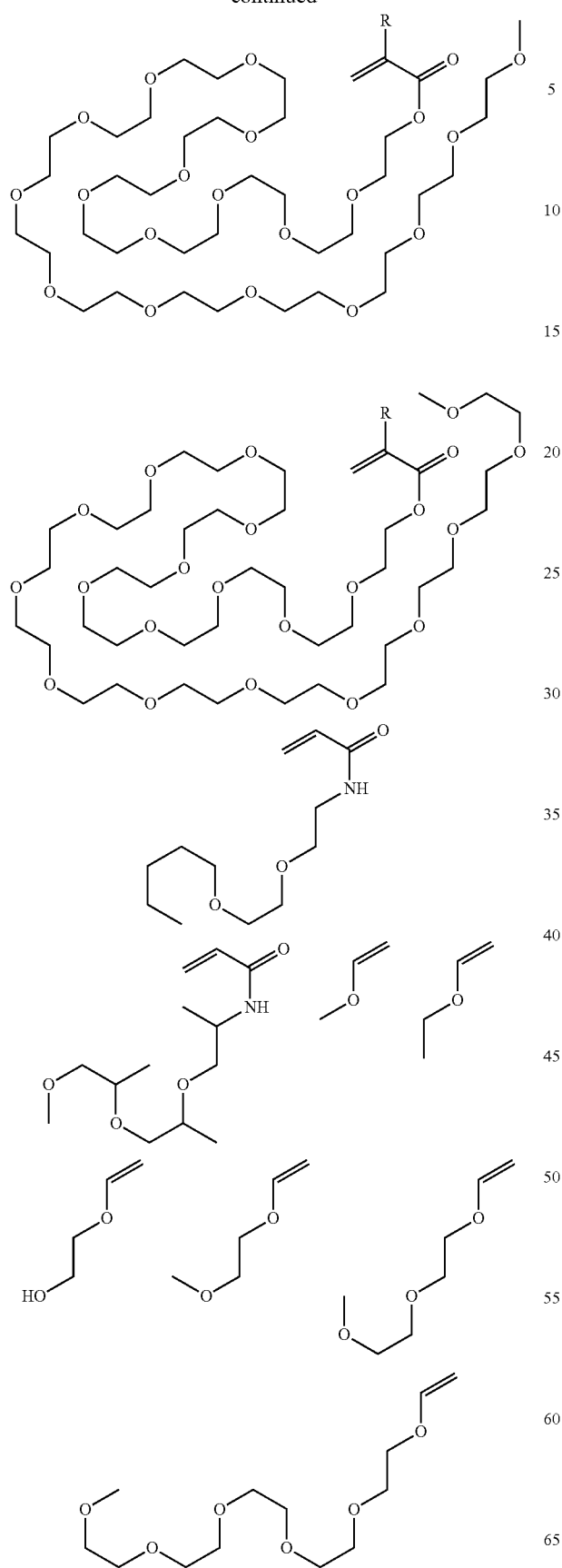
150
-continued
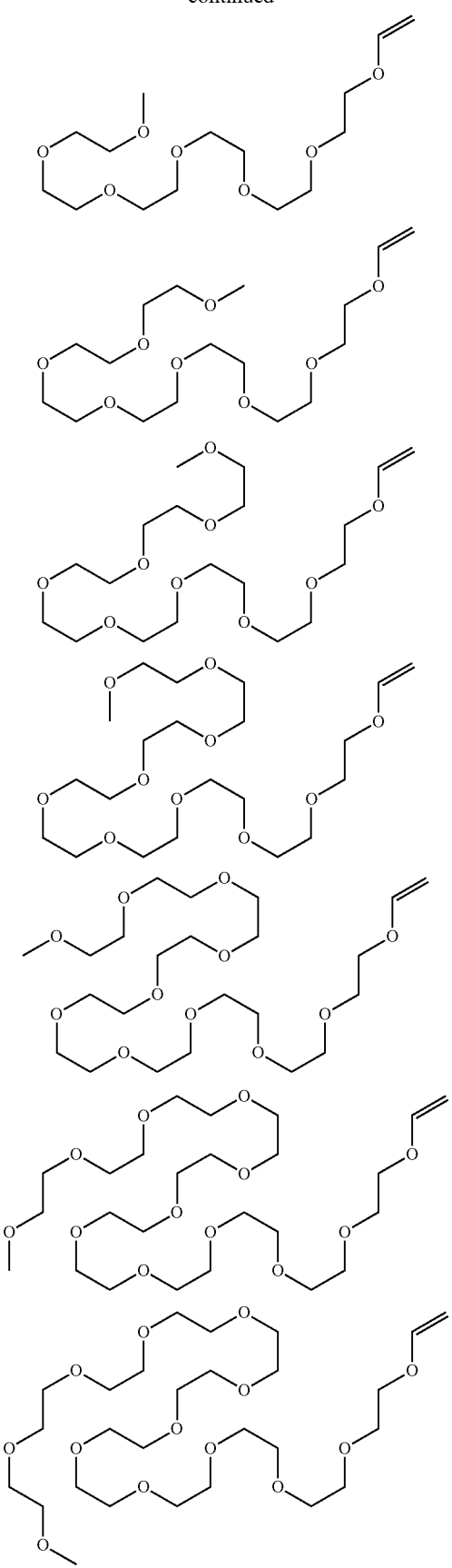

151
-continued
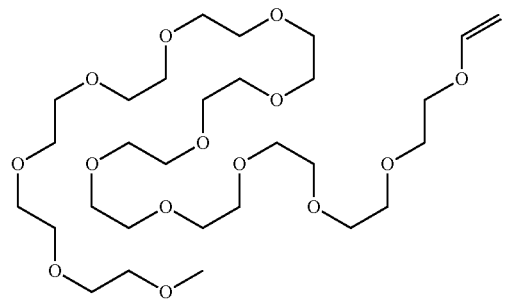
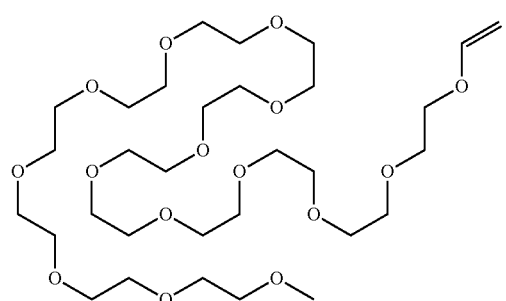
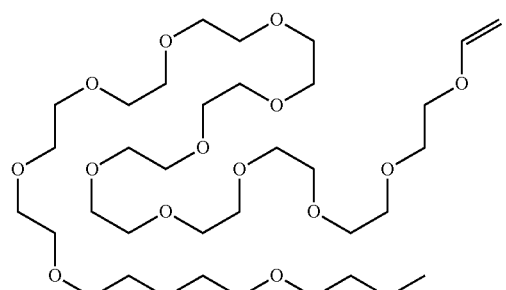
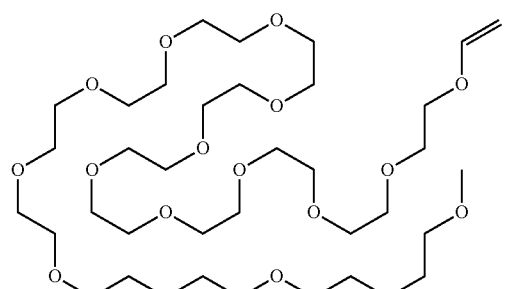
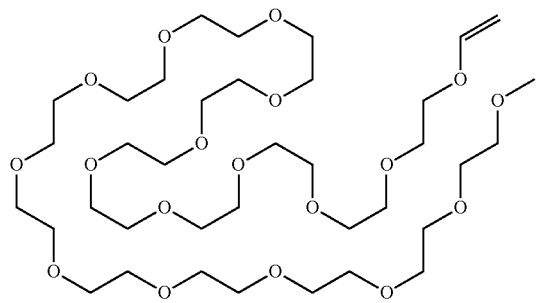
152
-continued
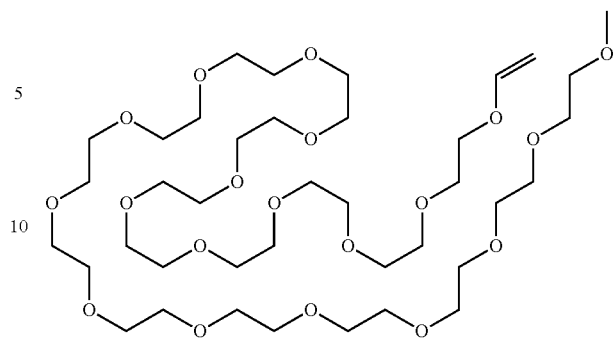
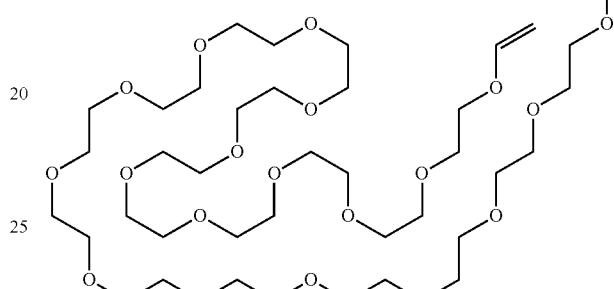
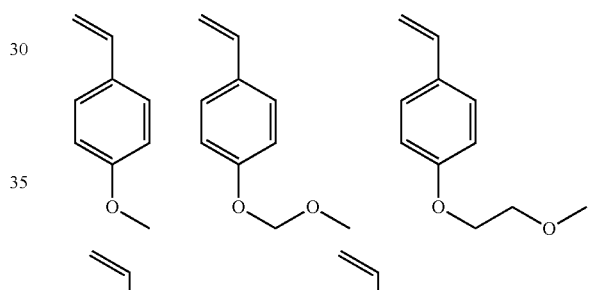
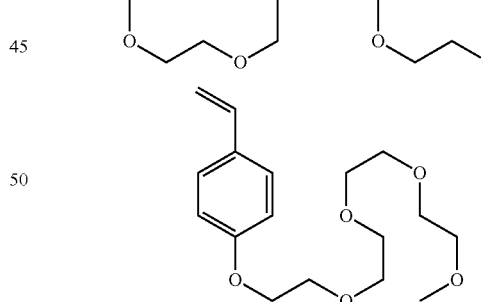
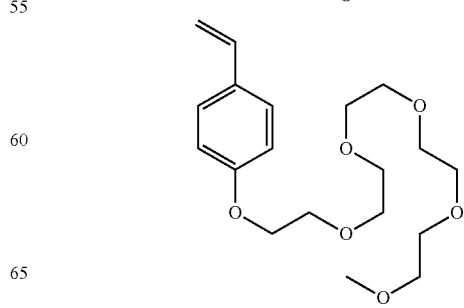

-continued

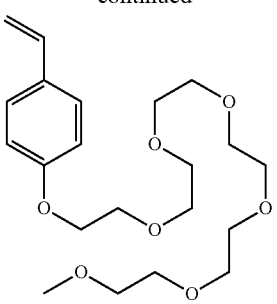
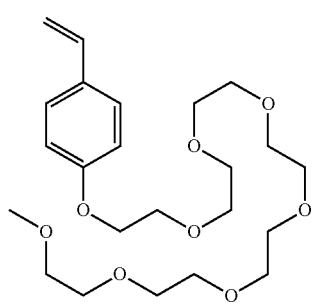
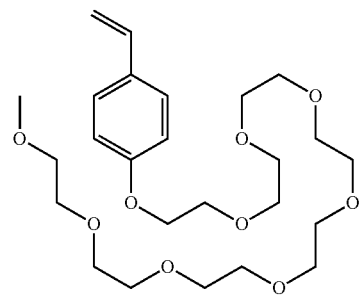
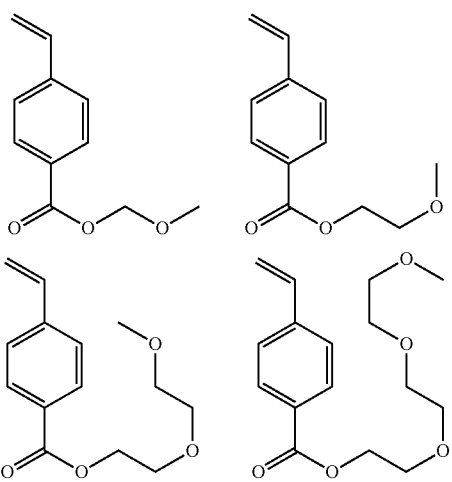
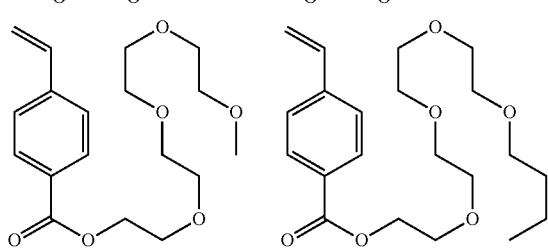

-continued

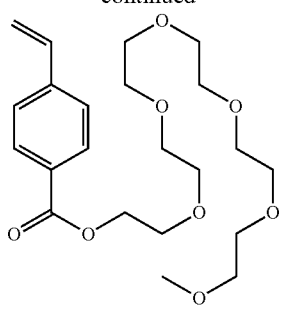
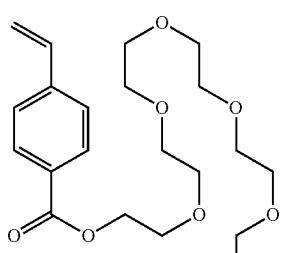
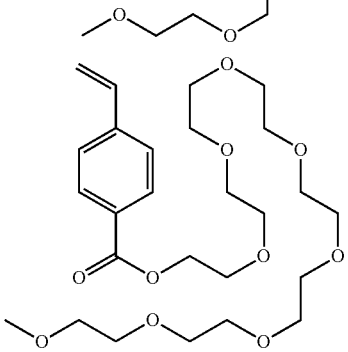

R represents a hydrogen atom or a methyl group.

(Repeating Unit-d)

In the component (A) of the inventive bio-electrode composition, a hydrophilic repeating unit-d having a hydroxy group, a carboxyl group, an ammonium salt, a betaine, an amide group, pyrrolidone, a lactone ring, a lactam ring, a sultone ring, a sodium salt of sulfonic acid or phosphoric acid, or a potassium salt of sulfonic acid can also be copolymerized with the repeating unit-a (e.g., the repeating units-a1 to -a7), the repeating unit-b, and the optional repeating unit-c, in order to improve the electric conductivity.

Specific examples of a monomer to give the hydrophilic repeating unit-d include the following. The copolymerization with repeating units containing such hydrophilic groups can increase the sensitivity of the dry electrode by increasing the sensitivity to ions released from skin.

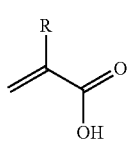
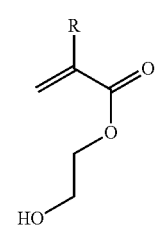
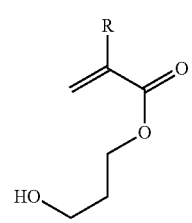

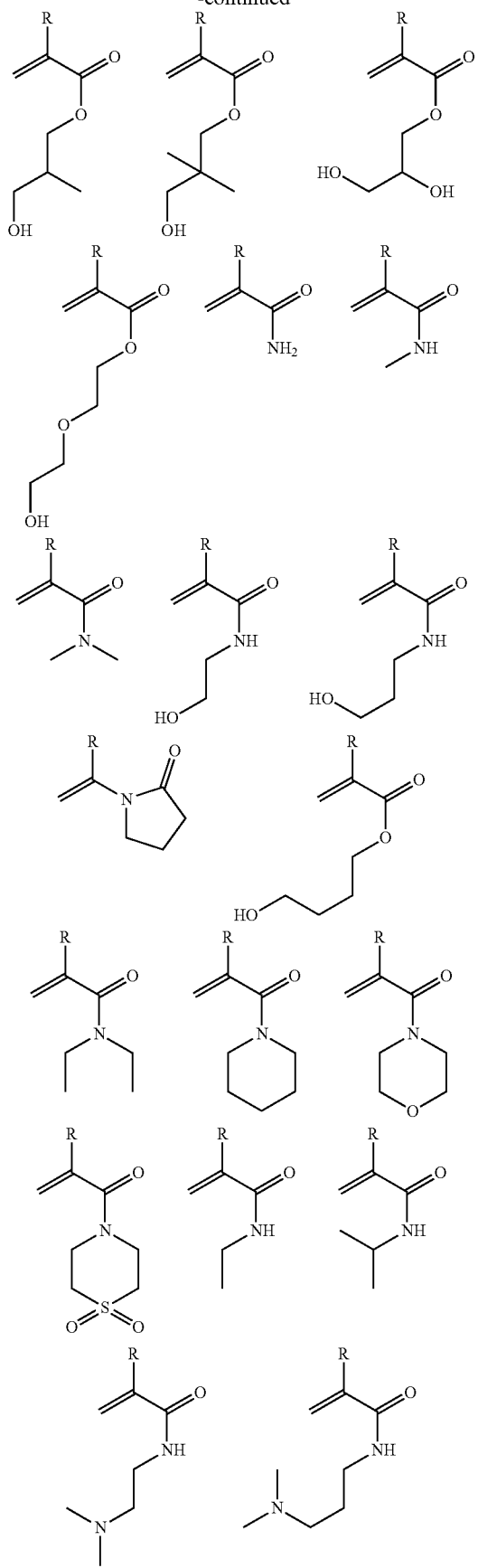
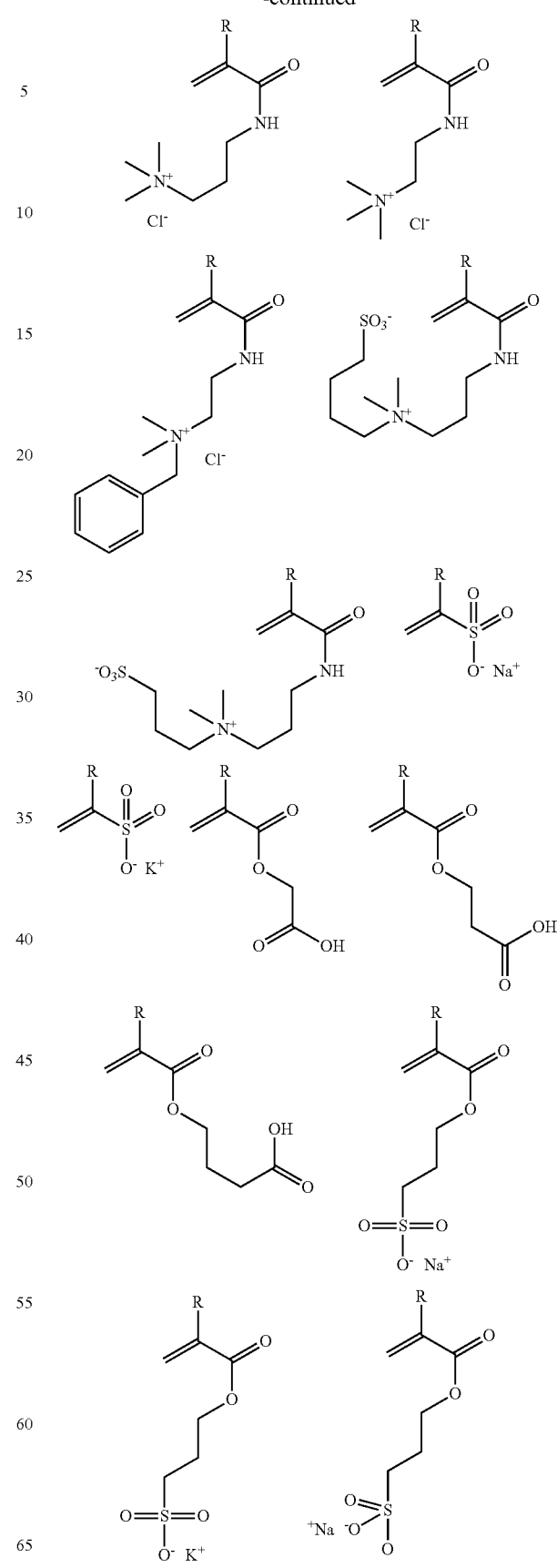

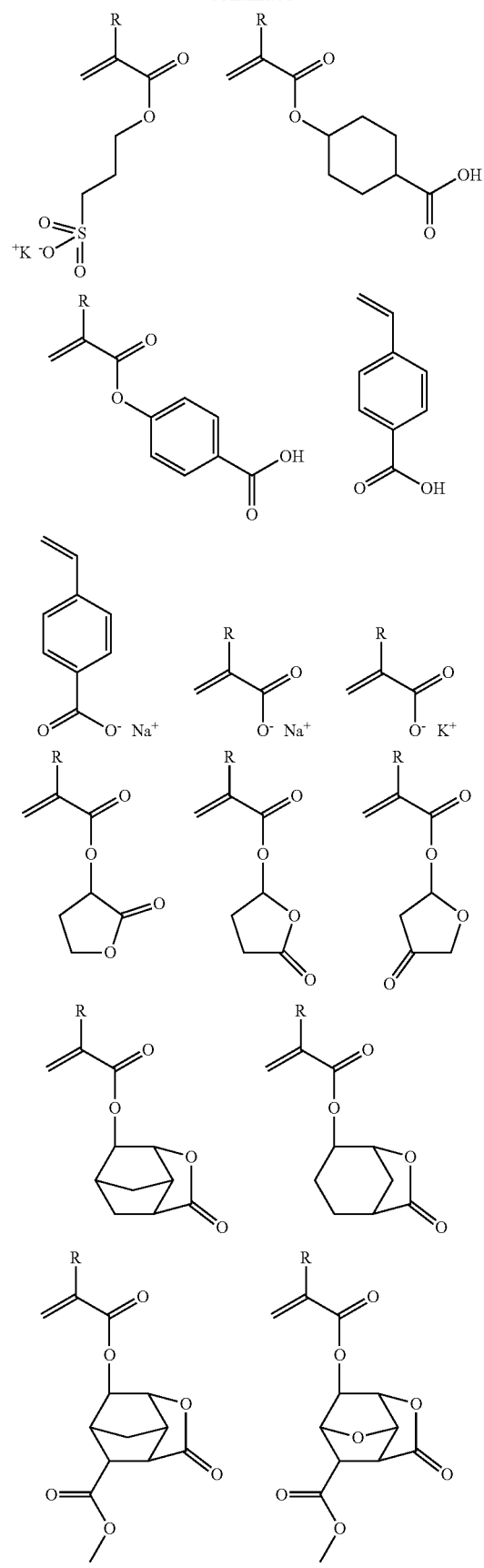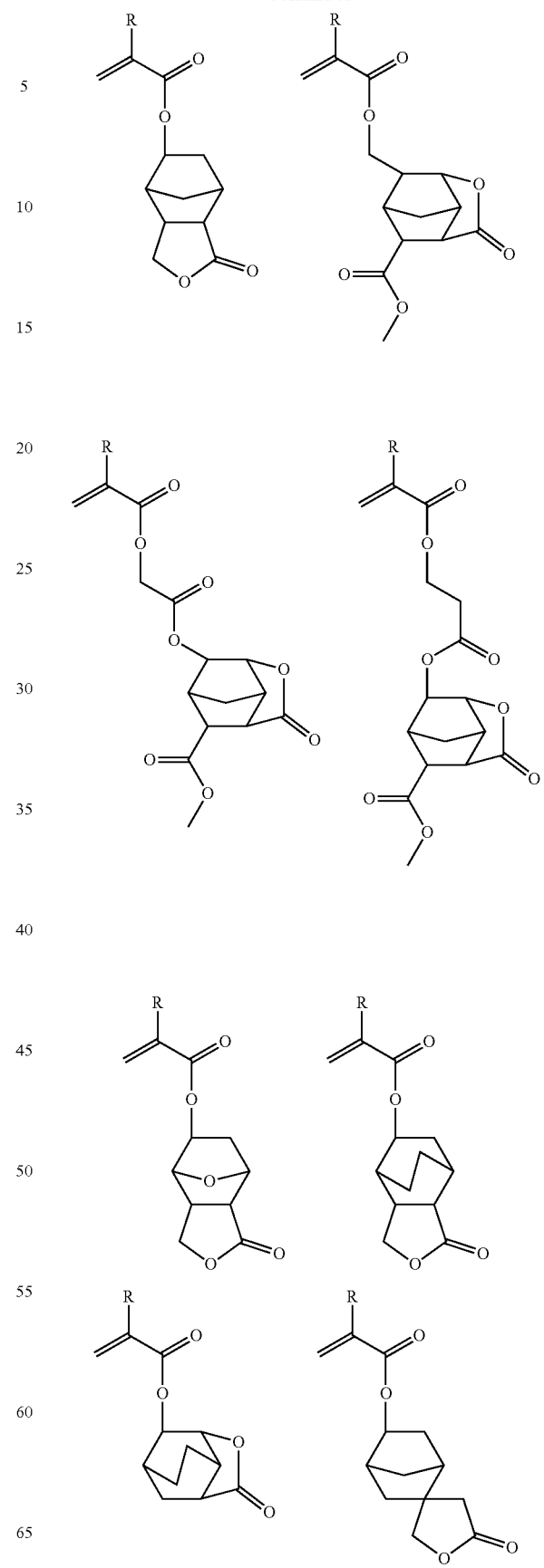

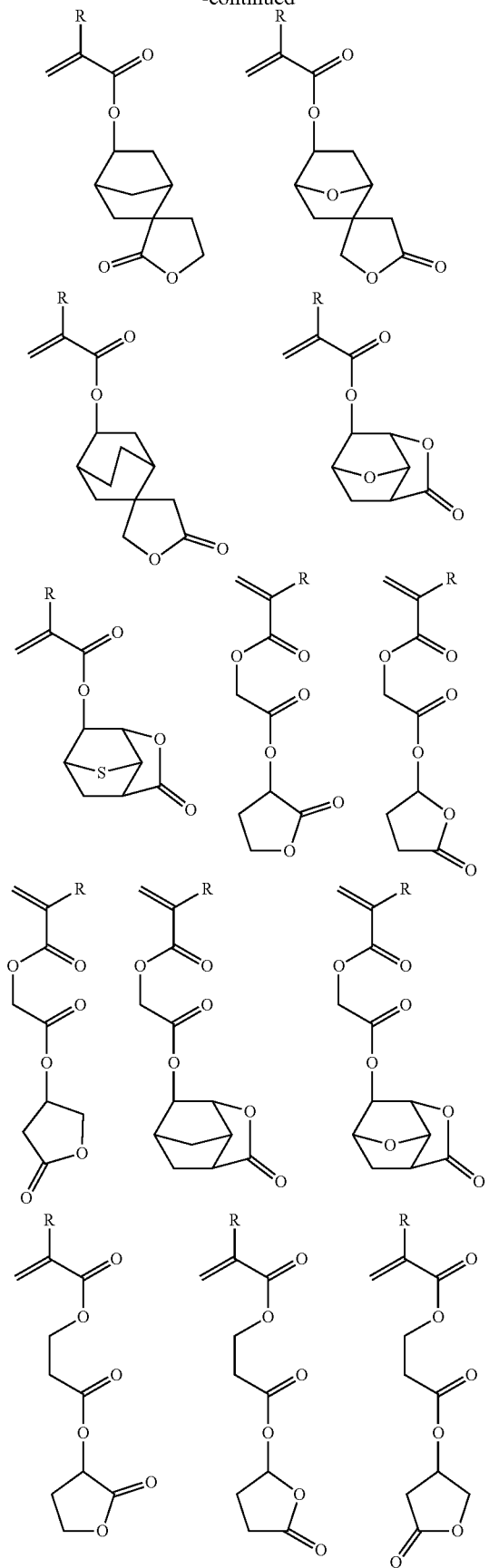
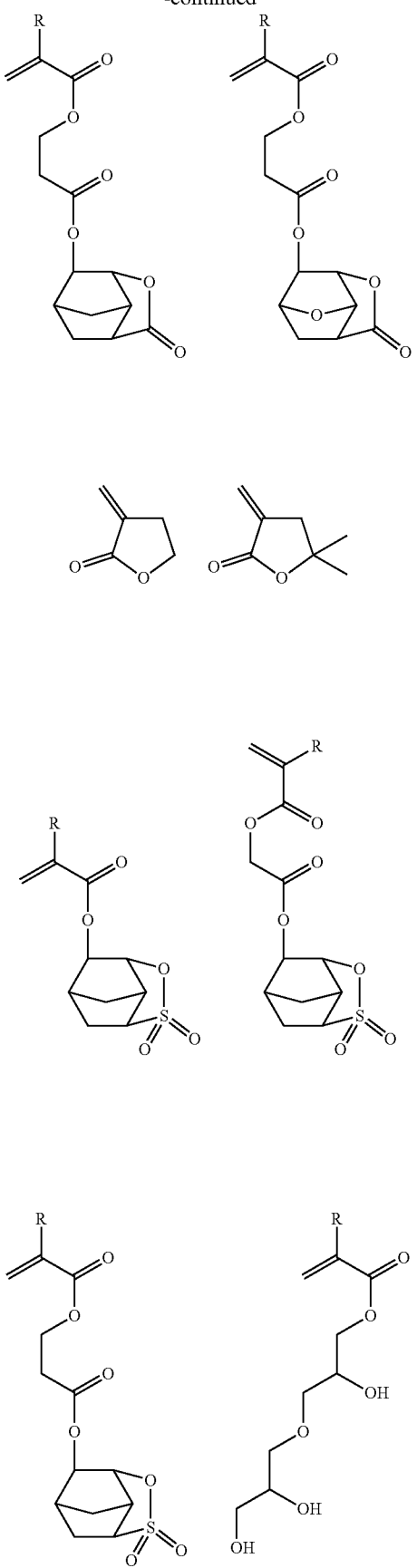

161
-continued
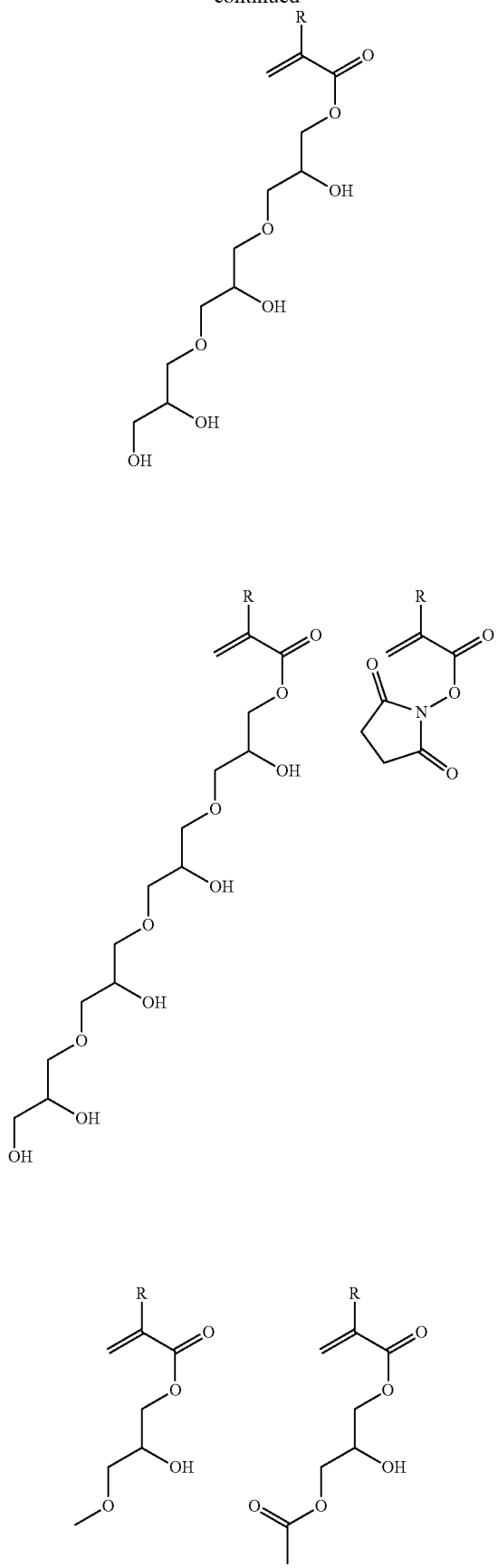
162
-continued
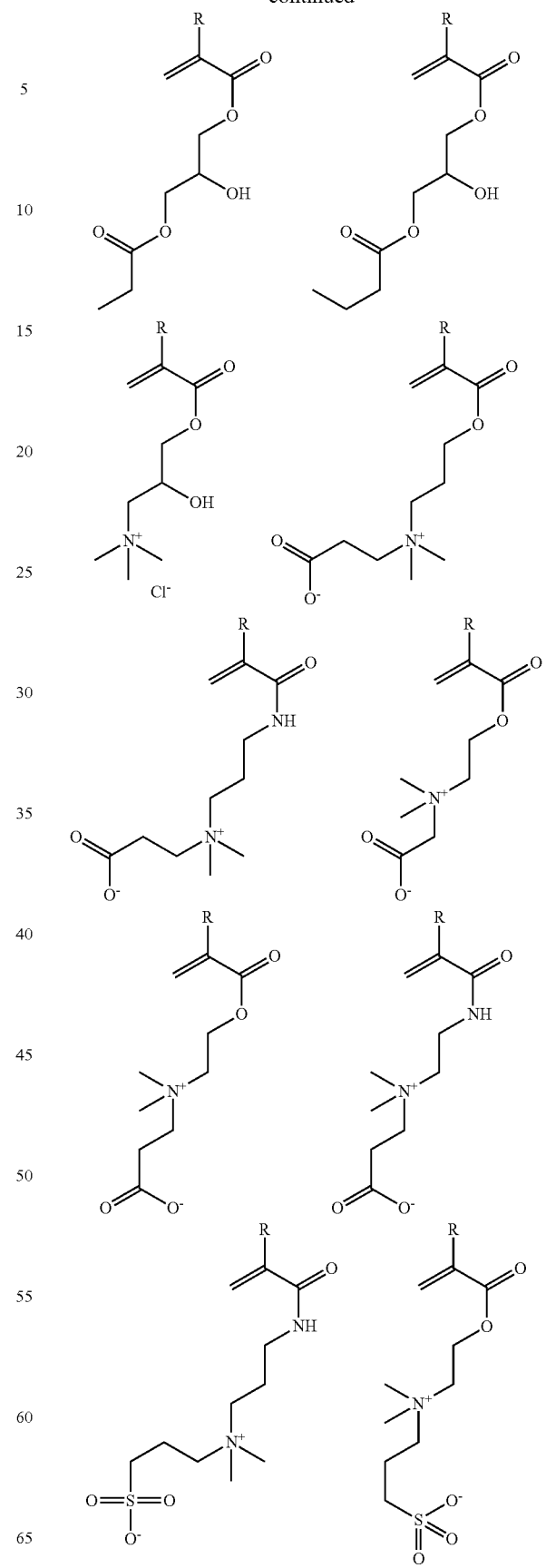

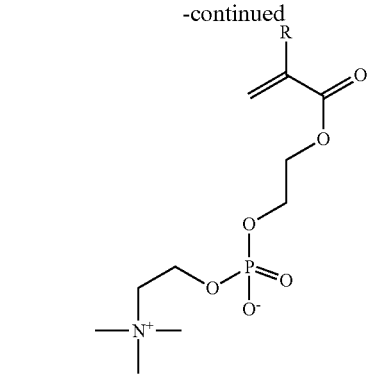
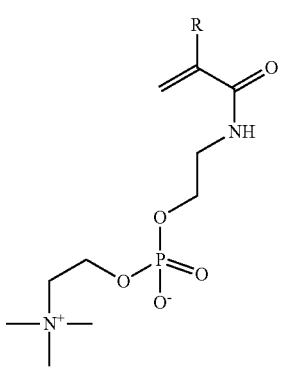
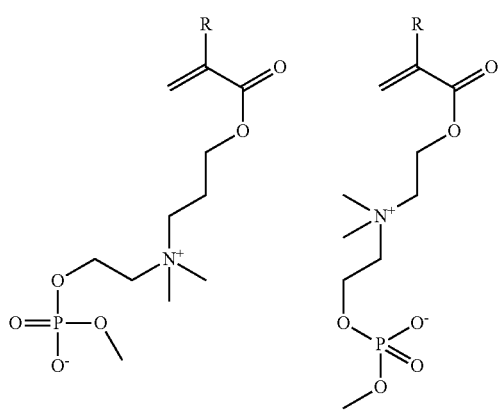
(Repeating Unit-e)
The polymer compound (A) in the inventive bio-electrode composition can contain a repeating unit-e to give adhesion properties.
Specific examples of a monomer to give the repeating unit-e include the following.
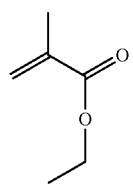
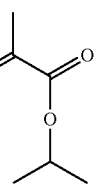
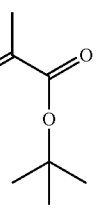
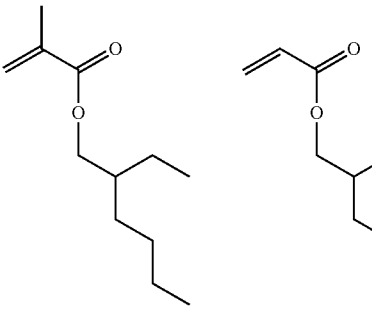
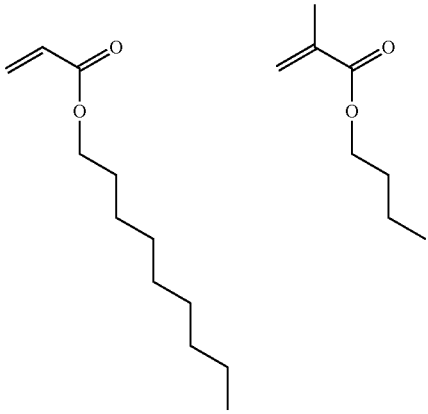
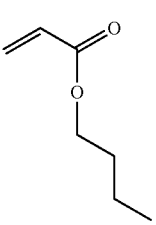
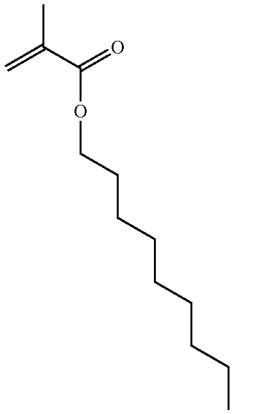
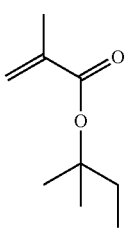
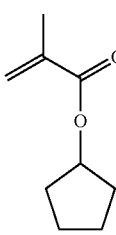
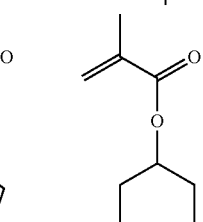
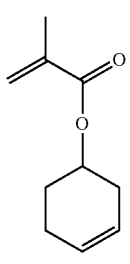
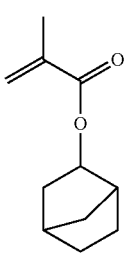
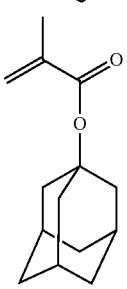

165
-continued
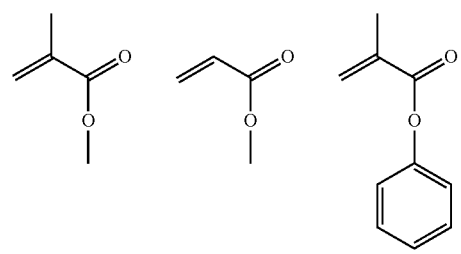
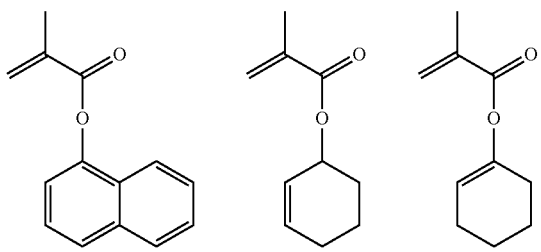
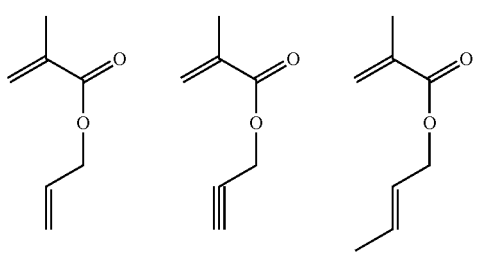
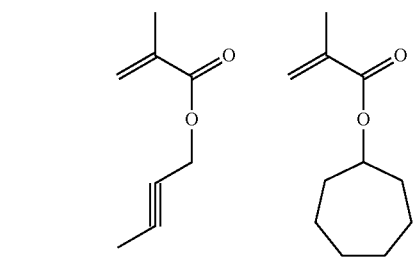
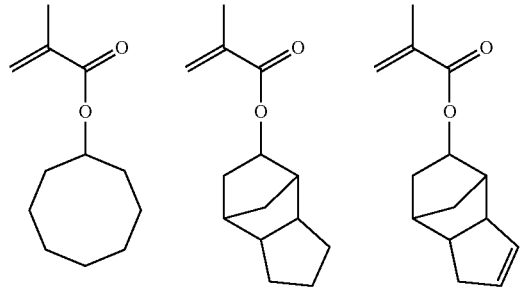
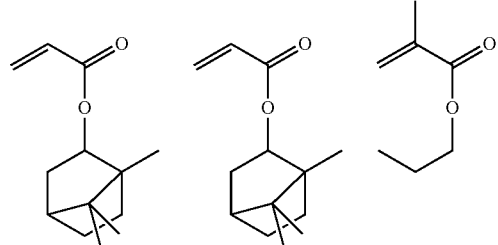
166
-continued
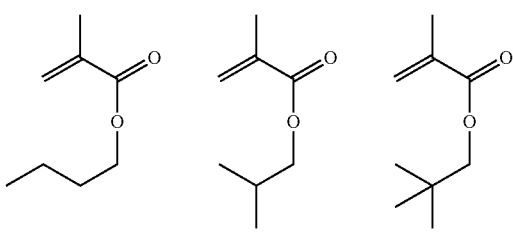
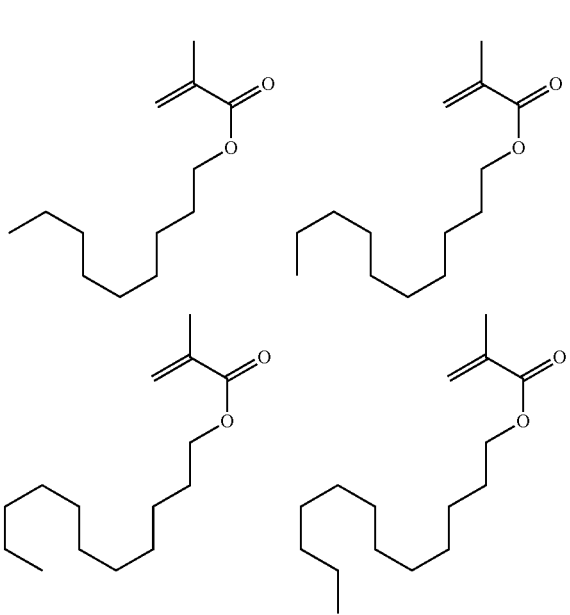
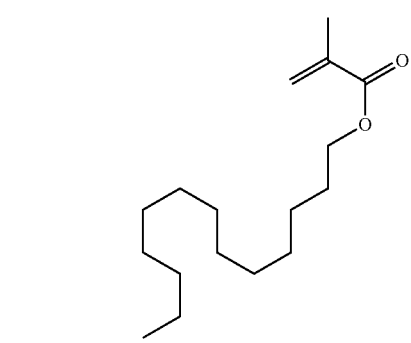
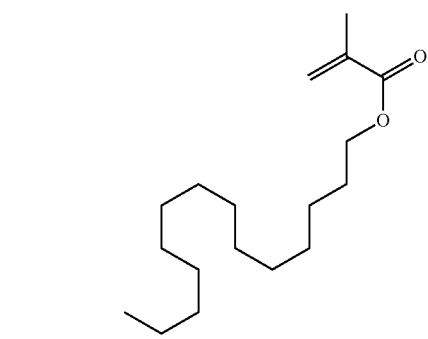

167
-continued
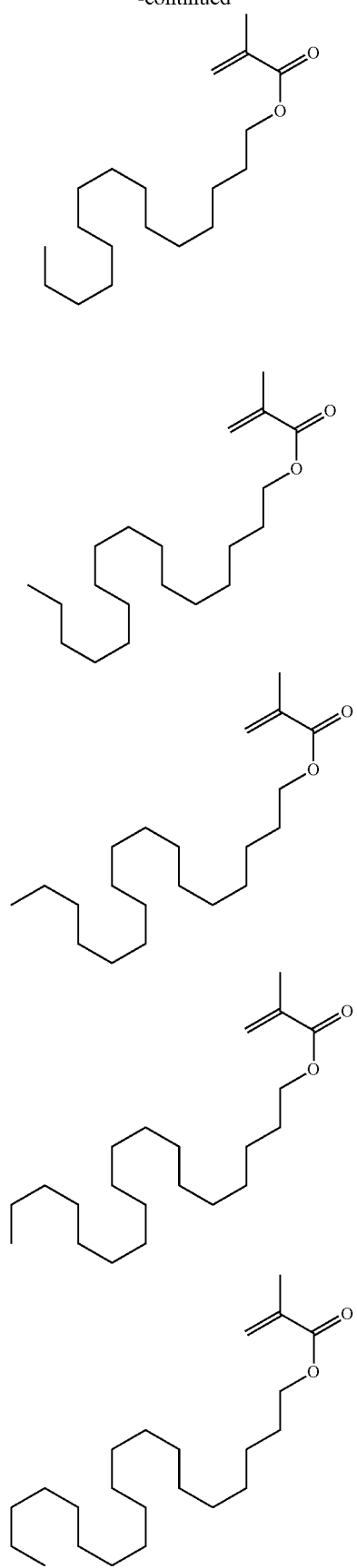
168
-continued
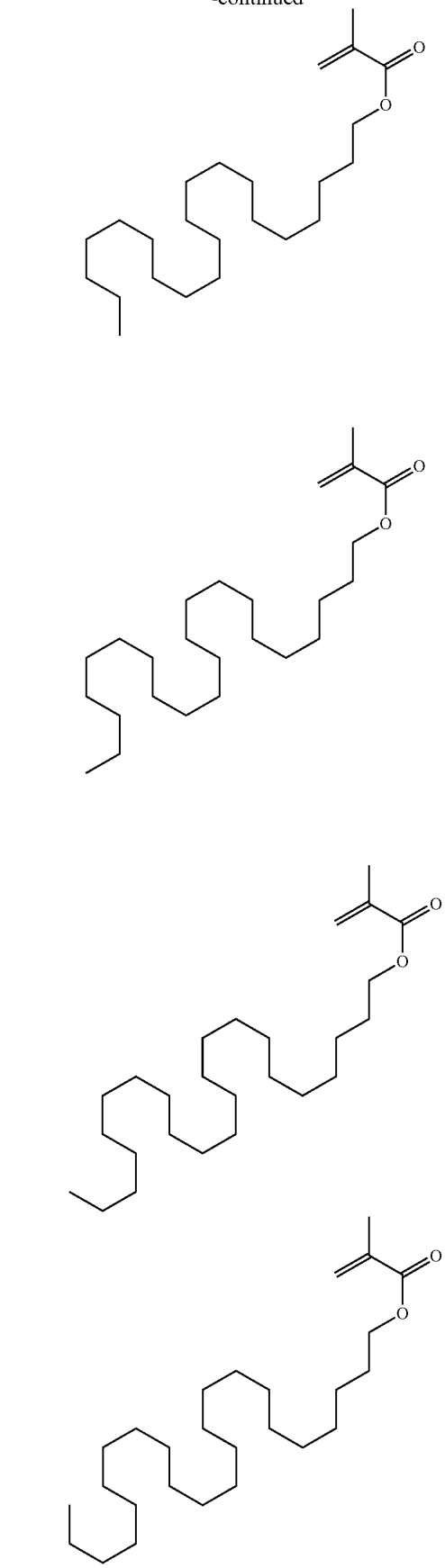

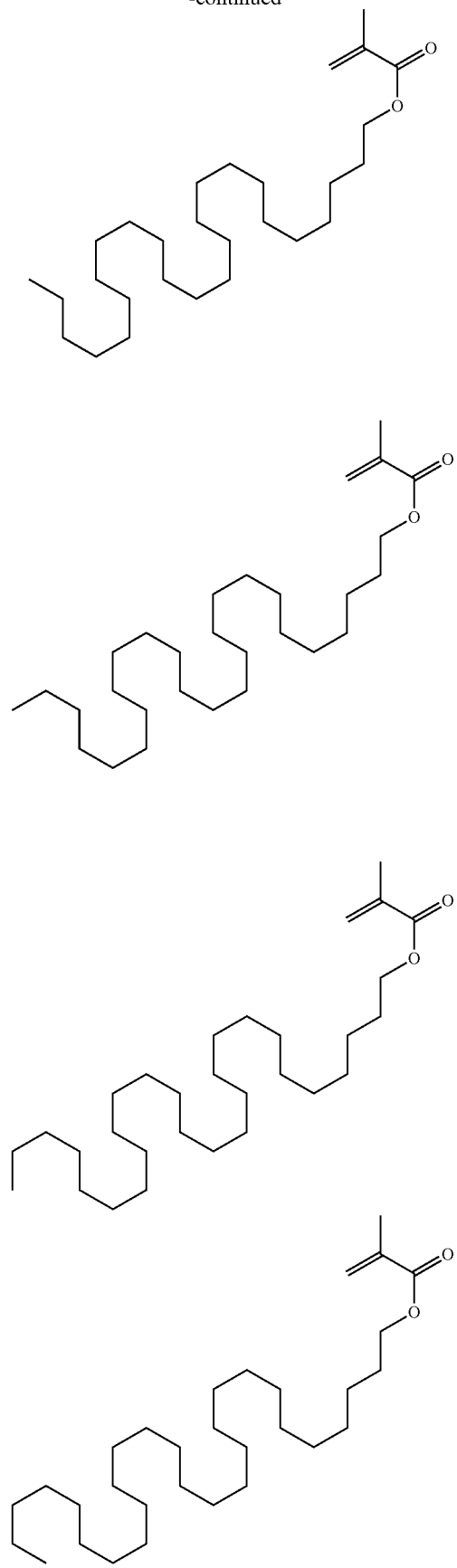
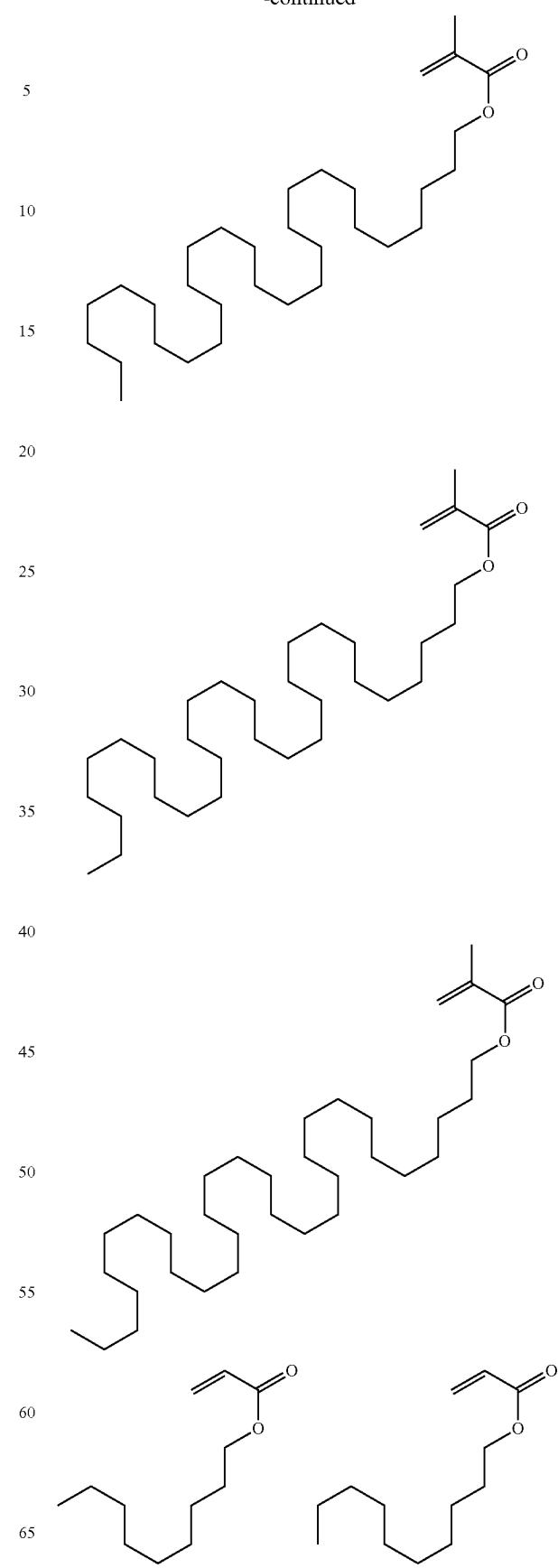

171
-continued
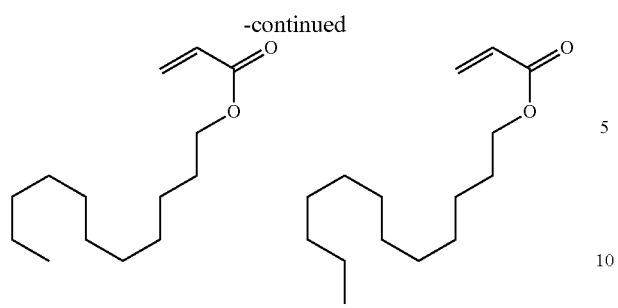
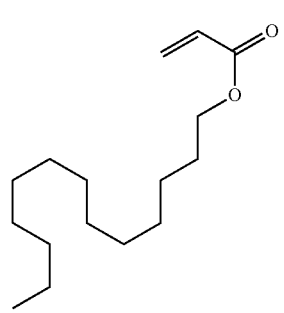
172
-continued
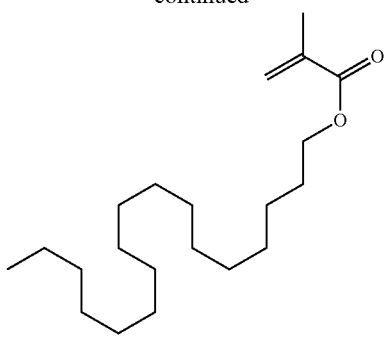
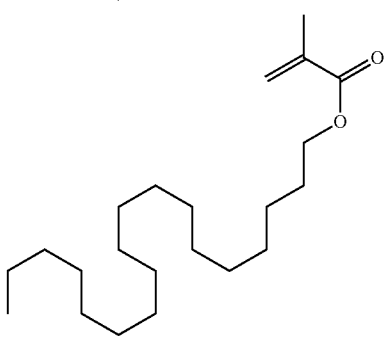
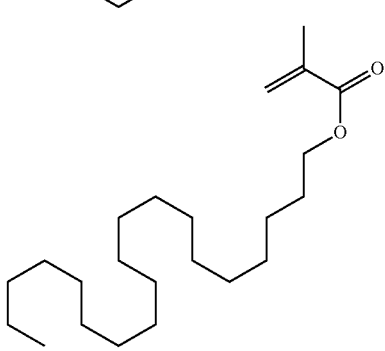
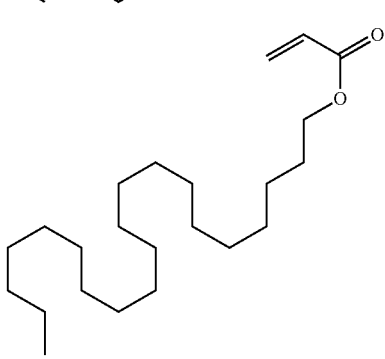
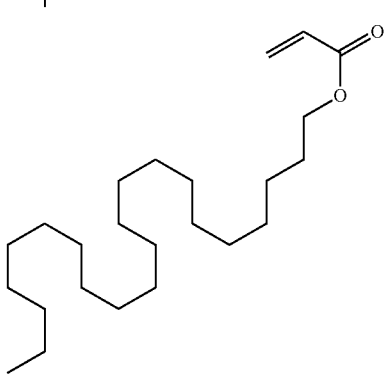

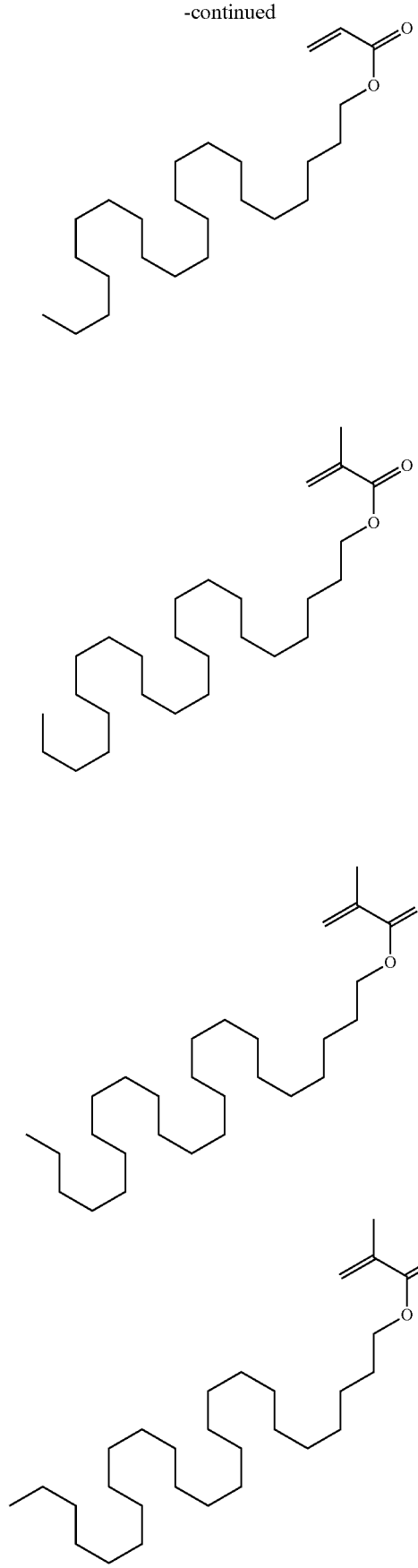
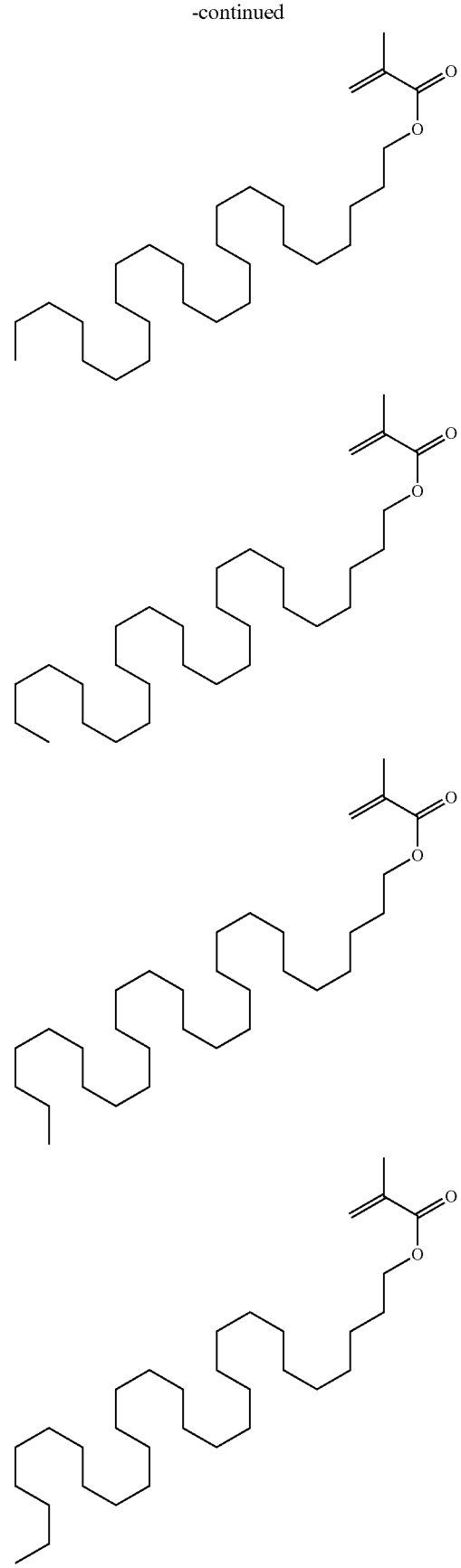

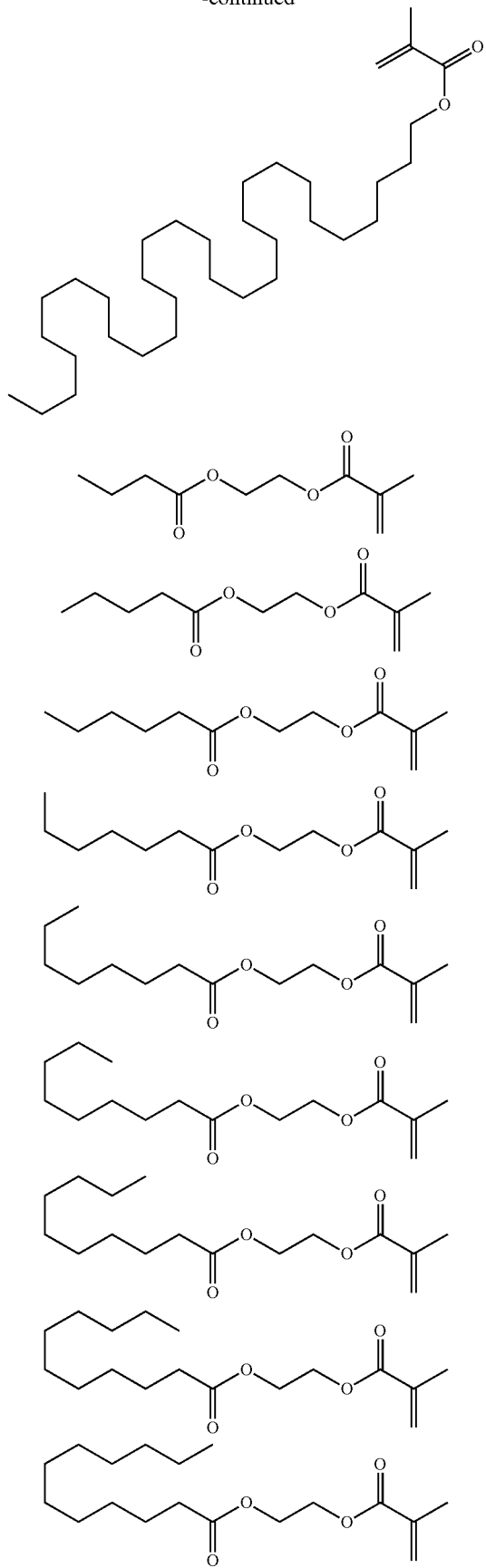
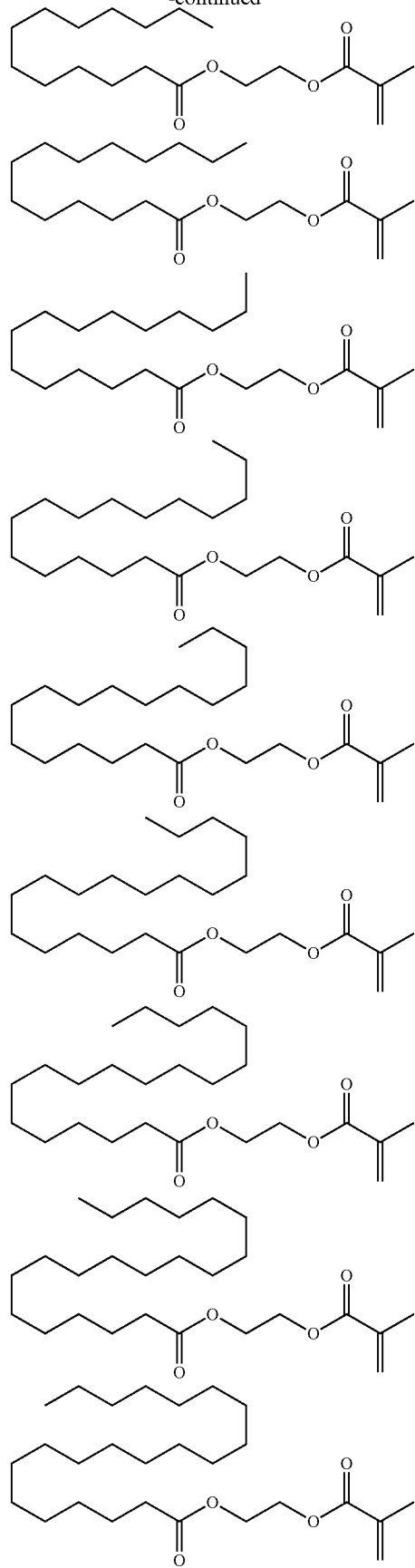

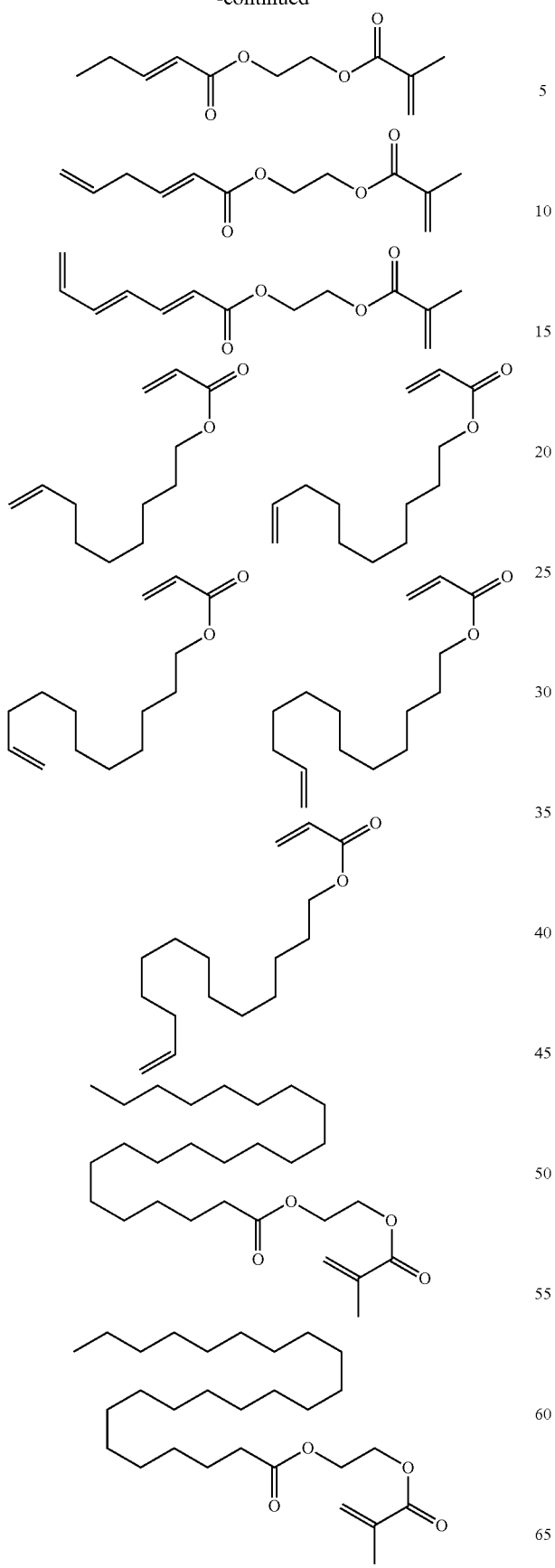
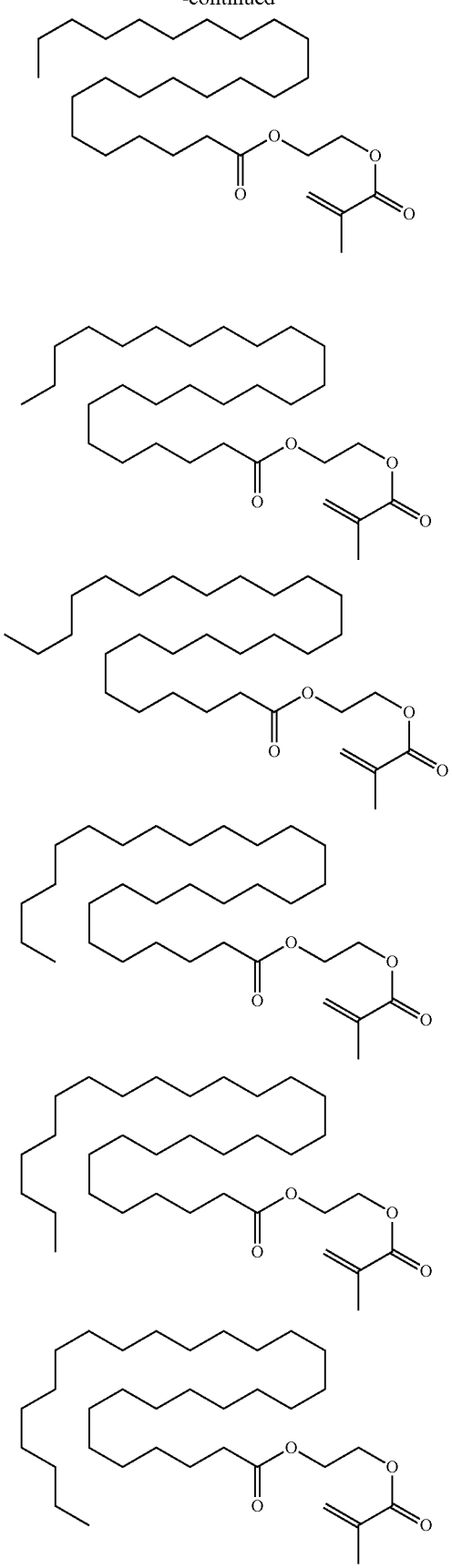

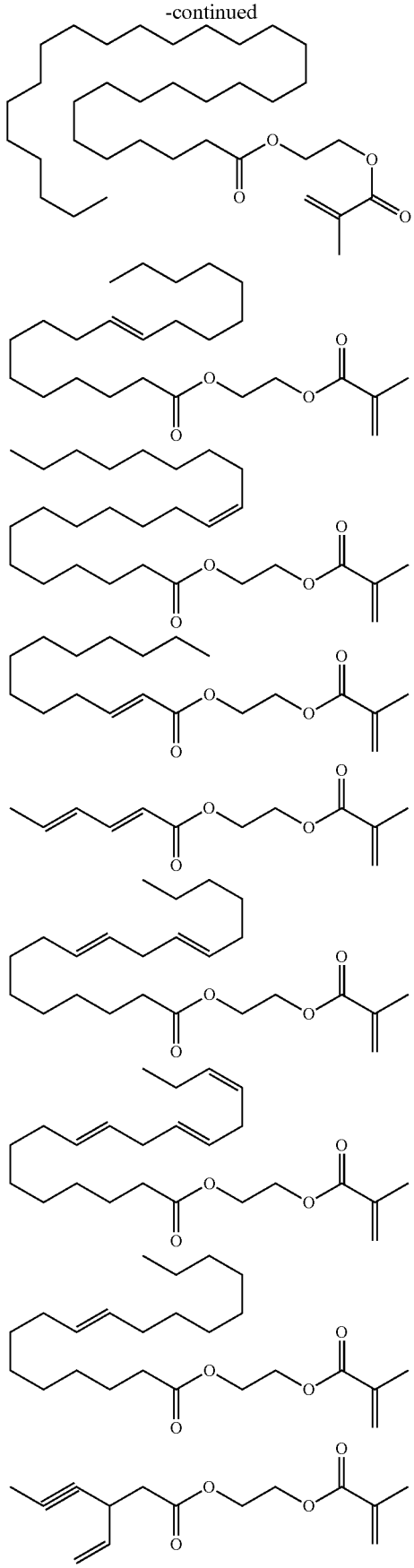
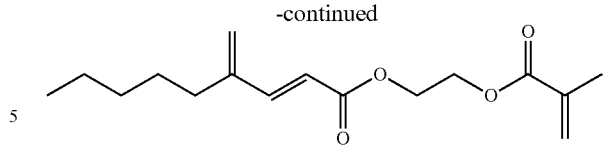
(Repeating Unit-f)
Further, it is also possible to copolymerize a crosslinkable repeating unit-f. Examples of the crosslinkable repeating unit include repeating units having an oxirane ring or an oxetane ring.
Specific examples of monomers to give the repeating unit-f having an oxirane ring or an oxetane ring include the following.
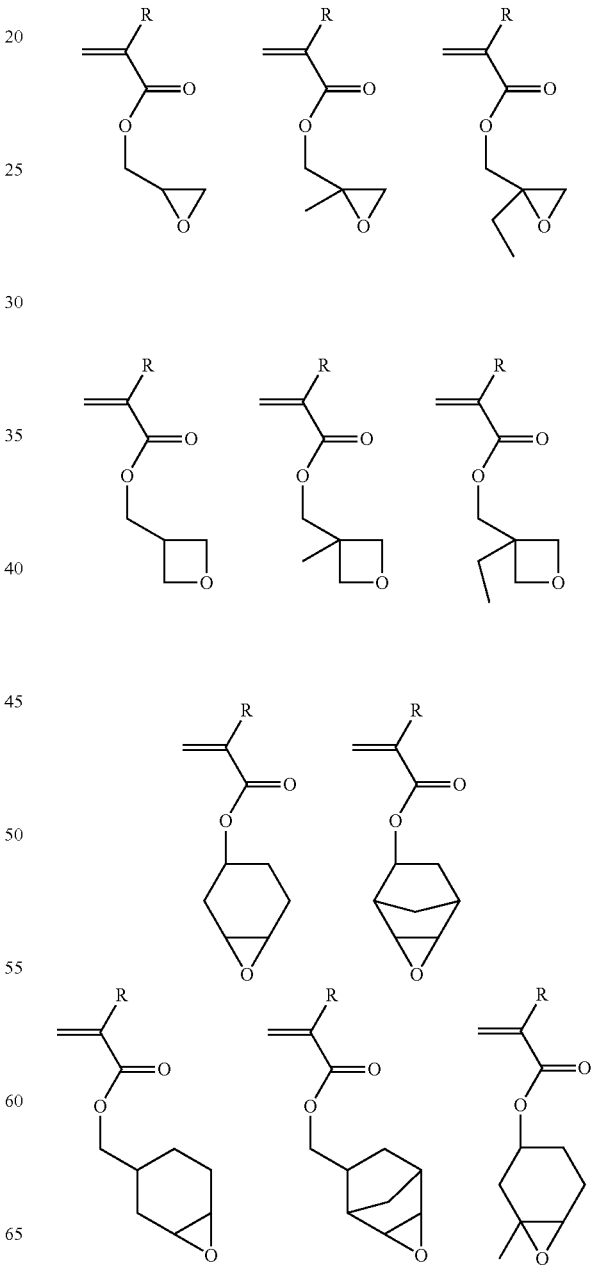

181
-continued
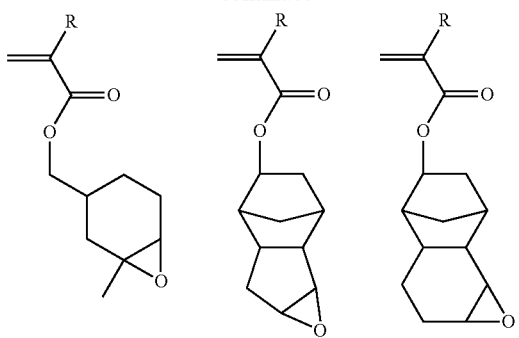
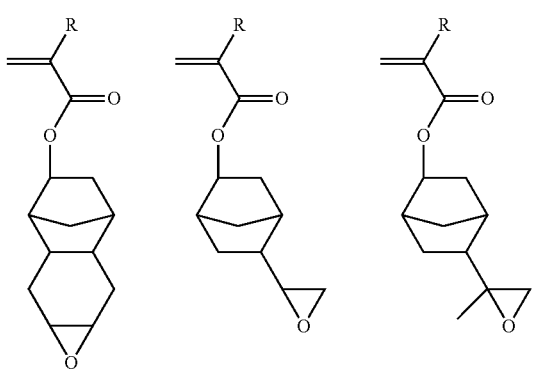
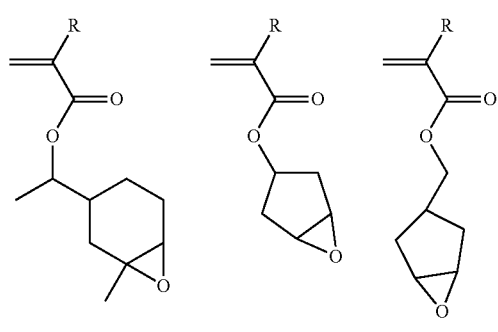
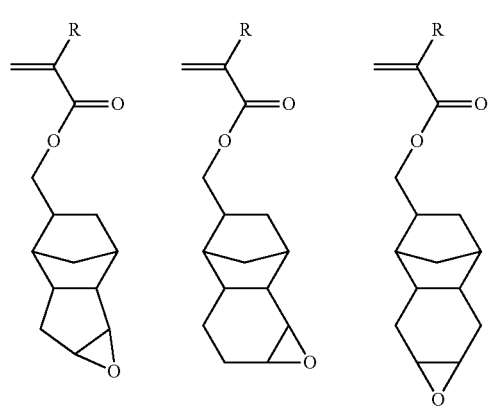
182
-continued
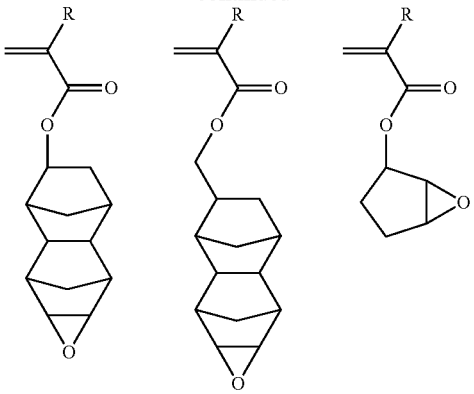
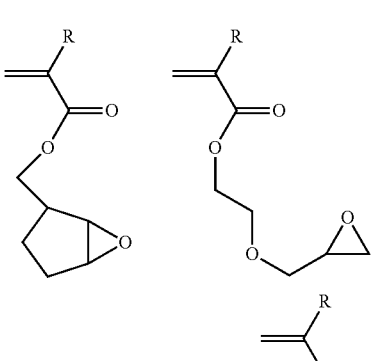
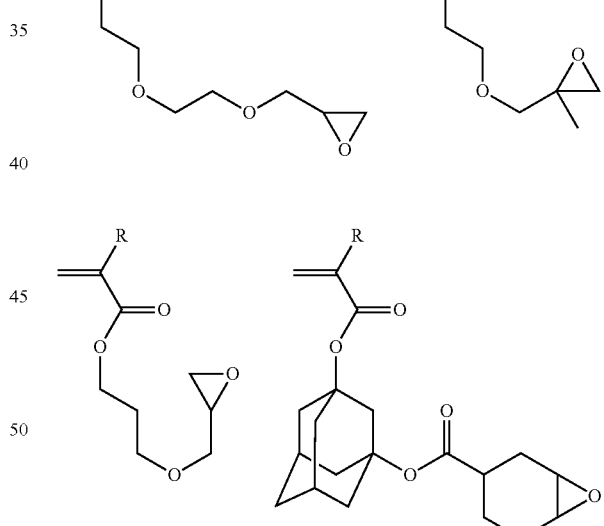
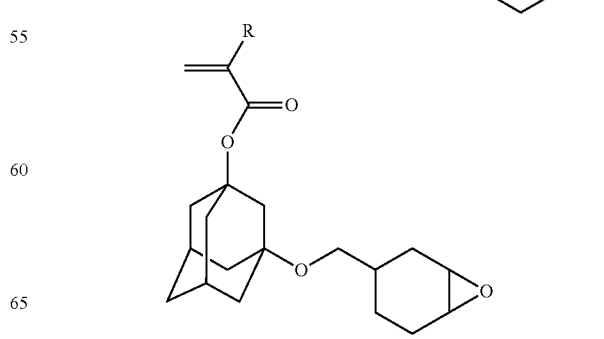

183
-continued
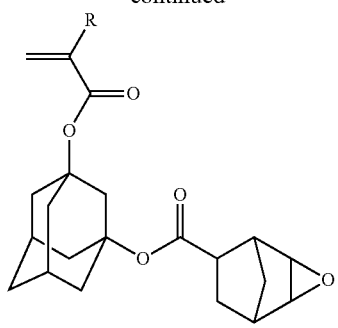
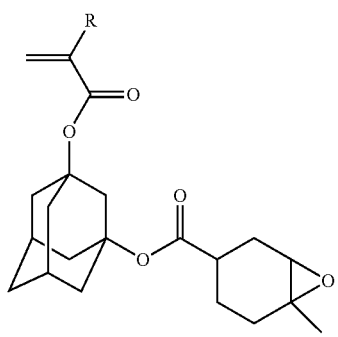
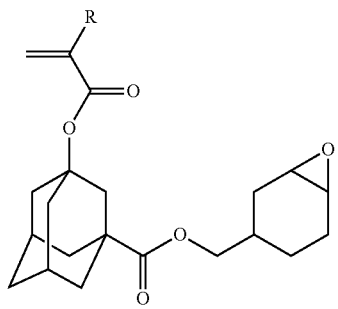
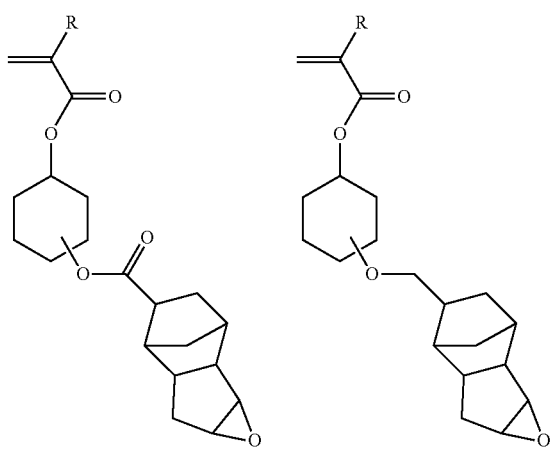
184
-continued
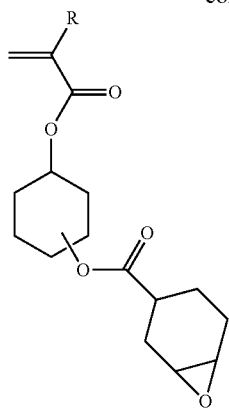
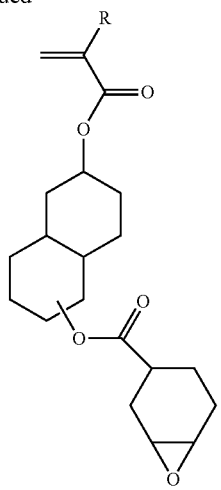
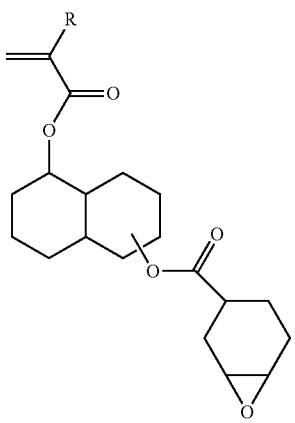
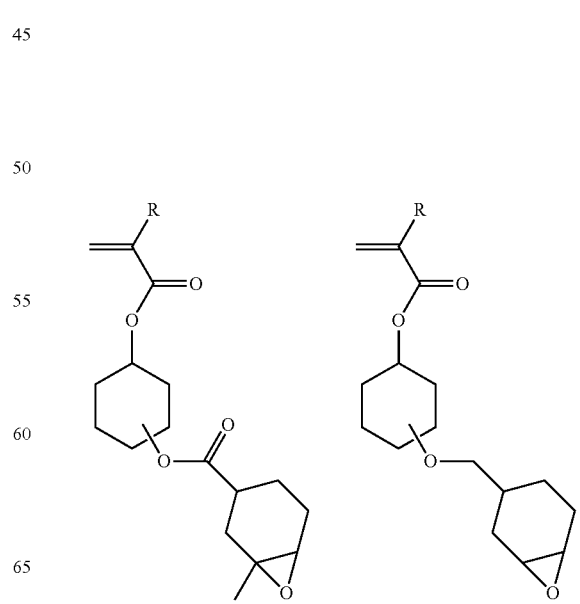

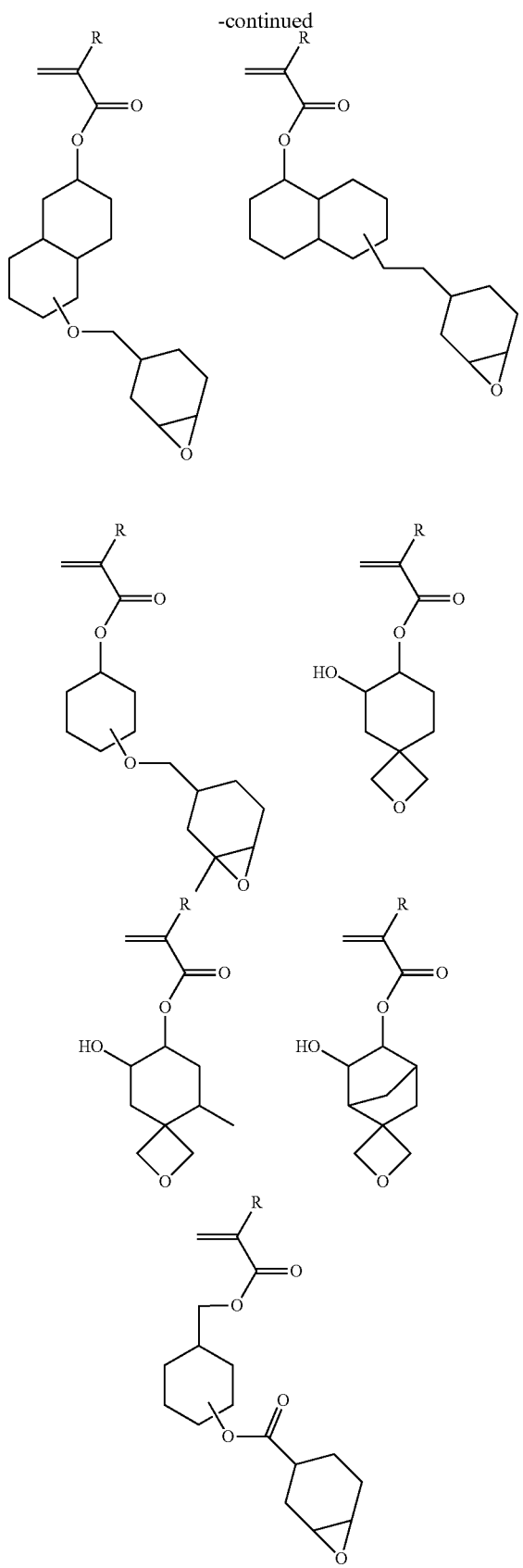

In these formulae, R represents a methyl group or a hydrogen atom.

(Repeating Unit-g)

The component (A) of the inventive bio-electrode composition can contain a repeating unit-g having silicon, in addition to the repeating unit-a (e.g., a1 to a7), the repeating unit-b, and the optional repeating unit(s) selected from the group consisting of the repeating units-c to -f. Specific examples of a monomer to give the repeating unit-g include the following.

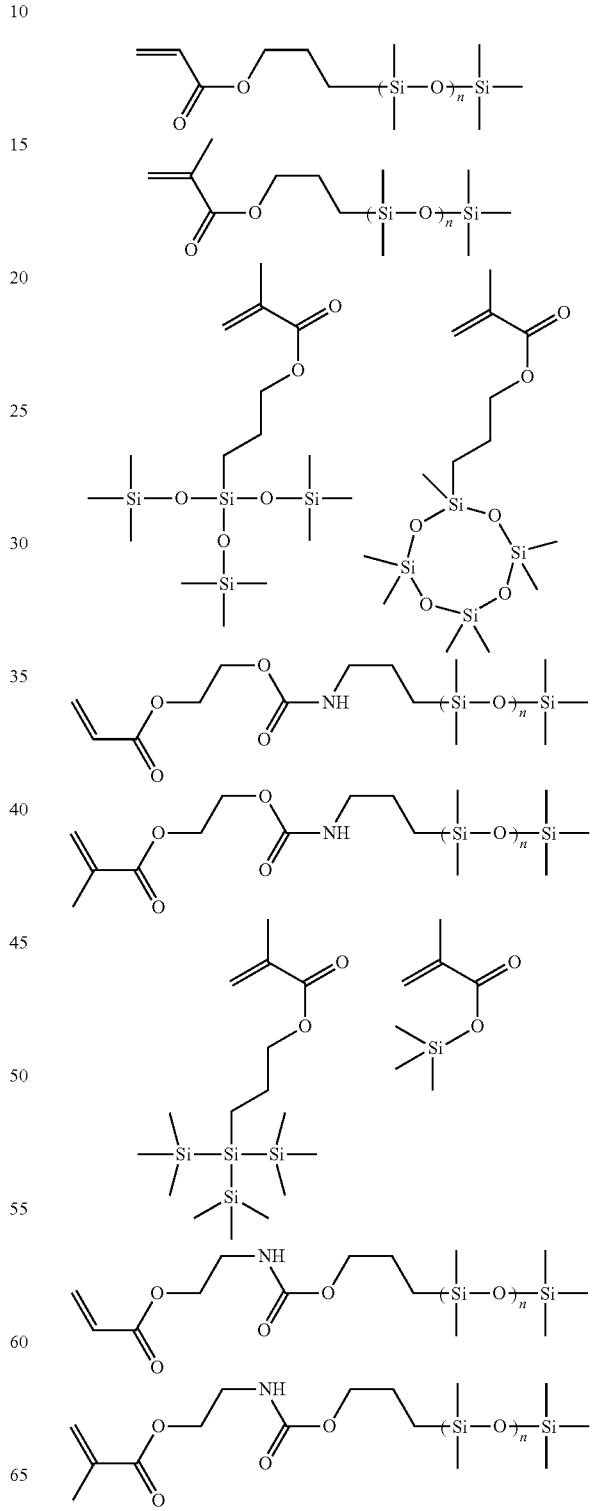

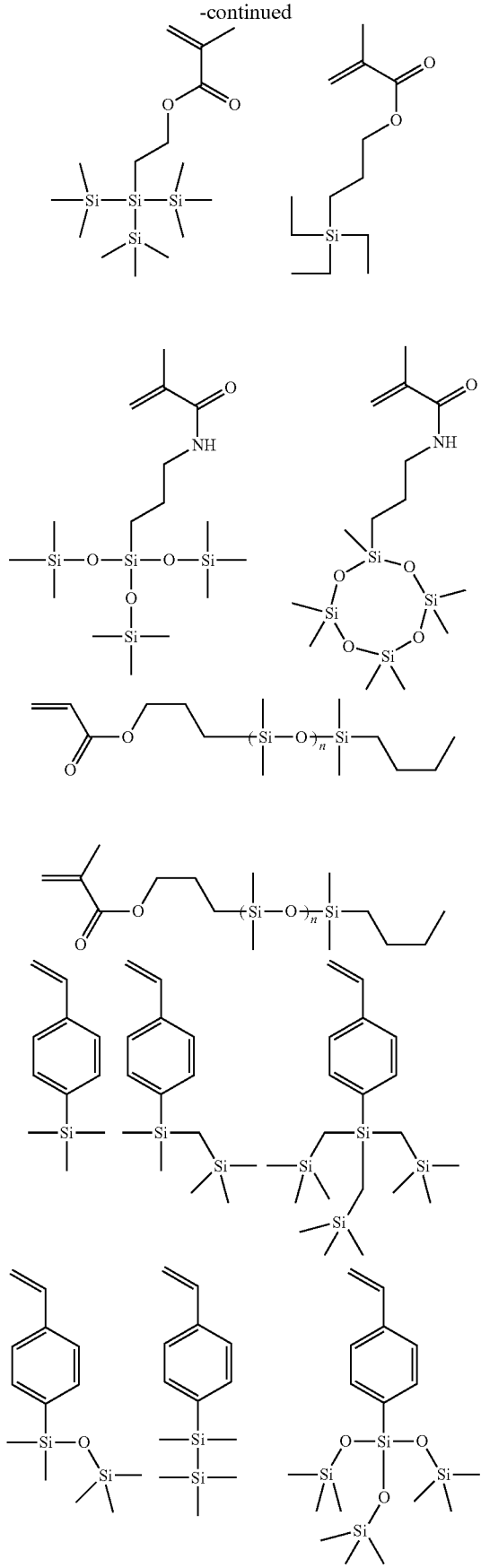
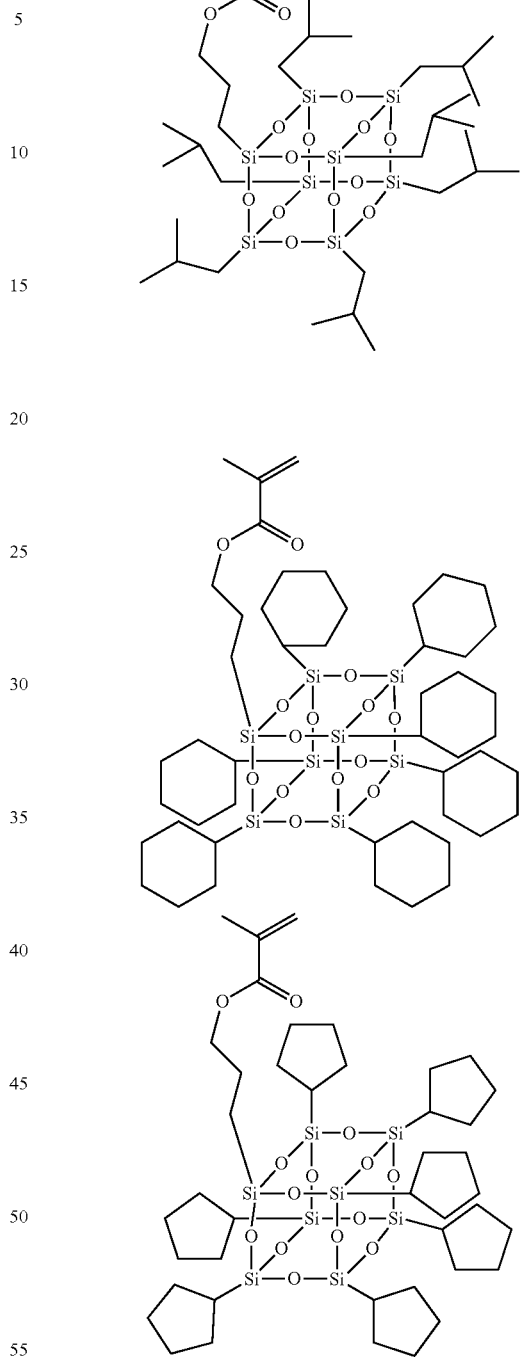

In the above formulae, "n" represents the number from 0 to 100.

(Repeating Unit-h)

The component (A) of the inventive bio-electrode composition can contain a repeating unit-h having fluorine, in addition to the repeating unit-a (e.g., a1 to a7), the repeating unit-b, and the optional repeating unit(s) selected from the group consisting of the repeating units-c to -g.

Specific examples of a monomer to give the repeating unit-h having fluorine include the following.

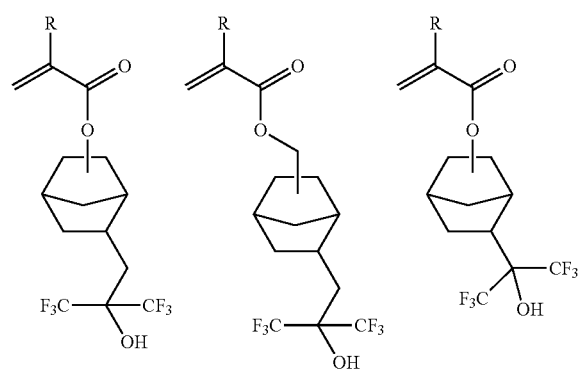
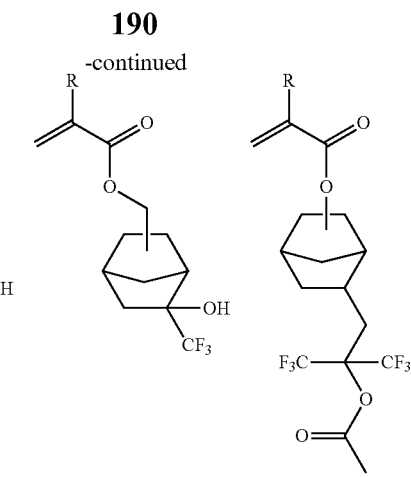
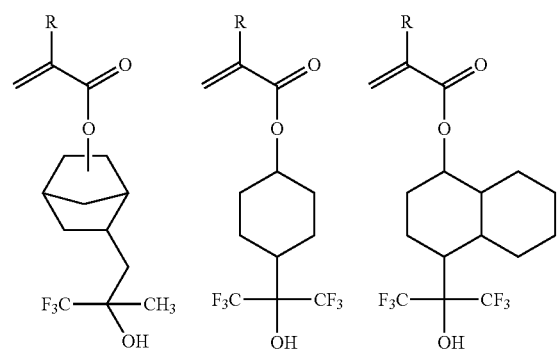
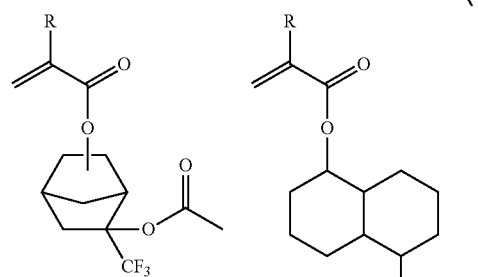
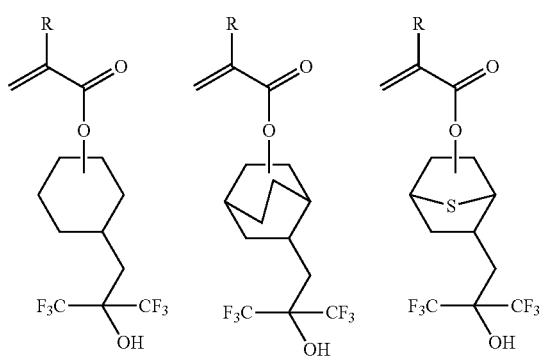
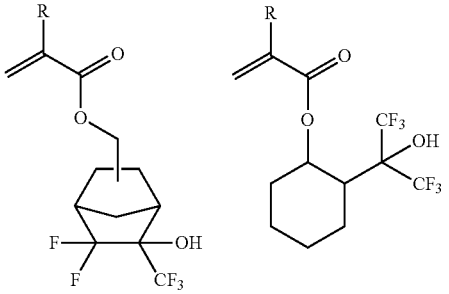
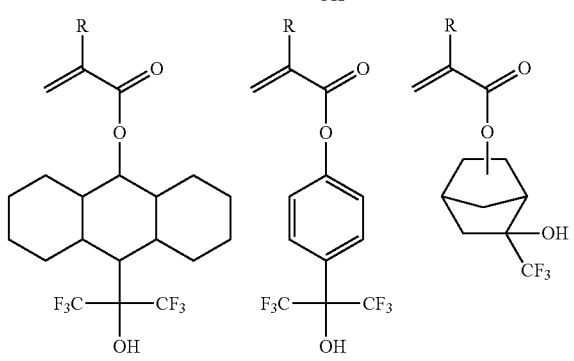
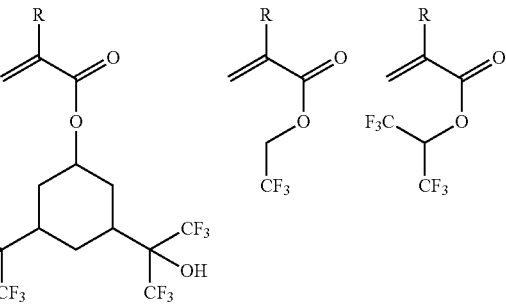
-continued

191
-continued
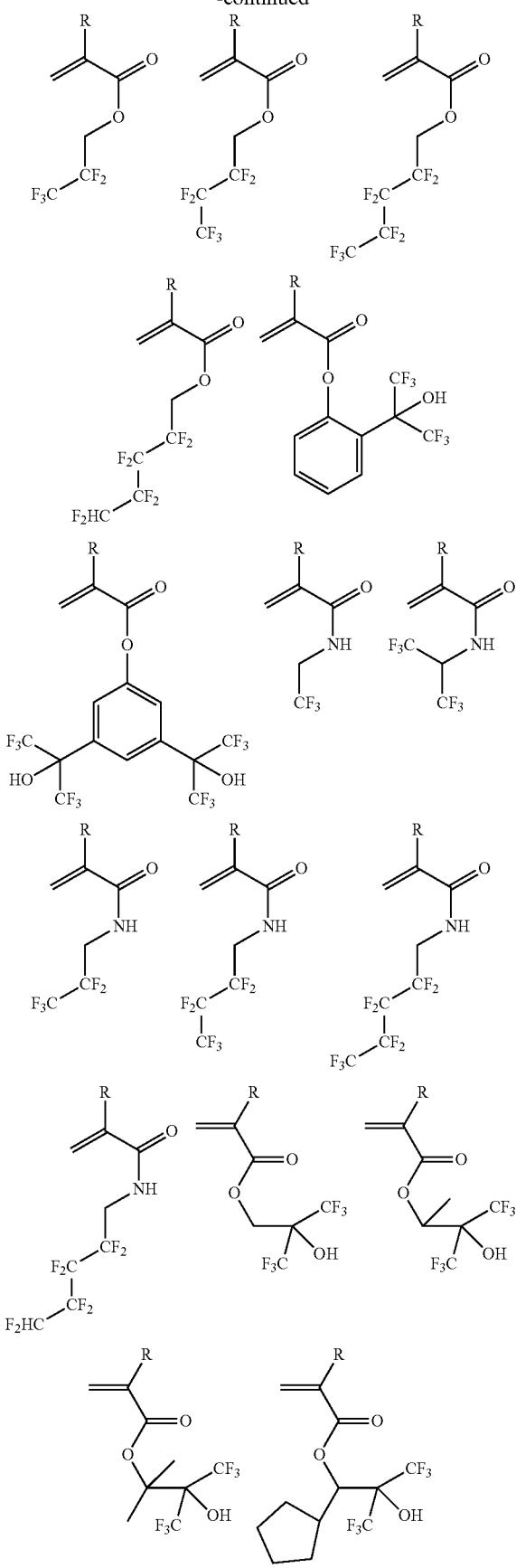
192
-continued
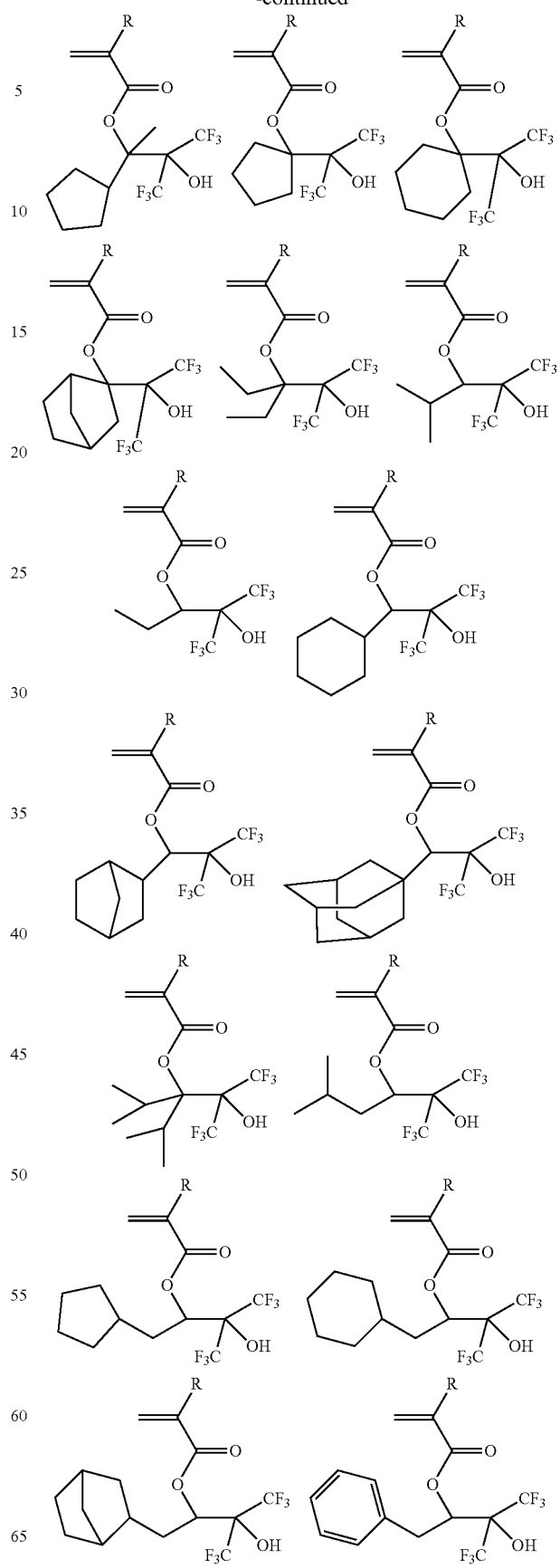

-continued
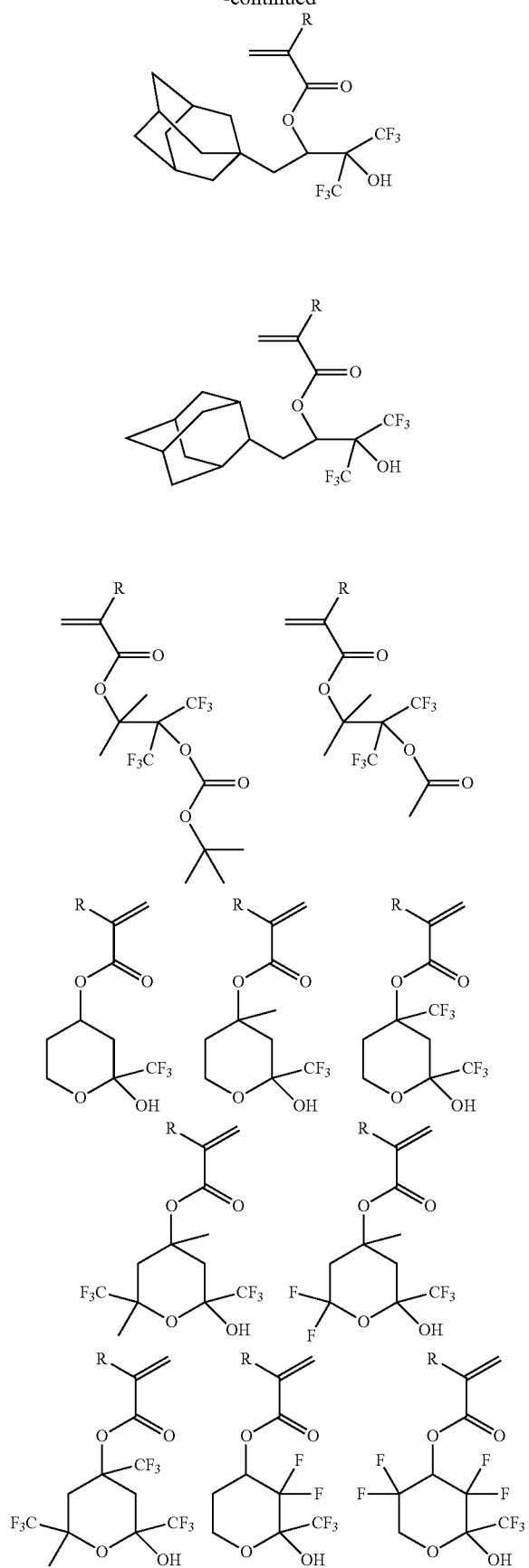
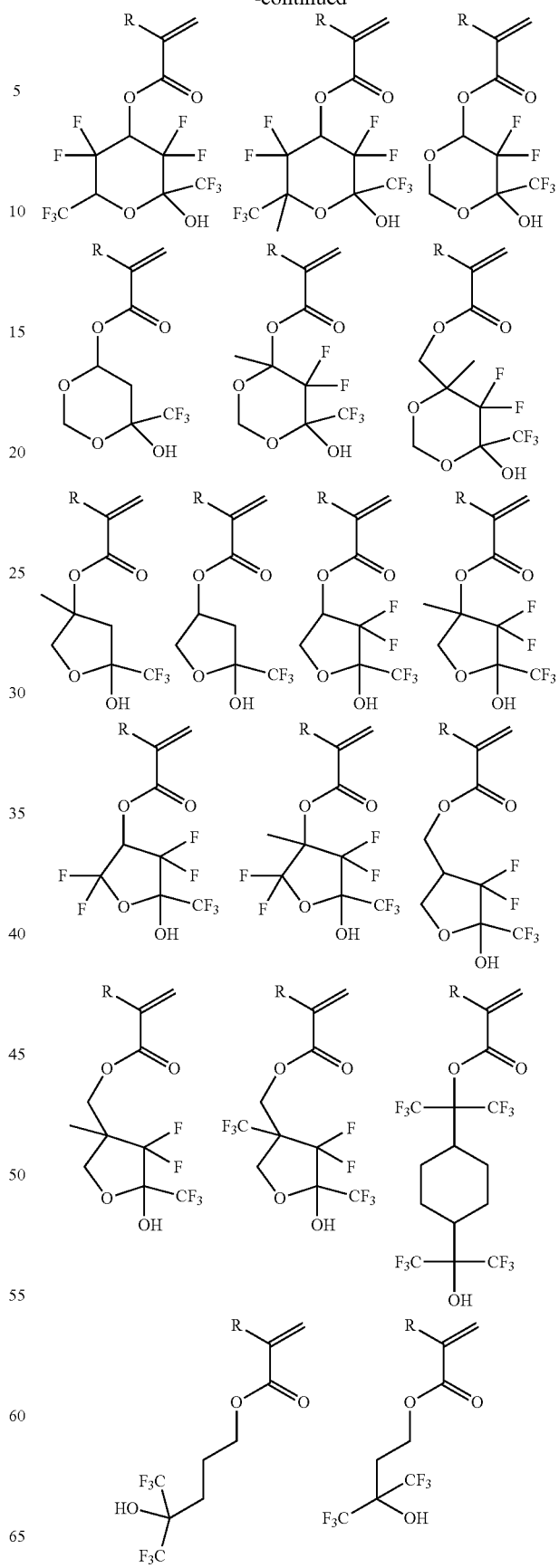

-continued
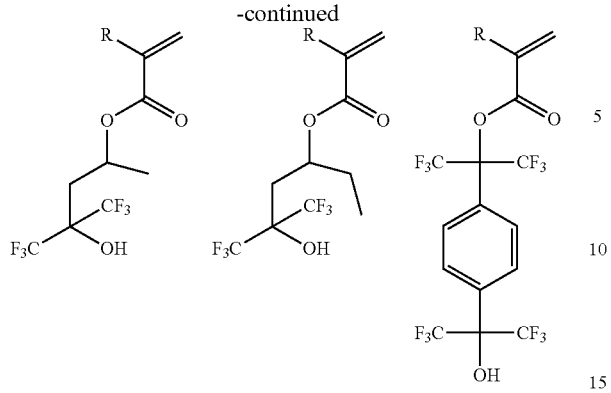
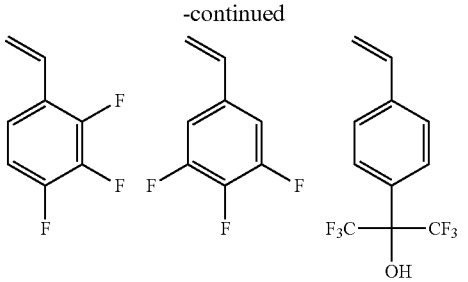
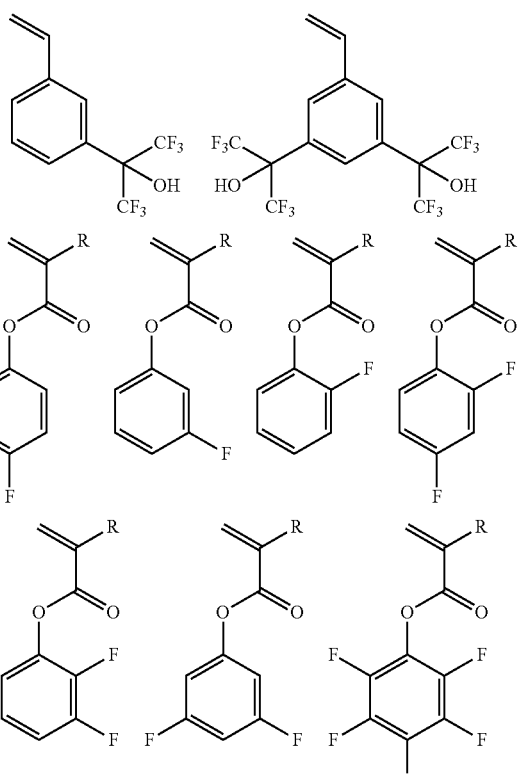
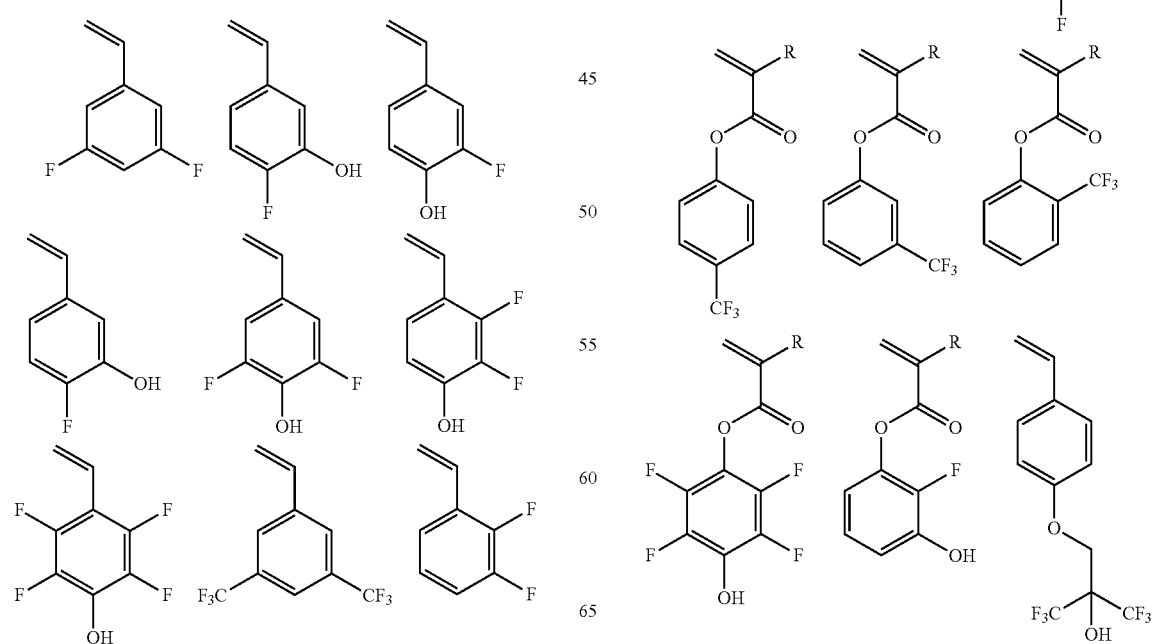

-continued

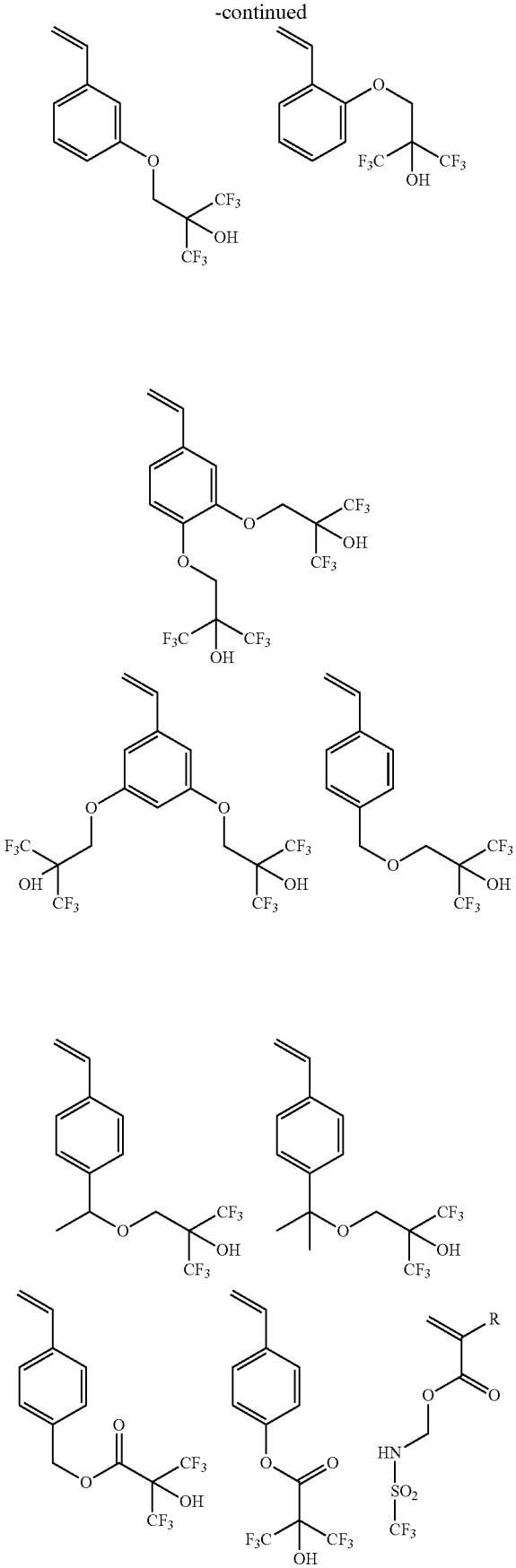

-continued

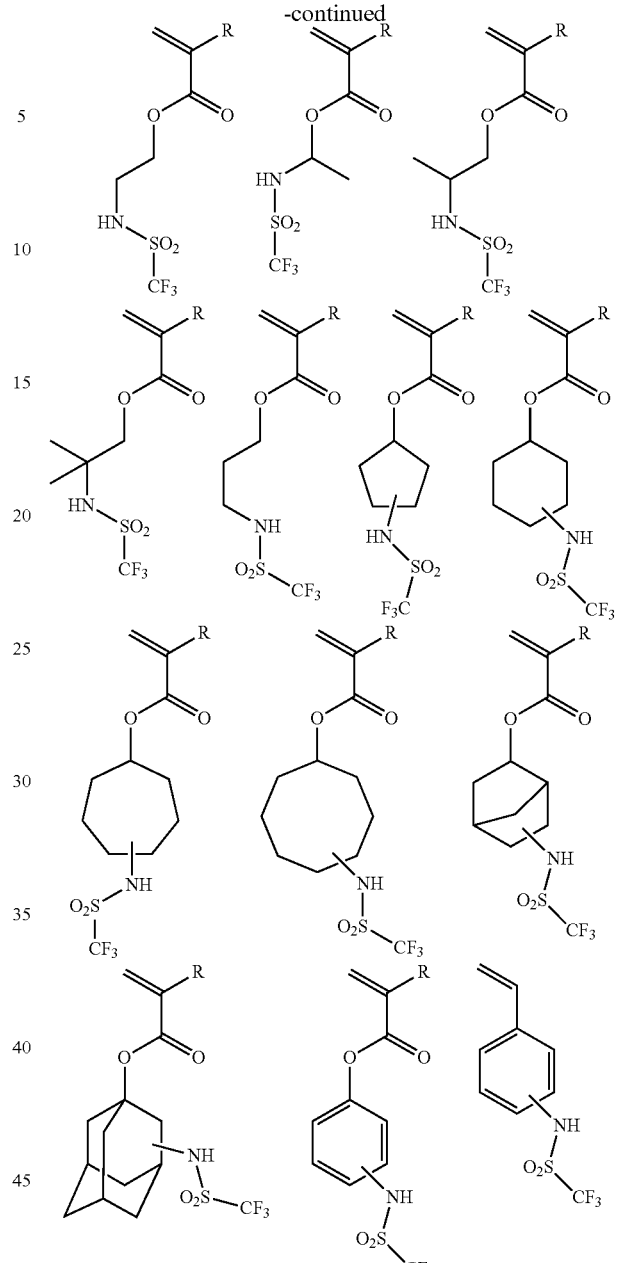

In these formulae, R represents a hydrogen atom or a methyl group.

(Synthesis Method)

As one of the method for synthesizing the component (A) that is the ionic polymer material (polymer compound), a copolymer compound can be obtained, for example, by a method in which the monomer to give the repeating unit-a (e.g., the repeating units-a1 to -a7) and the monomer to give the repeating unit-b as well as desired monomer(s) among the monomers to give the repeating units-c, -d, -e, -f, -g, and -h undergo heat polymerization in an organic solvent to which a radical polymerization initiator is added.

Examples of the organic solvent used in the polymerization include toluene, benzene, tetrahydrofuran, diethyl ether, dioxane, etc. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, etc. The heating temperature is preferably 50 to 80° C., and the reaction time is preferably 2 to 100 hours, more preferably 5 to 20 hours.

Here, the ratios of the repeating units-a1 to -a7, -b, -c, -d, -e, -f, -g, and -h in the ionic polymer material (polymer) (A) can be $0 \leq a1<1.0$, $0 \leq a2<1.0$, $0 \leq a3<1.0$, $0 \leq a4<1.0$, $0 \leq a5<1.0$, $0 \leq a6<1.0$, $0 \leq a7<1.0$, $0<a1+a2+a3+a4+a5+a6+a7<1.0$, $0<b<1.0$, $0 \leq c<1.0$, $0 \leq d<1.0$, $0 \leq e<0.9$, $0 \leq f<0.9$, $0 \leq g<0.9$, and $0 \leq h<0.9$; preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.9$, $0.001 \leq b \leq 0.8$, $0 \leq c \leq 0.8$, $0 \leq d \leq 0.8$, $0 \leq e<0.8$, $0 \leq f<0.8$, $0 \leq g<0.8$, and $0 \leq h<0.8$; more preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.8$, $0.01 \leq b \leq 0.7$, $0 \leq c \leq 0.7$, $0 \leq d \leq 0.5$, $0 \leq e<0.3$, $0 \leq f<0.7$, $0 \leq g<0.7$, and $0 \leq h<0.7$.

Incidentally, for example, $a1+a2+a3+a4+a5+a6+a7+b+c+d+e+f+g+h=1$ means that the total amount of the repeating units-a1, -a2, -a3, -a4, -a5, -a6, -a7, -b, -c, -d, -e, -f, -g, and -h is 100 mol % on the basis of the total amount of the whole repeating units in the polymer compound containing the repeating units-a1, -a2, -a3, -a4, -a5, -a6, -a7, -b, -c, -d, -e, -f, -g, and -h; and $a1+a2+a3+a4+a5+a6+a7+b+c+d+e+f+g+h<1$ means that the total amount of the repeating units-a1, -a2, -a3, -a4, -a5, -a6, -a7, -b, -c, -d, -e, -f, -g, and -h is less than 100 mol % on the basis of the total amount of the whole repeating units, which indicates that the polymer compound contains another repeating unit(s) besides the repeating units-a1, -a2, -a3, -a4, -a5, -a6, -a7, -b, -c, -d, -e, -f, -g, and -h.

To obtain the repeating unit-b, there is a method in which, for example, a precursor monomer thereof is polymerized with another monomer(s), and after the polymerization, the polymer is allowed to react at the portion corresponding to the repeating unit-b with a compound having a double bond, so that the repeating unit having the double bond can be obtained at the end of the side chain.

The precursor monomer is a monomer having a hydroxy group, a carboxyl group, an epoxy group, an oxetane group, or an isocyanate group. After the polymerization, this portion of the polymer is allowed to react with a compound having a double bond and a carboxyl group, an epoxy group, a hydroxy group, or an isocyanate group.

Regarding the molecular weight of the component (A), the weight-average molecular weight is preferably 500 or more, more preferably 1,000 or more and 1,000,000 or less, further preferably 2,000 or more and 500,000 or less. Regarding the ionic monomer (residual monomer) that is not incorporated into the component (A) after the polymerization, if the amount is small, the residual monomer can be prevented from permeating to skin in a biocompatibility test to cause allergy. Accordingly, it is preferable to decrease the amount of residual monomer(s). The amount of residual monomer(s) is preferably 10 parts by mass or less on the basis of 100 parts by mass of the whole component (A). One kind of the component (A) may be used singly, or there can be used a mixture of two or more kinds which differ in molecular weight, dispersity, and constitutive polymerizable monomer.

The weight-average molecular weight of the polymer material can be determined by gel permeation chromatography (GPC) using tetrahydrofuran (THF) as a solvent.

[(B) Resin]

A resin (B), which is blended into the inventive bio-electrode composition, is a component for: preventing elution of the ionic polymer material (salt) (A) by being compatibilized with the salt; holding an optional component, for example, an electric conductivity improver such as a metal powder and a carbon powder, and an ion receptivity improver such as a silicon powder and a lithium titanate powder; and for achieving adhesion. When the ionic polymer material (A) has adhesion, the resin (B) is not necessarily essential. It should be noted that this resin may be any resin other than the component (A), and is preferably either or both of a thermosetting resin and a photo-curable resin, particularly preferably one or more resins selected from the group consisting of silicone based, acrylic based, and urethane based resins. In other words, the inventive bio-electrode composition preferably contains, as the component (B), a resin containing any one or more of silicone, polyacrylate, and polyurethane.

The adherent (adhesive) silicone based resin include an addition-curable (addition reaction-curable) type and a radical curable (radical crosslinking reaction-curable) type. As the addition-curable type, it is possible to use one that contains diorganosiloxane having an alkenyl group(s), an MQ resin having $R_3SiO_{0.5}$ and $SiO_2$ units, organohydrogenpolysiloxane having a plurality of SiH groups, a platinum catalyst, an addition reaction inhibitor, and an organic solvent, for example, described in JP 2015-193803A. As the radical curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength by addition of it, but does not bind to the polysiloxane in molecular level because it is not crosslinkable. The adhesive strength can be increased by integrating the polysiloxane and the resin as described above.

The silicone resin may contain modified siloxane that has a group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic based resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane based resin, it is possible to use one having a urethane bond with a polyether bond, a polyester bond, a polycarbonate bond, or a siloxane bond described in JP 2016-065238A, for example.

In the inventive bio-electrode composition, the resin (B) preferably has high compatibility with the component (A) to prevent lowering of the electric conductivity due to elution of the component (A) from the living body contact layer. In the inventive bio-electrode composition, the resin (B) preferably has high adhesion to the electro-conductive base material (substrate) of the bio-electrode to prevent peeling of the living body contact layer from the electro-conductive base material. In order to increase the adhesion to the electro-conductive base material and the compatibility with the salt, a use of a resin with high polarity as the resin (B) is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin; etc. On the other hand, the living body contact layer is to be contacted with a living body, thereby being susceptible to perspiration. Accordingly, in the inventive bio-electrode composition, the resin (B) preferably has high repellency and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, silsesquioxane, siloxane having a (meth)acrylpropyl group, or the like can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating thereof. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s). Particularly, a polyurethane main chain having a silicone chain on a side chain as described in JP 2018-123304A and JP 2019-70109A is preferable because of the properties of high strength and high stretchability.

The silicon atom-containing polythiourethane resin can be obtained by reaction of a compound having a thiol group(s) and a compound having an isocyanate group(s), provided that either of them contains a silicon atom(s). It can also be photo-cured if (meth)acrylate groups are contained at the terminals.

The silicone based resin can be improved in compatibility with the foregoing salt by adding modified siloxane that has a group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as chloroplatinic acid, alcohol solution of chloroplatinic acid, reaction product of chloroplatinic acid and alcohol, reaction product of chloroplatinic acid and an olefin compound, reaction product of platinic chloride and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

The amount of the platinum catalyst added is preferably in a range of 5 to 2,000 ppm, particularly preferably 10 to 500 ppm, on the basis of 100 parts by mass of the resin including (A) and (B).

In the inventive bio-electrode composition, the component (B) is blended in an amount of preferably 0 to 2000 parts by mass, more preferably 10 to 1000 parts by mass, on the basis of 100 parts by mass of the ion polymer (A). One kind of each of the components (A) and (B) may be used singly or mixture of two or more kinds may be used.

When the addition curable silicone resin is used, an addition-reaction inhibitor may be added. This addition-reaction inhibitor is added as a quencher to prevent the action of the platinum catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The amount of the addition-reaction inhibitor added is preferably in a range of 0 to 10 parts by mass, particularly preferably 0.05 to 3 parts by mass, on the basis of 100 parts by mass of the resin.

[Radical Generator]

In crosslinking the radical-crosslinkable group in the component (A) in the present invention, it is effective to add a radical generator. Such a radical generator includes a photoradical generator and a thermal radical generator.

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

The amount of radical generator added is preferably in a range of 0.1 to 50 parts by mass on the basis of 100 parts by mass of the resin including the components (A) and (B).

As will be described later, the living body contact layer of the inventive bio-electrode is a cured material (cured product) of the inventive bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakayama, Maruzen Publishing Co., Ltd. (2013).

[Metal Powder]

The inventive bio-electrode composition can also contain a metal powder selected from the group consisting of gold, silver, platinum, copper, tin, titanium, nickel, aluminum, tungsten, molybdenum, ruthenium, chromium, and indium in order to improve electron conductivity. The amount of the metal powder added is preferably in a range of 1 to 50 parts by mass on the basis of 100 parts by mass of the resin.

As the kind of the metal powder, gold, silver, and platinum are preferable in view of electric conductivity; and silver, copper, tin, titanium, nickel, aluminum, tungsten, molybdenum, ruthenium, and chromium are preferable in view of cost.

In view of biocompatibility, noble metals are preferable. On the whole of these viewpoints, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 µm or less, a tapped density of not more than 5 g/cm$^3$, and a specific surface area of not less than 0.5 m$^2$/g.

[Carbon Material]

A carbon material can be added as an electric conductivity improver. Examples of the carbon material include carbon black, graphite, carbon nanotube, carbon fiber, etc. The carbon nanotube may be either single layer or multilayer, and the surface may be modified with an organic group(s). The amount of the carbon material added is preferably in a range of 1 to 50 parts by mass on the basis of 100 parts by mass of the resin.

[Silicon Powder]

The inventive bio-electrode composition may contain a silicon powder to enhance ion reception sensitivity.

Examples of the silicon powder include powders of silicon, silicon monoxide, or silicon carbide. The particle diameter of the powder is preferably smaller than 100 µm, more preferably 1 µm or less.

Since finer particles have a larger surface area, the resulting bio-electrode can receive a larger amount of ions and has higher sensitivity. The amount of the silicon powder added is preferably in a range of 1 to 50 parts by mass on the basis of 100 parts by mass of the resin.

[Lithium Titanate Powder]

The inventive bio-electrode composition may contain a lithium titanate powder to enhance ion reception sensitivity.

Examples of the lithium titanate powder include powders containing a compound shown by molecular formulae $Li_2TiO_3$, $LiTiO_2$, or $Li_4Ti_5O_{12}$ with a spinel structure. Lithium titanate having a spinel structure is preferable. It is also possible to use carbon-incorporated lithium titanate particles. The particle diameter of the powder is preferably smaller than 100 µm, more preferably 1 µm or less.

Since finer particles have a larger surface area, the bio-electrode can receive a larger amount of ions, and has higher sensitivity. The aforementioned powders may be composite powders with carbon. The amount of the lithium titanate powder added is preferably in a range of 1 to 50 parts by mass on the basis of 100 parts by mass of the resin.

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass on the basis of 100 parts by mass of the resin.

[Crosslinking Catalyst]

The inventive bio-electrode composition may also contain a catalyst for crosslinking the epoxy groups or the oxetane groups. As this catalyst, ones described in paragraphs 0027 to 0029 of JP 2019-503406A can be used. The amount of the catalyst added is preferably 0.01 to 10 parts by mass on the basis of 100 parts by mass of the resin.

[Ionic Additive]

The inventive bio-electrode composition may contain an ionic additive to increase ionic conductivity. In consideration of biocompatibility, examples of the ionic additive include sodium chloride, potassium chloride, calcium chloride, saccharin, acesulfame K, and salts disclosed in JP 2018-44147A, JP 2018-59050A, JP 2018-59052A, and JP 2018-130534A.

[Organic Solvent]

Further, the inventive bio-electrode composition may contain an organic solvent. Specific examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvent such as γ-butyrolactone; water; etc.

The amount of the organic solvent added is preferably in a range of 10 to 50,000 parts by mass on the basis of 100 parts by mass of the resin.

[Other Additives]

The inventive bio-electrode composition can be mixed with silica particles, polyether silicone, or polyglycerin silicone. Silica particles have hydrophilic surfaces and favorable compatibility with the hydrophilic ion polymer, polyether silicone, and polyglycerin silicone, and can improve the dispersibility of the ion polymer, polyether silicone, and polyglycerin silicone in the hydrophobic silicone adhesive. The silica particles may be either dry type or wet type both of which are preferably usable.

As has been described above, the inventive bio-electrode composition makes it possible to form a living body contact layer for a bio-electrode that is capable of efficiently conducting electric signals from skin to a device (i.e., excellent in electric conductivity), and preventing residue on the skin even when peeled from the skin after long-time attachment to the skin. Thus, the inventive bio-electrode composition is capable of forming a living body contact layer for a bio-electrode to enable signal collection immediately after attachment to skin and prevention of residue on the skin after peeling from the skin. Moreover, the inventive bio-electrode composition can form a living body contact layer for a bio-electrode which does not cause allergy even when attached to skin for a long time (i.e., excellent in biocompatibility), which is light-weight and manufacturable at low cost, and which prevents significant reduction in the electric conductivity even when wetted with water or dried. In addition, it is possible to further improve the electric conductivity by adding a carbon material, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer.

<Bio-Electrode>

The present invention also provides a bio-electrode comprising an electro-conductive base material and a living body contact layer formed on the electro-conductive base material, wherein the living body contact layer is a cured material of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is a cured material as one example of the inventive bio-electrode composition described above. More specifically, the living body contact layer 3 is a layer in which an ionic polymer material (ionic polymer) 4 and an additive 5 are dispersed in a resin 6.

When the bio-electrode 1 as shown in FIG. 1 is used, the living body contact layer 3 (i.e., the layer in which the ionic polymer material 4 and the additive 5 are dispersed in the resin 6) is brought into contact with a living body 7 as shown in FIG. 2. Electric signals are picked from the living body 7 through the ionic polymer 4 and the additive 5, and then conducted to a sensor device etc. (not shown) via the electro-conductive base material 2.

As described above, the inventive bio-electrode is capable of coping with both electric conductivity and biocompatibility by using the ionic polymer material (ionic polymer) described above, and obtaining electric signals from skin stably in high sensitivity because the contact area with skin is kept constant due to the adhesion thereof.

Moreover, since the inventive bio-electrode has the living body contact layer formed from the cured material of the inventive bio-electrode composition described above, this enables signal collection immediately after attachment to skin and prevention of residue on the skin after peeling from the skin.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from the group consisting of gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode includes a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above; that is, a resin layer containing: the ionic polymer material (salt) (A), and optional additive(s) such as the resin (B). The living body contact layer is for example an adherent resin layer.

The living body contact layer preferably has adhesive strength in a range of 0.5 N/25 mm or more and 20 N/25 mm or less. The adhesive strength is commonly measured by the method shown in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and as low as that of Teflon (registered trademark). Human skin is hard to adhere.

The living body contact layer of the bio-electrode has a thickness of preferably 1 μm or more and 5 mm or less, more preferably 2 μm or more and 3 mm or less. As the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be provided with an adherent film separately on the living body contact layer as in conventional bio-electrodes (e.g., the bio-electrode described in JP 2004-033468A) in order to prevent peeling off of the bio-electrode from a living body during the use. When the adherent film is provided separately, the adherent film may be formed by using a raw material for the adherent film such as an acrylic type, a urethane type, and a silicone type. Particularly, the silicone type is suitable because of: the high oxygen permeability, which enables dermal respiration while the electrode is attached to the skin, the high water repellency, which decreases lowering of adhesion due to perspiration, and the low irritation to skin. It is to be noted that the inventive bio-electrode does not necessarily require this adherent film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ the ones described in JP 2004-033468A.

As described above, since the inventive bio-electrode includes the living body contact layer formed from the cured material of the aforementioned inventive bio-electrode composition, the inventive bio-electrode is capable of efficiently conducting electric signals from skin to a device (i.e., excellent in electric conductivity), collecting signals immediately after attachment to the skin, and preventing residue on the skin after peeling from the skin. Moreover, since the living body contact layer is formed from the cured material of the inventive bio-electrode composition, the inventive bio-electrode does not cause allergy even when attached to skin for a long time (i.e., excellent in biocompatibility), and is light-weight and manufacturable at low cost. The bio-electrode prevents significant reduction in the electric conductivity even when wetted with water or dried. In addition, it is possible to further improve the electric conductivity by adding a metal powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

The electro-conductive base material, the bio-electrode composition, etc. used for the inventive method for manufacturing a bio-electrode may be the same as those described above.

The method for applying the bio-electrode composition onto the electro-conductive base material is not limited to particular ones. Examples of the suitable method include dip coating, spray coating, spin coating, roll coating, flow coating, doctor coating, screen printing, flexographic printing, gravure printing, stencil printing, inkjet printing, etc.

The method for curing the resin can be appropriately selected based on the kind of the ionic polymer material (A) used for the bio-electrode composition without being limited to particular methods. For example, the bio-electrode composition is preferably cured by either or both of heat and light. The foregoing bio-electrode composition can also be cured by adding a catalyst in advance to generate acid or base to the bio-electrode composition, which causes a cross-linking reaction.

The curing is particularly preferably performed under a condition where radical polymerization takes place on the repeating unit-b of the ionic polymer material (A).

The heating temperature is not particularly limited and may be appropriately selected based on the kind of the ionic polymer material (A) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

Water droplets may be attached to the surface of the cured film (living body contact layer); alternatively, the film may be immersed in water; alternatively, the surface of the cured film may be sprayed with water vapor or mist. These treatments improve the compatibility with skin, and the resulting film can obtain biological signals quickly. Water mixed with alcohol can be used to reduce size of water vapor or mist.

The aqueous solution to be sprayed as the water vapor etc. may contain a salt selected from the group consisting of sodium salts, potassium salts, and calcium salts.

The salt selected from the group consisting of sodium salts, potassium salts, and calcium salts is preferably a salt selected from the group consisting of sodium chloride, potassium chloride, calcium chloride, saccharin, acesulfame K, sodium carboxylate, potassium carboxylate, calcium carboxylate, sodium sulfonate, potassium sulfonate, and calcium sulfonate.

The aqueous solution to be sprayed as the water vapor etc. may contain a monohydric alcohol or polyhydric alcohol having 1 to 4 carbon atoms.

As the polyhydric alcohol, it is possible to use glycerin, polyethylene glycol, polypropylene glycol, polyglycerin, or a silicone compound having a polyglycerin structure.

The skin to which the bio-electrode is attached may be wiped with a nonwoven fabric, such as gauze, impregnated with water or alcohol to thus remove the oily substance on the skin to freshen and moisturize the outermost skin layer simultaneously. Such treatment is effective in collecting biological signals immediately after the attachment.

As described above, the inventive method for manufacturing a bio-electrode makes it possible to manufacture the inventive bio-electrode easily at low cost, with the bio-electrode enabling signal collection immediately after attachment to skin and prevention of residue on the skin after peeling from the skin. Moreover, the manufactured bio-electrode is light-weight and excellent in electric conductivity and biocompatibility, and prevents significant reduction in the electric conductivity even when wetted with water or dried.

EXAMPLE

Hereinafter, the present invention will be specifically described by giving Examples and Comparative Examples, but the present invention is not limited thereto.

(Synthesis of Ionic Polymer Materials)

Ionic polymers 1 to 21, which were blended as the ionic polymer material (conductive material) to bio-electrode composition solutions, were synthesized as follows.

First, 30 mass % solution of each monomer in cyclopentanone was introduced into a reaction vessel and mixed. The reaction vessel was cooled to −70° C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.01 moles per 1 mole of the whole monomers. This was warmed to a temperature of 60° C. and then allowed to react for 15 hours. After the polymerization, the polymer solution was allowed to react with a compound having a double bond, and thereby a polymerizable unit as the repeating unit-b was formed. After drying the solvent, the composition of the resulting polymer was identified by $^1$H-NMR. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 21 are shown below.

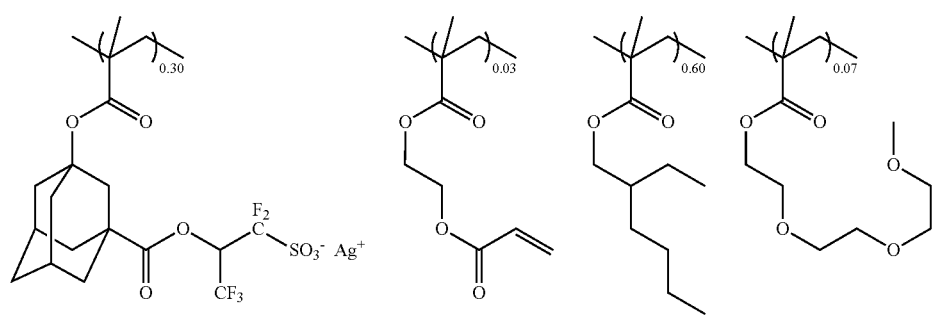
Ionic polymer 1
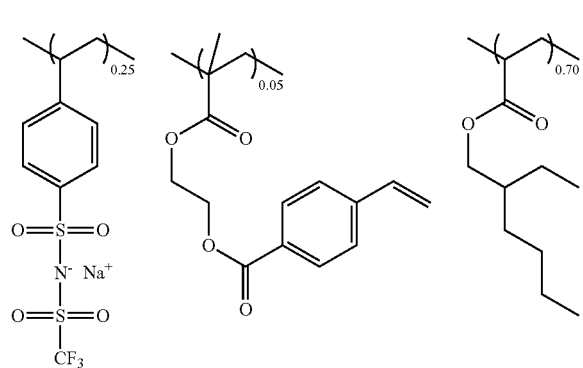
Ionic polymer 2
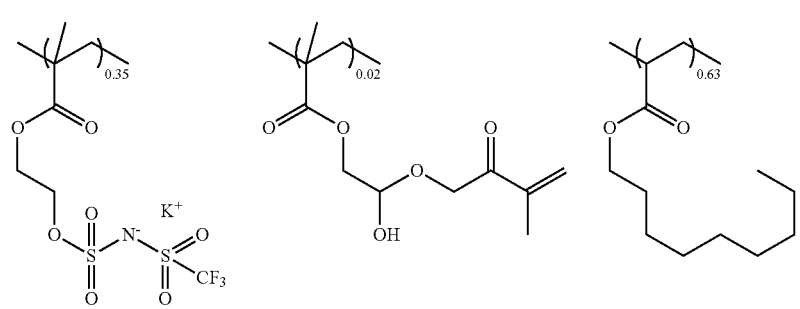
Ionic polymer 3

The repeating number in each formula shows the average value.
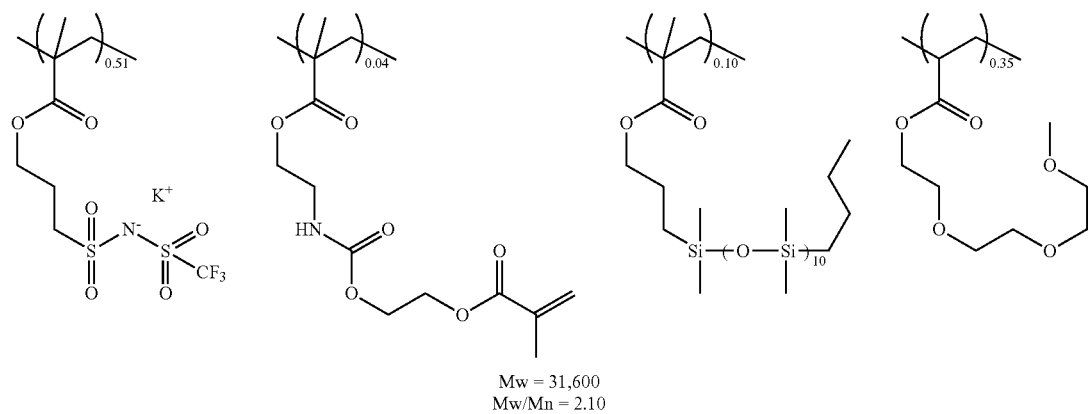
Ionic polymer 4
Mw = 31,600
Mw/Mn = 2.10
The repeating number in each formula shows the average value.
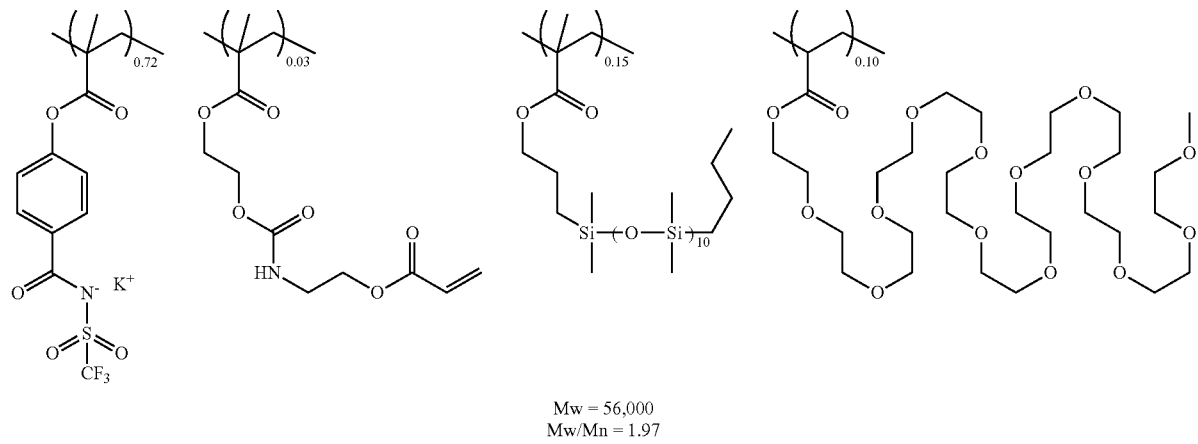
Ionic polymer 5
Mw = 56,000
Mw/Mn = 1.97

The repeating number in each formula shows the average value. The same shall apply hereinafter.
Ionic polymer 6
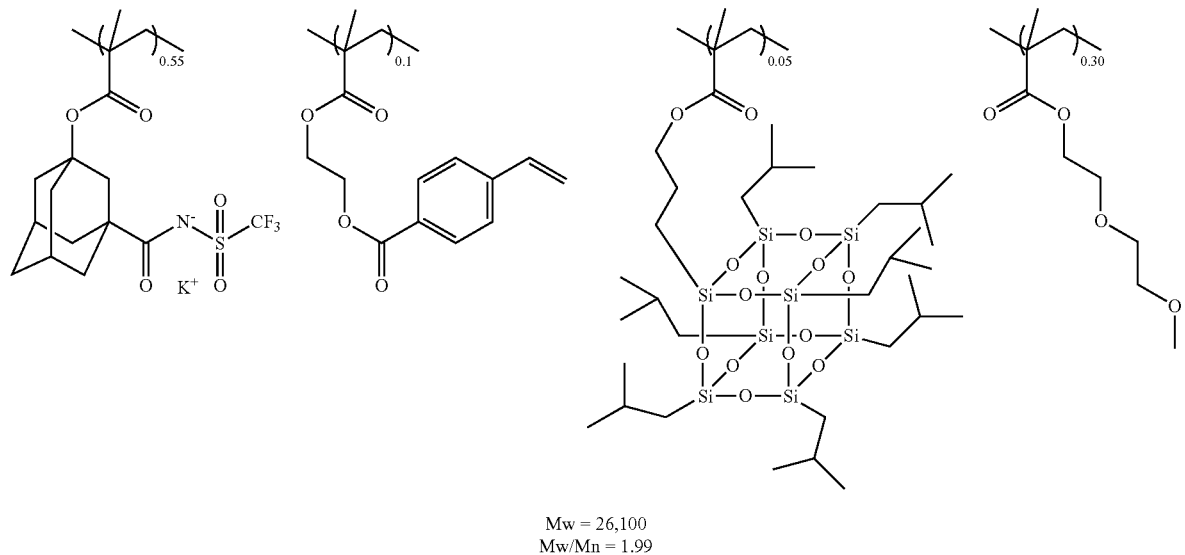
Mw = 26,100
Mw/Mn = 1.99
Ionic polymer 7
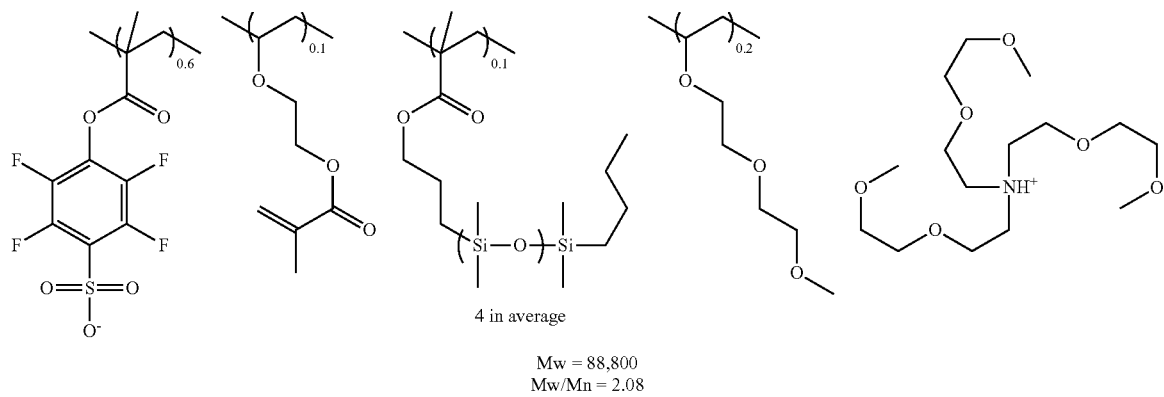
4 in average
Mw = 88,800
Mw/Mn = 2.08
Ionic polymer 8
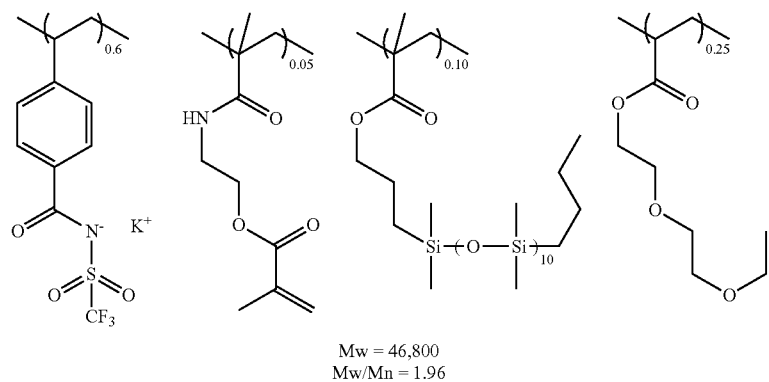
Mw = 46,800
Mw/Mn = 1.96

-continued
Ionic polymer 9
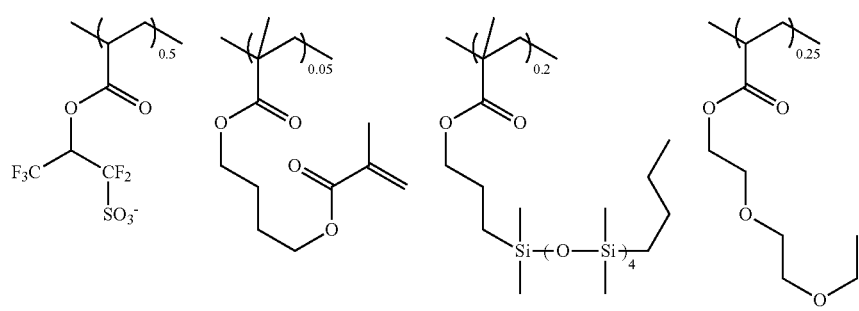
Mw = 98,300
Mw/Mn = 2.05
Ionic polymer 10
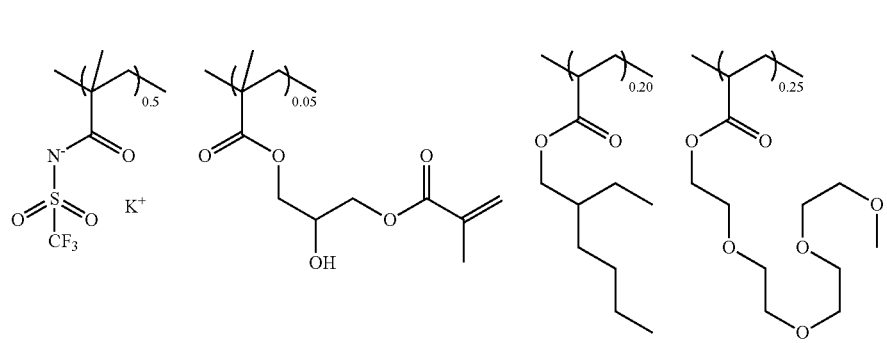
Mw = 97,100
Mw/Mn = 2.20
Ionic polymer 11
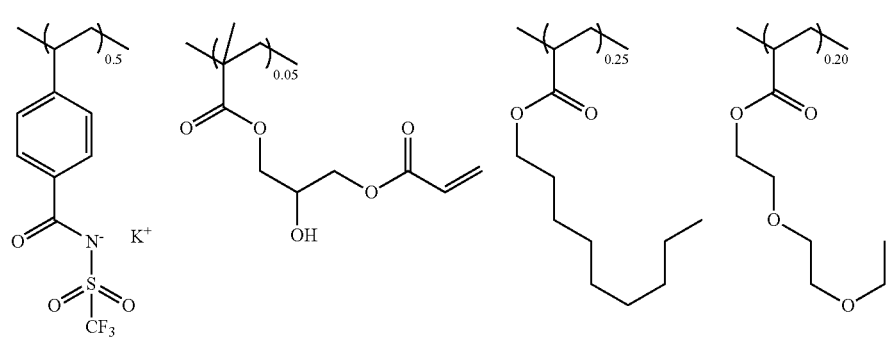
Mw = 32,800
Mw/Mn = 1.98
Ionic polymer 12
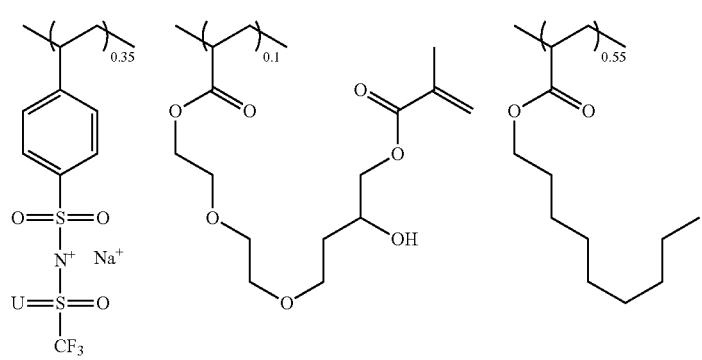
Mw = 35,700
Mw/Mn = 1.78

-continued
Ionic polymer 13
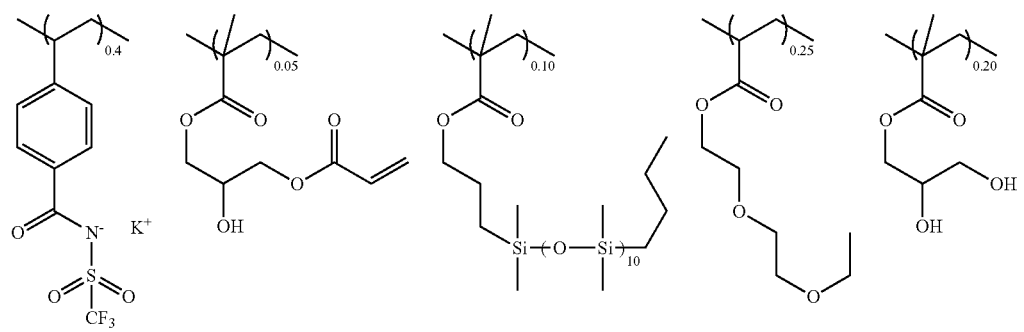
Mw = 46,100
Mw/Mn = 1.76
Ionic polymer 14
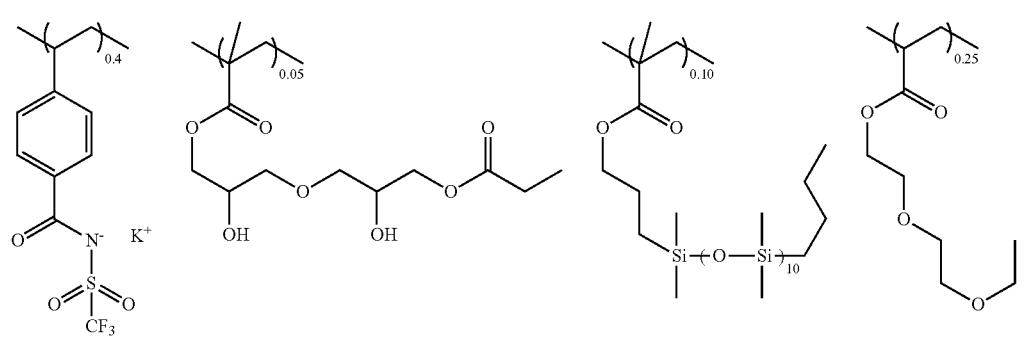
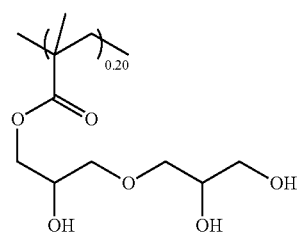
Mw = 46,100
Mw/Mn = 1.76
Ionic polymer 15
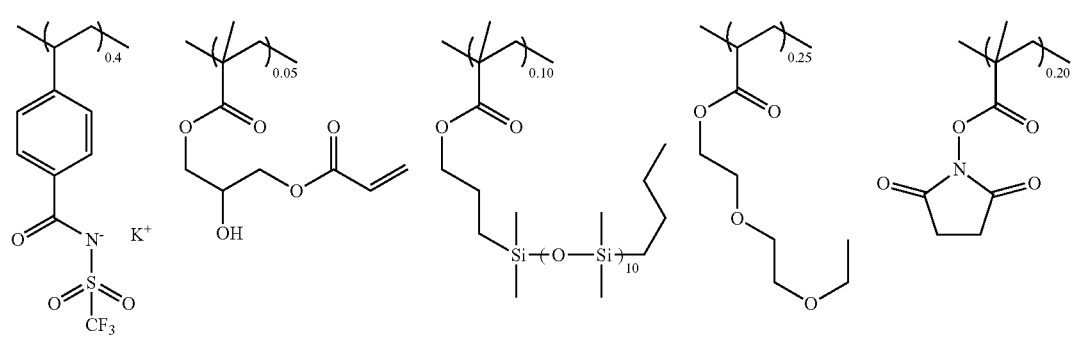
Mw = 36,000
Mw/Mn = 1.97

Ionic polymer 16
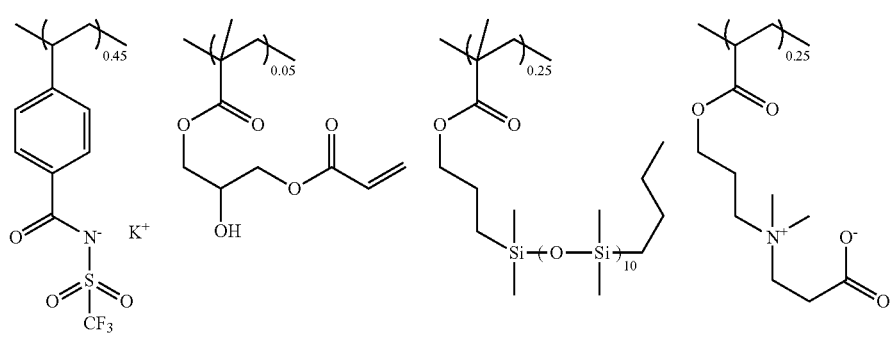
Mw = 16,000
Mw/Mn = 1.91
Ionic polymer 17
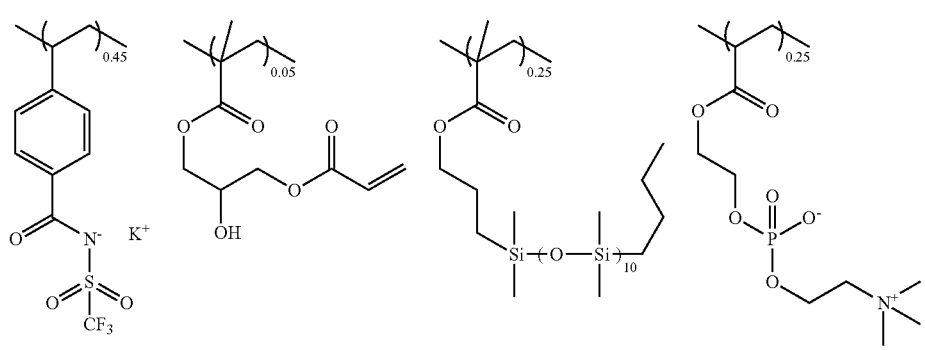
Mw = 23,000
Mw/Mn = 1.93
Ionic polymer 18
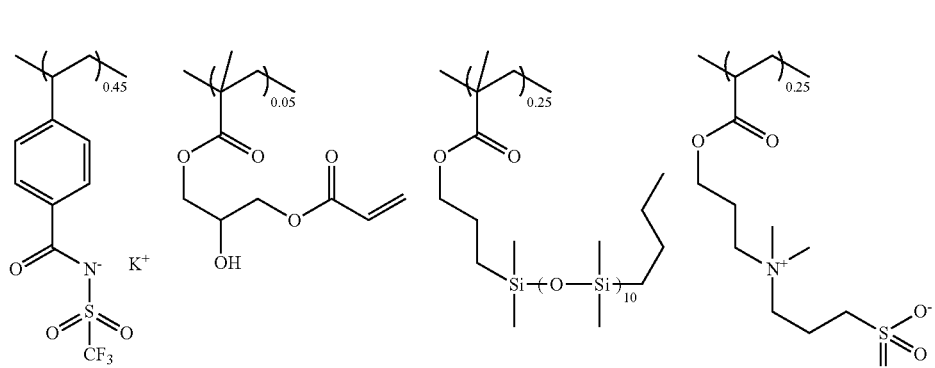
Mw = 15,000
Mw/Mn = 1.96
Ionic polymer 19
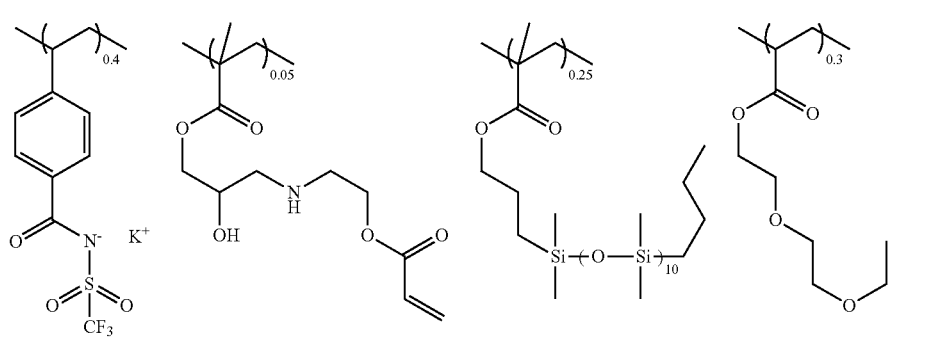
Mw = 41,600
Mw/Mn = 1.86

-continued

Ionic polymer 20

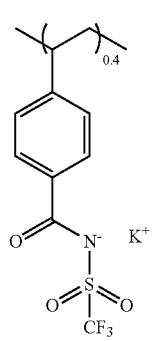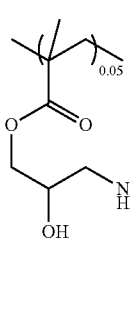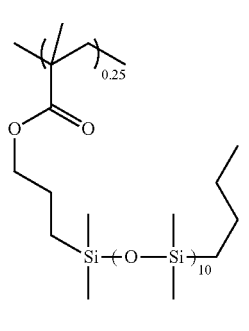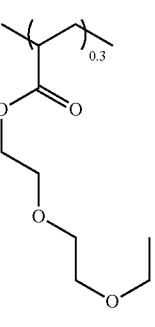

Mw = 41,100
Mw/Mn = 1.82

Ionic polymer 21

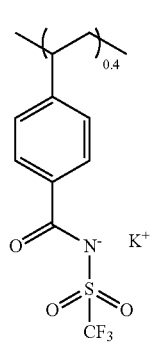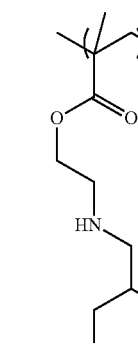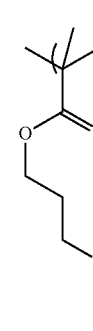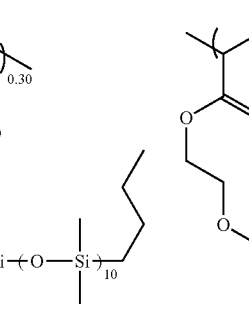

Mw = 41,400
Mw/Mn = 1.86

Comparative salts 1, 2 (Comparative ionic polymers), which were each blended as an ionic material to bio-electrode composition solutions of Comparative Examples, are shown below.

Comparative ionic polymer 1

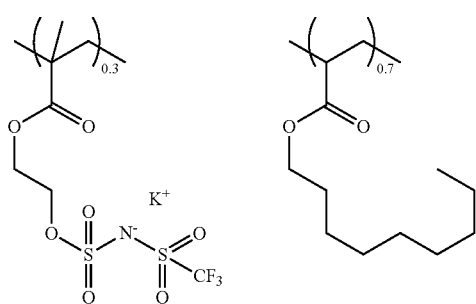

Comparative ionic polymer 1
Mw = 46,000
Mw/Mn = 2.02

Comparative ionic polymer 2

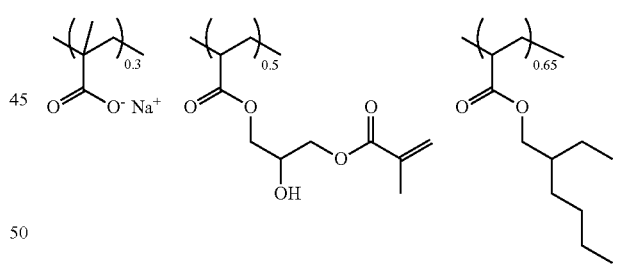

Comparative ionic polymer 2
Mw = 57,900
Mw/Mn = 1.89

Siloxane compounds 1 to 4, which were each blended as a silicone based resin to the bio-electrode composition solutions, are shown below. Hereinbelow, Me represents a methyl group, and Vi represents a vinyl group.

(Siloxane Compound 1)

Siloxane compound 1 was vinyl group-containing polydimethylsiloxane having an alkenyl group-content of 0.007 mol/100 g in which the terminals of molecular chain were capped with SiMe$_2$Vi groups, with the 30% solution in toluene having a viscosity of 27,000 mPa s.

(Siloxane Compound 2)

Siloxane compound 2 was a 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene.

(Siloxane compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were capped with OH groups, with the 30% solution in toluene having a viscosity of 42,000 mPa-s; 100 parts by mass of 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene; and 26.7 parts by mass of toluene) with refluxing for 4 hours, followed by cooling.

(Siloxane Compound 4)

As methylhydrogensilicone oil (Siloxane compound 4), KF-99 manufactured by Shin-Etsu Chemical Co., Ltd. was used.

Silicone pendant urethane (meth)acrylates 1 to 3 and Urethane (meth)acrylate 1, which were blended to the bio-electrode composition solutions, are shown below.

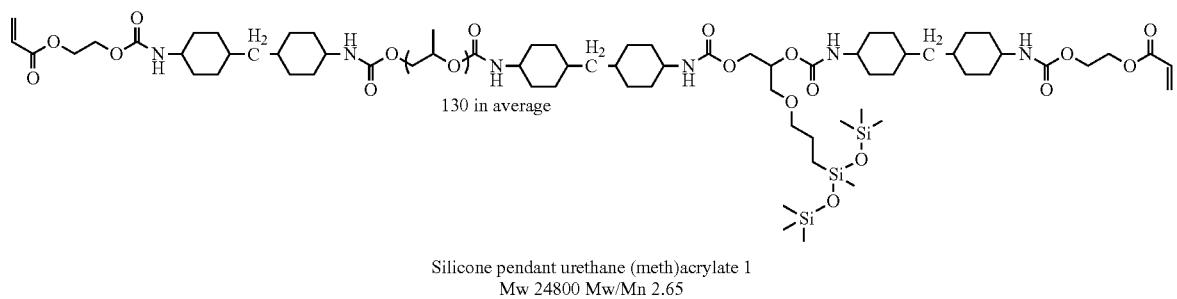

Silicone pendant urethane (meth)acrylate 1
Mw 24800 Mw/Mn 2.65

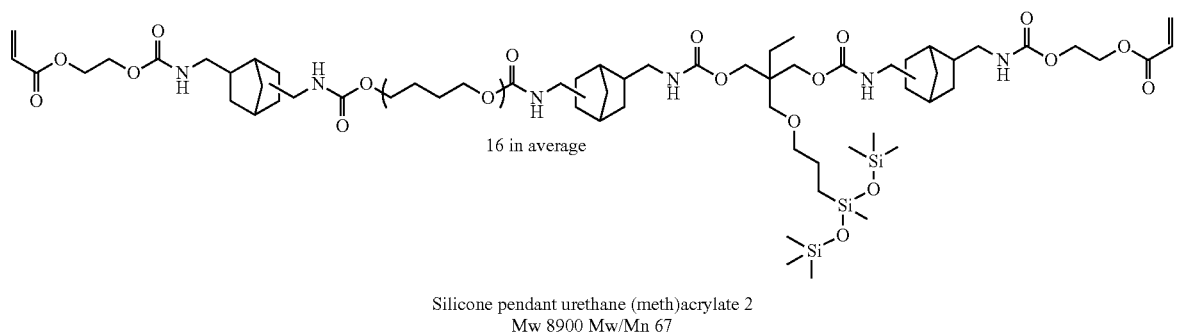

Silicone pendant urethane (meth)acrylate 2
Mw 8900 Mw/Mn 67

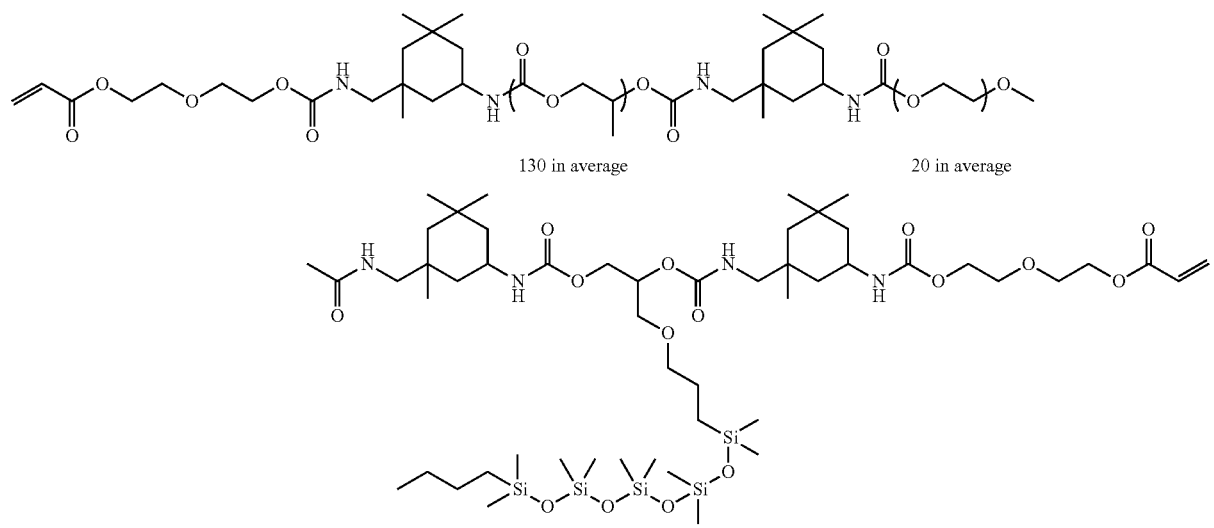

Silicone pendant urethane (meth)acrylate 3
Mw 8100 Mw/Mn 2.98

-continued

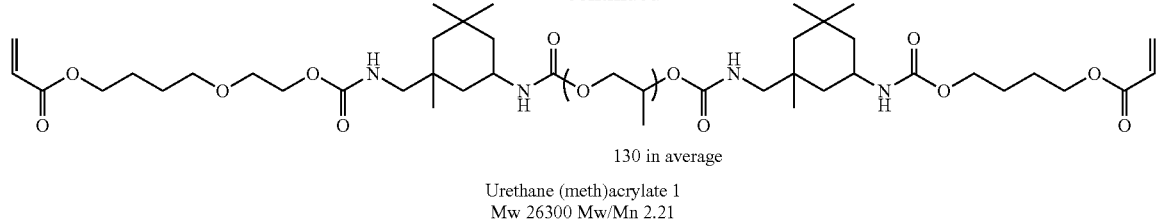

130 in average

Urethane (meth)acrylate 1
Mw 26300 Mw/Mn 2.21

The repeating number in each formula shows the average value.

Acrylic polymer blended as an acrylic based resin into the bio-electrode composition solutions is shown below.

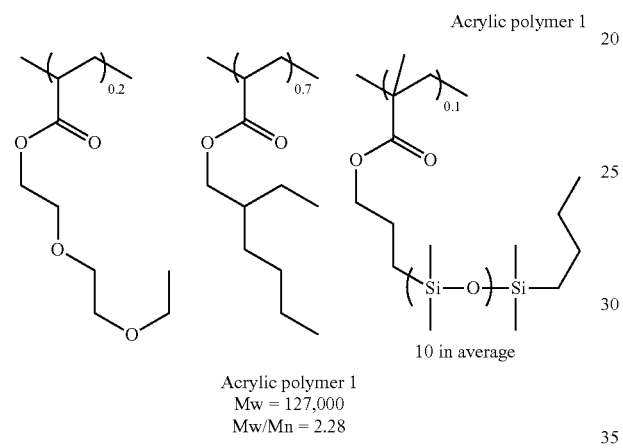

Acrylic polymer 1
Mw = 127,000
Mw/Mn = 2.28

The repeating number in each formula shows the average value.

Organic solvents blended into the bio-electrode composition solutions are shown below. Specific names of the other solvents used are shown in Tables 1 to 3.

EDE: diethylene glycol diethyl ether
BE: diethylene glycol butyl ether
ISOPAR G (manufactured by Exxon Mobile Corporation): isoparaffin A lithium titanate powder, a radical generator, a platinum catalyst, and electric conductivity improvers (carbon black, carbon nanotube), which were blended into the bio-electrode composition solutions as additives, are shown below.

Lithium titanate powder, spinel: manufactured by Sigma-Aldrich Co. LLC., with the size of 200 nm or less
Radical generator: IRGACURE TPO manufactured by BASF SE
Platinum catalyst: CAT-PL-50T manufactured by Shin-Etsu Chemical Co., Ltd.
Carbon black: DENKA BLACK Li-400 manufactured by Denka Co., Ltd.
Multilayer carbon nanotube: manufactured by Sigma-Aldrich Co. LLC., with the diameter of 110 to 170 nm and length of 5 to 9 μm Examples 1 to 27, Comparative Examples 1, 2

(Preparation of Bio-Electrode Compositions)

On the basis of the compositions shown in Tables 1 to 3, the ionic polymer material (salt), the resin, the organic solvent, and the additives (radical generator, platinum catalyst, electric conductivity improver, ion receptivity improver, ionic additive) were blended to prepare bio-electrode compositions (Bio-electrode composition solutions 1 to 24, Comparative bio-electrode composition solutions 1, 2).

TABLE 1

| Bio-electrode composition solution | Ionic polymer material (parts by mass) | Resin (parts by mass) | Organic solvent (parts by mass) | Additive (parts by mass) |
|---|---|---|---|---|
| Bio-electrode composition solution 1 | Ionic polymer 1 (100) | — | BE(60) cyclopentanone(70) | IRGACURE TPO(1) |
| Bio-electrode composition solution 2 | Ionic polymer 2 (100) | — | BE(60) cyclopentanone(70) | IRGACURE TPO(1) |
| Bio-electrode composition solution 3 | Ionic polymer 3 (100) | — | BE(60) cyclopentanone(70) | IRGACURE TPO(1) |
| Bio-electrode composition solution 4 | Ionic polymer 4 (40) | Siloxane compound 1(40) Siloxane compound 2(100) Siloxane compound 4(3) | ISOPAR G(60) cyclopentanone(70) | CAT-PL-50T(0.7) lithium titanate powder(12) silver flake(8) IRGACURE TPO(1) |
| Bio-electrode composition solution 5 | Ionic polymer 5 (40) | Siloxane compound 3(126) Siloxane compound 4(3) | n-octane(40) n-decane(20) cyclopentanone(70) | CAT-PL-50T(1.5) carbon black(5) IRGACURE TPO(1) |
| Bio-electrode composition solution 6 | Ionic polymer 6 (40) | Siloxane compound 3(126) Siloxane compound 4(3) | n-nonane(60) 2-heptanone(14) | CAT-PL-50T(1.5) carbon black(5) IRGACURE TPO(1) |
| Bio-electrode composition solution 7 | Ionic polymer 7 (40) | Siloxane compound 3(126) Siloxane compound 4(3) | ISOPAR G(60) cyclopentanone(60) | CAT-PL-50T(1.5) carbon black(6) IRGACURE TPO(1) |

TABLE 1-continued

| Bio-electrode composition solution | Ionic polymer material (parts by mass) | Resin (parts by mass) | Organic solvent (parts by mass) | Additive (parts by mass) |
|---|---|---|---|---|
| Bio-electrode composition solution 8 | Ionic polymer 8 (40) | Siloxane compound 3(126) Siloxane compound 4(3) | n-decane(30) n-octane(30) 2-heptanone(14) | CAT-PL-50T (1.5) IRGACURE TPO(1) |
| Bio-electrode composition solution 9 | Ionic polymer 9 (40) | Siloxane compound 3(126) Siloxane compound 4(3) | ISOPAR G(60) cyclopentanone(70) | CAT-PL-50T(1.5) multilayer carbon nanotube(3) IRGACURE TPO(1) |
| Bio-electrode composition solution 10 | Ionic polymer 10 (60) | Acrylic polymer 1(40) | EDE(60) cyclopentanone(70) | IRGACURE TPO(1) |
| Bio-electrode composition solution 11 | Ionic polymer 11 (60) | Silicone pendant urethane (meth)acrylate 1(40) | EDE(60) cyclepentanone(70) | IRGACURE TPO(1) |
| Bio-electrode composition solution 12 | Ionic polymer 12 (60) | Silicone pendant urethane (meth)acrylate 2(40) | EDE(60) cyclopentanone(70) | IRGACURE TPO(1) |
| Bio-electrode composition solution 13 | Ionic polymer 12 (60) | Silicone pendant urethane (meth)acrylate 3(40) | EDE(60) cyclopentanone(70) | IRGACURE TPO(1) |
| Bio-electrode composition solution 14 | Ionic polymer 12 (60) | Urethane (meth)acrylate 1(40) | BE(120) water(10) | IRGACURE TPO(1) sodium chloride(2) |
| Bio-electrode composition solution 15 | Ionic polymer 12 (60) | Silicone pendant urethane (meth)acrylate 1(40) | BE(120) water(10) | IRGACURE TPO(1) potassium chloride(2) |

TABLE 2

| Bio-electrode composition solution | Ionic material (parts by mass) | Resin (parts by mass) | Organic solvent (parts by mass) | Additive (parts by mass) |
|---|---|---|---|---|
| Bio-electrode composition solution 16 | Ionic polymer 13(60) | Silicone pendant urethane (meth)acrylate 2(40) | EDE(60) cyclopentanone(70) | IRGACURE TPO(1) |
| Bio-electrode composition solution 17 | Ionic polymer 14(60) | Silicone pendant urethane (meth)acrylate 3(40) | EDE(60) cyclopentanone(70) | IRGACURE TPO(1) |
| Bio-electrode composition solution 18 | Ionic polymer 15(60) | Silicone pendant urethane (meth)acrylate 3(40) | EDE(60) cyclopentanone(70) | IRGACURE TPO(1) |
| Bio-electrode composition solution 19 | Ionic polymer 16(60) | Silicone pendant urethane (meth)acrylate 3(40) | EDE(60) ethyl lactate(70) | IRGACURE TPO(1) |
| Bio-electrode composition solution 20 | Ionic polymer 17(60) | Silicone pendant urethane (meth)acrylate 3(40) | EDE(60) ethyl lactate(70) | IRGACURE TPO(1) |
| Bio-electrode composition solution 21 | Ionic polymer 18(60) | Silicone pendant urethane (meth)acrylate 3(40) | EDE(60) ethyl lactate(70) | IRGACURE TPO(1) |
| Bio-electrode composition solution 22 | Ionic polymer 19(60) | Silicone pendant urethane (meth)acrylate 3(40) | EDE(60) ethyl lactate(70) | IRGACURE TPO(1) |
| Bio-electrode composition solution 23 | Ionic polymer 20(60) | Silicone pendant urethane (meth)acrylate 3(40) | EDE(60) ethyl lactate(70) | IRGACURE TPO(1) |
| Bio-electrode composition solution 24 | Ionic polymer 21(60) | Silicone pendant urethane (meth)acrylate 3(40) | EDE(60) ethyl lactate(70) | IRGACURE TPO(1) |

TABLE 3

| Bio-electrode composition solution | Ionic polymer material (parts by mass) | Resin (parts by mass) | Organic solvent (parts by mass) | Additive (parts by mass) |
|---|---|---|---|---|
| Comparative bio-electrode composition solution 1 | Comparative ionic polymer 1(100) | — | BE(60) cyclopentanone(70) | IRGACURE TPO(1) |
| Comparative bio-electrode composition solution 2 | Comparative ionic polymer 2(100) | — | BE(60) cyclopentanone(70) | IRGACURE TPO(1) |

(Preparation of Samples for Biological Signal Evaluation)

A thermoplastic urethane (TPU) film ST-604 (manufactured by Bemis Associates Inc.) was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern including a circular portion with a diameter of 2 cm and a rectangular portion. Then, one of the bio-electrode composition solutions shown in Tables 1 to 3 was applied onto the circular portion of the printed electro-conductive pattern by screen printing. After air-dried at room temperature for 10 minutes, the coating film was baked using an oven at 125° C. for 10 minutes to evaporate the solvent and cure the film. The resulting films were further cured by irradiation with a xenon lamp at a radiant exposure level of 200 mJ/cm$^2$ under a nitrogen atmosphere. By the curing, cured materials of the bio-electrode compositions were obtained as living body contact layers. In Examples 16 and 18, the cured bio-electrodes respectively prepared in Examples 1, 4, and 12 were left standing in a 30° C. and 90%-humidity environment for 1 hour to perform humidification treatment.

FIG. 3 is a schematic view of the printed bio-electrodes prepared in each Example. As shown in FIG. 3, multiple bio-electrodes 1 were prepared on the thermoplastic urethane film 20. The bio-electrodes 1 each include the keyhole-shaped electro-conductive pattern 2 as the electro-conductive base material, and the living body contact layer 3 formed to cover the circular portion of the electro-conductive pattern 2.

Then, as shown in FIG. 4, the urethane film 20 with the printed bio-electrodes 1 was cut out and pasted on a double-sided tape 21. In this manner, three bio-electrode samples 10 (samples for biological signal evaluation) were prepared for each of the composition solutions.

(Thickness Measurement of Living Body Contact Layer)

The thickness of the living body contact layer of each bio-electrode sample prepared as described above was measured with a micrometer. Tables 4 and 5 show the result.

(Biological Signal Measurement)

The electro-conductive wiring pattern formed from the electro-conductive paste of each bio-electrode was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. Immediately after the attachments, the electrocardiogram measurement was started to measure the time until an electrocardiogram waveform including P, Q, R, S, and T waves appeared as shown in FIG. 6. Further, whether or not a residue remained on the skin was checked after the electrodes were peeled. Tables 4 and 5 show the results.

TABLE 4

| Example | Bio-electrode composition solution | Resin thickness (μm) | Time (min.) until ECG signal appeared | Presence/absence of residue on skin after peeling of bio-electrode |
|---|---|---|---|---|
| Example 1 | Bio-electrode composition solution 1 | 22 | 1.5 | absent |
| Example 2 | Bio-electrode composition solution 2 | 22 | 2 | absent |
| Example 3 | Bio-electrode composition solution 3 | 25 | 2 | absent |
| Example 4 | Bio-electrode composition solution 4 | 33 | 1.3 | absent |
| Example 5 | Bio-electrode composition solution 5 | 32 | 1.5 | absent |
| Example 6 | Bio-electrode composition solution 6 | 39 | 1.8 | absent |
| Example 7 | Bio-electrode composition solution 7 | 31 | 1.6 | absent |
| Example 8 | Bio-electrode composition solution 8 | 36 | 1.8 | absent |
| Example 9 | Bio-electrode composition solution 9 | 33 | 2 | absent |
| Example 10 | Bio-electrode composition solution 10 | 29 | 2 | absent |
| Example 11 | Bio-electrode composition solution 11 | 26 | 2 | absent |
| Example 12 | Bio-electrode composition solution 12 | 28 | 2 | absent |
| Example 13 | Bio-electrode composition solution 13 | 29 | 2 | absent |
| Example 14 | Bio-electrode composition solution 14 | 31 | 2 | absent |
| Example 15 | Bio-electrode composition solution 15 | 36 | 2 | absent |
| Example 16 | Bio-electrode composition solution 1 | 23 | 0.1 | absent |

TABLE 4-continued

| Example | Bio-electrode composition solution | Resin thickness (μm) | Time (min.) until ECG signal appeared | Presence/absence of residue on skin after peeling of bio-electrode |
|---|---|---|---|---|
| Example 17 | Bio-electrode composition solution 4 | 31 | 0.1 | absent |
| Example 18 | Bio-electrode composition solution 12 | 29 | 0.1 | absent |
| Comparative Example 1 | Comparative bio-electrode composition solution 1 | 20 | 2 | present |
| Comparative Example 2 | Comparative bio-electrode composition solution 2 | 21 | N/A | absent |

TABLE 5

| Example | Bio-electrode composition solution | Resin thickness (μm) | Time (min.) until ECG signal appeared | Presence/absence of residue on skin after peeling of bio-electrode |
|---|---|---|---|---|
| Example 19 | Bio-electrode composition solution 16 | 22 | 1.5 | absent |
| Example 20 | Bio-electrode composition solution 17 | 21 | 1.0 | absent |
| Example 21 | Bio-electrode composition solution 18 | 22 | 1.5 | absent |
| Example 22 | Bio-electrode composition solution 19 | 24 | 1.5 | absent |
| Example 23 | Bio-electrode composition solution 20 | 25 | 1.4 | absent |
| Example 24 | Bio-electrode composition solution 21 | 24 | 1.2 | absent |
| Example 25 | Bio-electrode composition solution 22 | 25 | 1.0 | absent |
| Example 26 | Bio-electrode composition solution 23 | 24 | 1.0 | absent |
| Example 27 | Bio-electrode composition solution 24 | 21 | 1.0 | absent |

As shown in Tables 4 and 5, in Examples 1 to 27 in each of which the living body contact layer was formed using the inventive bio-electrode composition including the ionic polymer material containing the ionic repeating unit-a having a particular structure and the repeating unit-b having a radical-polymerizable (crosslinkable) double bond, biological signals (ECG signals) were detected within short times after the attachment to the body, and no residue remained on the skin after the peeling.

Particularly, in Examples 16 to 18 where the humidification treatment was performed, the bio-electrodes were capable of obtaining biological signals within shorter time after the attachment to the body, and no residue remained on the skin after the peeling, as well.

In contrast, in Comparative Example 1 in which the living body contact layer was formed using the bio-electrode composition including the ionic polymer compound not containing the repeating unit having a crosslinkable double bond, residue was observed on the skin after the peeling. Meanwhile, in Comparative Example 2 in which the living body contact layer was formed using the bio-electrode composition including the ionic polymer compound not containing an ionic component having a particular structure, no biological signal was obtained.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A bio-electrode composition comprising
(A) an ionic polymer material, wherein
the ionic polymer material (A) is a polymer compound comprising:
a repeating unit-a having a structure selected from the group consisting of salts of ammonium, sodium, potassium, and silver formed with any of fluorosulfonic acid, fluorosulfonimide, and N-carbonylfluorosulfonamide; and
a repeating unit-b having a side chain with a radical-polymerizable double bond in a structure selected from the group consisting of (meth)acrylate, vinyl ether, and styrene.

2. The bio-electrode composition according to claim 1, wherein the repeating unit-a is shown by any of the following general formulae (1)-1 to (1)-4,

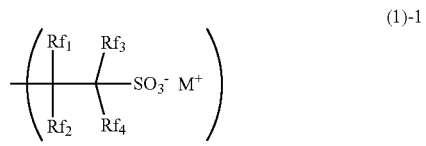

(1)-1

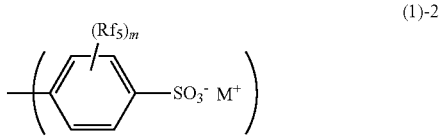

(1)-2

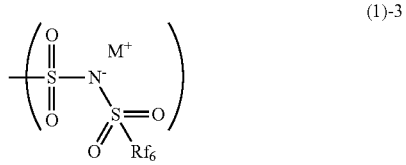

(1)-3

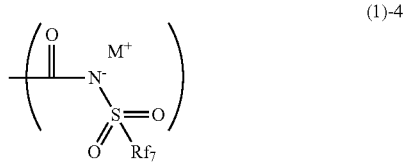

(1)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; and $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group;

Rf$_5$, Rf$_6$, and Rf$_7$ each represent a fluorine atom, or a linear or branched alkyl group having 1 to 4 carbon atoms and at least one or more fluorine atoms;

M$^+$ represents an ion selected from the group consisting of an ammonium ion, a sodium ion, a potassium ion, and a silver ion; and "m" represents an integer of 1 to 4.

3. The bio-electrode composition according to claim 1, wherein the repeating unit-a comprises at least one repeating unit selected from the group consisting of repeating units-a1 to -a7 shown by the following general formula (2),

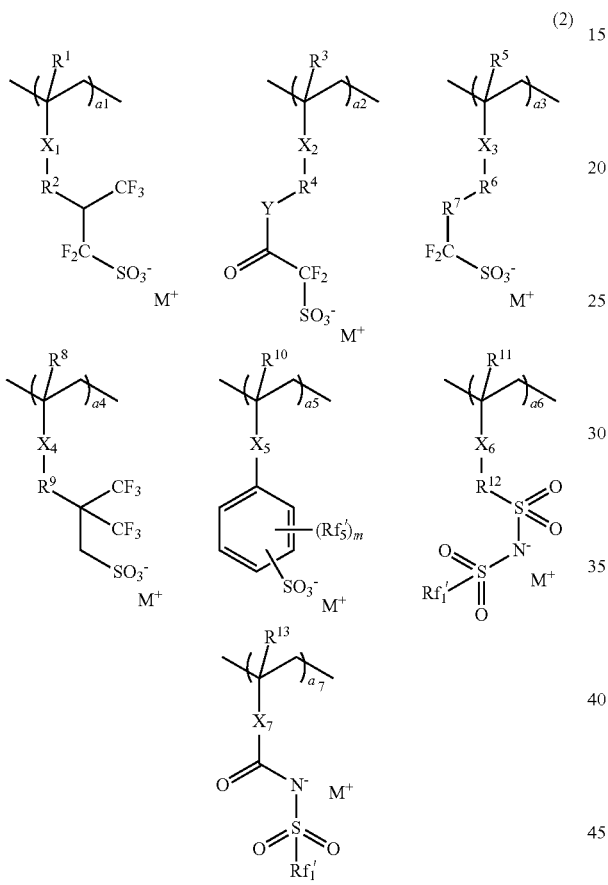

(2)

wherein R$^1$, R$^3$, R$^5$, R$^8$, R$^{10}$, R$^{11}$, and R$^{13}$ each independently represent a hydrogen atom or a methyl group; R$^2$, R$^4$, R$^6$, R$^9$, and R$^{12}$ each independently represent a single bond, or a linear, branched, or cyclic hydrocarbon group having 1 to 12 carbon atoms, the hydrocarbon group optionally having either or both of an ester group and an ether group; R$^7$ represents a linear or branched alkylene group having 1 to 4 carbon atoms, and one or two hydrogen atoms in R$^7$ are optionally substituted with a fluorine atom; X$_1$, X$_2$, X$_3$, X$_4$, X$_6$, and X$_7$ each independently represent any of a single bond, a phenylene group, a naphthylene group, an ether group, an ester group, and an amide group; X$_5$ represents any of a single bond, an ether group, and an ester group; Y represents an oxygen atom or a —NR$^{19}$— group; R$^{19}$ represents a hydrogen atom, or a linear or branched alkyl group having 1 to 4 carbon atoms; Rf$_1'$ represents a fluorine atom or a trifluoromethyl group; Rf$_5'$ represents a fluorine atom, or a linear or branched alkyl group having 1 to 4 carbon atoms and at least one or more fluorine atoms; "m" represents an integer of 1 to 4; a1, a2, a3, a4, a5, a6, and a7 satisfy 0≤a1<1.0, 0≤a2<1.0, 0≤a3<1.0, 0≤a4<1.0, 0≤a5<1.0, 0≤a6<1.0, 0≤a7<1.0, and 0<a1+a2+a3+a4+a5+a6+a7<1.0; and M$^+$ represents an ion selected from the group consisting of an ammonium ion, a sodium ion, a potassium ion, and a silver ion.

4. The bio-electrode composition according to claim 2, wherein the ionic polymer material (A) comprises an ammonium ion shown by the following general formula (3) as the M$^+$,

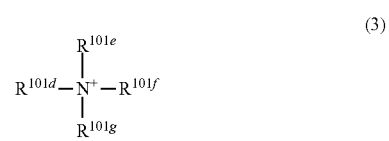

(3)

wherein R$^{101d}$, R$^{101e}$, R$^{101f}$, and R$^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and R$^{101d}$ and R$^{101e}$, or R$^{101d}$, R$^{101e}$, and R$^{101f}$, are optionally bonded to each other together with a nitrogen atom bonded therewith to form a ring in which R$^{101d}$ and R$^{101e}$, or R$^{101d}$, R$^{101e}$, and R$^{101f}$, represent an alkylene group having 3 to 10 carbon atoms, or to form a heteroaromatic ring having the nitrogen atom in the formula (3) within the ring.

5. The bio-electrode composition according to claim 1, wherein the repeating unit-b is shown by the following general formula (4),

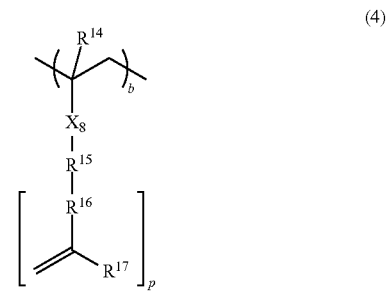

(4)

wherein R$^{14}$ and R$^{17}$ each represent a hydrogen atom or a methyl group; X$_8$ represents any of a single bond, a phenylene group, a naphthylene group, an ether group, an ester group, and an amide group; R$^{15}$ represents a single bond, a linear, branched, or cyclic alkylene group having 1 to 20 carbon atoms, or an aryl group having 6 to 10 carbon atoms, the alkylene group optionally having an ether group, an ester group, a hydroxy group, an alkoxy group, an alkoxycarbonyl group, a urethane group, a carbonate group, or an amino group; R$^{16}$ represents an ether group, an ester group, or a phenylene group; "p" represents an integer of 1 to 3; and "b" represents a number satisfying 0<b<1.0.

6. The bio-electrode composition according to claim 1, comprising, in addition to the ionic polymer material (A), a resin component (B) which is a resin containing any one or more of silicone, polyacrylate, and polyurethane.

7. The bio-electrode composition according to claim 6, wherein the resin containing any one or more of silicone, polyacrylate, and polyurethane as the resin component (B) has adhesion.

8. The bio-electrode composition according to claim 1, further comprising a radical generator.

9. The bio-electrode composition according to claim 1, further comprising an organic solvent.

10. The bio-electrode composition according to claim 1, further comprising any one or more of a carbon material, a silicon powder, a silver powder, and a lithium titanate powder having a spinel structure.

11. A bio-electrode comprising an electro-conductive base material and a living body contact layer formed on the electro-conductive base material, wherein
the living body contact layer is a cured material of the bio-electrode composition according to claim 1.

12. A bio-electrode comprising an electro-conductive base material and a living body contact layer formed on the electro-conductive base material, wherein
the living body contact layer is a cured material of the bio-electrode composition according to claim 2.

13. A bio-electrode comprising an electro-conductive base material and a living body contact layer formed on the electro-conductive base material, wherein
the living body contact layer is a cured material of the bio-electrode composition according to claim 3.

14. The bio-electrode according to claim 11, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

15. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition to form the living body contact layer.

16. A method for manufacturing a bio-electrode having an electro-conductive base material and a living body contact layer formed on the electro-conductive base material, comprising:
applying the bio-electrode composition according to claim 2 onto the electro-conductive base material; and
curing the bio-electrode composition to form the living body contact layer.

17. A method for manufacturing a bio-electrode having an electro-conductive base material and a living body contact layer formed on the electro-conductive base material, comprising:
applying the bio-electrode composition according to claim 3 onto the electro-conductive base material; and
curing the bio-electrode composition to form the living body contact layer.

18. The method for manufacturing a bio-electrode according to claim 15, wherein the living body contact layer is formed by curing the bio-electrode composition through light irradiation.

19. The method for manufacturing a bio-electrode according to claim 15, wherein after the living body contact layer is formed, the living body contact layer is immersed in water, or the living body contact layer is humidified.

20. The method for manufacturing a bio-electrode according to claim 15, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

* * * * *